US011954925B2

(12) United States Patent
Mizutani et al.

(10) Patent No.: US 11,954,925 B2
(45) Date of Patent: Apr. 9, 2024

(54) SUBSTANCE PREPARATION EVALUATION SYSTEM

(71) Applicant: Beckman Coulter, Inc., Brea, CA (US)

(72) Inventors: Takayuki Mizutani, Edina, MN (US); Katsuhiro Seo, Kanagawa (JP); Shigeru Fujii, Shizuoka (JP); Kazuki Umebara, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 222 days.

(21) Appl. No.: 17/682,809

(22) Filed: Feb. 28, 2022

(65) Prior Publication Data
US 2023/0045577 A1 Feb. 9, 2023

Related U.S. Application Data

(62) Division of application No. 16/345,658, filed as application No. PCT/US2017/058838 on Oct. 27, 2017, now Pat. No. 11,263,433.
(Continued)

(51) Int. Cl.
*G06V 20/69* (2022.01)
*C12M 1/34* (2006.01)
(Continued)

(52) U.S. Cl.
CPC ............. *G06V 20/69* (2022.01); *C12M 41/46* (2013.01); *G06T 7/62* (2017.01); *G06V 10/50* (2022.01);
(Continued)

(58) Field of Classification Search
CPC ........ G06V 20/69; G06V 10/50; G06V 20/50; G06V 10/255; G06V 20/693;
(Continued)

(56) References Cited

U.S. PATENT DOCUMENTS 7,771,659 B2 * 8/2010 Ziegler .................. G01N 15/05
422/65
8,321,055 B2 * 11/2012 Chen ...................... B25J 9/1697
700/32
(Continued)

FOREIGN PATENT DOCUMENTS

EP 0908724 4/1999
EP 2182371 5/2010
(Continued)

OTHER PUBLICATIONS

Search Report for Brazil Patent Application No. 112019008270-0, dated Apr. 11, 2023, 6 pages.
(Continued)

*Primary Examiner* — Michael S Osinski
(74) *Attorney, Agent, or Firm* — McAndrews, Held & Malloy, Ltd.

(57) ABSTRACT

Automatic substance preparation and evaluation systems and methods are provided for preparing and evaluating a fluidic substance, such as e.g. a sample with bodily fluid, in a container and/or in a dispense tip. The systems and methods can detect volumes, evaluate integrities, and check particle concentrations in the container and/or the dispense tip.

23 Claims, 80 Drawing Sheets

Related U.S. Application Data

(60) Provisional application No. 62/525,948, filed on Jun. 28, 2017, provisional application No. 62/414,655, filed on Oct. 28, 2016.

(51) Int. Cl.
    *G06T 7/62*     (2017.01)
    *G06V 10/50*     (2022.01)
    *G06V 20/50*     (2022.01)

(52) U.S. Cl.
    CPC .... *G06V 20/50* (2022.01); *G06T 2207/10024* (2013.01); *G06T 2207/30072* (2013.01)

(58) Field of Classification Search
CPC ........ G06V 20/698; C12M 41/46; G06T 7/62; G06T 2207/10024; G06T 2207/30072; G06T 2207/20081; G06T 7/90; G06T 2207/20072; G06T 2207/20084; G06T 7/0014; G06T 2207/20076; G06T 7/0012; G06T 2207/10056; G06T 2207/30242; G01N 2035/103; G01N 35/1011; G01N 35/1016; G01N 15/0227; G01N 15/1463; G01N 15/1475; G01N 15/1434; G01N 2015/1486; G01N 21/51; G01N 2015/0065; G01N 35/00732; G01N 15/1404; B01L 3/502715; B01L 2200/0647; B01L 2200/143; G02B 21/365

See application file for complete search history.

(56) References Cited

U.S. PATENT DOCUMENTS

| | | | |
|---|---|---|---|
| 9,816,949 B2* | 11/2017 | Santini | G06T 5/20 |
| 10,625,259 B1 | 4/2020 | Jones | |
| 11,574,460 B2* | 2/2023 | Sawhney | G06V 10/44 |
| 2006/0178578 A1 | 8/2006 | Tribble et al. | |
| 2008/0019584 A1* | 1/2008 | Lindberg | G06V 20/693 |
| | | | 382/134 |
| 2009/0059194 A1* | 3/2009 | Kanaya | G03F 7/70516 |
| | | | 250/559.1 |
| 2009/0076368 A1* | 3/2009 | Balas | A61B 1/042 |
| | | | 600/407 |
| 2009/0185714 A1* | 7/2009 | Lindberg | B01L 3/502715 |
| | | | 382/100 |
| 2009/0185734 A1* | 7/2009 | Lindberg | G06V 20/693 |
| | | | 382/133 |
| 2010/0102247 A1* | 4/2010 | Arvinte | G01N 21/51 |
| | | | 250/432 R |
| 2012/0086938 A1* | 4/2012 | Folkenberg | G01N 1/4077 |
| | | | 356/246 |
| 2013/0023007 A1 | 1/2013 | Zahniser et al. | |
| 2013/0122513 A1* | 5/2013 | Petersson | B03C 1/288 |
| | | | 435/7.1 |
| 2013/0263656 A1 | 10/2013 | Walsh et al. | |
| 2013/0293873 A1* | 11/2013 | Bentien | G01N 15/0227 |
| | | | 356/73 |
| 2013/0316934 A1* | 11/2013 | Matayoshi | G01N 15/06 |
| | | | 382/128 |
| 2013/0336567 A1* | 12/2013 | Chan | G01N 33/5094 |
| | | | 382/133 |
| 2014/0045170 A1 | 2/2014 | Patel et al. | |
| 2014/0273188 A1 | 9/2014 | Mohan et al. | |
| 2015/0118757 A1 | 4/2015 | Hamada et al. | |
| 2015/0233908 A1* | 8/2015 | Kelly | G01N 33/54326 |
| | | | 422/69 |
| 2015/0294461 A1 | 10/2015 | Satish et al. | |
| 2015/0347817 A1 | 12/2015 | Valvik et al. | |
| 2016/0041094 A1* | 2/2016 | Lei | G01N 15/1463 |
| | | | 250/573 |
| 2016/0228075 A1* | 8/2016 | Kitamura | A61B 6/12 |
| 2016/0291049 A1 | 10/2016 | Arumugam et al. | |
| 2017/0241894 A1 | 8/2017 | McCaffrey et al. | |
| 2017/0343542 A1 | 11/2017 | Jitsuhara et al. | |
| 2017/0345148 A1 | 11/2017 | Tomoda et al. | |
| 2017/0363851 A1* | 12/2017 | Xu | G02B 21/06 |
| 2018/0231446 A1 | 8/2018 | Svanback | |
| 2018/0231760 A1 | 8/2018 | Fradkin et al. | |
| 2019/0154560 A1 | 5/2019 | Matayoshi et al. | |
| 2019/0156475 A1* | 5/2019 | Markson | G06T 7/70 |
| 2019/0339189 A1 | 11/2019 | Takeda et al. | |
| 2020/0116610 A1 | 4/2020 | Wang et al. | |
| 2020/0232894 A1* | 7/2020 | Delubac | G01N 11/08 |
| 2020/0264207 A1* | 8/2020 | Kubota | G01N 35/1016 |
| 2020/0391138 A1 | 12/2020 | Chatterjee et al. | |
| 2023/0045577 A1* | 2/2023 | Mizutani | G06V 20/69 |

FOREIGN PATENT DOCUMENTS

| | | |
|---|---|---|
| EP | 2293024 | 3/2011 |
| EP | 2148205 | 1/2013 |
| EP | 1489303 | 6/2013 |
| EP | 2605020 | 6/2013 |
| EP | 2490814 | 1/2015 |
| EP | 2574907 | 7/2015 |
| EP | 2716215 | 11/2015 |
| EP | 2846916 | 6/2017 |
| EP | 1956360 | 1/2018 |
| JP | 2010175291 A | 8/2010 |
| JP | 2011058985 A | 3/2011 |
| JP | 2012-008077 A | 1/2012 |
| JP | 2014-504731 A | 2/2014 |
| WO | 2016133900 | 8/2016 |

OTHER PUBLICATIONS

PCT, International Search Report and Written Opinion regarding Appliation No. PCT/US2017/058838, 15 pgs., dated May 30, 2018.
European Patent Office, Official Communication regarding Application No. 178090778.3, 19 pgs., dated Dec. 23, 2020.
Indian Patent Office, Official Communication regarding Application No. 201947020101, 60 pgs., dated Jun. 20, 2022.

* cited by examiner

| | FIRST INTERFERENT | | SECOND INTERFERENT | | THIRD INTERFERENT | |
|---|---|---|---|---|---|---|
| | CONCENTRATION VALUE | CLASSIFICATION LABEL | CONCENTRATION VALUE | CLASSIFICATION LABEL | CONCENTRATION VALUE | CLASSIFICATION LABLE |
| | VALUE(S) 1-1 | ZERO | VALUE(S) 2-1 | ABSENT | VALUE(S) 3-1 | ZERO |
| | VALUE(S) 1-2 | MEDIUM | VALUE(S) 2-2 | PRESENT | VALUE(S) 3-2 | MEDIUM |
| | VALUE(S) 1-3 | HIGH | VALUE(S) 2-3 | PRESENT | VALUE(S) 3-3 | HIGH |

| SAMPLE CLASSIFICATION RESULT | FLAGGING RESULT |
| --- | --- |
| ZERO_ABSENT_ZERO | UNFLAGGED |
| ZERO_ABSENT_MEDIUM | UNFLAGGED |
| ZERO_ABSENT_HIGH | FLAGGED |
| ZERO_PRESENT_ZERO | FLAGGED |
| ZERO_PRESENT_MEDIUM | FLAGGED |
| ZERO_PRESENT_HIGH | FLAGGED |
| MEDIUM_ABSENT_ZERO | UNFLAGGED |
| MEDIUM_ABSENT_MEDIUM | FLAGGED |
| MEDIUM_ABSENT_HIGH | FLAGGED |
| MEDIUM_PRESENT_ZERO | FLAGGED |
| MEDIUM_PRESENT_MEDIUM | FLAGGED |
| MEDIUM_PRESENT_HIGH | FLAGGED |
| HIGH_ABSENT_ZERO | FLAGGED |
| HIGH_ABSENT_MEDIUM | FLAGGED |
| HIGH_ABSENT_HIGH | FLAGGED |
| HIGH_PRESENT_ZERO | FLAGGED |
| HIGH_PRESENT_MEDIUM | FLAGGED |
| HIGH_PRESENT_HIGH | FLAGGED |

*FIG. 55*

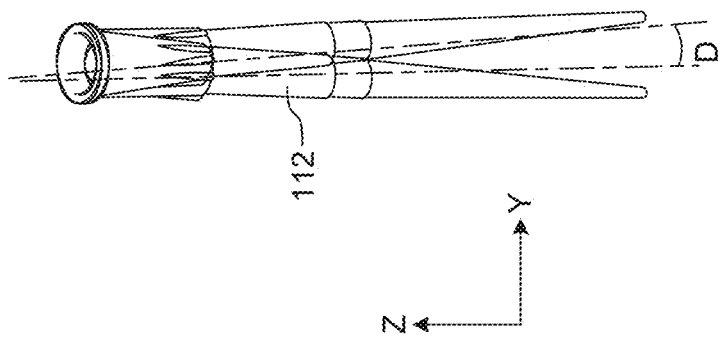
[Diagram 3: Side View from the Camera's Perspective]
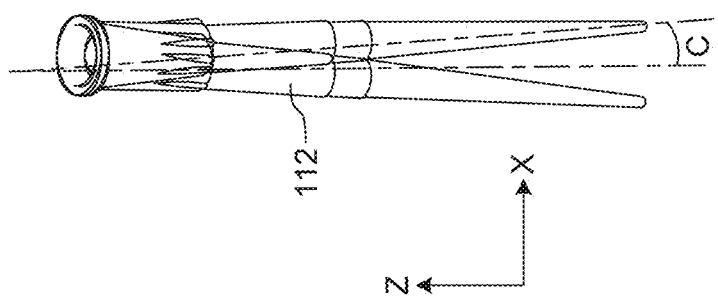
[Diagram 2: Front View from the Camera's Perspective]
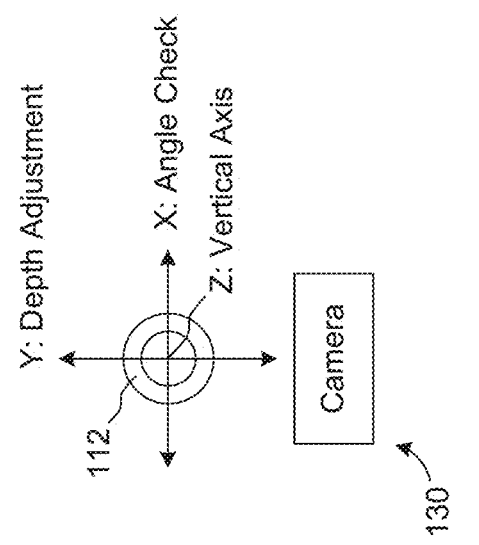
[Diagram 1: Top View]
FIG. 59

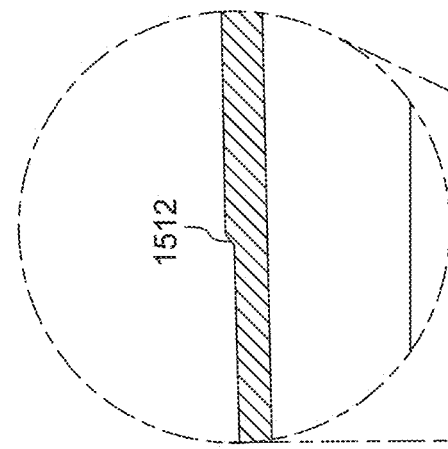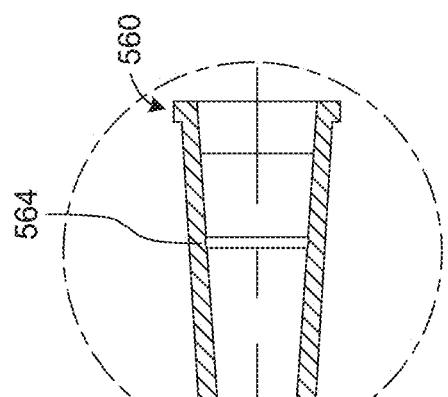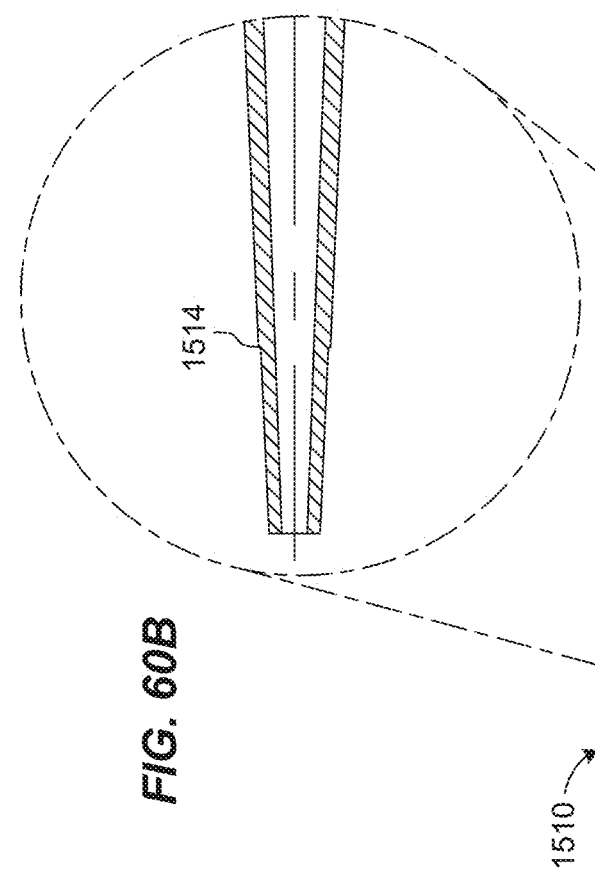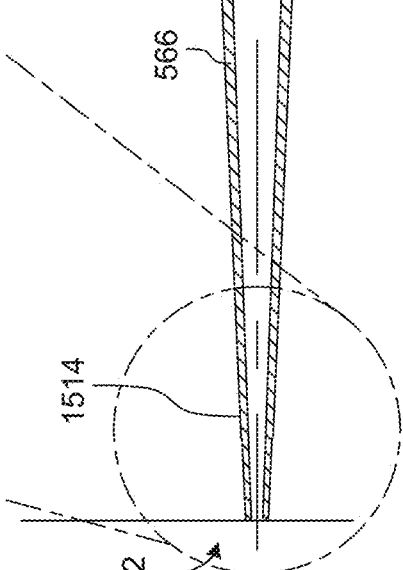
FIG. 60A  FIG. 60B  FIG. 60C

1750

| PmP % | PmP vol. | Substrate vol. |
|---|---|---|
| 100% | 200 µL | 0 µL |
| 90% | 180 µL | 20 µL |
| 80% | 160 µL | 40 µL |
| 70% | 140 µL | 60 µL |
| 60% | 120 µL | 80 µL |
| 50% | 100 µL | 100 µL |

*FIG. 74*

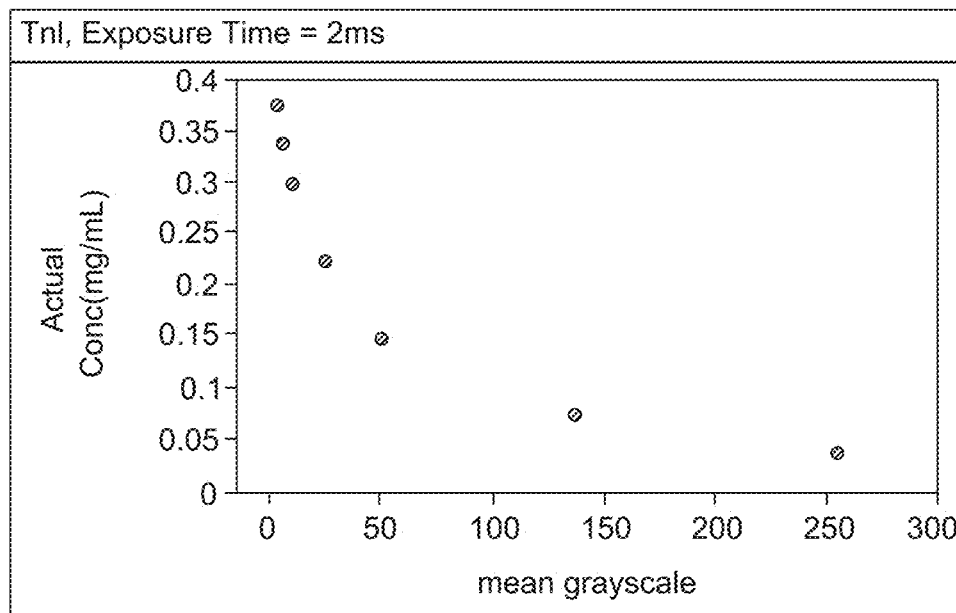
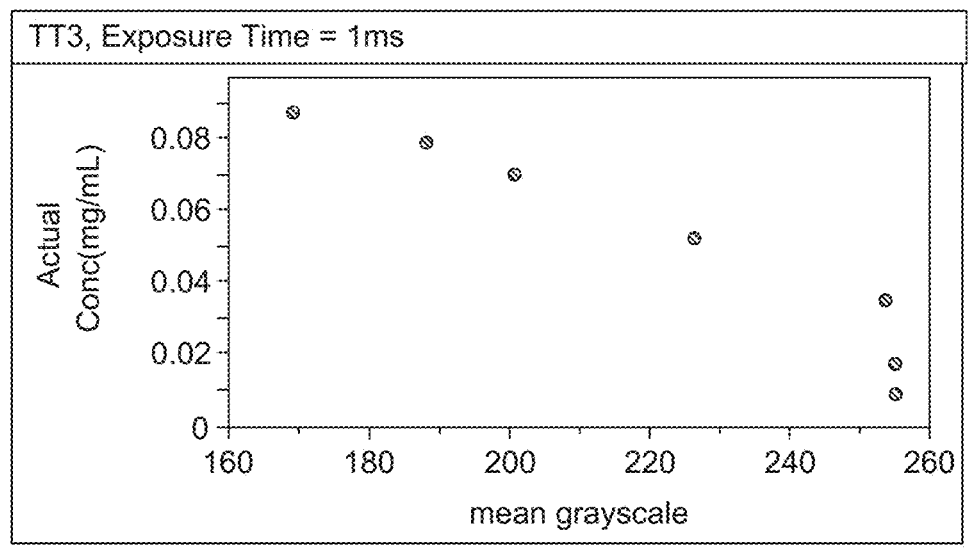
FIG. 75

| Test menu | Particle type | Particle conc. | Acceptable range |
|---|---|---|---|
| HBcAb | Estapor Direct | 6.7 mg/mL | ≥ 85 % |
| AFP | Estapor Direct | 2.1 mg/mL | ≥ 75 % |
| MYO | Estapor GxB | 1.5 mg/mL | ≥ 70 % |
| FSH | Estapor GxM | 1.0 mg/mL | ≥ 75 % |
| TSH2 | Dynal Epoxy | 1.0 mg/mL | ≥ 95 % |
| FT4 | Dynal SA | 0.35 mg/mL | ≥ 90 % |

FIG. 77

SUBSTANCE PREPARATION EVALUATION SYSTEM

CROSS REFERENCE TO RELATED APPLICATION(S)

This application is being filed as a divisional of U.S. Patent Application No. 11,263,433, filed on Apr. 26, 2019 which is a § 371 national stage entry of International Patent Application No. PCT/US2017/058838, filed on Oct. 27, 2017 and claims the benefit of priority to U.S. Provisional patent application Ser. No. 62/414,655, filed Oct. 28, 2016, and U.S. Provisional patent application Ser. No. 62/525,948, filed Jun. 28, 2017, the entire disclosures of which are incorporated by reference in their entireties.

FIELD OF THE INVENTION

The invention generally relates to the field of automatic substance preparation and evaluation. Particularly, the invention relates to methods and systems for evaluating a fluidic substance, such as e.g. a sample with bodily fluid, in a container and/or in a dispense tip. Further, the invention relates to computer program elements for instructing a computing device and/or a processing device to carry out steps of any of the methods of evaluating a fluidic substance. Moreover, the invention relates computer readable media storing such computer program elements.

SUMMARY OF THE INVENTION

It may be an objective of the present invention to provide improved methods and systems for automatically evaluating fluidic substances with improved reliability, improved quality, improved precision and improved throughput.

The objective of the present invention is solved by the subject-matter of the independent claims, wherein further embodiments are incorporated in the dependent claims and the following description.

According to a first aspect of the disclosure, a method of evaluating a fluidic substance in a container is provided. Among others, the method according to the first aspect may refer to a method for operating a dispense tip evaluation system, as exemplary described with reference to FIG. 1 and/or, to a method for operating a sample quality detection device, as exemplary described with reference to FIGS. 42 to 55. Also, the method according to the first aspect may refer to a method for operating a volume detection system, as exemplary described with reference to FIGS. 5 to 15 and/or FIGS. 9 to 21. Moreover, the method of the first aspect may refer to a method for operating a correlation data generation system, as exemplary described in with reference to FIGS. 8 to 21.

The method according to the first aspect comprises the steps of:
  capturing, using an image capture device, an image of at least a portion of the container, wherein the image capture device may comprise an image capture unit;
  obtaining, using at least one computing device and/or at least one processing device, a plurality of color parameters of at least a portion of the image; and
  generating a sample classification result for the fluidic substance contained in the container based on the plurality of color parameters.
Therein, the sample classification result is representative and/or indicative of a concentration of at least one interferent in the fluidic substance.

Here and in the following the image capture device and/or the image capture unit may refer to e.g. a dispense tip image capture unit.

According to an embodiment of the method of the first aspect, obtaining a plurality of color parameters includes:
  generating a histogram for at least a portion of the image, the histogram comprising a plurality of color channels; and
  obtaining a plurality of mean values and/or means for the plurality of color channels, wherein the plurality of color parameters includes the plurality of mean values for the plurality of color channels.
Therein, a mean and/or a mean value may be determined for each of the color channels or for a part of the color channels.

According to an embodiment of the method of the first aspect, obtaining a plurality of color parameters includes:
  generating a histogram for at least a portion of the image, the histogram comprising a plurality of color channels; and
  obtaining and/or determining a plurality of Riemann sums for the plurality of color channels, wherein the plurality of color parameters includes the plurality of Riemann sums for the plurality of color channels.
Therein, a Riemann sum may be obtained and/or determined for each of the color channels or for a part of the color channels.

According to an embodiment of the method of the first aspect, obtaining a plurality of color parameters includes:
  generating a histogram for at least a portion of the image, the histogram comprising a plurality of color channels;
  obtaining a plurality of modes for the plurality of color channels;
  obtaining a plurality of maximums for the plurality of color channels; and/or
  obtaining a plurality of minimums for the plurality of color channels, wherein the plurality of color parameters includes the plurality of modes, maximums, and/or minimums for the plurality of color channels.

According to an embodiment of the method of the first aspect, obtaining a plurality of color parameters includes:
  generating a histogram for at least a portion of the image, the histogram comprising a plurality of color channels;
  obtaining a plurality of histogram heads for the plurality of color channels;
  obtaining a plurality of histogram tails for the plurality of color channels;
  obtaining a plurality of histogram head percentages for the plurality of color channels; and/or
  obtaining a plurality of histogram tail percentages for the plurality of color channels, wherein the plurality of color parameters includes the plurality of histogram heads, histogram tails, histogram head percentages, and/or histogram tail percentages for the plurality of color channels.

According to an embodiment of the method of the first aspect, the plurality of color parameters includes at least one of a plurality of means for the color channels, a plurality of Riemann sum for the color channels, a plurality of modes for the color channels, a plurality of maximums for the color channels, a plurality of minimums for the color channels, a plurality of histogram heads for the color channels, a plurality of histogram tails for the color channels, a plurality of histogram head percentages for the color channels, a plurality of histogram tail percentages for the color channels, or any combination of the foregoing.

According to an embodiment of the method of the first aspect, the plurality of color channels include a red component, a green component, and a blue component, e.g. in a RGB model. However, also any other type of color model, such as e.g. a CMYK color model, may be used.

According to an embodiment of the method of the first aspect, the sample classification result comprises at least one classification identifier, wherein the at least one classification identifier is correlated with at least a part of the plurality of color parameters and/or is correlated with a concentration of the at least one interferent in the fluidic substance.

According to an embodiment of the method of the first aspect, the method further comprises generating a flagging result based on the sample classification result; wherein the flagging result is indicative of a quality of the fluidic substance. Alternatively or additionally a quality of the fluidic substance based on the sample qualification result.

According to an embodiment of the method of the first aspect, the at least one interferent is one or more selected from hemoglobin, icterus, and lipemia.

According to an embodiment of the method of the first aspect, the container is a dispense tip configured to aspirate the fluidic substance and/or a sample.

According to an embodiment of the method of the first aspect, the image capture device is configured and/or arranged to capture the image of the portion of the fluidic substance and/or the container from a side of the container.

According to an embodiment of the method of the first aspect, the method further comprises the steps of:
  identifying and/or determining, using the at least one computing device, a reference point in the image, which reference point is associated with the container;
  identifying and/or determining, using the at least one computing device, a surface level of the fluidic substance within the container in the image;
  determining and/or measuring a distance between the reference point and the surface level; and
  converting the distance to a volume of the fluidic substance based on correlation data, the correlation data including information about a correlation between volumes within the container and distances from the reference point to a plurality of surface levels within the container.

It is to be noted, however, that the term "correlation data" may also refer to an equation and/or a functional relation between the distance and the volume.

According to an embodiment of the method of the first aspect, the distance is measured by a pixel distance.

According to an embodiment of the method of the first aspect, the container is a dispense tip configured to aspirate the fluidic substance, wherein identifying a reference point includes identifying and/or determining a reference line formed on the dispense tip, e.g. a reference line formed on a body of the dispense tip.

According to an embodiment of the method of the first aspect, the reference line is identified based on pattern matching and/or based on segmentation of the captured image.

According to an embodiment of the method of the first aspect, identifying the reference line comprises searching a pattern representative of the reference line in the captured image.

According to an embodiment of the method of the first aspect, identifying the reference line comprises comparing at least a part of the captured image with a reference image.

According to an embodiment of the method of the first aspect, the method further comprises determining a matching rate, a matching score and/or a correlation value of the part of the captured image and the reference image.

According to an embodiment of the method of the first aspect, the method further comprises the steps of:
  supplying a liquid to a further container;
  determining a volume of the supplied liquid;
  capturing a further image of the container;
  determining a pixel distance between a reference point in the image associated with the further container; and
  correlating the determined volume with the determined pixel distance.

According to an embodiment of the method of the first aspect, the method further comprises generating correlation data based on the determined volume and the determined pixel distance.

According to an embodiment of the method of the first aspect, the correlation data are generated based on a plurality of correlations between a plurality of determined pixel distances and a plurality of determined volumes of liquid supplied to the further container.

According to an embodiment of the method of the first aspect, the supplied liquid comprises a dye solution. Alternatively or additionally the volume of the supplied liquid is determined based on spectrophotometry.

According to an embodiment of the method of the first aspect, determining the volume of the supplied liquid comprises determining a mass of the supplied liquid.

It is to be noted that any embodiment of the method according to the first aspect, as described above, may be combined with one or more further embodiments of the method according to the first aspect, as described above. This may allow to provide particularly advantageous synergistic effects.

According to a second aspect of the disclosure, a computer program element is provided, which when executed on a computing device of a system for evaluating a fluidic substance, instructs the computing device and/or the system to carry out the steps of the method according to the first aspect and/or according to any embodiment of the first aspect.

According to a third aspect of the disclosure, a non-transitory computer-readable medium is provided, on which a computer program element according to the second aspect of the disclosure is stored.

According to a fourth aspect of the disclosure, a system for evaluating a fluidic substance is provided. Among others, the system according to the fourth aspect may refer to a dispense tip evaluation system, as exemplary described with reference to e.g. FIG. 1, and/or to a sample quality detection device, as exemplary described with reference to e.g. FIGS. 42 to 55. Also, the system according to the fourth aspect may refer to a volume detection system, as exemplary described with reference to e.g. FIG. 1, FIGS. 6 to 15 and/or FIGS. 9 to 21. Moreover, the system according to the fourth aspect may refer to a correlation data generation system, as exemplary described with reference to e.g. FIGS. 8 to 21.

The system according to the fourth aspect comprises a sample pipetting device having a dispense tip. The sample pipetting device may refer to a substance pipetting device. Therein, the sample pipetting device is configured to at least partly engage the dispense tip and to aspirate a fluidic substance into the dispense tip. The system further comprises an image capture unit, and at least one computing device, which may comprise and/or refer to a processing device. Therein, the image capture unit is configured to capture an image of at least a portion of the fluidic substance in the dispense tip, wherein the computing device is configured to obtain a plurality of color parameters of at least a portion of the image, and to generate a sample classification result for the fluidic substance contained in the dispense tip based on the plurality of color parameters, wherein the sample classification result is representative and/or indicative of a concentration of at least one interferent in the fluidic substance.

Rephrasing, the system may comprise a sample pipetting device having a dispense tip, the sample pipetting device configured to engage a dispense tip, the sample pipetting device configured to aspirate a fluidic substance into the dispense tip. The system may further comprise an image capture unit configured to capture an image of at least a portion of the fluidic substance in the dispense tip, at least one computing device, and at least one computer readable storage media storing instructions that, when executed by at least one computing device, cause the system to: capture, using the image capture unit, an image of at least a portion of the fluidic substance in the dispense tip, obtain a plurality of color parameters of at least a portion of the image, and generate a sample classification result for the fluidic substance contained in the dispense tip based on the plurality of color parameters, the sample classification result being representative of a concentration of at least one interferent in the fluidic substance According to an embodiment of the system of the fourth aspect, the computing device is further configured to and/or the software instructions further cause the system to:
  generate a histogram for at least a portion of the image, the histogram comprising a plurality of color channels;
  obtain a plurality of mean values for the plurality of color channels; and/or
  obtain a plurality of Riemann sums for the plurality of color channels.
Therein, the plurality of color parameters include the plurality of means and/or the plurality of Riemann sum for the color channels.

According to an embodiment of the system of the fourth aspect, the sample classification result comprises at least one classification identifier, wherein the at least one classification identifier is correlated with at least a part of the plurality of color parameters and/or is correlated with a concentration of the at least one interferent in the fluidic substance. Therein, the sample classification result may include at least one of a plurality of classification identifiers, the plurality of classification identifiers being correlated with the plurality of color parameters.

According to an embodiment of the system of the fourth aspect, the computing device is further configured to and/or the software instructions further cause the system to:
  identify a reference point in the image, the reference point associated with the dispense tip;
  identify a surface level of the fluidic substance within the dispense tip in the image;
  determine and/or measure a distance between the reference point and the surface level; and
  convert the distance to a volume of the fluidic substance based on correlation data, the correlation data including information about a correlation between volumes within the dispense tip and distances from the reference point to a plurality of surface levels within the dispense tip.
Therein, the correlation data may also refer to an equation and/or to a functional relationship between the distance and the volume.

According to an embodiment of the system of the fourth aspect, the computing device is configured to determine a reference line formed on a body of the dispense tip and to determine the reference point based on the determined reference line. Therein, the reference point in the image may include a reference line formed on a body of the dispense tip.

According to an embodiment of the system of the fourth aspect, the computing device is configured to determine the reference line based on pattern matching and/or based on segmentation of the captured image.

According to an embodiment of the system of the fourth aspect, the computing device is configured to search and/or identify a pattern representative of the reference line in the captured image.

According to an embodiment of the system of the fourth aspect, the computing device is configured to compare at least a part of the captured image with a reference image.

According to an embodiment of the system of the fourth aspect, the computing device is configured to determine a matching rate, a matching score and/or a correlation value of the part of the captured image and the reference image.

According to an embodiment of the system of the fourth aspect, the image capture unit is configured and/or arranged to capture the image of the portion of the fluidic substance from a side of the dispense tip.

According to an embodiment of the system of the fourth aspect, the system further comprises a sample pipetting module, wherein the image capture unit is attached to the sample pipetting module.

According to an embodiment of the system of the fourth aspect, the system further comprises a light source positioned opposite the image capture unit and positioned at a side of the dispense tip, wherein the light source is configured to illuminate the dispense tip from the side of the dispense tip.

According to an embodiment of the system of the fourth aspect, the system further comprises a light source and a sample pipetting module, wherein the light source and the image capture unit are attached to the sample pipetting module; and/or wherein the light source and the image capture unit are configured to move, e.g. horizontally, together with the sample pipetting module so that an image of the dispense tip can be captured in any position of the sample pipetting module. Particularly, an image may be captured in any position along a trajectory and/or along a sample transfer guide of the sample pipetting module.

According to an embodiment of the system of the fourth aspect, the sample pipetting device is configured to aspirate a liquid into a further dispense tip, wherein the system is configured to determine a volume of the aspirated liquid, wherein the image capture unit is configured to capture a further image of the further dispense tip, and wherein the computing device is configured to determine a pixel distance between a reference point in the image associated with the further dispense tip and is configured to correlate the determined volume with the determined pixel distance.

According to an embodiment of the system of the fourth aspect, the computing device is configured to generate correlation data based on the determined volume and the determined pixel distance.

According to an embodiment of the system of the fourth aspect, the correlation data are generated based on a plurality of correlations between a plurality of determined pixel distances and a plurality of determined volumes of liquid aspirated into the further dispense tip.

According to an embodiment of the system of the fourth aspect, the aspirated liquid comprises a dye solution. Alternatively or additionally the system is configured to determine the volume of the aspirated liquid based on spectrophotometry.

According to an embodiment of the system of the fourth aspect, the system is configured to determine a mass of the aspirated liquid and to determine the volume of the aspirated liquid based on the determined mass of the aspirated liquid.

It is to be noted that any embodiment of the system according to the fourth aspect, as described above, may be combined with one or more further embodiments of the system according to the fourth aspect, as described above. This may allow to provide particularly advantageous synergistic effects.

Further, it is to be noted that any features, functions, characteristics and/or elements of the system according to the fourth aspect, as described above and in the following, may be features, functions, characteristics, steps and/or elements of the method according to the first aspect, as described above and in the following. Vice versa, any features, functions, characteristics, steps and/or elements of the method according to the first aspect, as described above and in the following, may be features, functions, characteristics, and/or elements of the system according to the fourth aspect, as described above and in the following.

According to a fifth aspect of the disclosure, a system for evaluating a fluidic substance is provided. Among others, the system according to the fifth aspect may refer to a tip alignment detection device, as exemplary described with reference to e.g. FIGS. 56 to 58. The system according to the fifth aspect may further refer to a dispense tip evaluation system and/or a volume detection system, as exemplary described with reference to e.g. FIG. 1, FIGS. 5 to 15, and/or FIGS. 9 21. Also, the system according to the fifth aspect may refer to a correlation data generation system, as exemplary described with reference to FIGS. 8 to 21.

The system according to the fifth aspect comprises a sample pipetting device configured to at least partly engage a dispense tip, the sample pipetting device is configured to aspirate a fluidic substance into the dispense tip, the dispense tip having at least one reference line. The sample pipetting device may refer to a substance pipetting device. The system further comprises an image capture unit configured to capture an image of at least a portion of the dispense tip, and at least one computing device, which may comprise a processing device, configured to:
  identify the at least one reference line of the dispense tip from the portion of the image of the dispense tip;
  determine at least one characteristic of the at least one reference line; and
  compare the at least one characteristic of the at least one reference line to a threshold value, which threshold value is representative of a misalignment of the dispense tip.

The computing device may be configured to determine whether the characteristic of the at least one reference line meets a threshold value, the threshold value being representative of a misalignment of the dispense tip. Therein, the misalignment may refer to a misalignment with respect to the image capture unit and/or with respect to a sample pipetting module.

The system may also comprise at least one computer readable data storage medium storing software instructions that, when executed by at least one processing device and/or by the computing device, cause the system to:
  identify the at least one reference line of the dispense tip from the image of the dispense tip;
  obtain one or more characteristics of the at least one reference line; and
  determine whether the characteristic of the at least one reference line meets a threshold value, the threshold value being representative of a misalignment of the dispense tip.

According to an embodiment of the system of the fifth aspect, the at least one reference line comprises a first reference line and a second reference line formed on the dispense tip.

According to an embodiment of the system of the fifth aspect, the at least one reference line comprises a first reference line and a second reference line formed on the dispense tip, wherein the at least one computing device is further configured to and/or the software instructions further cause the system to:
  obtain the at least one characteristic of the at least one reference line based on:
    determining and/or calculating a length of the first reference line;
    determining and/or calculating a length of the second reference line; and
    determining and/or calculating an angle of a line relative to at least one of the first reference line and the second reference line, the line connecting a predetermined point of the first reference line and a predetermined point of the second reference line; and
  determine the misalignment, e.g. the misalignment with respect to the image capture unit and/or with respect to a sample pipetting module, of the dispense tip based on at least one of the length of the first reference line, the length of the second reference line, and the angle of the line.

According to an embodiment of the system of the fifth aspect, the system is configured to and/or the software instructions further cause the system to, in response to determining the misalignment, prevent the sample pipetting device from aspirating the fluidic substance into the dispense tip. By way of example the computing device may be configured to generate and/or output an abort signal in response to determining the misalignment.

According to an embodiment of the system of the fifth aspect, the at least one computing device is further configured to and/or the software instructions further cause the system to, in response to determining the misalignment, flag and/or initiate aspiration of the fluidic substance into the dispense tip.

According to an embodiment of the system of the fifth aspect, the at least one computing device is further configured to and/or the software instructions further cause the system to:
  identify the at least one reference line of the dispense tip from the portion of the image of the dispense tip;
  identify a surface level of the fluidic substance within the dispense tip in the image;
  determine and/or measure a distance between the at least one reference line and the surface level; and
  determine a volume of the fluidic substance by converting the distance to the volume of the fluidic substance based on correlation data, the correlation data including information about a correlation between volumes within the dispense tip and distances from the at least one reference line to a plurality of surface levels within the dispense tip.

Therein, the correlation may also refer to an equation and/or a functional relationship between the distance and the volume.

According to an embodiment of the system of the fifth aspect, the computing device is configured to determine the reference line based on pattern matching and/or based on segmentation of the captured image.

According to an embodiment of the system of the fifth aspect, the computing device is configured to search a pattern representative of the reference line in the captured image.

According to an embodiment of the system of the fifth aspect, the computing device is configured to compare at least a part of the captured image with a reference image.

According to an embodiment of the system of the fifth aspect, the computing device is configured to determine a matching rate, a matching score and/or a correlation value of the part of the captured image and the reference image.

According to an embodiment of the system of the fifth aspect, the at least one reference line comprises a first reference line and a second reference line formed on the dispense tip, wherein the at least one computing device is further configured to and/or the software instructions further cause the system to:

determine and/or calculate a length of the first reference line in the image;

determine and/or calculate a length of the second reference line in the image;

determine and/or calculate an angle of a line relative to at least one of the first reference line and the second reference line, the line connecting a predetermined point of the first reference line and a predetermined point of the second reference line;

determine the misalignment, e.g. a misalignment with respect to the image capture unit and/or with respect to a sample pipetting module, of the dispense tip based on at least one of the length of the first reference line, the length of the second reference line, and the angle of the line; and adjust the volume of the fluidic substance based on the determination of the mis alignment.

According to an embodiment of the system of the fifth aspect, the misalignment of the dispense tip includes a side misalignment and a depth misalignment. Therein, the side misalignment may refer to a displacement of the dispense tip with respect to an optical axis of a camera and/or an image capture unit. The depth misalignment may refer to a displacement of the dispense tip along an optical axis of a camera and/or an image capture unit.

According to an embodiment of the system of the fifth aspect, the at least one reference line comprises a first reference line and a second reference line formed on the dispense tip, wherein the at least one computing device is further configured to and/or the software instructions further cause the system to:

identify a predetermined point of the first reference line in the image;

identify a predetermined point of the second reference line in the image;

define an alignment line that connects the predetermined point of the first reference line and the predetermined point of the second reference line;

determine an angle of the alignment line relative to at least one of the first reference line and the second reference line; and compare the angle to a threshold angle value, which threshold angle value is representative of a side misalignment of the dispense tip.

Therein, it may be determined whether the angle of the alignment line is less than a threshold angle value, the threshold angle value being representative of the side misalignment of the dispense tip.

According to an embodiment of the system of the fifth aspect, the predetermined point of the first reference line is a center point of the first reference line in in the image, and the predetermined point of the second reference line is a center point of the second reference line in the image.

According to an embodiment of the system of the fifth aspect, the system is configured to and/or the software instructions further cause the system to, in response to determining that the angle of the alignment line relative to at least one of the first reference line and the second reference line meets and/or exceeds the threshold angle value, prevent the sample pipetting device from aspirating the fluidic substance into the dispense tip. The system and/or the computing device may be configured to generate and/or output an abort signal in response to determining that the angle of the alignment line relative to at least one of the first reference line and the second reference line meets and/or exceeds the threshold angle value. Accordingly, the system may be configured to, in response to determining that the angle of the alignment line is not less than a threshold angle value, prevent the substance pipetting device and/or the sample pipetting device from aspirating the fluidic substance into the dispense tip.

According to an embodiment of the system of the fifth aspect, the at least one computing device is further configured to and/or the software instructions further cause the system to, in response to determining that the angle of the alignment line relative to at least one of the first reference line and the second reference line meets and/or exceeds the threshold angle value, flag aspiration of the fluidic substance into the dispense tip and/or initiate aspiration of the fluidic substance into the dispense tip, e.g. by flagging the aspiration. Accordingly, the system may be configured to, in response to determining that the angle of the alignment line is not less than a threshold angle value, flag aspiration of the fluidic substance into the dispense tip.

According to an embodiment of the system of the fifth aspect, the at least one computing device is further configured to and/or the software instructions further cause the system to:

determine and/or identify a length of the at least one reference line based on the captured image of the tip;

obtain an actual length of the at least one reference line;

calculate a ratio between the length of the at least one reference line and the actual length of the at least one reference line; and determine a depth misalignment of the dispense tip based on the ratio.

Alternatively or additionally, the software instructions further cause the system to:

identify a length of the first reference line from the captured image of the tip;

obtain an actual length of the first reference line;

calculate a ratio between the length of the first reference line and the actual length of the first reference line; and determine the depth misalignment of the dispense tip based on the ratio.

According to an embodiment of the system of the fifth aspect, the system is further configured to and/or the software instructions further cause the system to adjust the determined volume of the fluidic substance based on the ratio.

According to an embodiment of the system of the fifth aspect, the system further comprises a light source and a sample pipetting module, wherein the light source and the image capture unit are attached to the sample pipetting module, and/or wherein the light source and the image capture unit are configured to move, e.g. horizontally, together with the sample pipetting module so that an image of the dispense tip can be captured in any position of the sample pipetting module. By way of example an image may be captured in any position along a trajectory and/or along a sample transfer guide of the sample pipetting module.

According to an embodiment of the system of the fifth aspect, the sample pipetting device is configured to aspirate a liquid into a further dispense tip, wherein the system is configured to determine a volume of the aspirated liquid. The image capture unit is configured to capture a further image of the further dispense tip, wherein the computing device is configured to determine a pixel distance between a reference point in the image associated with the further dispense tip and is configured to correlate the determined volume with the determined pixel distance.

According to an embodiment of the system of the fifth aspect, the computing device is configured to generate correlation data based on the determined volume and the determined pixel distance.

According to an embodiment of the system of the fifth aspect, the correlation data are generated based on a plurality of correlations between a plurality of determined pixel distances and a plurality of determined volumes of liquid aspirated into the further dispense tip.

According to an embodiment of the system of the fifth aspect, the aspirated liquid comprises a dye solution, and/or wherein the system is configured to determine the volume of the aspirated liquid based on spectrophotometry.

According to an embodiment of the system of the fifth aspect, the system is configured to determine a mass of the aspirated liquid and to determine the volume of the aspirated liquid based on the determined mass of the aspirated liquid.

It is to be noted that any embodiment of the system according to the fifth aspect, as described above, may be combined with one or more further embodiments of the system according to the fifth aspect, as described above. This may allow to provide particularly advantageous synergistic effects.

According to a sixth aspect of the disclosure, a method of evaluating a fluidic substance in a container is provided. Among others, the method according to the sixth aspect may refer to a method for operating a tip alignment detection device, for operating a dispense tip integrity evaluation device, for operating a volume detection system, and/or for operating a dispense tip evaluation system, as exemplary described with reference to e.g. FIG. 1, FIGS. 5 to 15, FIGS. 9 to 21, and/or FIGS. 56 to 68.

The method according to the sixth aspect comprises the steps of
  capturing, using an image capture unit, an image of at least a portion of the container, wherein the container may be a dispense tip;
  determining and/or identifying, using at least one computing device, a first reference line and a second reference line of the container from the image of the container;
  determining and/or obtaining at least one characteristic of at least one of the first reference line and the second reference line.
Therein, the at least one characteristic comprises at least one of a length of the first reference line; a length of the second reference line, and an angle of a line relative to at least one of the first reference line and the second reference line, wherein the line connects a predetermined point of the first reference line and a predetermined point of the second reference line. The method according to the sixth aspect further comprises a step of comparing the at least one characteristic of at least one of the first reference line and the second reference line to a threshold value representative of a misalignment of the dispense tip.

Rephrasing, the method according to the sixth aspect may comprise the steps of:
  capturing, using an image capture unit, an image of at least a portion of the container;
  identifying, using at least one computing device, first and second reference lines of the dispense tip from the image of the dispense tip;
  obtaining one or more characteristics of the first and second reference lines, the characteristics including at least one of a length of the first reference line; a length of the second reference line; and an angle of a line relative to a reference line, the line connecting a predetermined point of the first reference line and a predetermined point of the second reference line; and
  determining whether the characteristics of the at least one reference line meets a threshold value, the threshold value being representative of a misalignment of the dispense tip.

According to an embodiment of the method of the sixth aspect, the first reference line and the second reference line are determined based on pattern matching and/or based on segmentation of the captured image.

According to an embodiment of the method of the sixth aspect, determining the first reference line and the second reference line comprises searching a pattern representative of the first reference line and/or the second reference line in the captured image.

According to an embodiment of the method of the sixth aspect, determining the first reference line and the second reference line comprises comparing at least a part of the captured image with a reference image.

According to an embodiment of the method of the sixth aspect, the method further comprises determining a matching rate, a matching score and/or a correlation value of the part of the captured image and the reference image.

According to an embodiment of the method of the sixth aspect, the container contains a fluidic substance, wherein the method further comprises:
  identifying a surface level of the fluidic substance within the container in the captured image;
  determining a distance between at least one of the first reference line and the second reference line and the surface level; and
  determining a volume of the fluidic substance by converting the distance to the volume of the fluidic substance based on correlation data, the correlation data including information about a correlation between volumes within the container and distances from at least one of the first reference line and the second reference line to a plurality of surface levels within the container.
Therein, the correlation data may also refer to an equation and/or a functional relationship between the distance and the volume.

According to an embodiment of the method of the sixth aspect, the method further comprises:
  determining a length of the first reference line in the image;
  determining a length of the second reference line in the image;
  determining an angle of a line relative to at least one of the first reference line and the second reference line, the line connecting a predetermined point of the first reference line and a predetermined point of the second reference line;

determining the misalignment of the container based on at least one of the length of the first reference line, the length of the second reference line, and the angle of the line; and adjusting the volume of the fluidic substance based on the determination of the misalignment.

Therein, the misalignment may refer to a misalignment with respect to the image capture unit and/or with respect to a sample pipetting module.

According to an embodiment of the method of the sixth aspect, the misalignment of the container includes a side misalignment and a depth misalignment. Therein, the side misalignment may refer to a displacement of the dispense tip with respect to an optical axis of a camera and/or of the image capture unit, and the depth misalignment may refer to a displacement of the dispense tip along the optical axis of a camera and/or of the image capture unit.

According to an embodiment of the method of the sixth aspect, the method further comprises:
  identifying a predetermined point of the first reference line in the image;
  identifying a predetermined point of the second reference line in the image;
  defining an alignment line that connects the predetermined point of the first reference line and the predetermined point of the second reference line;
  determining an angle of the alignment line relative to at least one of the first reference line and the second reference line; and
  comparing the angle to a threshold angle value, which threshold angle value is representative of a side misalignment of the container.

According to an embodiment of the method of the sixth aspect, the predetermined point of the first reference line is a center point of the first reference line in in the image, and the predetermined point of the second reference line is a center point of the second reference line in the image.

According to an embodiment of the method of the sixth aspect, the method further comprises, in response to determining that the angle of the alignment line relative to at least one of the first reference line and the second reference line meets and/or exceeds the threshold angle value, preventing aspiration of the fluidic substance into the container. Accordingly, an abort signal preventing aspiration may be generated in response to determining that the angle of the alignment line relative to at least one of the first reference line and the second reference line meets and/or exceeds the threshold angle value.

According to an embodiment of the method of the sixth aspect, the method further comprises, in response to determining that the angle of the alignment line relative to at least one of the first reference line and the second reference line meets and/or exceeds the threshold angle value, flagging aspiration of the fluidic substance into the container and/or initiating aspiration of the fluidic substance into the container.

According to an embodiment of the method of the sixth aspect, the method further comprises:
  determining a length of at least one of the first reference line and the second reference line based on the captured image of the container;
  obtaining, e.g. from a data storage device, an actual length of at least one of the first reference line and the second reference line;
  calculating a ratio between the length of at least one of the first reference line and the second reference line and the actual length of the at least one of the first reference line and the second reference line; and
  determining a depth misalignment of the container based on the ratio.

According to an embodiment of the method of the sixth aspect, the method further comprises adjusting a determined volume of the fluidic substance based on the ratio.

It is to be noted that any embodiment of the method according to the sixth aspect, as described above, may be combined with one or more further embodiments of the method according to the sixth aspect, as described above. This may allow to provide particularly advantageous synergistic effects.

Further, it is to be noted that any features, functions, characteristics and/or elements of the system according to the fifth aspect, as described above and in the following, may be features, functions, characteristics, steps and/or elements of the method according to the sixth aspect, as described above and in the following. Vice versa, any features, functions, characteristics, steps and/or elements of the method according to the sixth aspect, as described above and in the following, may be features, functions, characteristics, and/or elements of the system according to the fifth aspect, as described above and in the following.

According to a seventh aspect of the disclosure, a computer program element is provided, which when executed on a computing device of a system for evaluating a fluidic substance, instructs the computing device and/or the system to carry out the steps of the method according to the sixth aspect.

According to an eighth aspect of the disclosure, a non-transitory computer-readable medium is provided, on which a computer program element according the seventh aspect is stored.

According to a ninth aspect of the disclosure, a system for evaluating a fluidic substance is provided. The system according to the ninth aspect may refer to a particle concentration check system, as exemplary described with reference to e.g. FIGS. 69 to 79, to a volume detection system, as exemplary described with reference to e.g. FIGS. 5 to 15, a correlation data generation system, as exemplary described with reference to e.g. FIGS. 8 to 21, and/or a reaction vessel residual volume detection device, as exemplary described with reference to e.g. FIGS. 32 to 34.

The system according to the ninth aspect comprises a container carriage device configured to support and/or hold one or more containers, a sample pipetting device and/or a substance pipetting device configured to dispense a fluidic substance in at least one of the containers on the container carriage device, an image capture device configured to capture an image of at least one of the containers on the container carriage device, and at least one processing device and/or at least one computing device. Therein, the system is configured to:
  dispense, using the sample pipetting device, at least one fluidic substance into a container;
  capture, using the image capture device, an image of the container on the container carriage device;
  analyze, using the at least one processing device, the image of the container to determine a volume of the dispensed at least one fluidic substance in the container; and analyze, using the at least one processing device, the image of the container to determine a particle concentration of a total volume of fluidic substances in the container.

The system may comprise at least one computer readable data storage medium storing software instructions that, when executed by at least one processing device, cause the system to:
dispense one or more fluidic substances into a container;
obtain an image of the container on the container carriage device;
analyze the image of the container to determine a volume of the dispensed fluidic substances in the container; and
analyze the image of the container to determine a particle concentration of a total volume of fluidic substances in the container According to an embodiment of the system of the ninth aspect, the total volume of fluidic substances comprises at least one bodily fluid and/or at least one reagent.

According to an embodiment of the system of the ninth aspect, the system is further configured to and/or the software instructions further cause the system to:
capture and/or obtain, using the image capture device, a first image of the container after dispensing a reagent to the at least one fluidic substance contained in a container, wherein the at least one fluidic substance comprises at least one bodily fluid;
capture and/or obtain, using the image capture device, a second image of the container after mixing the added reagent with the at least one fluidic substance in the container;
analyze, using the at least one processing device, the first image of the container to determine the volume of the dispensed reagent in the container; and
analyze, using the at least one processing device, the second image of the container to determine a particle concentration of the total volume of fluidic substances in the container.

According to an embodiment of the system of the ninth aspect, the particle concentration comprises a concentration of paramagnetic particles.

According to an embodiment of the system of the ninth aspect, the at least one reagent comprises a chemiluminescent substrate.

According to an embodiment of the system of the ninth aspect, the first image is captured at approximately 0.2 second after the reagent is dispensed into the container, wherein the second image is captured after approximately 6.5 seconds of mixing.

According to an embodiment of the system of the ninth aspect, the image capture device is mounted to the container carriage device, and the image capture device is configured and/or arranged to capture the image of the container from a side of the container.

According to an embodiment of the system of the ninth aspect, the system further comprises a light source, wherein the light source and the image capture device are mounted to the container carriage device such that the light source is positioned opposite the image capture device.

According to an embodiment of the system of the ninth aspect, the container carriage device is a wash wheel comprising a rotatable plate, wherein the rotatable plate is configured to rotate the container to the image capture device.

According to an embodiment of the system of the ninth aspect, the system is further configured to and/or the software instructions further cause the system to detect if the container is present on the container carriage device, e.g. by appropriate hardware and/or software means.

According to an embodiment of the system of the ninth aspect, the at least one processing device is configured to and/or the software instructions further cause the system to:
determine and/or identify a reference point in the image, wherein the reference point is associated with the container;
determine and/or identify a surface level of the at least one fluidic substance within the container in the image;
determine and/or measure a distance between the reference point and the surface level; and
convert the distance to a volume of the dispensed at least one fluidic substance and/or a reagent based on correlation data, the correlation data including information about a correlation between volumes within the container and distances from the reference point to a plurality of surface levels within the container.

According to an embodiment of the system of the ninth aspect, determining and/or identifying a reference point includes determining and/or identifying a bottom portion of the container.

According to an embodiment of the system of the ninth aspect, the distance is measured by a pixel distance.

According to an embodiment of the system of the ninth aspect, the processing device is configured to determine the reference point based on pattern matching and/or based on segmentation of the captured image.

According to an embodiment of the system of the ninth aspect, the processing device is configured to search a pattern representative of the reference point in the captured image.

According to an embodiment of the system of the ninth aspect, the processing device is configured to compare at least a part of the captured image with a reference image.

According to an embodiment of the system of the ninth aspect, the processing device is configured to determine a matching rate, a matching score and/or a correlation value of the part of the captured image and the reference image.

According to an embodiment of the system of the ninth aspect, the sample pipetting device is configured to aspirate a liquid into a further container, wherein the system is configured to determine a volume of the aspirated liquid, wherein the image capture unit is configured to capture a further image of the further container, and wherein the processing device is configured to determine a pixel distance between a reference point in the image associated with the further container and is configured to correlate the determined volume with the determined pixel distance.

According to an embodiment of the system of the ninth aspect, the processing device is configured to generate correlation data based on the determined volume and the determined pixel distance.

According to an embodiment of the system of the ninth aspect, the correlation data are generated based on a plurality of correlations between a plurality of determined pixel distances and a plurality of determined volumes of liquid aspirated into the further container.

According to an embodiment of the system of the ninth aspect, the aspirated liquid comprises a dye solution. Alternatively or additionally the system is configured to determine the volume of the aspirated liquid based on spectrophotometry.

According to an embodiment of the system of the ninth aspect, the system is configured to determine a mass of the aspirated liquid and to determine the volume of the aspirated liquid based on the determined mass of the aspirated liquid.

According to an embodiment of the system of the ninth aspect, the at least one processing device is further configured to and/or the software instructions further cause the system to:
- obtain and/or determine a brightness of the total volume of the fluidic substances from the image of the container, e.g. based on receiving a brightness value from a sensor and/or e.g. based on image processing;
- determine a particle concentration of the total volume of fluidic substances based on the brightness of the fluidic substance and calibration data;
- compare the determined particle concentration to a threshold value; and
- in response to determining that the determined particle concentration is below the threshold value, flag the container containing the total volume of fluidic substances.

According to an embodiment of the system of the ninth aspect, the system is further configured to and/or the software instructions further cause the system to:
- aspirate, using the sample pipetting device, at least a portion of the fluidic substance from the container;
- capture, using the image capture device, a third image of at least a portion of the container;
- compare, using the at least one processing device, the third image with a reference image;
- determine, using the at least one processing device, a matching score based on a similarity between the third image and the reference image; and
- compare the generated matching score with a threshold.

According to an embodiment of the system of the ninth aspect, the system is further configured to and/or the software instructions further cause the system to determine, using the at least one processing device, an area of interest in the third image, wherein comparing the third image includes comparing the area of interest in the third image with at least a part of the reference image.

According to an embodiment of the system of the ninth aspect, the area of interest comprises a region adjacent to a bottom of the container.

According to an embodiment of the system of the ninth aspect, the system is further configured to and/or the software instructions further cause the system to:
- when the matching score is equal to and/or below the threshold, flagging a result of the aspiration from the container and/or
- when the matching score does not exceed the threshold, flagging a result of the aspiration from the container.

According to an embodiment of the system of the ninth aspect, the container carriage device comprises a plurality of container slots, wherein each container slot is configured to support a container, and wherein the system is further configured to and/or the software instructions further cause the system to:
- capture, using the image capture device, a fourth image of one of the plurality of container slots at a first position of the container carriage device;
- compare, using the at least one processing device, the fourth image with a reference image;
- generate, using the at least one processing device, a matching score based on a similarity between the fourth image and the reference image; and
- compare the matching score with a threshold.

According to an embodiment of the system of the ninth aspect, the matching score exceeding and/or meeting the threshold represents absence of the container at the one of the plurality of container slots.

According to an embodiment of the system of the ninth aspect, the system is configured to remove the container from the one of the plurality of container slots when the matching score is below the threshold, and/or the software instructions further cause the system to, when the matching score does not meet the threshold, removing the container from the one of the plurality of container slots.

According to an embodiment of the system of the ninth aspect, the system is configured to move the container carriage device to a second position after and/or in response to determining that the matching score exceeds and/or meets a threshold. Alternatively or additionally the software instructions further cause the system to, after determining that the matching score exceeds a threshold, moving the container carriage device to a second position.

It is to be noted that any embodiment of the system according to the ninth aspect, as described above, may be combined with one or more further embodiments of the system according to the ninth aspect, as described above. This may allow to provide particularly advantageous synergistic effects.

According to a tenth aspect of the disclosure, a method for evaluating a fluidic substance in a container is provided. The method according to the tenth aspect may refer to a method for operating a particle concentration check system, as exemplary described with reference to e.g. FIGS. 69 to 79, and/or to a method for operating a volume detection system, as exemplary described with reference to e.g. FIGS. 5 to 15.

The method according to the tenth aspect comprises the steps of:
- dispensing, using a sample pipetting device, at least one fluidic substance into a container;
- capturing and/or obtaining, using an image capture device, an image of at least a part of the container arranged on a container carriage device, which container carriage device is configured to support and/or hold one or more containers;
- analyzing, using at least one computing device, the image of the container to determine a volume of the at least one dispensed fluidic substance in the container; and
- analyzing, using the at least one computing device, the image of the container to determine a particle concentration of a total volume of fluidic substances in the container.

Therein, the term "total volume of fluidic substances" may refer to the at least one dispensed fluidic substance and optionally to at least one added reagent.

According to an embodiment of the method of the tenth aspect, capturing and/or obtaining the image of the container includes:
- capturing and/or obtaining, using the image capture device, a first image of the container after dispensing a reagent to the at least one fluidic substance contained in a container, wherein the at least one fluidic substance includes at least one bodily fluid;
- capturing and/or obtaining, using the image capture device, a second image of the container after adding and/or mixing a reagent, e.g. an added reagent, with the at least one fluidic substance in the container.

Therein, analyzing the image of the container to determine the volume of the at least one dispensed fluidic substance includes analyzing the first image of the container to determine the volume of the dispensed reagent contained in the container, wherein analyzing the image of the container to determine the particle concentration of the total volume of fluidic substances includes analyzing the second image of the container to determine a particle concentration of the total volume of fluidic substances in the container.

It is to be noted that any embodiment of the method according to the tenth aspect, as described above, may be combined with one or more further embodiments of the method according to the tenth aspect, as described above. This may allow to provide particularly advantageous synergistic effects.

Further, it is to be noted that any features, functions, characteristics and/or elements of the system according to the ninth aspect, as described above and in the following, may be features, functions, characteristics, steps and/or elements of the method according to the tenth aspect, as described above and in the following. Vice versa, any features, functions, characteristics, steps and/or elements of the method according to the tenth aspect, as described above and in the following, may be features, functions, characteristics, and/or elements of the system according to the ninth aspect, as described above and in the following.

According to an eleventh aspect of the disclosure, a computer program element is provided, which when executed on a computing device of a system for evaluating a fluidic substance, instructs the computing device and/or the system to carry out the steps of the method according the tenth aspect.

According to a twelfth aspect of the disclosure, a non-transitory computer-readable medium is provided, on which a computer program element according to the eleventh aspect is stored.

According to a thirteenth aspect of the disclosure, a method for evaluating a fluidic substance in a container is provided. The method of the thirteenth aspect may refer to a method for operating a volume detection system, as exemplary described with reference to e.g. FIGS. 5 to 15, a method for operating a dispensing adjustment system, as exemplary described with reference to e.g. FIGS. 35 to 36, a method for operating a correlation data generation system, as exemplary described with reference to e.g. FIGS. 8 to 21, and/or to a method for operating a residual volume detection device, as exemplary described with reference to e.g. FIGS. 32 to 34.

The method according to the thirteenth aspect comprises the steps of:
dispensing, using a substance dispense device, a fluidic substance to a container;
determining and/or measuring, using at least one computing device, a volume of the fluidic substance in the container;
receiving operational information of the substance dispense device, the operational information including operational parameters of the fluidic substance dispense device;
receiving a target dispense volume of the fluidic substance;
comparing the determined volume of the fluidic substance with the target dispense volume;
generating calibration information for the substance dispense device; and
adjusting the operational parameters of the substance dispense device based on the calibration information.

According to an embodiment of the method of the thirteenth aspect, determining and/or measuring the volume of the fluidic substance includes:
capturing, using an image capturing device, an image of at least a portion of the container;
identifying, using at least one computing device, a reference point in the image, the reference point associated with the container;
identifying, using the at least one computing device, a surface level of the fluidic substance within the container in the image;
determining a distance between the reference point and the surface level; and
converting the distance to a volume of the fluidic substance based on correlation data, the correlation data including information about a correlation between volumes within the container and distances from the reference point to a plurality of surface levels within the container.

According to an embodiment of the method of the thirteenth aspect, the method further comprises:
supplying a liquid to a further container;
determining a volume of the supplied liquid;
capturing a further image of the container;
determining a pixel distance between a reference point in the image associated with the further container; and
correlating the determined volume with the determined pixel distance.

According to an embodiment of the method of the thirteenth aspect, the method further comprises generating correlation data based on the determined volume and the determined pixel distance.

According to an embodiment of the method of the thirteenth aspect, the correlation data are generated based on a plurality of correlations between a plurality of determined pixel distances and a plurality of determined volumes of liquid supplied to the further container.

According to an embodiment of the method of the thirteenth aspect, the supplied liquid comprises a dye solution. Alternatively or additionally the volume of the supplied liquid is determined based on spectrophotometry.

According to an embodiment of the method of the thirteenth aspect, determining the volume of the supplied liquid comprises determining a mass of the supplied liquid.

According to an embodiment of the method of the thirteenth aspect, the method further comprises:
aspirating at least a portion of the fluidic substance from the container;
capturing, using an image capturing device, an image of at least a portion of the container;
comparing the image with a reference image;
generating a matching score based on a similarity between the image and the reference image.

According to an embodiment of the method of the thirteenth aspect, the method further comprises:
comparing the matching score with a threshold; and/or
determining that the matching score exceeds a threshold.

According to an embodiment of the method of the thirteenth aspect, the method further comprises determining an area of interest in the image, wherein comparing the image includes comparing the area of interest in the image with at least a part of the reference image.

According to an embodiment of the method of the thirteenth aspect, the area of interest includes a region adjacent to a bottom of the container.

According to an embodiment of the method of the thirteenth aspect, the method further comprises, when the matching score meets and/or is below the threshold, flagging a result of the aspiration from the container.

According to an embodiment of the method of the thirteenth aspect, the method further comprises:
arranging a plurality of containers in a plurality of container slots of a container carriage device;
capturing, using an image capturing device, an image of one of the plurality of container slots at a first position of the container carriage device;
comparing the image with a reference image;
generating a matching score based on a similarity between the image and the reference image.

According to an embodiment of the method of the thirteenth aspect, the method further comprises:
comparing the matching score with a threshold; and/or
determining that the matching score exceeds and/or meets a threshold, wherein the matching score exceeding the threshold represents absence of the container at the one of the plurality of container slots.

According to an embodiment of the method of the thirteenth aspect, the method further comprises, when the matching score is below the threshold, removing the container from the one of the plurality of container slots.

According to an embodiment of the method of the thirteenth aspect, the method further comprises, after determining that the matching score exceeds and/or meets a threshold, moving the container carriage device to a second position.

It is to be noted that any embodiment of the method according to the thirteenth aspect, as described above, may be combined with one or more further embodiments of the method according to the thirteenth aspect, as described above. This may allow to provide particularly advantageous synergistic effects.

Further, it is to be noted that any features, functions, characteristics and/or elements of the system according to the ninth aspect, as described above and in the following, may be features, functions, characteristics, steps and/or elements of the method according to the thirteenth aspect, as described above and in the following. Vice versa, any features, functions, characteristics, steps and/or elements of the method according to the thirteenth aspect, as described above and in the following, may be features, functions, characteristics, and/or elements of the system according to the ninth aspect, as described above and in the following.

According to a fourteenth aspect of the disclosure, a computer program element is provided, which when executed on a computing device of a system for evaluating a fluidic substance, instructs the computing device and/or the system to carry out the steps of the method according to the thirteenth aspect.

According to a fifteenth aspect of the disclosure, a non-transitory computer-readable medium is provided, on which a computer program element according to the fourteenth aspect is stored.

BRIEF DESCRIPTION OF THE DRAWINGS

FIG. 50 is an example table of interferent values being parsed into classification labels.

FIG. 51 is an example set of sample classification identifiers.

FIG. 55 is an example data set of sample classification results and associated flagging results.

FIG. 59 illustrates possible types of misalignment of a dispense tip.

FIG. 60A is a cross sectional side view of an example dispense tip usable with the tip alignment detection device.

FIG. 60B is an expanded view of a portion of the dispense tip of FIG. 60A.

FIG. 60C is an expanded view of a portion of the dispense tip of FIG. 60A.

FIG. 74 is a table of example substances used to generate the calibration data.

FIG. 75 shows example calibration curves plotted from the calibration data.

FIG. 77 is an example table of example concentration thresholds for different assay substances.

DETAILED DESCRIPTION

Figure 1:
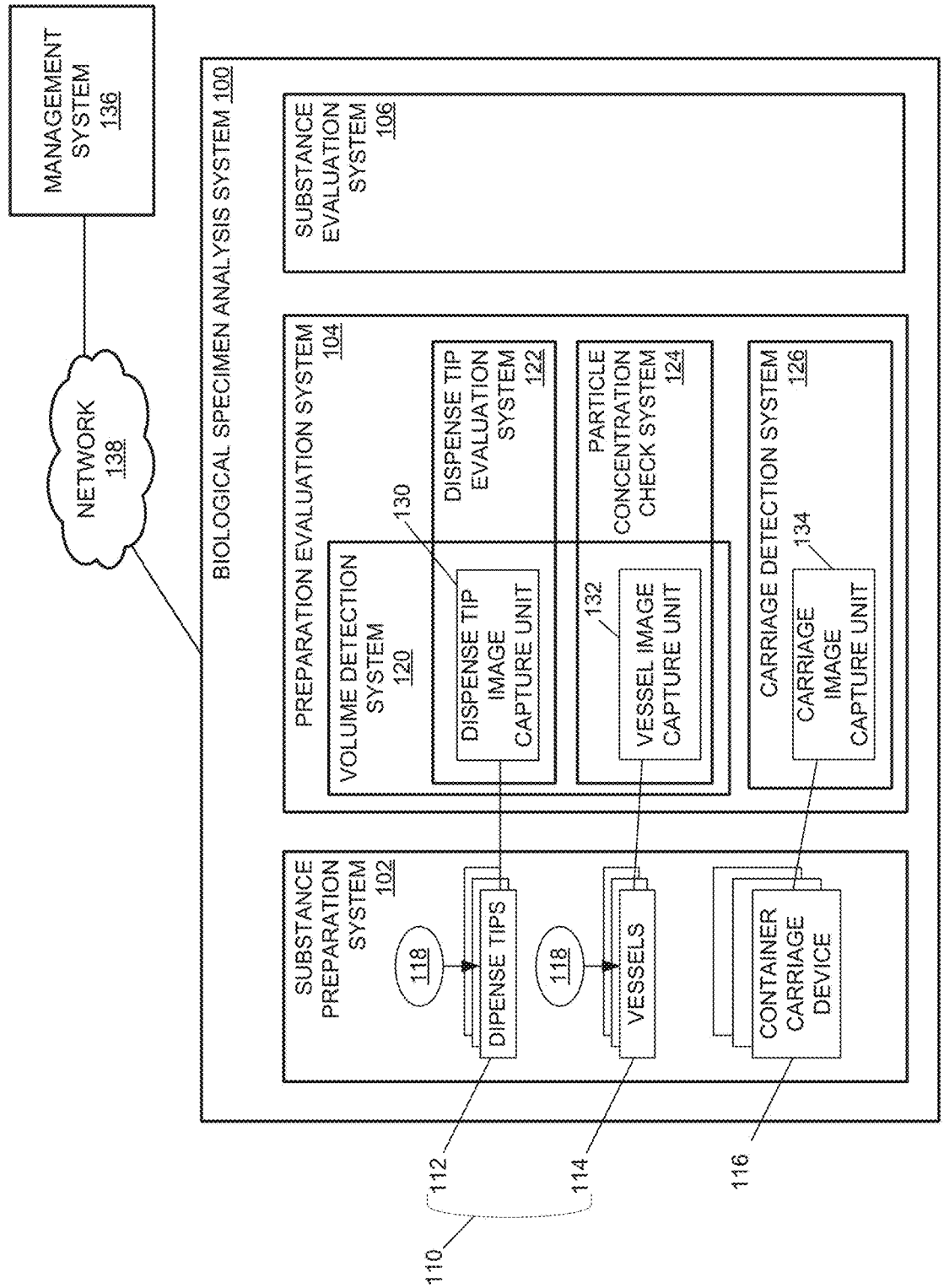
FIG. 1 is a block diagram of an example instrument for analyzing a biological specimen.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a block diagram of an example instrument 100 for analyzing a biological specimen. In some embodiments, the instrument 100 includes a substance preparation system 102, a preparation evaluation system 104, and a substance evaluation system 106. One or more containers 110 are used with the systems of the instrument 100 and include dispense tips 112 and vessels 114. Also shown are one or more container carriage devices 116 that are provided in the instrument 100. Further, the preparation evaluation system 104 includes a volume detection system 120, a dispense tip evaluation system 122, and a carriage detection system 126. In some embodiments, the volume detection system 120 utilizes a dispense tip image capture unit 130 and a vessel image capture unit 132. In some embodiments, the dispense tip evaluation system 122 uses the dispense tip image capture unit 130, and the particle concentration check system 124 uses the vessel image capture unit 132. In some embodiments, the carriage detection system 126 uses a carriage image capture unit 134.

It is to be noted that the systems for evaluating a fluidic substance according to the fourth aspect, the fifth aspect, and/or the ninth aspect, as described in the summary part of the present disclosure, each may refer to the instrument 100 for analyzing biological specimen and/or each may refer to one or more components and/or devices of the instrument 100. Further, the methods for evaluating a fluidic substance according to the first aspect, the sixth aspect, the tenth aspect, and/or the thirteenth aspect, as described in the summary part of the present disclosure, each may refer to a method for operating the instrument 100 and/or each may refer to a method for operating one or more components and/or devices of instrument 100.

The biological specimen analysis instrument 100 operates to analyze a biological specimen for various purposes. In some embodiments, the biological specimen analysis instrument 100 is configured to analyze a blood sample and operates to collect, test, process, store, and/or transfuse blood and its components.

The substance preparation system 102 operates to prepare one or more substances for further analysis by the substance evaluation system 106. In some embodiments, the substance preparation system 102 operates to aliquot substances 118 with containers 110, aspirate substances 118 from containers 110 and dispense substances 118 to containers 110.

The preparation evaluation system 104 operates to evaluate the preparation of substances for subsequent analysis by the substance evaluation system 106. In some embodiments, the preparation evaluation system 104 utilizes one or more image capture units to determine whether substances 118 have been appropriately prepared for analysis. As described herein, the preparation evaluation system 104 provides direct and simple measurements of volume or integrity of a substance 118 to determine whether the substance 118 is appropriately prepared so that the substance evaluation system 106 produces a reliable result using the substance 118.

The substance evaluation system 106 operates to evaluate the substance 118 that is prepared by the substance preparation system 102. By way of example, the substance evaluation system 106 performs an immunoassay as described with reference to FIG. 2.

The containers 110 are used to prepare one or more substances 118 to be analyzed by the substance evaluation system 106. The containers 110 can be of various types, such as specimen tubes (also referred to herein as sample tubes), pipetting tips, and vessels. In some embodiments, the containers 110 include dispense tips 112 and vessels 114.

The dispense tips 112 are provided to the substance preparation system 102 to aliquot or aspirate substances 118 from other containers, such as vessels 114. For example, the dispense tips 112 are used to aliquot samples from specimen tubes or aspirate samples or reagents from sample vessels or reagent vessels. An example of the dispense tip 112 is described and illustrated in more detail with reference to FIGS. 13 and 14.

The vessels 114 are provided to the substance preparation system 102 to contain substances 118 for preparation and analysis. In some embodiments, the substance preparation system 102 dispenses substances 118 into vessels 114. Examples of vessels 114 include sample vessels, diluent vessels, and reaction vessels, which are described herein in more detail.

The container carriage devices 116 are configured to hold and carry the containers 110 at various locations in the instrument 100 so that the substance preparation system 102, the preparation evaluation system 104, and the substance evaluation system 106 use the containers 110 in various manners. Examples of container carriage devices 116 include vessel racks (e.g., a sample rack, a reagent rack, and a diluent rack), a sample presentation unit, vessel carriage units (e.g., a sample carriage unit, a reaction vessel carriage unit, and a reagent carriage unit), vessel transfer units (e.g., a sample transfer unit, a reagent transfer unit, an incubator transfer unit, and an reaction vessel transfer unit), and vessel holding plates or wheels (e.g., a sample wheel, an incubator, and a wash wheel)), which are described and illustrated in more detail with reference to FIG. 2.

The substances 118 are prepared, evaluated, and examined for various tests and analyses in the instrument 100. The substances 118 include any substances that can be aliquoted, aspirated, and dispensed in the instrument 100. In some embodiments, the substances 118 have fluidic characteristics and are therefore referred to herein as fluidic substances. In some embodiments, the fluidic substance 118 is a single fluidic substance. In other embodiments, the fluidic substance 118 is a mixture of a plurality of substances.

The volume detection system 120 of the preparation evaluation system 104 operates to detect a volume of a fluidic substance 118 in a container 110 and determine whether the volume held in the container 110 is appropriate as targeted. As described herein, the volume detection system 120 is configured to detect a volume at a dispense tip 112 using the dispense tip image capture unit 130, and a volume at a vessel 114 using the vessel image capture unit 132.

The dispense tip evaluation system 122 of the preparation evaluation system 104 operates to evaluate the integrity of a fluidic substance 118. In some embodiments, the dispense tip evaluation system 122 detects any interferents, which can interfere with an analytic procedure and may generate incorrect results. As described herein, the dispense tip evaluation system 122 is configured to determine a quality of a fluidic substance 118 at a dispense tip 112 using the dispense tip image capture unit 130, and an alignment of the dispense tip 112 with respect to the dispense tip image capture unit 130.

The particle concentration check system 124 operates to determine a particle concentration in a fluidic substance contained in a vessel, such as a reaction vessel, a sample vessel, a dilution vessel, a cuvette, or any suitable type of vessel, which is used throughout the process in the instrument 100. In some embodiments, the reaction vessel particle concentration check system 1700 uses the vessel image capture unit 132.

The dispense tip image capture unit 130 operates to capture images of dispense tips 112 in one or more locations. In some embodiments, the dispense tip image capture unit 130 is fixed at a particular location in the instrument 100. In other embodiments, the dispense tip image capture unit 130 is movably disposed in the instrument 100, which can move either independently from other components of the instrument 100 or together with one or more components of the instrument 100. Some embodiments of the instrument 100 include a plurality of dispense tip image capture units 130.

Figure 11:
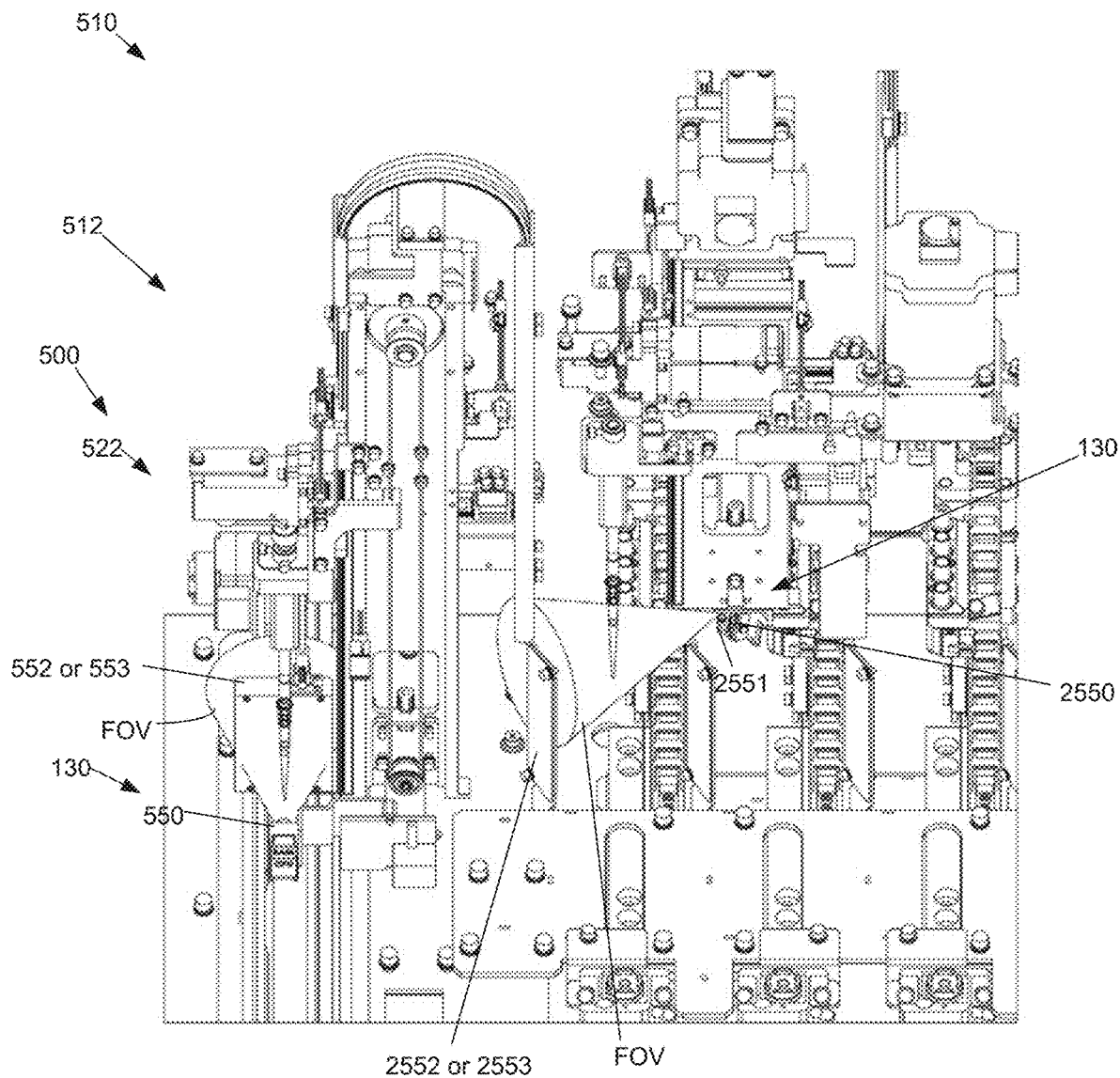
FIG. 11 is a perspective view of the sample aspiration system of FIG. 10.
Figure 67:
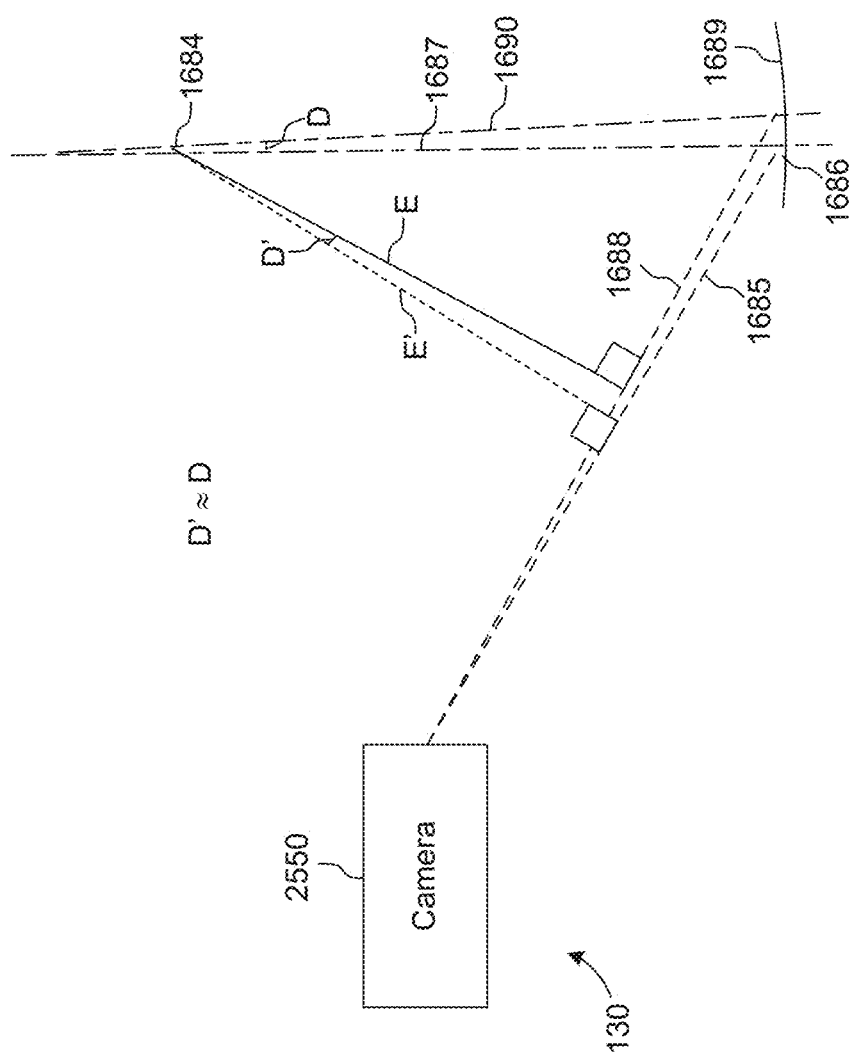
FIG. 67 schematically illustrates a depth misalignment of the dispense tip with respect to a camera unit.

As described herein, the dispense tip image capture unit 130 can include a camera unit 550 (e.g., FIG. 11) and a camera unit 2550 (FIGS. 11 and 67).

The vessel image capture unit 132 operates to capture images of vessels 114 in one or more locations. In some embodiments, the vessel image capture unit 132 is fixed at a particular location in the instrument 100. In other embodiments, the vessel image capture unit 132 is movably disposed in the instrument 100, which can move either independently from other components of the instrument 100 or together with one or more components of the instrument 100. Some embodiments of the instrument 100 include a plurality of vessel image capture units 132. As described herein, the vessel tip image capture unit 132 includes a camera unit 730 (e.g., FIG. 24).

The carriage image capture unit 134 operates to capture images of container carriage devices 116 with or without containers 110 in one or more locations. In some embodiments, the carriage image capture unit 134 is fixed at a particular location in the instrument 100. In other embodiments, the carriage image capture unit 134 is movably disposed in the instrument 100, which can move either independently from other components of the instrument 100 or together with one or more components of the instrument 100. Some embodiments of the instrument 100 include a plurality of carriage image capture units 134.

With continued reference to FIG. 1, in some embodiments, the instrument 100 operates to communicate with a management system 136 via a data communication network 138. For example, the instrument 100 includes a communication device (such as a communication device 246 in FIG. 3) through which the instrument 100 communicates with the management system 136.

In some embodiments, the management system 136 is remotely located from the instrument 100 and configured to perform diagnosis based on data from the instrument 100. In addition, the instrument 100 can evaluate performance of the instrument and generate a report. One example of the management system 136 includes one or more computing devices executing PROSevice Remote Service Application available from Beckman Coulter, Inc., Brea, CA The Beckman Coulter PROService Remote Service Application can provide a secure and continuous connection between the biological sample analysis instrument 100 and a remote diagnosis command center (e.g., the management system 136) over a network (e.g., the network 138). The biological specimen analysis instrument 100 may be connected to the remote diagnosis command center by way of the Internet via Ethernet port, Wi-Fi, or cellular network.

Still referring to FIG. 1, the data communication network 138 communicates digital data between one or more computing devices, such as between the data collection device 108 and the data processing system 136. Examples of the network 138 include a local area network and a wide area network, such as the Internet. In some embodiments, the network 138 includes a wireless communication system, a wired communication system, or a combination of wireless and wired communication systems. A wired communication system can transmit data using electrical or optical signals in various possible embodiments. Wireless communication systems typically transmit signals via electromagnetic waves, such as in the form of optical signals or radio frequency (RF) signals. A wireless communication system typically includes an optical or RF transmitter for transmitting optical or RF signals, and an optical or RF receiver for receiving optical or RF signals. Examples of wireless communication systems include Wi-Fi communication devices (such as utilizing wireless routers or wireless access points), cellular communication devices (such as utilizing one or more cellular base stations), and other wireless communication devices.

Figure 2:
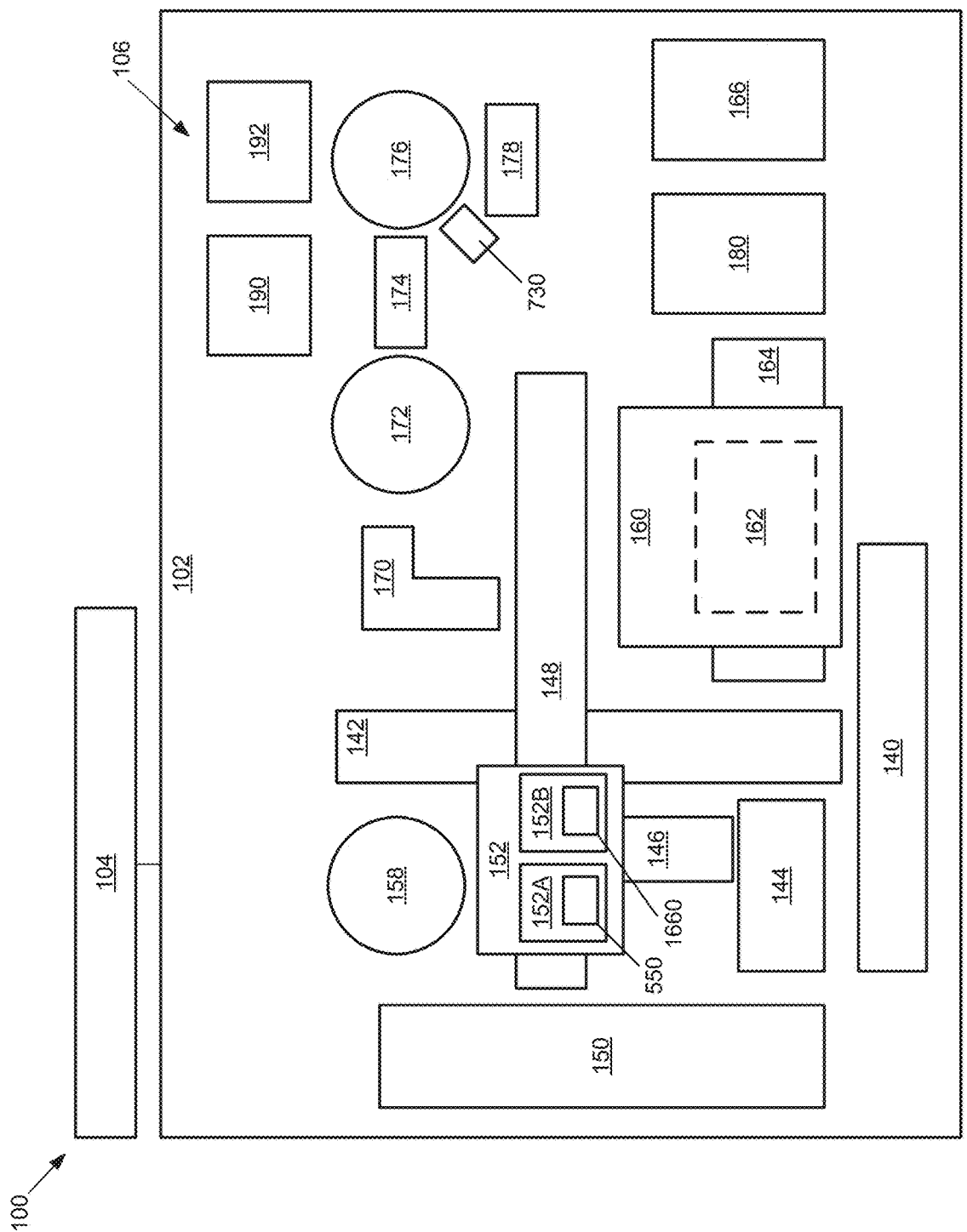
FIG. 2 schematically illustrates an example of the biological specimen analysis instrument of FIG. 1.

FIG. 2 schematically illustrates an example of the biological specimen analysis instrument 100 of FIG. 1. In the illustrated example, the instrument 100 is configured as an immunoassay analyzer. As described above, the instrument 100 includes the substance preparation system 102, the preparation evaluation system 104, and the substance evaluation system 106. In some embodiments, the substance preparation system 102 includes a sample supply board 140, a sample presentation unit 142, a reaction vessel feeder 144, a reaction vessel carriage unit 146, a sample transfer unit 148, a pipetting tip feeder 150, a sample pipetting device 152, a sample wheel 158, a reagent carriage unit 160, a reagent pipetting device 162, a reagent storage device 164, a reagent load device 166, an incubator transfer unit 170, an incubator 172, an reaction vessel transfer unit 174, a wash wheel 176, and a substrate load device 180. In some embodiments, the substance evaluation system 106 includes a light measurement device 190 and an evaluation processing device 192. Some embodiments of the substance evaluation system 106 are further associated with at least some operations performed by the incubator transfer unit 170, the incubator 172, the reaction vessel transfer unit 174, the wash wheel 176, and the substrate load device 180.

The sample supply board 140 is configured to receive a plurality of sample tubes in a plurality of sample racks. In some embodiments, a user (e.g., a laboratory technician) loads one or more racks of sample tubes to the sample supply board 140. The sample supply board 140 can move the racks to the sample presentation unit 142 for pipetting, and receives the pipetted racks returned by the sample presentation unit 142 after pipetting.

The sample presentation unit 142 operates to transfer one or more racks of sample tubes to designated locations. In some embodiments, the sample supply board 140 operates to provide one sample rack to the sample presentation unit 142. Further, the sample presentation unit 142 can operate to identify the rack and the sample ID on the rack. The sample presentation unit 142 transfers the rack to a sample pipetting location at which sample pipettors aliquot from the sample tubes in the rack. When a sample pipettor aliquots from one of the sample tubes in the rack, the sample presentation unit 142 indexes to another sample tube in the rack for the next pipetting. After all of the sample tubes have been pipetted, the sample presentation unit 142 returns the rack to the sample supply board 140. The sample presentation unit 142 can include a sample rack presentation unit. In other embodiments, the sample presentation unit 142 is configured to transfer a puck that carries a single tube. It is understood that the sample presentation unit 142 is also configured and used for other types of containers, such as cups or vessels.

The reaction vessel feeder 144 supplies a plurality of reaction vessels to the reaction vessel carriage unit 146. A user can load a large quantity of new, empty reaction vessels in the reaction vessel feeder 144. In some embodiments, the reaction vessel feeder 144 operates to orient the reaction vessels when supplying the reaction vessels to the reaction vessel carriage unit 146.

The reaction vessel carriage unit 146 operates to transfer reaction vessels from the reaction vessel feeder 144 to the sample transfer unit 148. In some embodiments, the reaction vessel carriage unit 146 picks up one or more reaction vessels from the reaction vessel feeder 144 and transfer the reaction vessels to the sample transfer unit 148.

The sample transfer unit 148 operates to transfer empty reaction vessels from the reaction vessel carriage unit 146 to the sample wheel 158 and the reagent carriage unit 160. Further, the sample transfer unit 148 operates to transfer aliquoted sample vessels to the reagent carriage unit 160, and transfer the sample vessels from the reagent carriage unit 160 back to the sample wheel 158. The sample transfer unit 148 can further operates to dispose the sample vessels and the diluent vessels that have been used for predetermined processes.

The pipetting tip feeder 150 supplies pipetting tips to the sample pipetting device 152. In this document, pipetting tips are examples of the dispense tips 112 and, therefore, can be also referred to herein as dispense tips 112. In some embodiments, a plurality of pipetting tips in racks is loaded in an array in the pipetting tip feeder 150. The pipetting tips are transferred and engaged to the sample pipetting device 152 for pipetting. Once used, the pipetting tips are disengaged from the sample pipetting device 152 to waste and the sample pipetting device 152 can return to the pipetting tip feeder 150. The user can discard solid waste including the used pipetting tips.

The sample pipetting device 152 performs various pipetting operations. The sample pipetting device 152 receives a pipetting tip from the pipetting tip feeder 150 and engages the pipetting tip to the sample pipetting device 152. In some embodiments, the sample pipetting device 152 engages a pipetting tip by pressing a pipettor mandrel into the pipetting tip and lifts the pipettor mandrel that fits the pipetting tip. As described herein, some embodiments of the pipetting tips are disposable after a single use or multiple uses.

In some embodiments, the sample pipetting device 152 includes a sample aliquot pipetting unit ("Sample Aliquot Gantry") 152A and a sample precise pipetting unit ("Sample Precision Gantry") 152B.

The sample aliquot pipetting unit 152A operates to pipette an aliquot of sample from a sample tube located in the sample presentation unit 142, and dispense the aliquot of sample into a sample vessel on the sample wheel 158. The sample aliquot pipetting unit can dispose the used pipetting tip when the pipetting is completed for each sample. As described herein, the sample aliquot pipetting unit 152A can include a camera unit 550, which is further described herein with reference to, for example, FIGS. 11, 12A, and 12B.

The sample precise pipetting unit 152B operates to pipette the sample from a sample vessel located on the reagent carriage unit 160. Then, the sample precise pipetting unit can dispense the sample to a reaction vessel. In some embodiments, the sample can be dispensed first to a dilution vessel to create a sample dilution (for example, with wash buffer provided by the reagent pipetting device 162) before being dispensed to a reaction vessel. The sample precise pipetting unit can dispose the used pipetting tip when a predetermined test is completed. As described herein, the sample precise pipetting unit 152B can include a camera unit 2550, which is further described herein with reference to FIGS. 11, 12A, 12B, and 67.

The sample wheel 158 stores the aliquoted samples in the sample vessels thereon. In some embodiments, the sample wheel 158 operates to maintain the samples in a lower temperature, such as around 4-10° C., to reduce analyte concentration changed by evaporation. The sample vessels can be transferred back to the sample wheel 158 after reagent pipetting, if additional tests are requested.

The reagent carriage unit 160 is configured to support a plurality of vessels and transfer the vessels to different locations. In some embodiments, the reagent carriage unit 160 is configured to hold a plurality of four vessels (e.g., three or four vessels), which can be used simultaneously for each reagent pipettor of the reagent pipetting device 162. In some embodiments, the reagent carriage unit 160 is thermally controlled at about 30° C. to 40° C. In other embodiments, the reagent carriage unit 160 is maintained about 37° C. to ensure enzyme consistent kinetic reaction, for example.

In some embodiments, the reagent carriage unit 160 is configured to hold a reaction vessel, a dilution vessel, and a sample vessel, and convey the vessels for sample pipetting and reagent pipetting. In some embodiments, the reagent carriage unit 160 includes a carriage shuttle that is movable along a predetermined path. For example, the reagent carriage unit 160 is moved close to the sample transfer unit 148 to accept the reaction vessel, the dilution vessel, and the sample vessel from the sample transfer unit 148. Further, the reagent carriage unit 160 can move to the reagent pipetting device 162 for pipetting reagents, and to the sample precise pipetting unit 152B for pipetting the sample. In some embodiments, the reagent carriage unit 160 moves to the sample transfer unit 148 to remove the dilution vessel and the sample vessel, and to the incubate transfer unit 170 to remove the reaction vessel.

The reagent pipetting device 162 operates to pipette reagents from the reagent storage device 164 to the reaction vessels on the reagent carriage unit 160. In some embodiments, the reagent pipetting device 162 includes a plurality of pipettors, which can perform pipetting on different tests concurrently to support throughput. In some embodiments, the reagent pipetting device 162 is thermally controlled at about 30° C. to 40° C. In other embodiments, the reagent pipetting device 162 is maintained about 37° C. to ensure enzyme reaction consistent binding kinetics, for example.

The reagent storage device 164 stores reagents. The reagent storage device includes a reagent transfer unit configured to transfer reagent packs to predetermined locations. In some embodiments, the reagent storage device 164 can transfer reagent packs from the reagent load device 166 to the reagent storage device 164, from the reagent storage device 164 to the pipetting location for pipetting by the reagent pipetting device 162, from the pipetting location to the reagent storage device 164, from the pipetting location to a waste location if the reagents are consumed, from the reagent storage device 164 to the waste location if the reagents expire, and from the reagent storage device 164 to the reagent load device 166 for unloading the reagent packs. In some embodiments, the reagent storage device 164 is thermally controlled at about 2° C. to 15° C. In other embodiments, the reagent storage device 164 is maintained about 4° C. to 10° C.

The reagent load device 166 operates to load one or more reagent packs. A user can load reagent packs to the reagent load device 166.

The incubator transfer unit 170 transfers the reaction vessels to and from the incubator 172. In some embodiments, the incubator transfer unit 170 transfers one or more of the pipetted reaction vessels from the reagent carriage unit 160 to the incubator 172. Further, the incubator transfer unit 170 can transfer one or more reaction vessels from the incubator 172 to the reagent carriage unit 160. The incubator transfer unit 170 can also remove from the incubator 172 the reaction vessels that have been read or completed.

The incubator 172 is thermally controlled to maintain a predetermine temperature. In some embodiments, the incubator 172 is maintained about 30° C. to 40° C. In other embodiments, the incubator 172 is maintained about 37° C. to ensure immunological reaction and enzyme reaction, for example. By way of example, the incubator 172 performs assay incubation.

The reaction vessel transfer unit 174 transfers the reaction vessels to and from the incubator 172. In some embodiments, the reaction vessel transfer unit 174 transfers incubated reaction vessels from the incubator 172 to the wash wheel 176, transfers assay reaction vessels from the wash wheel 176 to the incubator 172, transfers reaction vessels containing substrate from the wash wheel 176 to the incubator 172 for substrate incubation or enzyme reaction, transfers washed reaction vessels from the incubator 172 to the light measurement device 190 after substrate incubation, and transfers the reaction vessels that have been read or completed from the light measurement device 190 to the incubator 172. The used reaction vessels can be delivered to a waste location.

The wash wheel 176 receives and supports reaction vessels thereon such that various aspects of diagnostic process are performed with the substance evaluation system 106. An example of the wash wheel 176 is described and illustrated in more detail with reference to FIGS. 23-25. In some embodiments, the wash wheel 176 is a thermally controlled device to separate bound or free analytes from particles after incubation. In some embodiments, the wash wheel 176 is maintained about 30° C. to 40° C. In other embodiments, the wash wheel 176 is maintained about 37° C. to ensure enzyme reaction, for example.

The substrate pipetting device 178 operates to dispense a substrate to a washed reaction vessel. One example of the substrate is a chemiluminescent substrate for immunoassay-enzyme reaction, such as Lumi-Phos 530, which can produce light provide detection of corresponding to the quantity of analytes captured on magnetic particles.

The substrate load device 180 operates to load one or more substrates to be supplied. In some embodiments, the substrate load device 180 includes a set of two bottles, one of which is in use and the other of which is arranged for unloading and new loading processed. The substrate pipetting device 178 can operate to draw the substrate from the bottle in use.

The light measurement device 190 operates to detect and measure light (e.g., light L in FIG. 4) resulting from immunological analysis. In some embodiments, the light measurement device 190, which can also referred to as a luminometer, includes a light tight enclosure containing a photomultiplier tube (PMT) for reading a magnitude of chemiluminescence light from the reaction vessel containing the substrate. The reaction vessel can be transferred to, and removed from, the light measurement device 190 by the reaction vessel transfer unit 174.

The evaluation processing device 192 operates to receive information about the amount of light detected by the light measurement device 190 and evaluate the analysis based on the information.

Figure 3:
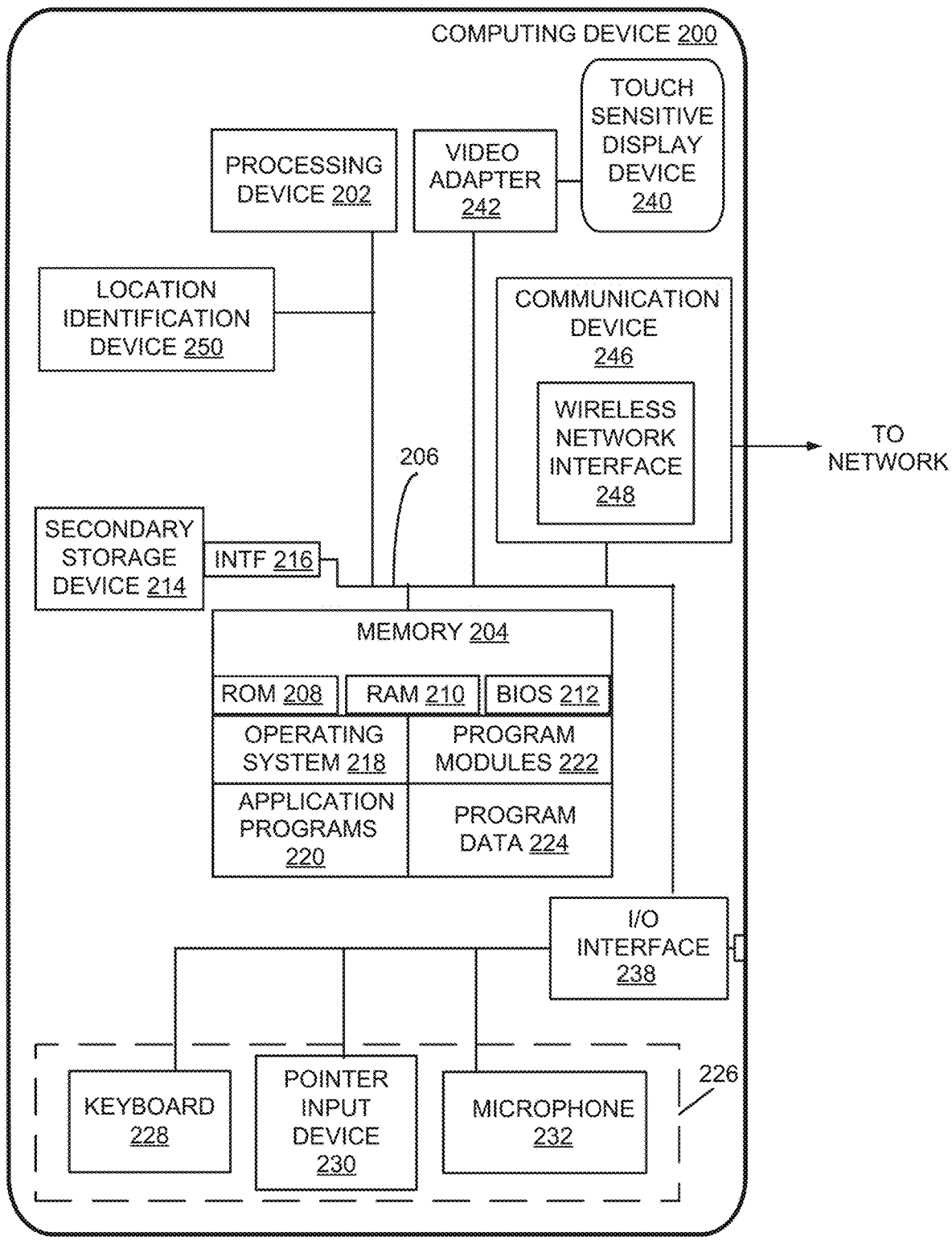
FIG. 3 illustrates an exemplary architecture of a computing device that can be used to implement aspects of the present disclosure.

FIG. 3 illustrates an exemplary architecture of a computing device that can be used to implement aspects of the present disclosure, including the biological specimen analysis instrument 100 or various systems of the instrument 100, such as the substance preparation system 102, the preparation evaluation system 104, and the substance evaluation system 106. Further, one or more devices or units included in the systems of the instrument 100 can also be implemented with at least some components of the computing device as illustrated in FIG. 3. Such a computing device is designated herein as reference numeral 200. The computing device 200 is used to execute the operating system, application programs, and software modules (including the software engines) described herein.

The computing device 200 includes, in some embodiments, at least one processing device 202, such as a central processing unit (CPU). A variety of processing devices are available from a variety of manufacturers, for example, Intel or Advanced Micro Devices. In this example, the computing device 200 also includes a system memory 204, and a system bus 206 that couples various system components including the system memory 204 to the processing device 202. The system bus 206 is one of any number of types of bus structures including a memory bus, or memory controller; a peripheral bus; and a local bus using any of a variety of bus architectures.

Examples of computing devices suitable for the computing device 200 include a desktop computer, a laptop computer, a tablet computer, a mobile device (such as a smart phone, an iPod® mobile digital device, or other mobile devices), or other devices configured to process digital instructions.

The system memory 204 includes read only memory 208 and random access memory 210. A basic input/output system 212 containing the basic routines that act to transfer information within computing device 200, such as during start up, is typically stored in the read only memory 208.

The computing device 200 also includes a secondary storage device 214 in some embodiments, such as a hard disk drive, for storing digital data. The secondary storage device 214 is connected to the system bus 206 by a secondary storage interface 216. The secondary storage devices and their associated computer readable media provide nonvolatile storage of computer readable instructions (including application programs and program modules), data structures, and other data for the computing device 200.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

A number of program modules can be stored in secondary storage device 214 or memory 204, including an operating system 218, one or more application programs 220, other program modules 222, and program data 224.

In some embodiments, computing device 200 includes input devices to enable a user to provide inputs to the computing device 200. Examples of input devices 226 include a keyboard 228, pointer input device 230, microphone 232, and touch sensitive display 240. Other embodiments include other input devices 226. The input devices are often connected to the processing device 202 through an input/output interface 238 that is coupled to the system bus 206. These input devices 226 can be connected by any number of input/output interfaces, such as a parallel port, serial port, game port, or a universal serial bus. Wireless communication between input devices and interface 238 is possible as well, and includes infrared, BLUETOOTH® wireless technology, WiFi technology (802.11a/b/g/n etc.), cellular, or other radio frequency communication systems in some possible embodiments.

In this example embodiment, a touch sensitive display device 240 is also connected to the system bus 206 via an interface, such as a video adapter 242. The touch sensitive display device 240 includes touch sensors for receiving input from a user when the user touches the display. Such sensors can be capacitive sensors, pressure sensors, or other touch sensors. The sensors not only detect contact with the display, but also the location of the contact and movement of the contact over time. For example, a user can move a finger or stylus across the screen to provide written inputs. The written inputs are evaluated and, in some embodiments, converted into text inputs.

In addition to the display device 240, the computing device 200 can include various other peripheral devices (not shown), such as speakers or a printer.

The computing device 200 further includes a communication device 246 configured to establish communication across the network. In some embodiments, when used in a local area networking environment or a wide area networking environment (such as the Internet), the computing device 200 is typically connected to the network through a network interface, such as a wireless network interface 248. Other possible embodiments use other wired and/or wireless communication devices. For example, some embodiments of the computing device 200 include an Ethernet network interface, or a modem for communicating across the network. In yet other embodiments, the communication device 246 is capable of short-range wireless communication. Short-range wireless communication is one-way or two-way short-range to medium-range wireless communication. Short-range wireless communication can be established according to various technologies and protocols. Examples of short-range wireless communication include a radio frequency identification (RFID), a near field communication (NFC), a Bluetooth technology, and a Wi-Fi technology.

The computing device 200 typically includes at least some form of computer-readable media. Computer readable media includes any available media that can be accessed by the computing device 200. By way of example, computer-readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 200.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

Blood samples are whole blood, serum, plasma, and other blood components or fractions. In some embodiments, the biological specimen analysis instrument 100 is configured to analyze one or more bodily fluid sample types. Bodily fluids are blood, urine, saliva, cerebral spinal fluid, amniotic fluid, feces, mucus, cell or tissue extracts, and nucleic acid extracts. Specimens, also referred to as samples, are collected at donor centers, physician's offices, phlebotomist's offices, hospitals, clinics, and other healthcare settings, but not limited thereto. The collected bodily fluid and its components are then often processed, tested, and distributed at or through clinical laboratories, hospitals, blood banks, physicians's offices, or other healthcare settings. In the present disclosure, the instrument 100 is primarily described to perform immunoassay, which measures the presence or concentration of a macromolecule in a solution through the use of an antibody or immunoglobulin. Such a macromolecule is also referred to herein as an analyte. In other embodiments, however, the instrument 100 includes a biological specimen analyzer of any type. For example, the instrument 100 can be a clinical chemistry analyzer, a blood type analyzer, a nucleic acid analyzer, a microbiology analyzer, or any other type of in-vitro diagnostic (IVD) analyzer.

Figure 4:
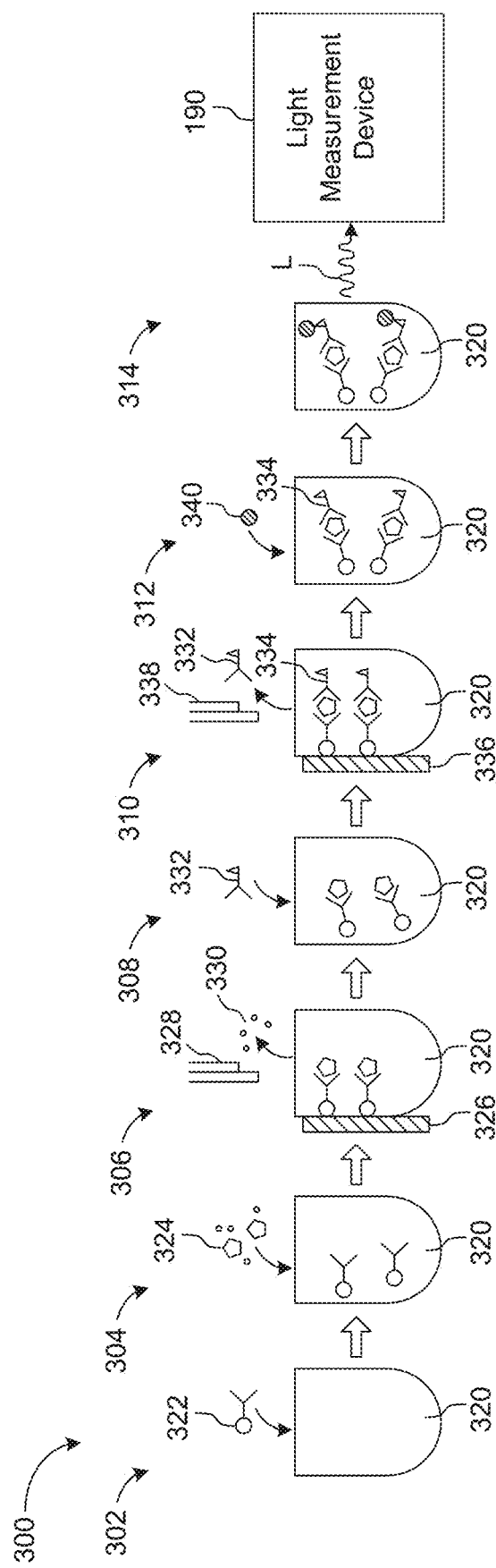
FIG. 4 is a schematic diagram that illustrates an example method for immunological analysis.

FIG. 4 is a schematic diagram that illustrates an example method 300 for immunological analysis. In some embodiments, the method 300 includes operations 302, 304, 306, 308, 310, 312, and 314. In some embodiments, at least some of the operations in the method 300 are performed by the substance preparation system 102, the preparation evaluation system 104, and/or the substance evaluation system 106 of the instrument 100.

At operation 302, a cuvette 320 (e.g., a reaction vessel) is transported to a predetermined position, and a first reagent including magnetic particles 322 is dispensed into the cuvette 320. In some embodiments, the cuvette 320 is a reaction vessel and transported to the wash wheel 176.

At operation 304, a sample or specimen 324 is dispensed into the cuvette 320. In some embodiments, the sample pipetting device 152, to which a pipetting tip supplied from the pipetting tip feeder 150 is engaged, aspirates the sample 324 from a sample vessel that has been transported to a predetermined position. Once the sample is dispensed into the cuvette 320, the cuvette 320 is may be subjected to mixing, if required, so as to produce magnetic particle carriers each formed of the antigen and the magnetic particle in the sample 324 bonded together.

At operation 306, the cuvette 320 is subjected to a first cleaning process in which the magnetic particle carriers is magnetically collected by a magnetic collecting unit 326, and a bound-free separation is carried out by a bound-free cleaning aspiration nozzle 328. As a result, an unreacted substance 330 in the cuvette 320 is removed.

At operation 308, a second reagent 332, such as a labeling reagent including a labeled antibody is dispensed into the cuvette 320. As a result, immune complexes 334 each formed of the magnetic particle carrier and the labeled antibody 332 bonded together are produced.

At operation 310, a second bound-free cleaning process is performed to magnetically collect the magnetic particle carriers by a magnetic collecting structure 336. Further, a bound-free separation is performed by a bound-free cleaning aspiration nozzle 338. As a result, the labeled antibody 332 that is not bonded with the magnetic particle carrier is removed from the cuvette 320.

At operation 312, a substrate including an enzyme 340 is dispensed into the cuvette 320, which is then mixed. After a certain reaction time necessary for the enzyme reaction passes, the cuvette 320 is transported to a photometric system, such as the light measurement device 190.

At operation 314, the enzyme 340 and the immune complex 334 are bonded together through the substrate 340 reactions with the enzyme on the labeled antibody 332, and light L is emitted from the immune complex 334 and measured by a photometric system, such as the light measurement device 190. The light measurement device 190 operates to calculate an amount of antigen, which is included in the specimen, according to the quantity of light measured.

Referring to FIGS. 5-39, an example of the volume detection system 120 is described.

Figure 5:
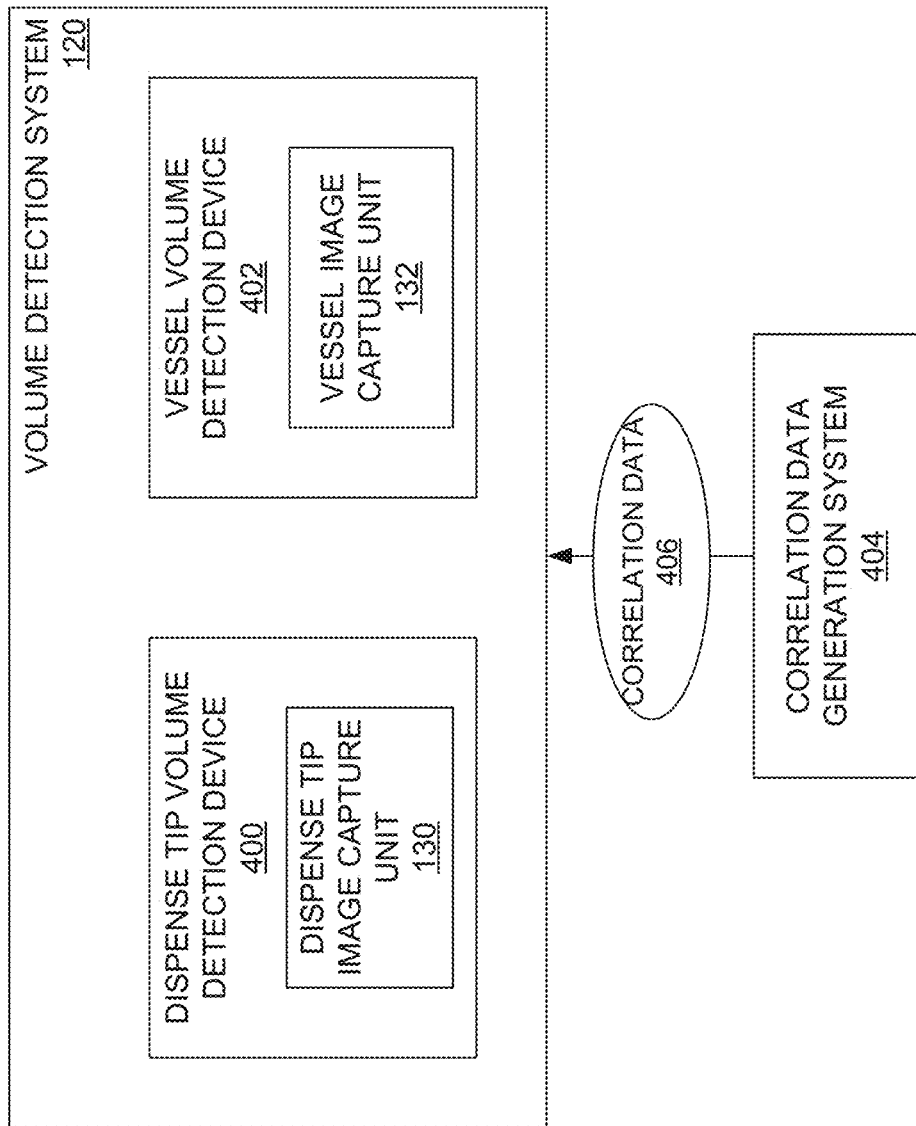
FIG. 5 is a block diagram of an example of a volume detection system of FIG. 1.

FIG. 5 is a block diagram of an example of the volume detection system 120 of FIG. 1. In some embodiments, the volume detection system 120 includes a dispense tip volume detection device 400 and a vessel volume detection device 402. The volume detection system 120 further includes a correlation data generation system 404 that generates correlation data 406.

The dispense tip volume detection device 400 operates to detect a volume of a fluidic substance 118 aspirated into a dispense tip 112.

Fluidic substance 118 may be of any type suitable for being dispensed in a container and presented for further analysis. In various embodiments, the fluidic substance 118 may be a specimen to be subjected to analysis, sample preparation components, diluents, buffers, reagents, or any combinations of the foregoing. Where the fluidic substance 118 involves blood or its components, examples of the fluidic substance 118 include whole blood, blood plasma, serum, red blood cells, white blood cells, platelets, diluents, reagents, or any combinations thereof. Fluidic substance 118 may be other types of bodily fluidic substances, such as saliva, cerebral spinal fluid, urine, amniotic fluid, feces, mucus, cell or tissue extracts, nucleic acids, or any other type of bodily fluid, tissue or material which is suspected of containing an analyte of interest. Where the fluidic substance 118 is a reagent, the reagent may be of various types known for use in analysis of biological specimens. Some examples of reagents include liquid reagents containing labeled specific-binding reagents, for example antibody or nucleic acid probes, liquid reagents containing reactive and/or non-reactive substances, red blood cells suspensions, and particle suspensions. In other embodiments, the reagent can be a chemiluminescent substrate.

As described herein, the dispense tip 112 can be of various types and used for different processes. One example of the dispense tip 112 is a pipetting tip that can be used with the sample pipetting device 152. The dispense tip volume detection device 400 can utilize the dispense tip image capture unit 130. An example of the dispense tip volume detection device 400 is illustrated and described in more detail with reference to FIGS. 9-21.

The vessel volume detection device 402 operates to detect a volume of a fluidic substance 118 contained within a vessel 114. As described herein, the vessel 114 can be of various types and used for different processes. Examples of the vessel 114 include a reaction vessel, a sample vessel, and a dilution vessel, which are used throughout the process in the instrument 100. The vessel volume detection device 402 can utilize the vessel image capture unit 132. An example of the vessel volume detection device 402 is illustrated and described in more detail with reference to FIGS. 22-39.

The correlation data generation system 404 generates correlation data 406. The correlation data 406 provide information used by the volume detection system 120 to determine a volume of the fluidic substance 118 received in the container 110. In some embodiments, the correlation data generation system 404 is an independent apparatus from the volume detection system 120. In other embodiments, the correlation data generation system 404 is configured to use at least some resources of the volume detection system 120.

Figure 6:
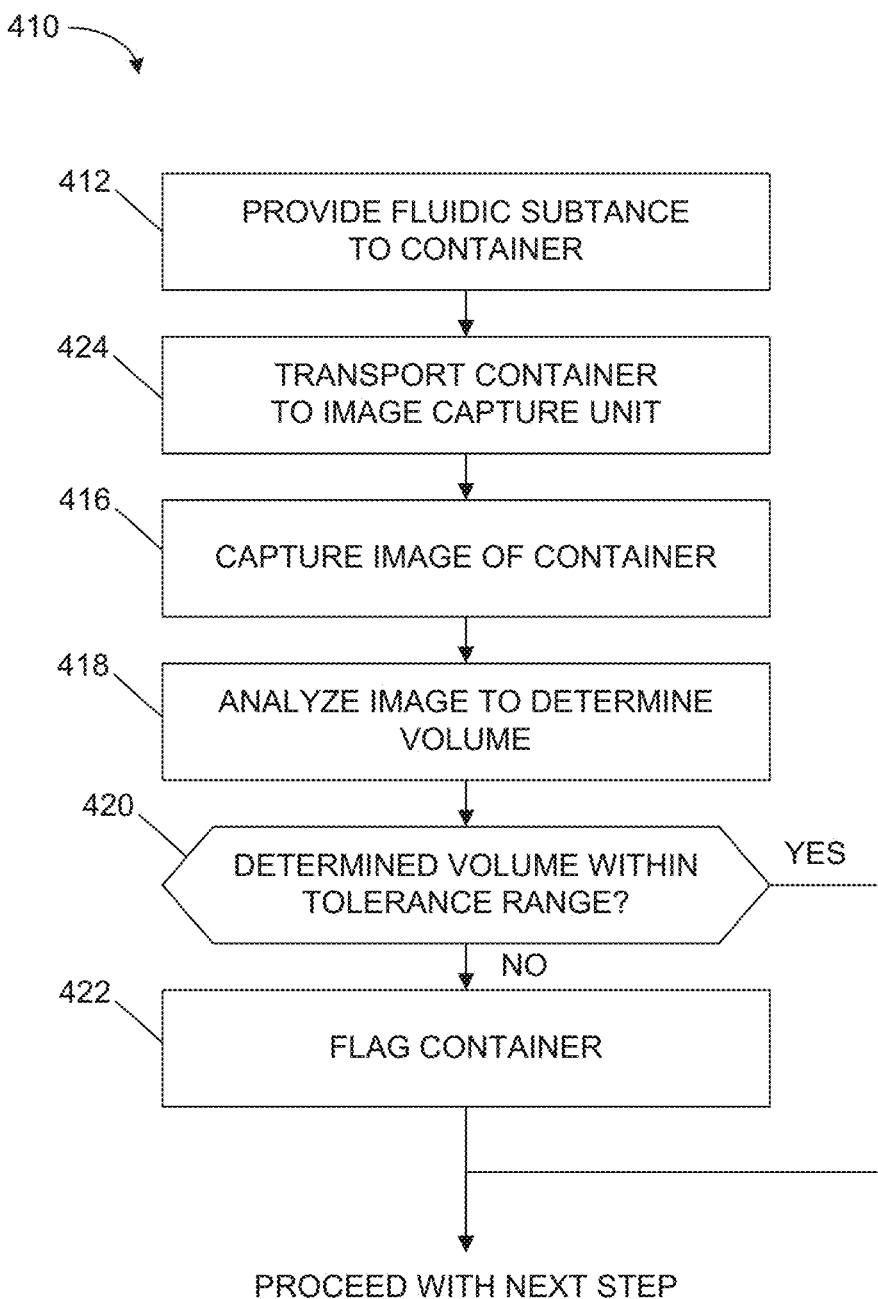
FIG. 6 is a flowchart illustrating an example method of operating the volume detection system.

FIG. 6 is a flowchart illustrating an example method 410 of operating the volume detection system 120. In some embodiments, at least some of the operations in the method 410 are performed by the substance preparation system 102, the preparation evaluation system 104, and/or the substance evaluation system 106 of the instrument 100. In other embodiments, other components, units, and devices of the instrument 100 are used to perform at least one of the operations in the method 410.

At operation 412, a fluidic substance 118 is provided into a container 110. In some embodiments, the substance preparation system 102 can perform the operation 412. In other embodiments, the container 110 is preloaded with the fluidic substance 118 before the container 110 is loaded into, and used by, the instrument 100.

At operation 414, the container 110 including the fluidic substance 118 is transported to an image capture unit, such as the dispense tip image capture unit 130 and the vessel image capture unit 132.

At operation 416, the image capture unit captures an image of the container 110. In some embodiments, the image of the container 110 is a digital image of a predetermined resolution.

At operation 418, the preparation evaluation system 104 (e.g., the volume detection system 120) analyzes the image to determine a volume of the fluidic substance 118 within the container 110. An example of the operation 416 is described in more detail with respect to FIG. 7.

At operation 420, the preparation evaluation system 104 (e.g., the volume detection system 120) determines whether the determined volume falls within a tolerance range. When the determined volume is outside a tolerance range, the provision of the fluidic substance 118 into the container 110 is considered to have been inappropriate. In some embodiments, such a tolerance range is determined based on an allowable deviation from a target volume of the fluidic substance 118 that is intended to be provided into the container 110. When the detected volume is determined to fall within the tolerance range ("YES" at the operation 420), the method 410 proceeds to perform a predetermined next step. Otherwise ("NO" at the operation 420), the method 410 moves on to operation 422.

At operation 422, the preparation evaluation system 104 (e.g., the volume detection system 120) flags the container 110 to indicate that the volume of the fluidic substance 118 within the container 110 is not appropriate for subsequent processes. Alternatively, the preparation evaluation system 104 operates to stop an associated test or analytic process in the instrument 100. In other embodiments, the evaluation result can be used to automatically adjust a test result that may be erroneous due to the inappropriate volume of the fluidic substance. In yet other embodiments, as described herein, the evaluation result can be used to automatically adjust the volume of the fluidic substance in response to the volume determination.

Figure 7:
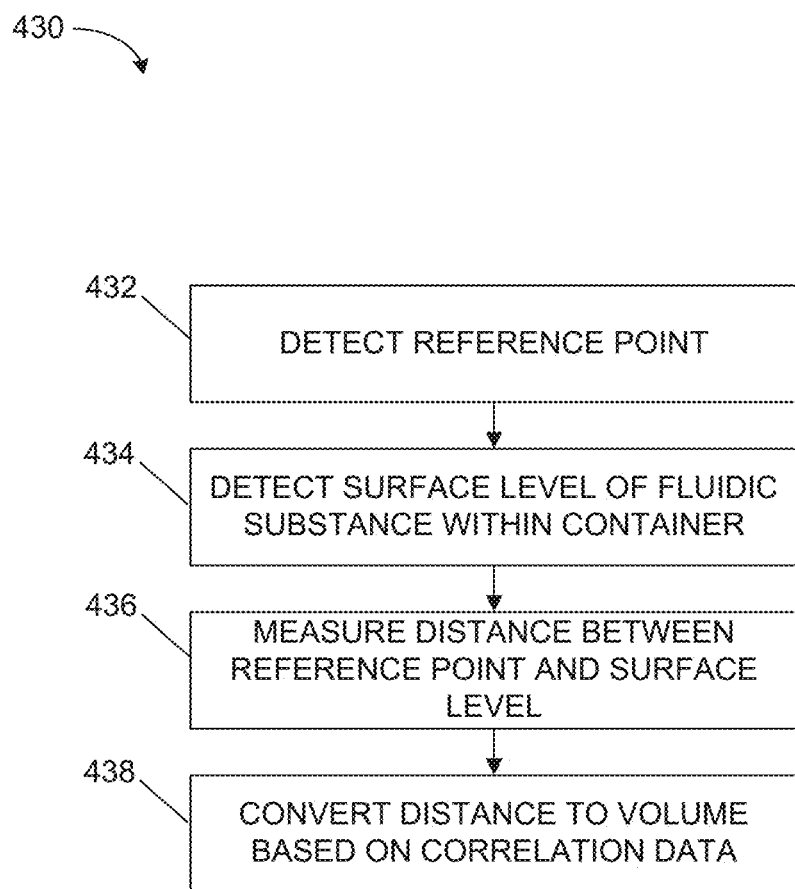
FIG. 7 is a flowchart illustrating an example method for performing an operation of the volume detection system of FIG. 6.

FIG. 7 is a flowchart illustrating an example method 430 for performing the operation 418 of FIG. 6. In particular, the method 430 provides processes for analyzing the captured image of a container 110 to determine a volume of fluidic substance 118 contained in the container 110.

At operation 432, the preparation evaluation system 104 (e.g., the volume detection system 120) detects a reference point in the image. The reference point is associated with the container 110. In some embodiments, the reference point includes a location or portion of a detectable structure formed on the container 110. In other embodiments, the reference point is configured as a portion of the container 110. Other examples of the reference point are also possible. Various image processing methods can be used to detect the surface level of the fluidic substance 118 in the image.

At operation 434, the preparation evaluation system 104 (e.g., the volume detection system 120) detects a surface level of the fluidic substance 118 within the container 110 in the image. Various image processing methods can be used to detect the surface level of the fluidic substance 118 in the image.

At operation 436, the preparation evaluation system 104 (e.g., the volume detection system 120) measures a distance between the reference point and the surface level. In some embodiments, the distance is measured by a pixel distance between the reference point and the surface level in the image. In some embodiments, the pixel distance is calculated based on a Euclidean distance between two pixel points.

At operation 438, the preparation evaluation system 104 (e.g., the volume detection system 120) converts the distance to a volume based on correlation data 406. The correlation data 406 include information about a correlation between volumes within the container 110 and distances from the reference point to a plurality of different surface levels within the container 110. An example method of generating the correlation data is described with reference to FIG. 8.

Figure 8:
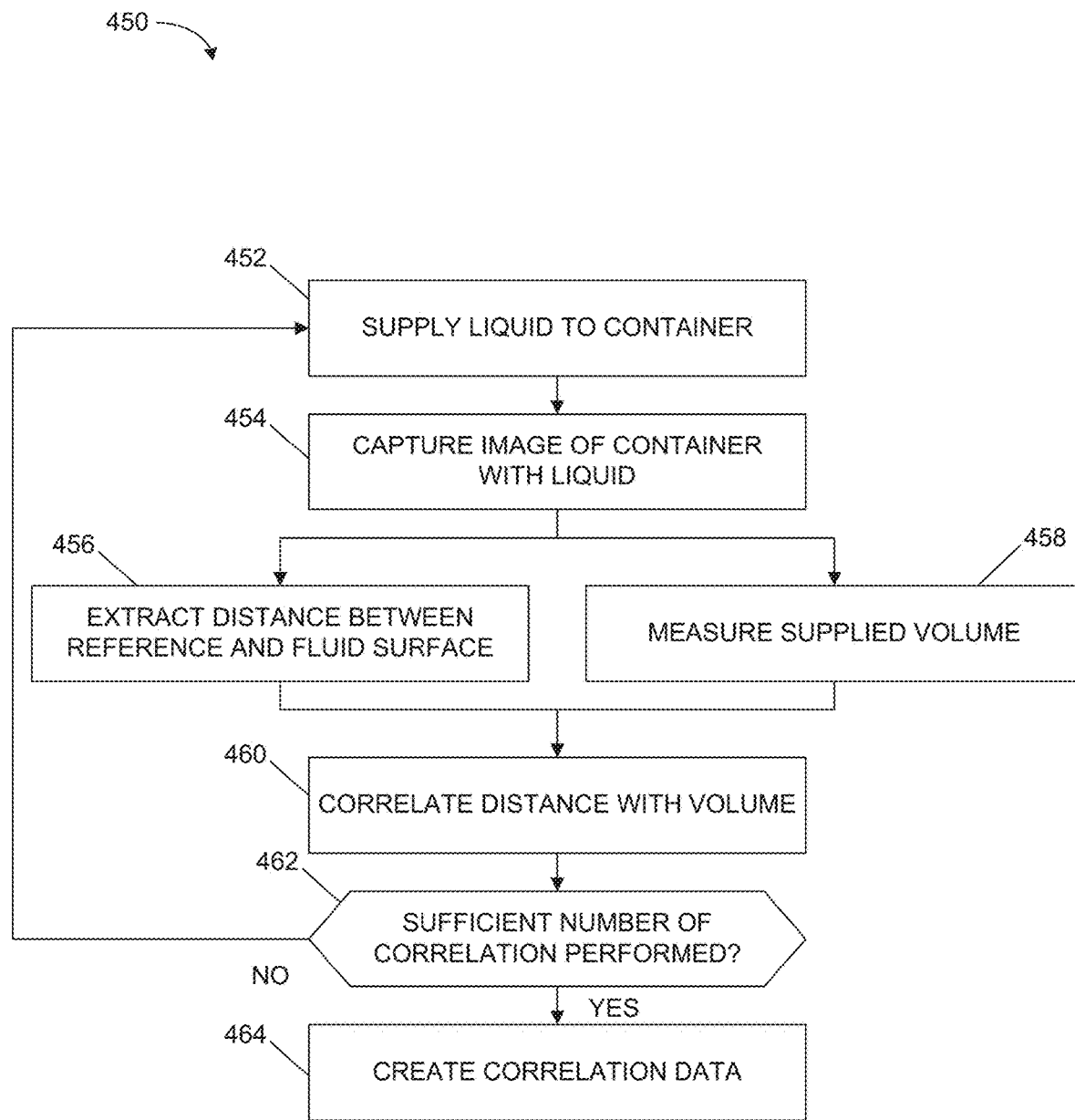
FIG. 8 is a flowchart illustrating an example method for operating a correlation data generation system to generate correlation data.

FIG. 8 is a flowchart illustrating an example method 450 for operating the correlation data generation system 404 to generate correlation data 406. In some embodiments, at least part of the instrument 100 is used as the correlation data generation system 404. In other embodiments, the correlation data generation system 404 generates the correlation data independently from the instrument 100.

At operation 452, the correlation data generation system 404 supplies a liquid to a container. The container used in the method 450 is the same container 110 that is subjected to volume detection process herein. The liquid used in the method 450 need not be identical to the fluidic substance 118 used in the instrument 100.

At operation 454, the correlation data generation system 404 captures an image of the container having the liquid.

At operation 456, the correlation data generation system 404 extracts a distance between a reference point (i.e., the reference point as described in the operation 432) and a fluid surface in the image captured in the operation 454. In some embodiments, the distance can be determined similarly to at least some of the operations of the method 430, such as the operations 432, 434, and 436.

At operation 458, the correlation data generation system 404 measures a volume of the liquid supplied to the container. Various methods can be used to determine the liquid volume within the container. Some of such methods are described in this document.

At operation 460, the correlation data generation system 404 correlates the distance calculated at the operation 456 and the volume measured at the operation 458.

At operation 462, the correlation data generation system 404 determines whether a sufficient number of correlations have been performed to generate the correlation data 406. If so ("YES" at the operation 470), the method 450 moves on to operation 464. Otherwise ("NO" at the operation 470), the method 450 returns to operation 452, in which the liquid is supplied to the container, and the subsequent operations are performed to determine additional correlations between the distance and the volume of the liquid within the container. To obtain a sufficient range of correlation data, the quantity of liquid supplied to the container can change in different cycles of correlation process. In addition, the quantity of liquid supplied to the container can remain roughly the same for some of the correlation cycles so as to obtain reliable results for particular volumes or volume ranges.

At operation 464, the correlation data generation system 404 creates the correlation data 408 based on a plurality of correlations made at the operation 460. In some embodiments, the correlation data 408 can be extrapolated to infer the relationship between the distance and the volume. For example, a correlation curve, a lookup table, or a mathematical formula can be created from the correlation data 408 to fit the data and estimate the relationship between the distance and the volume within the container.

Referring to FIGS. 9-21, an example of the dispense tip volume detection device 400 of FIG. 5 is described.

Figure 9:
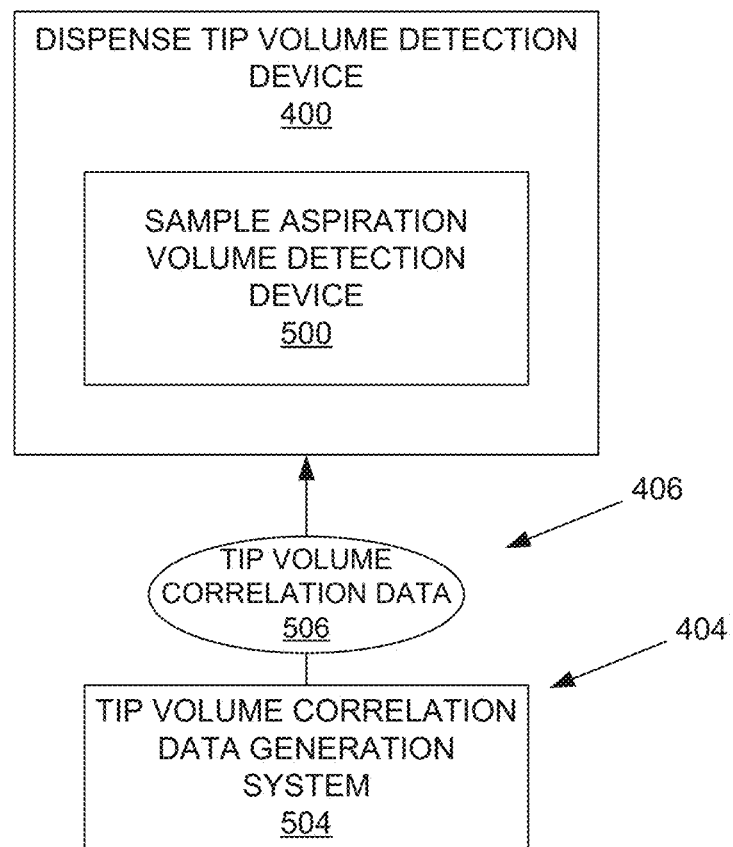
FIG. 9 illustrates an example of a dispense tip volume detection device of FIG. 5.

FIG. 9 illustrates an example of the dispense tip volume detection device 400 of FIG. 5. In some embodiments, the dispense tip volume detection device 400 includes a sample aspiration volume detection device 500. Further, the dispense tip volume detection device 400 uses tip volume correlation data 506 generated by a tip volume correlation data generation system 504.

The sample aspiration volume detection device 500 operates to determine a volume of the sample aspirated into a sample pipetting tip of the sample pipetting device 152. An example of the structure and operation of the sample aspiration volume detection device 500 is described below.

The tip volume correlation data generation system 504 generates the tip volume correlation data 506. The tip volume correlation data 506 provide information used by the dispense tip volume detection device 400 to determine a volume of fluidic substance received in a dispense tip (e.g., a sample pipetting tip). In some embodiments, the tip volume correlation data generation system 504 is an independent apparatus from the dispense tip volume detection device 400. In other embodiments, the tip volume correlation data generation system 504 is configured to use at least some resources of the dispense tip volume detection device 400. The tip volume correlation data generation system 504 and the tip volume correlation data 506 are included in, or examples of, the correlation data generation system 404 and the correlation data 406 as illustrated in FIG. 5.

Reliable clinical diagnosis requires accurate and precise aspiration and dispensing of a substance to be analyzed. For example, in an automatic analyzer which analyzes a specimen such as blood or any other bodily fluid, fluctuation in a dispensed amount of a specimen and other substances such as a reagent in a reaction vessel relative to a specified amount can affect an analysis result and degrade reliability of inspection and analysis. Therefore, it is beneficial to establish a technology for measuring an aspirated or dispensed amount with high accuracy and selecting only the aspirated or dispensed specimens whose amount is within a suitable range. One way to measure a liquid volume is to detect the level of a liquid surface by determining the height of liquid inside the vessel using resonant frequency. In other cases, air pressure is used to determine the viscosity of a liquid (e.g., sample) aspirated by a dispense tip. In yet other cases, a flow sensor is used to determine a flow rate of a liquid aspirated or dispensed.

However, these approaches have various disadvantages. For example, the detection of a liquid surface level using resonant frequency, and the detection of fluid viscosity using air pressure, can determine a liquid volume in a container, but cannot quantify a liquid volume that is aspirated or dispensed. Flow sensors can quantify a volume of liquid passing the tubing to which the flow sensors are arranged, but cannot reliably measure a liquid volume that is aspirated or dispensed. These methods do not have processes for identifying inaccurate sample aspirations in case of erroneous results.

As described herein in more detail, the dispense tip volume detection device 400 employs an image processing method for quantifying a volume of a fluidic substance (e.g., sample) aspirated. The volume of a fluidic substance is aspirated in a transparent or translucent container, such as a cone-shaped dispense tip. The container is imaged and a reference point is detected in the image. The dispense tip volume detection device measures a distance from the meniscus of the fluidic substance to the reference point, and correlates the distance to a volume using a volume calibration curve. If the volume aspirated inside the container is not within specifications for precision or accuracy of aspiration, the aspiration, or the entire test, is flagged. A user or operator can receive information about the result of aspiration.

Figure 10:
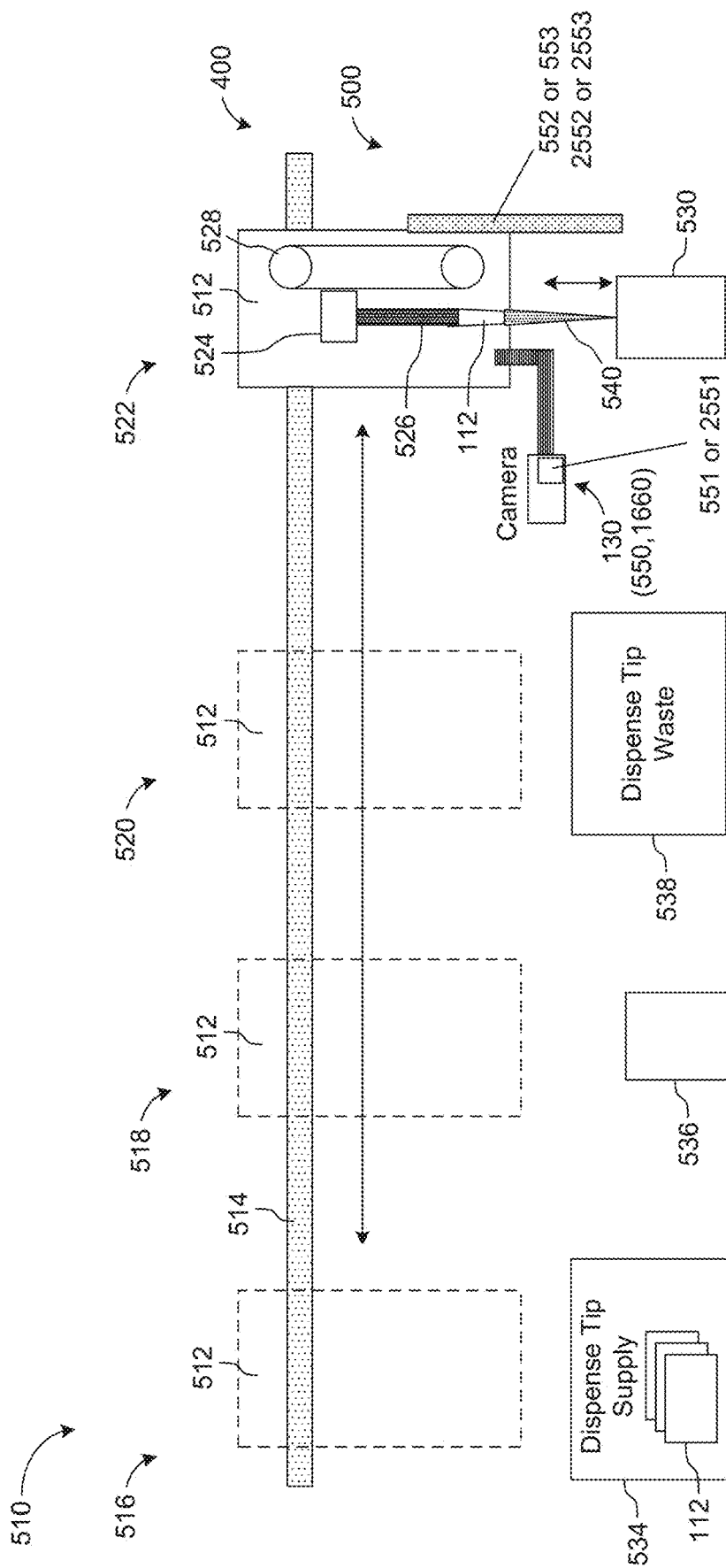
FIG. 10 schematically illustrates an example structure of a sample aspiration system in connection with the dispense tip volume detection device.

FIG. 10 schematically illustrates an example structure of a sample aspiration system 510 in connection with the sample aspiration volume detection device 500. In the illustrated example, the sample aspiration volume detection device 500 is primarily described and illustrated as an example of the dispense tip volume detection device 400. It is understood, however, that any types of the dispense tip volume detection device 400 can be used in the same or similar manner as the sample aspiration volume detection device 500.

In some embodiments, the sample aspiration system 510 includes a sample pipetting module 512 that is movable between different positions along a sample transfer guide 514. The sample pipetting module 512 can move to a tip supply position 516, a sample dispense position 518, a tip waste position 520, and a sample aspiration position 522. In some embodiments, the sample pipetting module 512 includes a base 524 and a mandrel 526 supported at the base 524. The sample pipetting module 512 includes a vertical transfer unit 528 configured to vertically move the base 524 including the mandrel 526 relative to a sample container 530. The mandrel 526 is configured to mount a dispense tip 112, which is also referred to herein as a pipetting tip or probe, an aspiration tip or probe, or a disposable tip or probe. 112

On the instrument 100, samples are aspirated by dispense tips to avoid contamination risks. The sample pipetting module 512 can move to the tip supply position 516 and vertically lower the base 524 of the module 512 to insert the mandrel 526 into a dispense tip 112 that is supplied by a dispense tip supply unit 534. Then, the sample pipetting module 512 moves to the sample aspiration position 522, in which the sample pipetting module 512 operates to aspirate a predetermined volume of sample 540 from the sample container 530. Once the sample is aspirated, the sample aspiration volume detection device 500 detects the volume of sample aspirated in the dispense tip 112. In some embodiments, the sample aspiration volume detection device 500 includes the dispense tip image capture unit 130 to capture an image of the dispense tip 112 as part of the process of volume detection. After that, the sample pipetting module 512 moves to the sample dispense position 518 to dispense the aspirated volume of sample into a reaction container 536, and then moves to the tip waste position 520 to discard the dispense tip 112 into a dispense tip waste unit 538.

In some embodiments, the sample aspiration system 510 is implemented with at least some components of the instrument 100 as illustrated in FIG. 2. For example, the sample pipetting module 512 corresponds to the sample pipetting device 152 (including the sample aliquot pipetting unit 152A and the sample precise pipetting unit 152B) of the instrument 100. The sample container 530 can correspond to a sample tube. The dispense tip supply unit 534 can correspond to the pipetting tip feeder 150. The reaction container 536 can correspond to a sample vessel, a reaction vessel, or any other vessel.

Figure 12A:
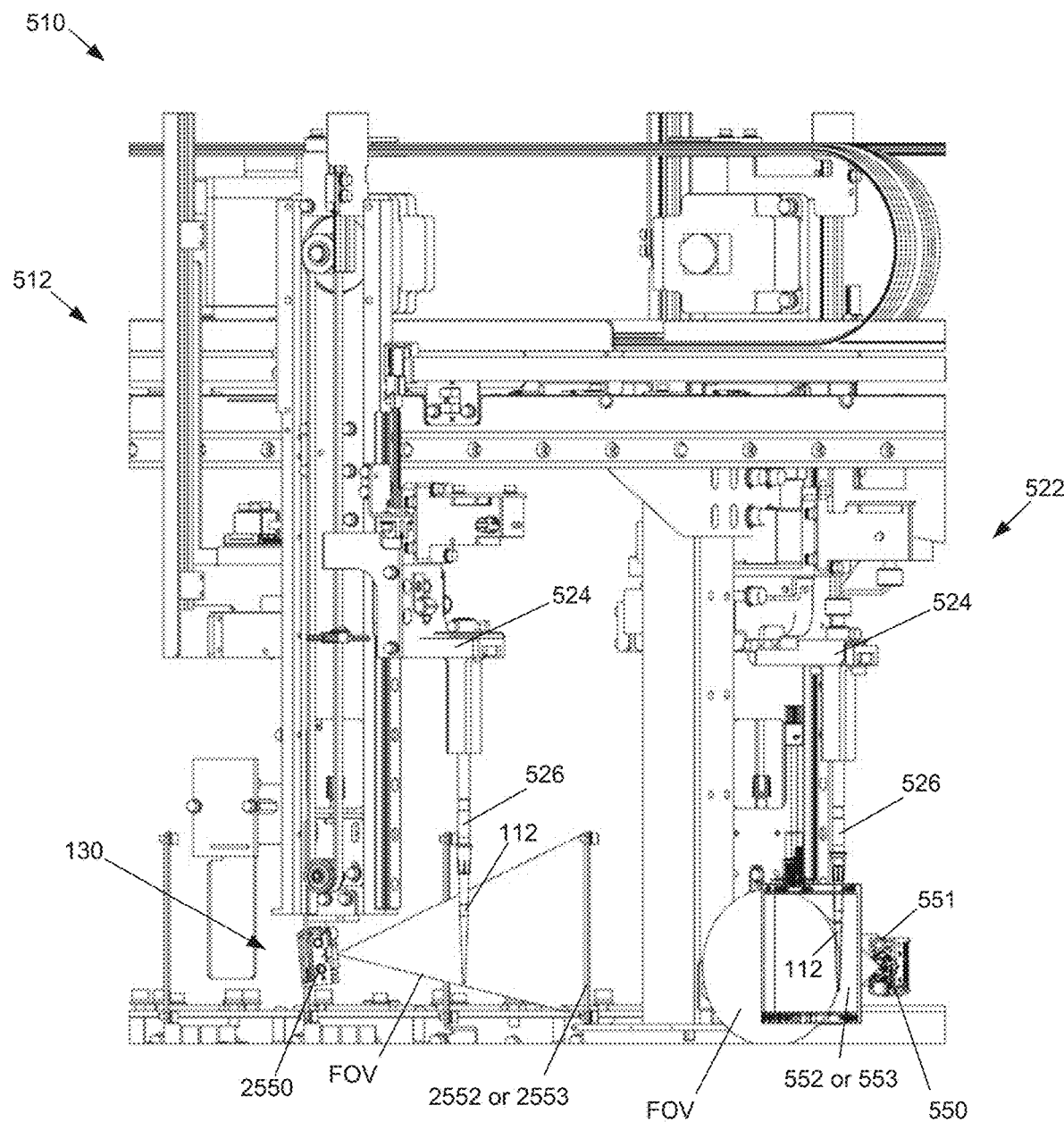
FIG. 12A is a side view of the sample aspiration system of FIG. 10.
Figure 12B:
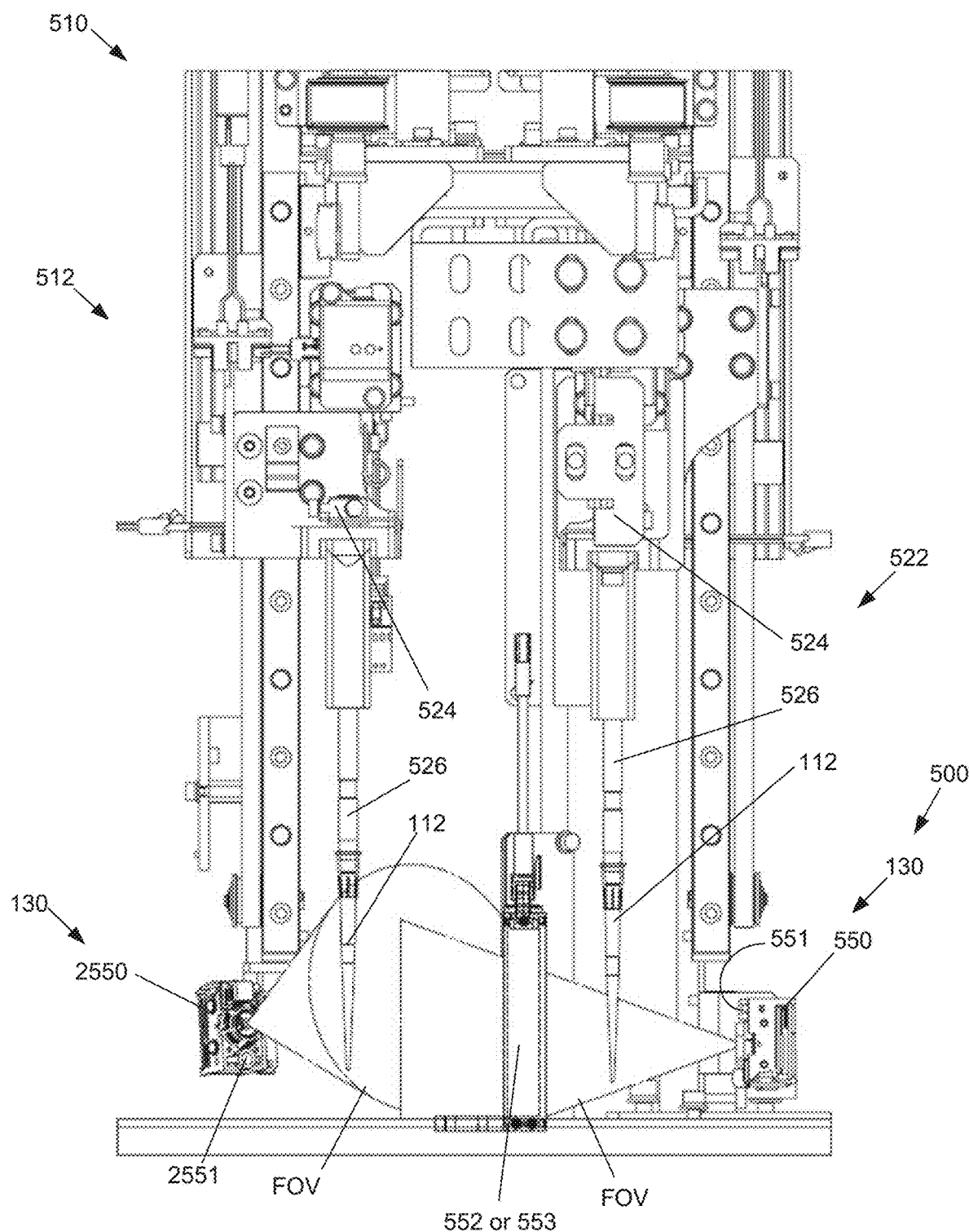
FIG. 12B is another side view of the sample aspiration system of FIG. 10.

FIGS. 11, 12A and 12B illustrate the sample aspiration system 510 of FIG. 10. FIG. 11 is a perspective view of the sample aspiration system of FIG. 10, FIG. 12A is a side view of the sample aspiration system 510, and FIG. 12B is another side view of the sample aspiration system 510, illustrating that the sample pipetting module 512 is in the sample aspiration position 522 for volume detection using the sample aspiration volume detection device 500.

As illustrated, the dispense tip image capture unit 130 includes a first camera unit 550 and its associated components, which are mounted to the sample aliquot pipetting unit 152A. In some embodiments, the first camera unit 550 and such other components are configured to move together with the corresponding mandrel and dispense tip of the sample aliquot pipetting unit 152A.

In some embodiments, the camera unit 550 includes a complementary metal-oxide-semiconductor (CMOS) image sensor for obtaining a color digital image. In other embodiments, the camera unit 550 includes a charge-coupled device (CCD) image sensor for obtaining a color digital image. As shown in FIG. 12, the camera unit 550 is located to a side of the dispense tip 112. Other embodiments of the camera unit 550 are configured to obtain black-and-white or grayscale pictures. One example of the camera unit 550 includes a model named ADVANTAGE 102, which is available from Cognex Corporation (Natick, MA), such as AE3-IS Machine Vision Color Camera+IO board (e.g., part number AE3C-IS-CQBCKFS1-B).

The dispense tip image capture unit 130 can further includes a light source 552 for the camera 550. The light source 552 is used to illuminate the dispense tip 112 and its surroundings to be photographed as desired. The light source 552 can be arranged in various locations. In the illustrated example, the light source 552 is positioned at the back of the dispense tip 112 opposite to the camera unit 550 and thus used as a backlight. Other locations of the light source 552 are also possible. One example of the light source 552 includes MDBL Series available from Moritex Corporation (Japan).

In other embodiments, the camera unit 550 includes a light source 551, such as a LED light, which is operable to emit light toward the dispense tip 112. In this configuration, the light source 552 can be replaced by a screen 553 which is arranged to be opposite to the camera unit 550 so that the dispense tip 112 is positioned between the camera unit 550 and the screen 553. The screen 553 is used to cast light back in the direction of the field of view (FOV) of the camera unit by reflecting light toward the camera's aperture. The screen 553 is made of one or more various materials which can provide different reflection intensities. For example, the screen 553 includes a retroreflective sheeting, one example of which includes 3M™ Scotchlite™ Sheeting 7610, available from 3M Company (Maplewood, MN). In other embodiment, the light source 552 can be used together with the light source 551 from the camera unit 550 and the screen 553.

In some embodiments, the camera unit 550 and the light source 552 (or the screen 553) are attached on the sample pipetting module 512 and configured to move horizontally together with the sample pipetting module 512 so that an image of the dispense tip 112 is captured in any positions of the sample pipetting module 512. For example, an image of the dispense tip 112 containing the aspirated sample can be taken in any position after the sample is aspirated (i.e., the sample aspiration position 522) and before the sample is dispensed (i.e., the sample dispense position 518). In other embodiments, the camera unit 550 is attached to the sample pipetting module 512 while the light source 552 (or the screen 553) is not attached to the sample pipetting module 512. In yet other embodiments, the camera unit 550 is not attached to the sample pipetting module 512 while the light source 552 (or the screen 553) is attached to the sample pipetting module 512. In yet other embodiments, neither of the camera unit 550 and the light source 552 (or the screen 553) is attached to the sample pipetting module 512.

In addition, the dispense tip image capture unit 130 can include a second camera unit 2550 and its associated components, which are mounted to the sample precise pipetting unit 152B. The second camera unit 2550 and its associated components can be configured similar to the first camera unit 550 and its associated components.

In some embodiments, the second camera unit 2550 and such other components are configured to move together with the corresponding mandrel and dispense tip of the sample aliquot pipetting unit 152A.

The second camera unit 2550 can be configured to similar to the first camera unit 550. One example of the camera unit 2550 includes a model named ADVANTAGE 102, available from Cognex Corporation (Natick, MA), such as AE3-IS Machine Vision Camera+IO board, (e.g., part number AE3-IS-CQBCKFP2-B).

The dispense tip image capture unit 130 can further includes a light source 2552 for the camera 2550. The light source 2552 is used to illuminate the dispense tip 112 and its surroundings to be photographed as desired. The light source 2552 can be arranged in various locations. In the illustrated example, the light source 2552 is positioned at the back of the dispense tip 112 opposite to the camera unit 2550 and thus used as a backlight. Other locations of the light source 2552 are also possible. One example of the light source 2552 includes MDBL Series available from Moritex Corporation (Japan).

In other embodiments, the camera unit 550 includes a light source 2551, such as a LED light, which is operable to emit light toward the dispense tip 112. In this configuration, the light source 2552 can be replaced by a screen 2553 which is arranged to be opposite to the camera unit 550 so that the dispense tip 112 is positioned between the camera unit 2550 and the screen 2553. The screen 2553 is used to cast light back in the direction of the field of view (FOV) of the camera unit by reflecting light toward the camera's aperture. The screen 2553 is made of one or more various materials which can provide different reflection intensities. For example, the screen 2553 includes a retroreflective sheeting, one example of which includes 3M™ Scotchlite™ Sheeting 7610, available from 3M Company (Maplewood, MN). In other embodiment, the light source 2552 can be used together with the light source 2551 from the camera unit 2550 and the screen 2553.

In some embodiments, the camera unit 2550 and the light source 2552 (or the screen 2553) are configured to stationary and independent of the movement of the sample pipetting module 512. Other configurations are also possible in other embodiments.

As described herein, the camera unit 2550 and its associated components can be used for tip alignment detection, as further illustrated in FIG. 67.

Figure 13:
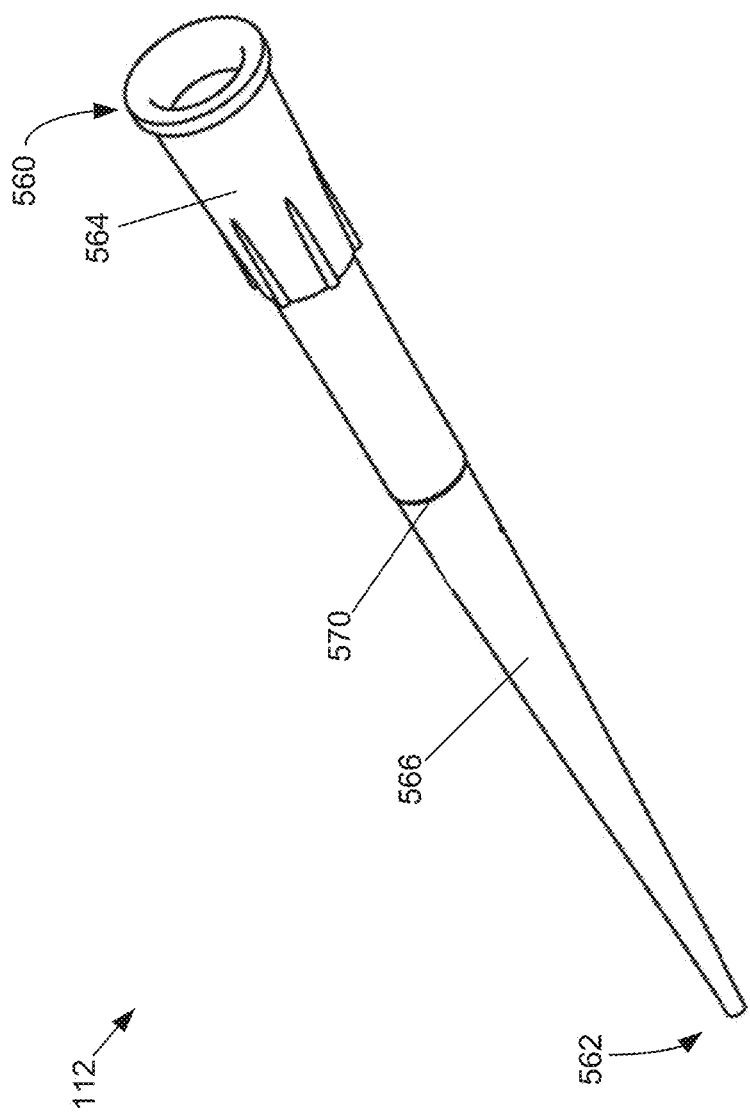
FIG. 13 is a schematic perspective view of an example dispense tip.
Figure 14:
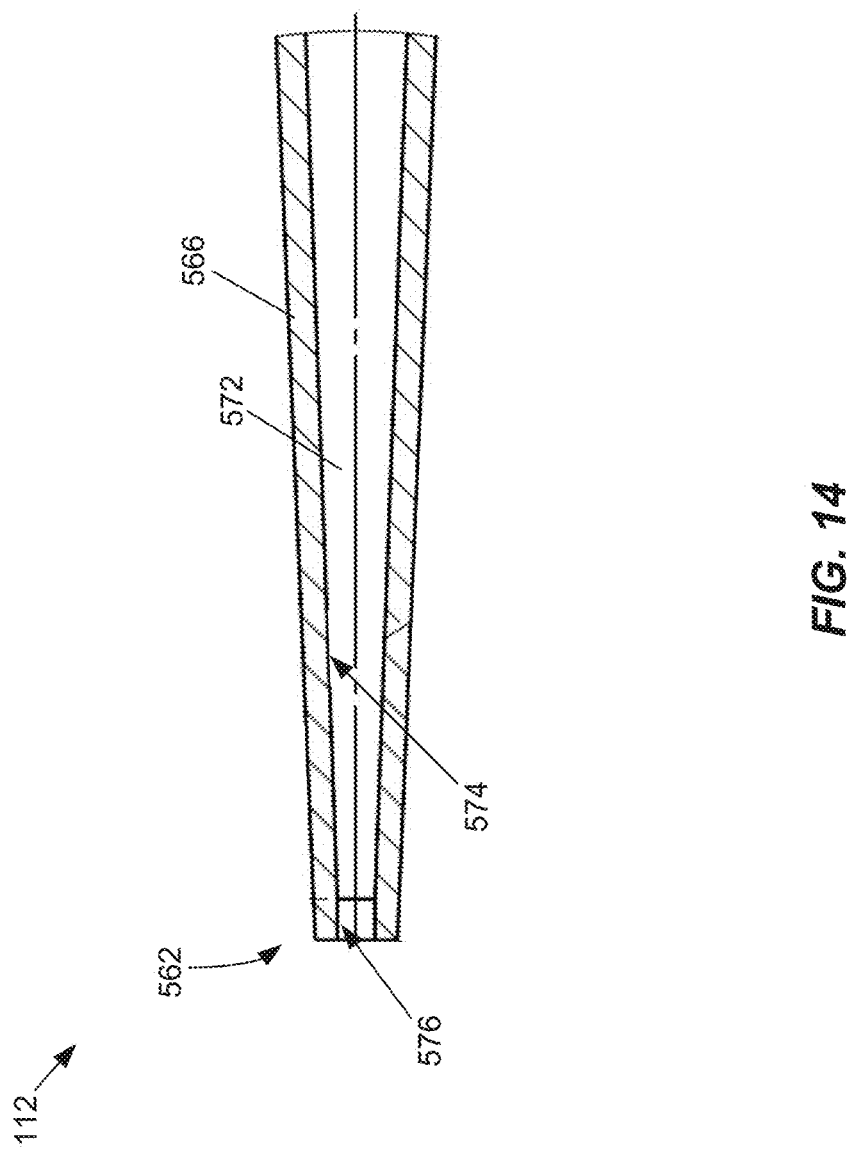
FIG. 14 is a cross sectional view of a distal end of the dispense tip of FIG. 13.

Referring to FIGS. 13 and 14, an example of the dispense tip 112 is described. In particular, FIG. 13 is a schematic perspective view of an example of the dispense tip 112, and FIG. 14 is a cross sectional view of a distal end of the dispense tip 112.

The dispense tip 112 extends from a proximal end 560 and a distal end 562. The dispense tip 112 includes a base portion 564 at the proximal end 560, which is configured to attach the dispense tip 112 to the mandrel 526 of the sample pipetting module 512. The dispense tip 112 further includes an elongated body portion 566 extending from the base portion 564. The dispense tip 112 including the base portion 564 and the body portion 566 defines a pipetting passage (or channel) 572 for aspirating, containing, and dispensing a fluidic substance. In some embodiments, the dispense tip 112 (including the dispense tip 112) is disposable. In other embodiments, the dispense tip 112 (including the dispense tip 112) is non-disposable or usable multiple tiles before being disposed.

In some embodiments, the dispense tip 112 includes a reference line 570 that is detectable by the dispense tip image capture unit 130. The reference line 570 can be formed in various locations of the dispense tip 112. In some embodiments, the reference line 570 is formed on the body portion 566 of the dispense tip 112. In other embodiments, the reference line 570 is formed on the base portion 564 of the dispense tip 112. Some examples of the reference line 570 are located such that a surface level or meniscus of the fluidic substance aspirated in the dispense tip 112 is arranged between the reference line 570 and the distal end 562 of the dispense tip 112. In other embodiments, the reference line 570 is located such that the meniscus of the aspirated fluidic substance is arranged above the reference line 570 relative to the distal end 562 (i.e., between the reference line 570 and the proximal end 560).

The reference line 570 is provided to the dispense tip 112 in various manners. In some embodiments, the reference line 570 is a detectable structure, such as a projection, ridge, indentation, notch, or any other visible element formed on the dispense tip 112. In other embodiments, the reference line 570 is a marker or indicator that is painted or attached on the dispense tip 112. The reference line 570 can be integrally formed or molded to the dispense tip 112. Alternatively, the reference line 570 is separately made and attached to the dispense tip 112.

The reference line 570 is used as a reference point when an image of the dispense tip 112 is analyzed to determine if the sample has been properly aspirated for analytic test. As described herein, the sample aspiration volume detection device 500 measures the aspirated sample volume in the dispense tip 112 by measuring a distance between the reference line 570 and the sample meniscus. Since the reference line 570 is formed on the dispense tip 112, the reference line 570 provides a consistent reference point for volume measurement, compared to any reference points provided by other structures than the dispense tip 112. For example, where a portion or point in the mandrel 526 is used as a reference point, the position of the mandrel 526 relative to the dispense tip 112 can vary depending on the insertion depth of the dispense tip 112 to the mandrel 526, thereby causing inaccurate volume measurement. In contrast, the reference line 570 is stationary relative to the dispense tip 112 and thus can provide accurate measurement.

As illustrated in FIG. 14, the pipetting passage 572 includes a tapered section 574 in which an inner diameter becomes smaller from the proximal end 560 to the distal end 562. The pipetting passage 572 further includes a straight section 576 that has a constant inner diameter at or adjacent to the distal end 562. The straight section 576 can improve accuracy and precision in aspirating a small volume, such as about 2-5 µL, while still providing the dispense tip 112 capable of aspirating a large volume, such as 250 µL, for aliquotting.

Figure 15:
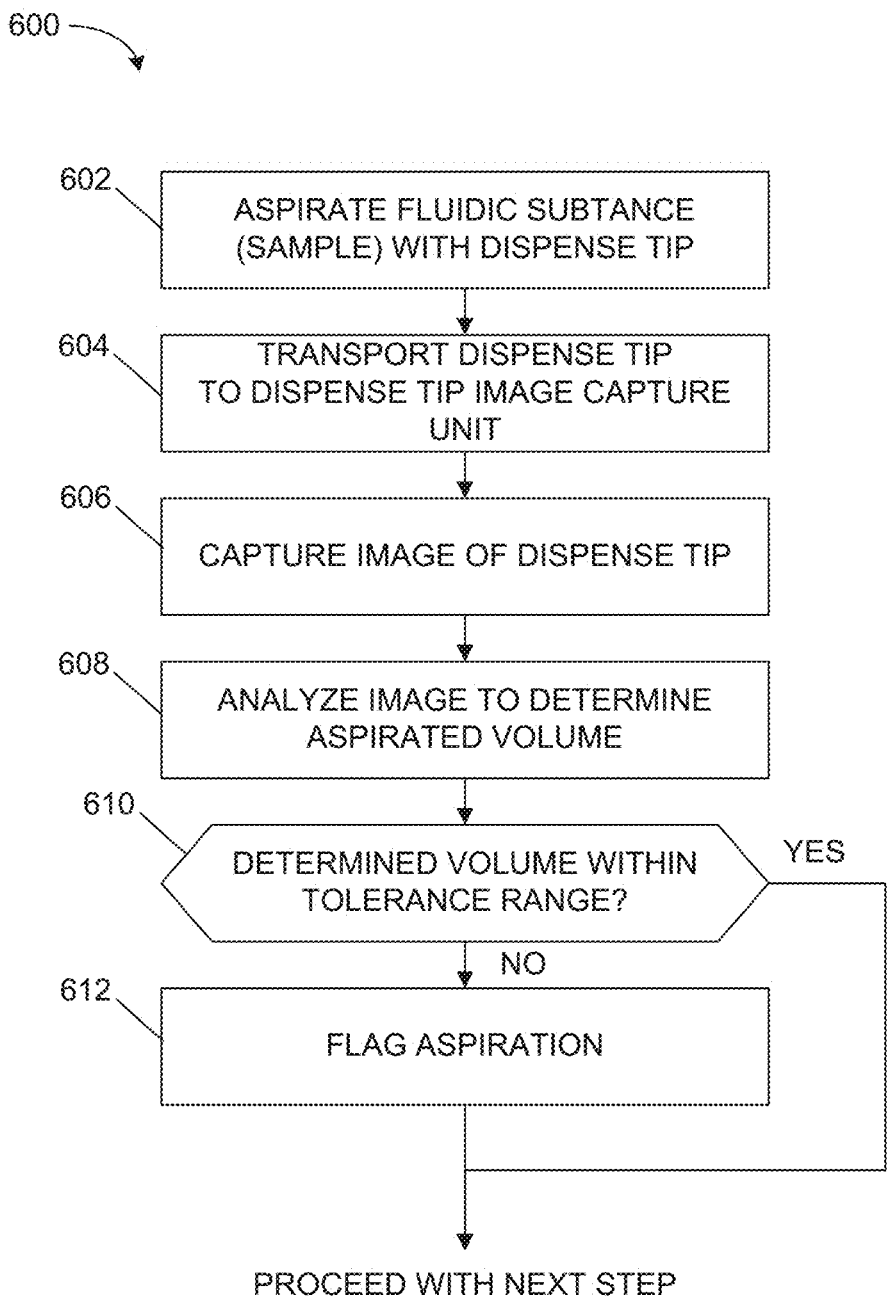
FIG. 15 is a flowchart illustrating an example method of operating the dispense tip volume detection device.

FIG. 15 is a flowchart illustrating an example method 600 of operating the dispense tip volume detection device 400. In the illustrated example, the method 600 is primarily described with respect to the sample aspiration volume detection device 500. However, the method 600 is also similarly applicable to other types of the dispense tip volume detection device 400. In some embodiments, the method 600 is performed by the sample aspiration system 510 and the sample aspiration volume detection device 500.

In general, the method 600 performs analysis of an aspirated volume in a dispense tip using a metering algorithm and flags aspiration results or test results if the calculated aspiration volume is outside a tolerance range.

At operation 602, the sample aspiration system 510 operates to aspirate a fluidic substance, such as a sample 540 (FIG. 10), into a dispense tip 112 as programmed At operation 604, the sample aspiration system 510 transports the dispense tip 112 containing the aspirated sample 540 to the dispense tip image capture unit 130. In some embodiments, the dispense tip image capture unit 130 is arranged to capture an image of the dispense tip 112 after aspiration without transportation.

At operation 606, the dispense tip image capture unit 130 of the sample aspiration volume detection device 500 captures an image of the dispense tip 112. In some embodiments, the image of the dispense tip 112 is a digital image of a predetermined resolution.

At operation 608, the sample aspiration volume detection device 500 analyzes the image to determine a volume of the sample 540 within the dispense tip 112. An example of the operation 608 is described in more detail with respect to FIGS. 16-19.

At operation 610, the sample aspiration volume detection device 500 determines whether the determined volume falls within a tolerance range. When the determined volume is outside a tolerance range, the aspiration of the sample 540 in the dispense tip 112 is considered to be inappropriate. In some embodiments, such a tolerance range is determined based on an allowable deviation from a target aspiration volume of the sample 540 that is intended to be aspirated into the dispense tip 112. The tolerance range can vary depending on the target aspiration volume. An example of the tolerance range is as follows:

TABLE 1

| Target Aspiration Volume (V) | Tolerance Range |
|---|---|
| 2 µL ≤ V < 10 µL | 100 ± 30% |
| 10 µL ≤ V < 50 µL | 100 ± 15% |
| 50 µL ≤ V < 110 µL | 100 ± 10% |

When the detected volume is determined to fall within the tolerance range ("YES" at the operation 610), the method 600 proceeds to perform a predetermined next step. Otherwise ("NO" at the operation 610), the method 600 moves on to operation 612.

At operation 612, the sample aspiration volume detection device 500 flags the aspiration to indicate that the aspirated sample volume in the dispense tip 112 is not appropriate for subsequent processes. In other embodiments, the entire test result that has used the aspirated sample can be flagged to indicate or suggest that the test result can be improper. Alternatively, the sample aspiration volume detection device 500 operates to stop an associated test or analytic process in the instrument 100. In other embodiments, the evaluation result can be used to automatically adjust a test result that may be erroneous due to the inappropriate volume of the fluidic substance. In yet other embodiments, as described herein, the evaluation result can be used to automatically adjust the volume of the fluidic substance in response to the volume determination.

Figure 16:
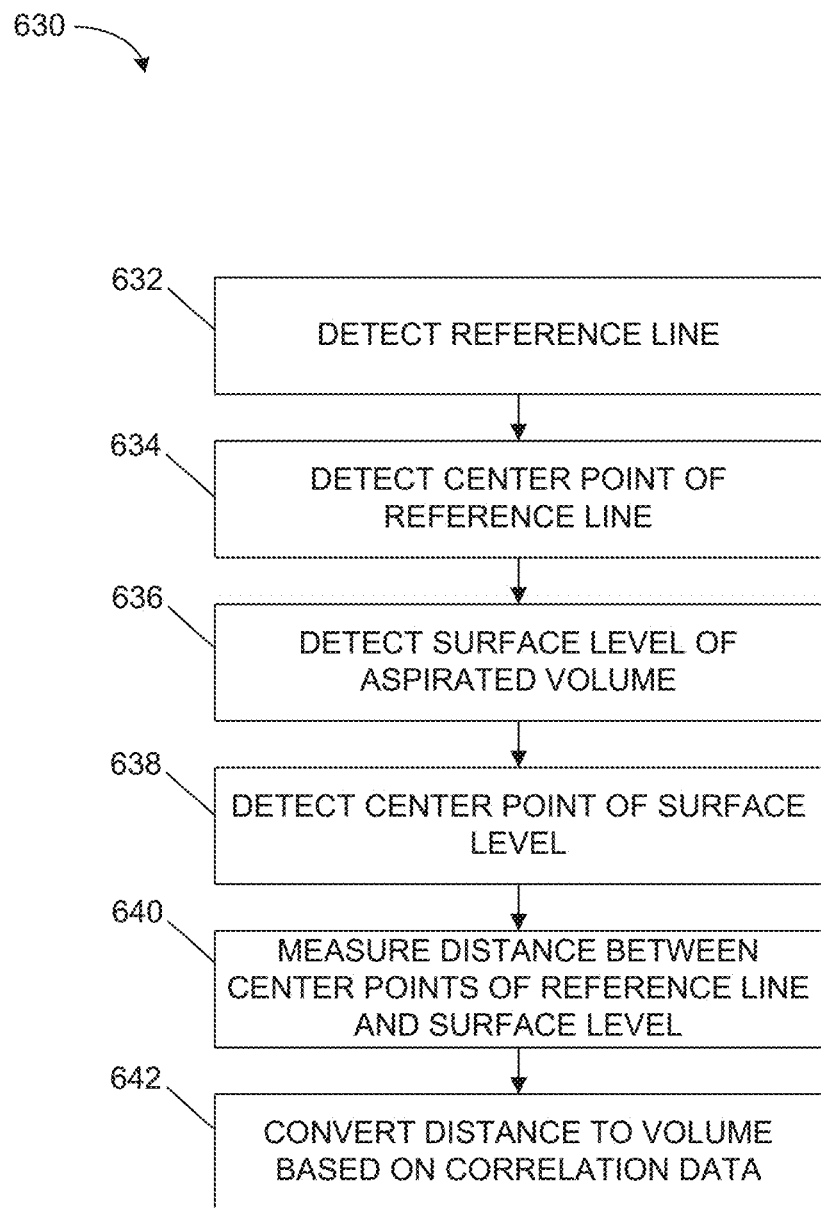
FIG. 16 is a flowchart illustrating an example method for performing an operation of the dispense tip volume detection device of FIG. 15.

Referring to FIGS. 16-19, an example of the operation 608 of FIG. 15, in which a captured image is analyzed to determine a sample volume in the dispense tip, is described. In particular, FIG. 16 is a flowchart illustrating an example method 630 for performing the operation 608 of FIG. 15. The method 630 is described with also reference to FIGS. 17-19, which illustrate an example analysis of a captured image 620 of the dispense tip.

At operation 632, the sample aspiration volume detection device 500 detects the reference line 570 of the dispense tip 112 in the captured image 620. Various image processing methods can be used to detect the reference line 570 in the image 620. In some embodiments, the reference line 570 is detected by pattern matching function, which searches a pattern representative of the reference line based on a pre-trained reference image. For example, such pattern matching function executes a pattern search that scans the captured image for a pattern that has been stored in the system and recognized as the reference line. A correlation value, or matching rate (e.g., % matching), is adjustable. Other methods are also possible in other embodiments. One example of such image processing methods can be implemented by Cognex In-Sight Vision Software, available from Cognex Corporation (Natick, MA), which provides various tools, such as edge detection ("Edge"), pattern matching ("Pattern Match"), and histogram analysis ("Histogram").

Figure 17:
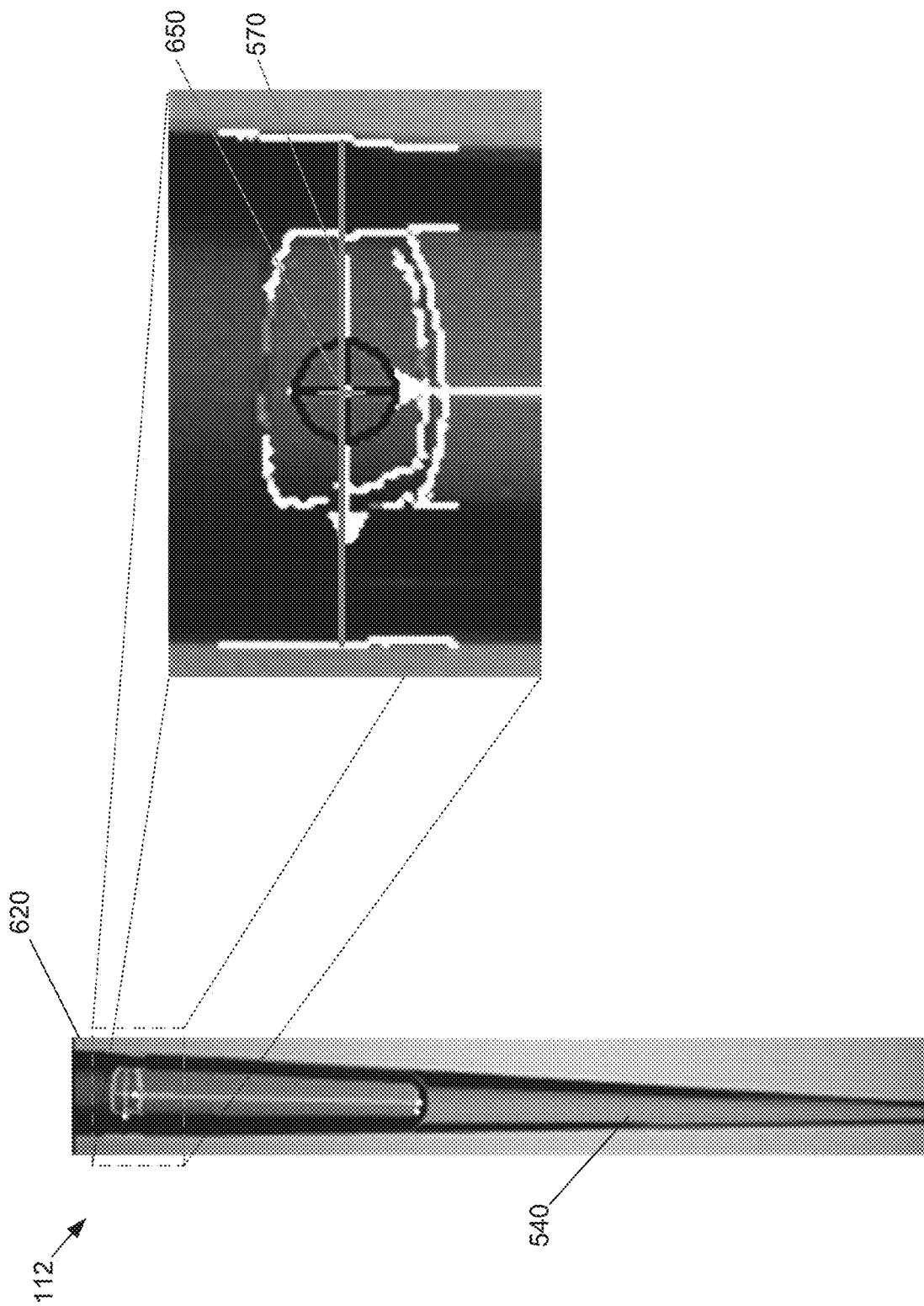
FIG. 17 illustrates an example analysis of a captured image of the dispense tip.

At operation 634, the sample aspiration volume detection device 500 detects a center point 650 of the reference line 570. As illustrated in FIG. 17, once the reference line 570 is detected, the center point 650 can be calculated as the middle point of the reference line 570.

At operation 636, the sample aspiration volume detection device 500 detects a surface level 652 (FIG. 18) of the aspirated sample volume in the dispense tip 112. Various image processing methods can be used to detect the surface level 652 in the image. In some embodiments, similarly to the operation 632, the surface level 652 is detected by pattern matching function based on a pre-trained reference image. Other methods are also possible in other embodiments.

Figure 18:
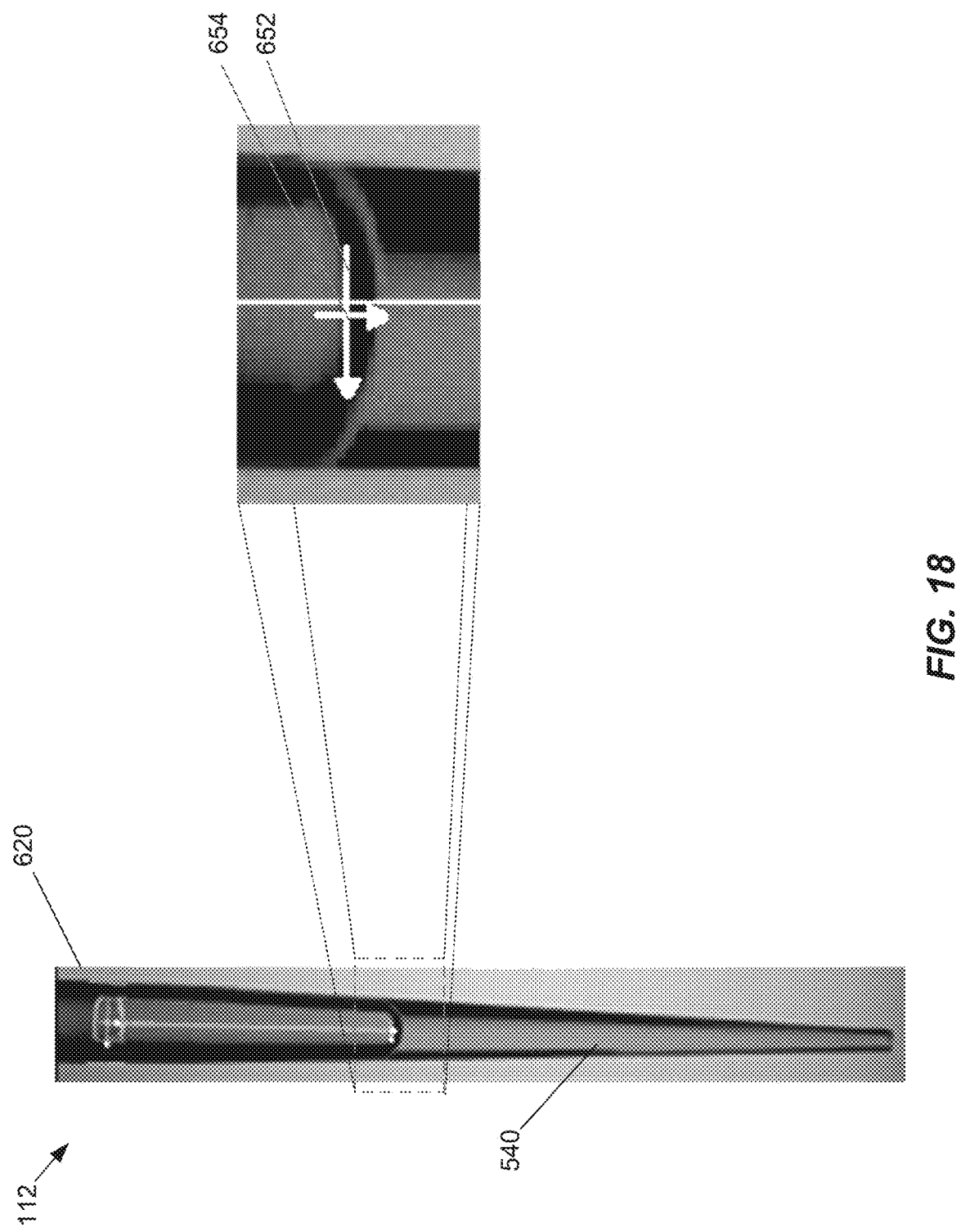
FIG. 18 illustrates the analysis of the captured image of FIG. 17.
Figure 19:
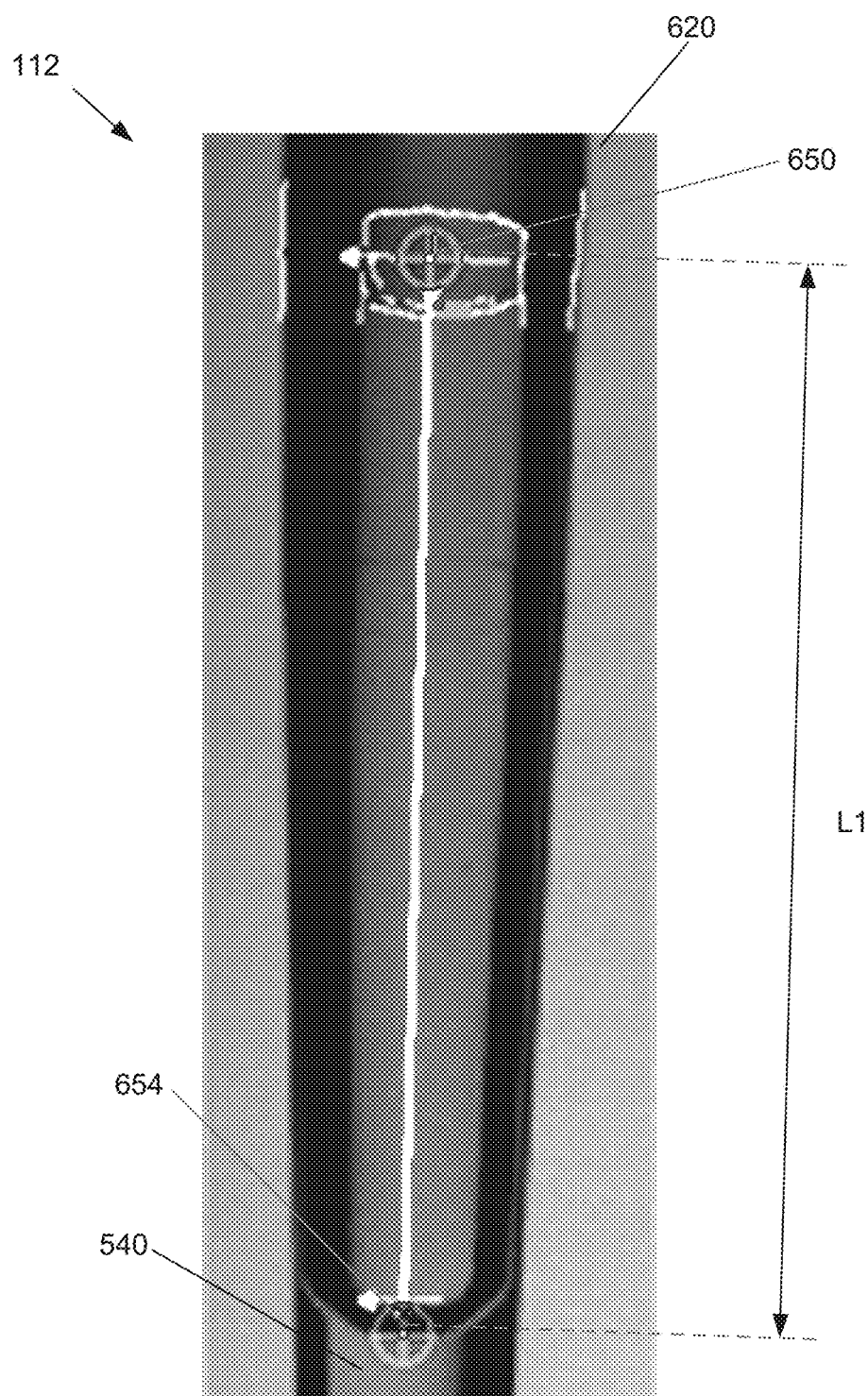
FIG. 19 illustrates the analysis of the captured image of FIG. 17.

At operation 638, the sample aspiration volume detection device 500 detects a center point 654 of the surface level 652. As illustrated in FIG. 18, once the surface level 652 is detected, the center point 654 can be calculated as the middle point of the line of the surface level 652.

At operation 640, the sample aspiration volume detection device 500 measures a distance L1 (FIG. 19) between the center point 650 of the reference line 570 and the center point 654 of the surface level 652. In some embodiments, the distance L1 is measured by a pixel distance between the center points 650 and 654 in the image 620. In some embodiments, the pixel distance is calculated based on a Euclidean distance between two pixel points.

Figure 20:
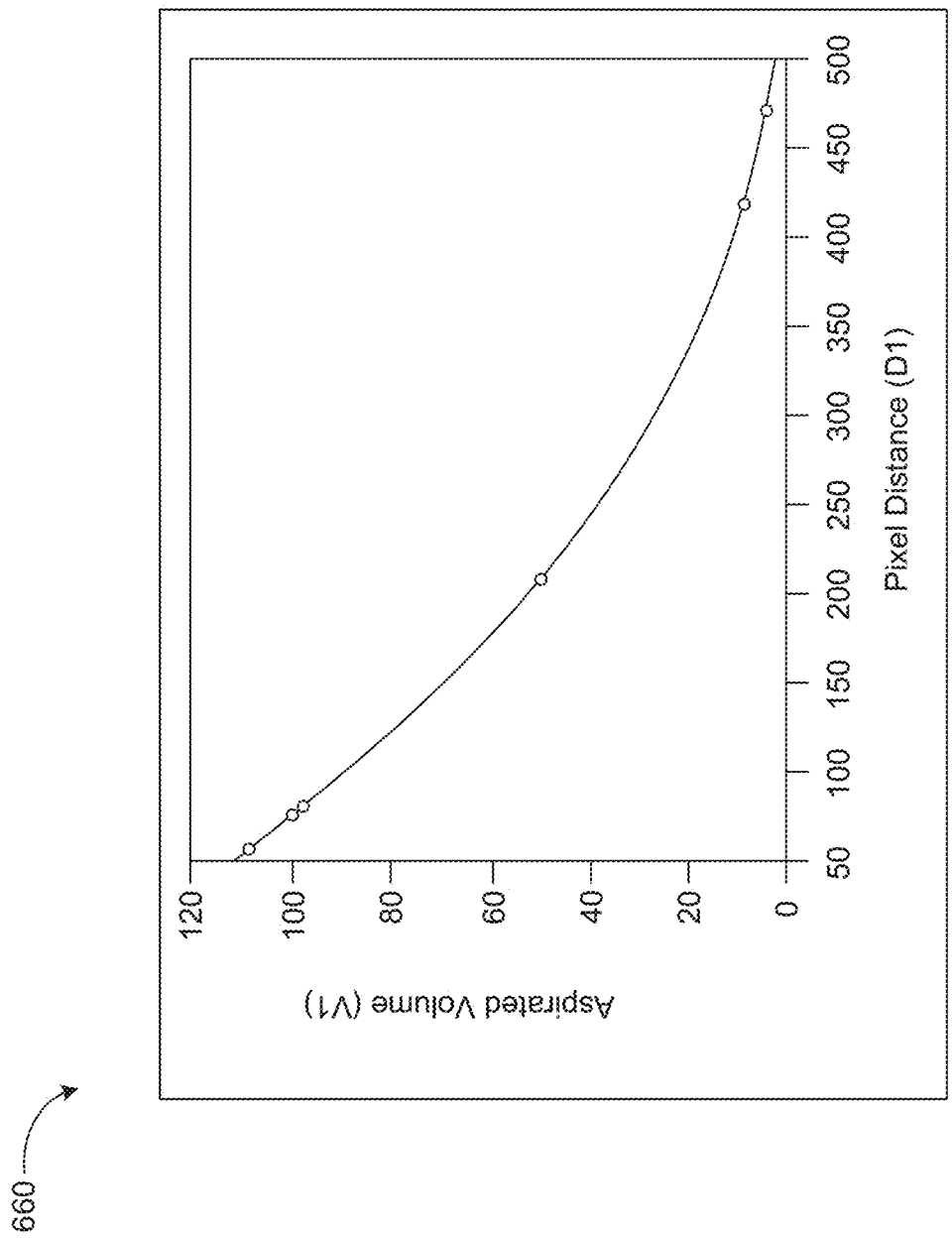
FIG. 20 is an example correlation curve corresponding to tip volume correlation data.

At operation 642, the sample aspiration volume detection device 500 converts the distance L1 to a volume based on the tip volume correlation data 506. The correlation data 506 include information about a correlation between volumes within the dispense tip 112 and distances L1 between the center point 650 of the reference line 570 and the center points 654 of a plurality of different surface levels 652 in the dispense tip 112. In some embodiments, the correlation data 506 can be plotted to a correlation curve 660 as illustrated in FIG. 20. An example method of generating the correlation data 506 is described with reference to FIG. 21.

FIG. 20 is an example correlation curve 660 corresponding to the correlation data 506. In some embodiments, the correlation curve 660 shows a relationship between the distance L1 (e.g., pixel distance) between the center points 650 and 654 and the volume V1 of aspirated sample in the dispense tip 112. The correlation curve 660 can be obtained by plotting a plurality of discrete data points include in the correlation data 506, which is described with reference to FIG. 21. As illustrated in FIG. 20, the correlation curve indicates that the aspirated volume V1 generally decreases as the distance L1 increases. Since the reference line 570 is formed on the dispense tip 112 to be arranged above the surface level 652, the distance L1 is generally inversely correlated with the volume V1.

Figure 21:
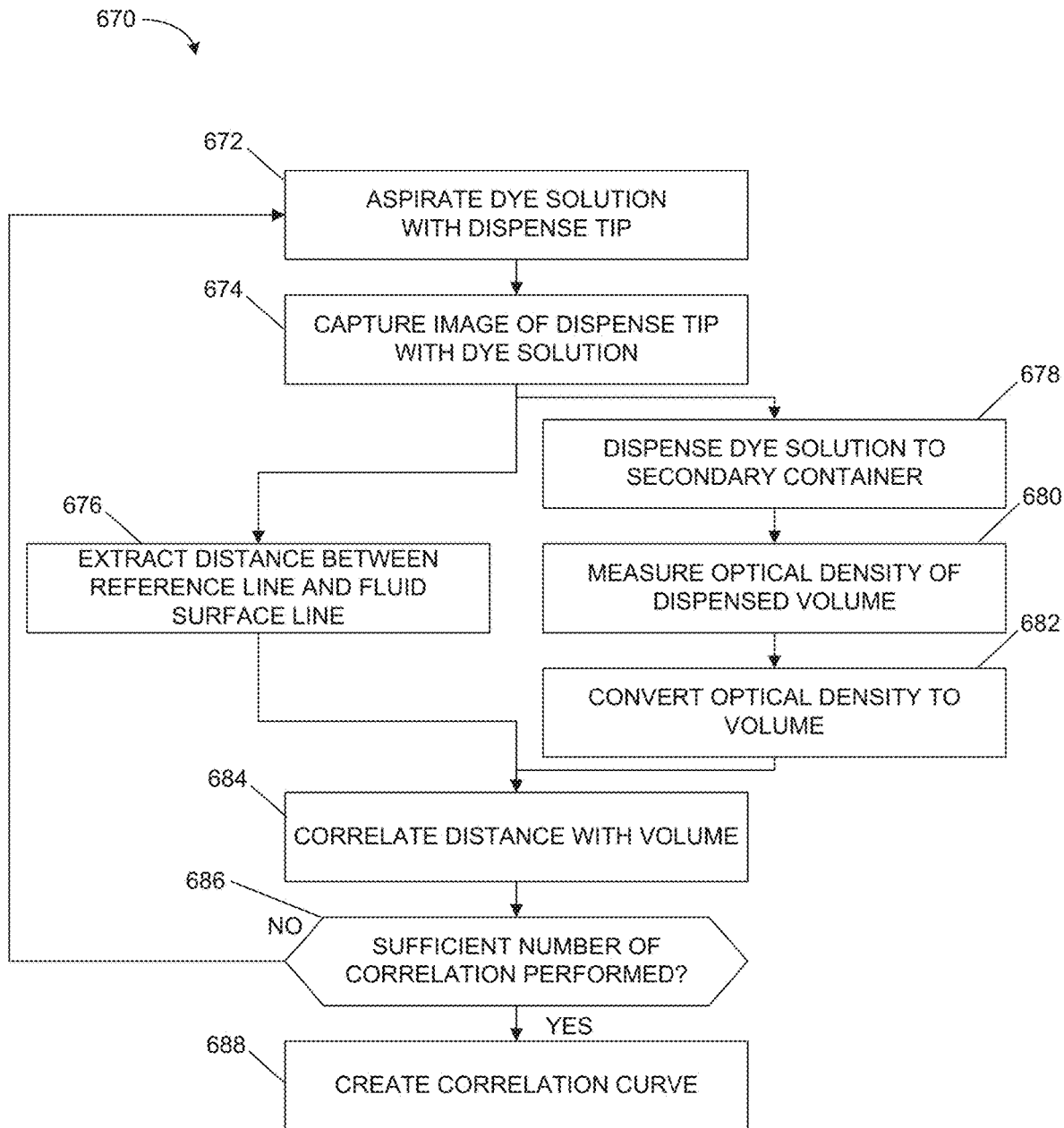
FIG. 21 is a flowchart illustrating an example method for operating a tip volume correlation data generation system to generate the tip volume correlation data.

FIG. 21 is a flowchart illustrating an example method 670 for operating the tip volume correlation data generation system 504 to generate the tip volume correlation data 506.

In some embodiments, the correlation data 506 is created using spectroscopic techniques. For example, the tip volume correlation data generation system 504 uses a dye solution to show a correlation between extracted pixel distance information and fluidic volume information in a dispense tip. The spectrophotometer can be used to measure the absorbance of the dye at a specific wavelength. In some embodiments, the tip volume correlation data generation system 504 selects a plurality of points within a target volume range (e.g., 5, 10, 50, 100, and 110 µL), aspirate these volume setting by dispense tips, and take images of the dispense tips for pixel distance calculation. Then, the tip volume correlation data generation system 504 draws a calibration curve between pixel distances calculated from the images and volumes calculated by a spectrophotometer.

At operation 672, the tip volume correlation data generation system 504 aspirates a dye solution to a dispense tip 112.

At operation 674, the tip volume correlation data generation system 504 captures an image of the dispense tip 112 containing the dye solution.

At operation 676, the tip volume correlation data generation system 504 extracts a distance between the reference line 570 and a surface line of the dye solution in the image captured in the operation 674. In some embodiments, the distance is measured by a pixel distance. In some embodiments, the distance is determined similarly to at least some of the operations of the method 630, such as the operations 632, 634, 636, 638, and 640. Other methods are also possible in other embodiments.

During operations 678, 680, and 682, the tip volume correlation data generation system 504 measures a volume of the dye solution aspirated in the dispense tip 112. Various methods can be used to determine the dye solution volume. In the illustrated example, spectroscopic approaches are used as described below.

At operation 678, the tip volume correlation data generation system 504 dispenses the dye solution to a secondary container having a known volume of diluent.

At operation 680, the tip volume correlation data generation system 504 measures an optical density of the diluted dye solution dispensed in the secondary container. In some embodiments, a spectrophotometer is used to measure the optical density of the dye solution. A spectrophotometer measures the amount of light of a specified wavelength which passes through the diluted dye solution in the secondary container.

At operation 682, the tip volume correlation data generation system 504 converts the optical density to a volume of the dye solution in the dispense tip.

At operation 684, the tip volume correlation data generation system 504 correlates the distance calculated at the operation 676 and the volume obtained at the operation 682.

At operation 686, the tip volume correlation data generation system 504 determines whether a sufficient number of correlations have been performed to generate the tip volume correlation data 506. If so ("YES" at the operation 686), the method 670 moves on to operation 688. Otherwise ("NO" at the operation 686), the method 670 returns to operation 672, in which the dye solution is aspirated to the dispense tip 112, and the subsequent operations are performed to determine additional correlations between the distance and the volume of the dye solution within the dispense tip. To obtain a sufficient range of correlation data, different quantities of dye solution are aspirated in the dispense tip 112 in different correlation cycles. In addition, the quantity of dye solution aspirated in the dispense tip can remain generally the same for some of the correlation cycles so as to obtain reliable results for particular volumes or volume ranges.

At operation 688, the tip volume correlation data generation system 504 creates the tip volume correlation data 506 based on a plurality of correlations made at the operation 684. In some embodiments, the correlation data is illustrated as a correlation curve (e.g., the correlation curve 660 in FIG. 20) by plotting each image's pixel distance with the corresponding aspirated volume measured by the spectrophotometer. The correlation curve is used to estimate the relationship between the distance and the volume in the dispense tip 112.

The dispense tip volume detection device 400, as described with reference to FIGS. 9-21, can be modified to be suitable for various applications. In some embodiments, the dispense tip volume detection device 400 is used for any fluidic substance other than a patient sample. In some embodiments, the dispense tip image capture unit of the dispense tip volume detection device 400 does not use a backlight setting. Further, the dispense tip image capture unit can be executed with a fixed camera and backlight setting, as opposed to the set of camera and backlight moving together with the sample pipetting module and other associated devices. The reference line of a dispense tip can be anything other than a line formed on the dispense tip. In some embodiments, the mandrel for a dispense tip is used as a reference point. In some embodiments, the pattern matching function in connection with the dispense tip volume detection device 400 employs various algorithms, such as finding lines or segments. In some embodiments, the measurement volume range can be greater than 110 µL. In some embodiments, the dispense tip volume detection device 400 is used for any container in various shapes (e.g., cylindrical, conical, rectangular, and square) other than the sample pipetting tip as illustrated herein. In other embodiments, the tip volume correlation data generation system 504 employs any liquid other than a dye solution and uses techniques other than spectroscopy. For example, a JIG tip with multiple reference lines corresponding to known volumes can be used.

One example of image processing methods used above can be implemented by Cognex In-Sight Vision Software, available from Cognex Corporation (Natick, MA), which provides various tools, such as edge detection ("Edge"), pattern matching ("Pattern Match"), and histogram analysis ("Histogram").

In some embodiments, the measured volumes of aspirated sample can be used to adjust the relative light units (RLUs) of test results. Since sample volumes (as well as substrate/reagent volumes, etc.) correlate with RLUs for immunoassay, this correlation can be measured and used as the basis for adjustment. Further, the measured volumes can be used as a feedback to adjust reagent volumes for improved ratio matching and assay performance Referring now to FIGS. 22-39, an example of the vessel volume detection device 402 of FIG. 5 is described.

Figure 22:
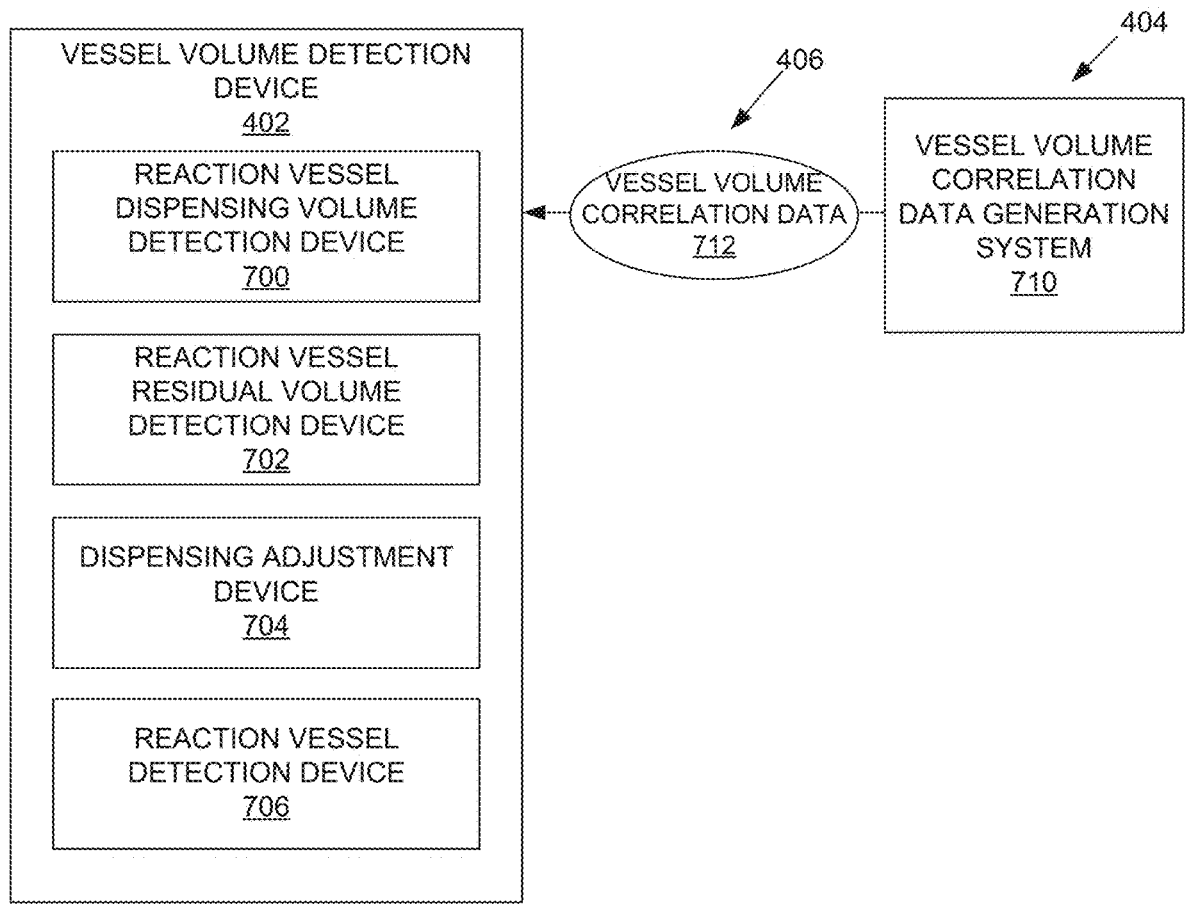
FIG. 22 illustrates an example of a vessel volume detection device of FIG. 5.

FIG. 22 illustrates an example of the vessel volume detection device 402 of FIG. 5. In some embodiments, the vessel volume detection device 402 includes a reaction vessel dispensing volume detection device 700, a reaction vessel residual volume detection device 702, a dispensing adjustment device 704, and a reaction vessel detection device 706. The reaction vessel dispensing volume detection device 700 uses vessel volume correlation data 712 generated by a vessel volume correlation data generation system 710.

The reaction vessel dispensing volume detection device 700 operates to determine a volume of a fluidic substance 118 dispensed into a vessel 114, such as a reaction vessel. An example of the structure and operation of the reaction vessel dispensing volume detection device 700 is described and illustrated with reference to FIG. 27-31.

The reaction vessel residual volume detection device 702 operates to determine a volume of a fluidic substance 118 that remains in a vessel 114, such as a reaction vessel. An example of the reaction vessel residual volume detection device 702 is described and illustrated with reference to FIGS. 32-34.

The dispensing adjustment device 704 operates to adjust operations of substance dispense devices, such as pipettors and pump devices, based on measurements of fluidic substance volumes dispensed to vessels 114, such as reaction vessels. An example of the dispensing adjustment device 704 is described and illustrated with reference to FIGS. 35 and 36.

The reaction vessel detection device 706 operates to detect presence or absence of vessels 114, such as reaction vessels. An example of the reaction vessel detection device 706 is described and illustrated with reference to FIGS. 37-39.

The vessel volume correlation data generation system 710 generates the vessel volume correlation data 712. The vessel volume correlation data 712 provide information used by the vessel volume detection device 402 to determine a volume of fluidic substance dispensed into a vessel (e.g., a reaction vessel). In some embodiments, the vessel volume correlation data generation system 710 is an independent apparatus from the vessel volume detection device 402. In other embodiments, the vessel volume correlation data generation system 710 is configured to use at least some resources of the vessel volume detection device 402. The vessel volume correlation data generation system 710 and the vessel volume correlation data 712 are included in, or examples of, the correlation data generation system 404 and the correlation data 406 as illustrated in FIG. 5.

Prior to turning to FIGS. 23-26, it is noted that reliable clinical diagnosis requires accurate and precise aspiration and dispensing of a substance to be analyzed. For example, in an automatic analyzer which analyzes a specimen such as blood or any other type of bodily fluid, fluctuation in the amount of dispensed or aspirated specimen and other substances, such as a reagent, in a container (e.g., pipetting tips or reaction vessels) relative to a specified amount can affect an analysis result and degrades reliability of inspection and analysis. Further, it is difficult in clinical diagnostic industry to accurately and precisely control and match the volumes of fluid dispensed from different pump units. Therefore, it is beneficial to establish a technology for measuring an aspirated or dispensed amount with high accuracy and selecting only the aspirated or dispensed specimens whose amount is within a suitable range. One way to measure a liquid volume is to monitor fluid pressure in fluidic lines and correlate the fluid pressure to the dispensed volume. In other cases, a flow sensor is used to determine a flow rate of a liquid aspirated or dispensed. In yet other cases, chemiluminescent signals from a controlled dispense of IA reagents are used to the presence of excessive residual volume in a vessel after aspiration from the vessel. In yet other cases, chemiluminescent signals from a controlled dispense of IA reagents are used to determine the volume-dispensing characteristics of multiple pump devices.

However, these approaches have several disadvantages. For example, pressure sensors can determine fluid viscosity, but cannot quantify dispensed volumes. Flow sensors can quantify a volume of liquid passing the tubing to which the flow sensors are arranged, but cannot reliably measure a liquid volume that is aspirated or dispensed. Further, it is difficult to correlate a low volume measurement in-line to an exact reaction vessel due to the offset in location. Moreover, chemiluminescent signals cannot detect small amounts of residual fluid volume following an aspiration. Chemiluminescent signals do not provide precise, direct estimates of volume-matching characteristics among different pump devices. Chemiluminescent signals confuse reagent characteristics and lot variations with system variables of interest, such as dispensed volume or residual volume.

As described herein in more detail, the vessel volume detection device 402 employs an image processing method for quantifying a volume of a fluidic substance dispensed and aspirated in a vessel (e.g., reaction vessel). The volume of a fluidic substance is dispensed or aspirated in a transparent or translucent container, such as a clear cylindrical vessel. The vessel is imaged and a reference point is detected in the image. In some embodiments, the bottom feature of the vessel is used as the reference point within the image. The vessel volume detection device measures a distance from the meniscus of the fluidic substance to the reference point, and correlates the distance to a volume using a volume calibration curve. If the volume dispensed within the container is not within specifications for accuracy of dispensing, the dispensing or the entire test is flagged. A user or operator can receive information about the result of dispensing.

In addition, the measured volumes of fluidic substance dispensed in the vessels are recorded with respect to different combinations of pumps and pipettors in the system, and used to calibrate the combinations of pumps and pipettors to improve accuracy in controlling different pumps and pipettors in the system.

Further, the vessel volume detection device 402 can detect the presence of very small amounts of residual fluidic substance remaining in a vessel following aspiration. In some embodiments, pattern-recognition algorithms are used for such residual volume detection.

Referring to FIGS. 23-26, example structure and operation of a container carriage device 720 in which the vessel volume detection device 402 is included are described.

Figure 23:
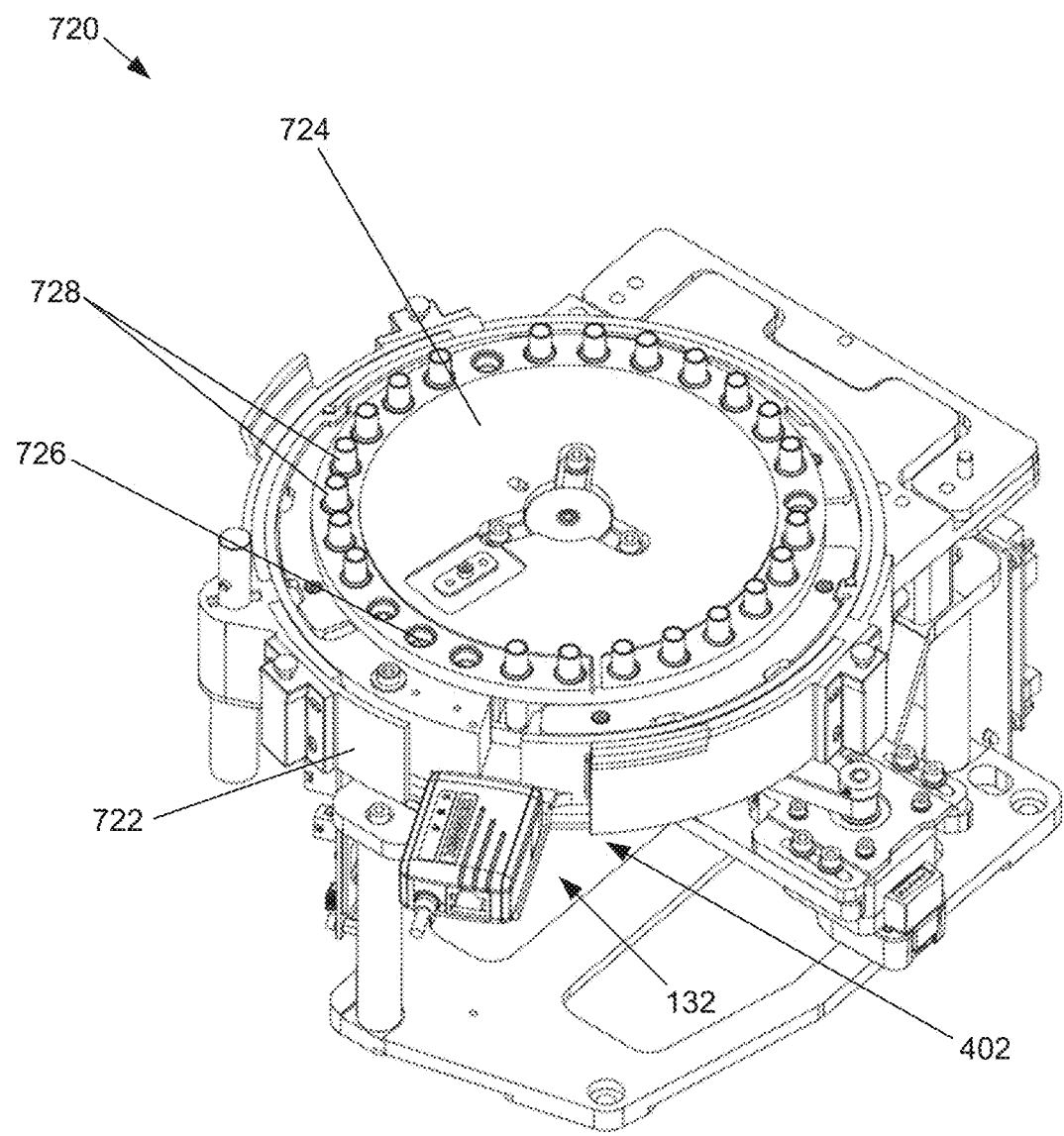
FIG. 23 illustrates an example container carriage device in which the vessel volume detection device is included.

FIG. 23 illustrates an example container carriage device 720 in which the vessel volume detection device 402 is included. In the illustrated example, the container carriage device 720 is implemented as a wash wheel, such as the wash wheel 176 (FIG. 2), in the instrument 100. Therefore, the container carriage device 720 is also referred to herein as the wash wheel 720. In the embodiments, other types of container carriage device 720 are used with the vessel volume detection device 402.

As illustrated, the container carriage device or wash wheel 720 is configured to perform various aspects of a diagnostic process. In some embodiments, the wash wheel 720 includes a housing unit 722 and a rotatable plate 724 relative to the housing unit 722. The wash wheel 720 includes a plurality of container seats 726 formed in the rotatable plate 724 and configured to receive and support containers 728. Where the container carriage device 720 is configured as a wash wheel, such containers 728 include reaction vessels. Thus, the containers 728 are also referred to herein as reaction vessels 728.

In some embodiments, the vessel volume detection device 402 is mounted to the wash wheel 720. As described above, the vessel volume detection device 402 includes the vessel image capture unit 132. An example structure of the vessel image capture unit 132 is described in more detail with reference to FIGS. 24 and 25.

Figure 24:
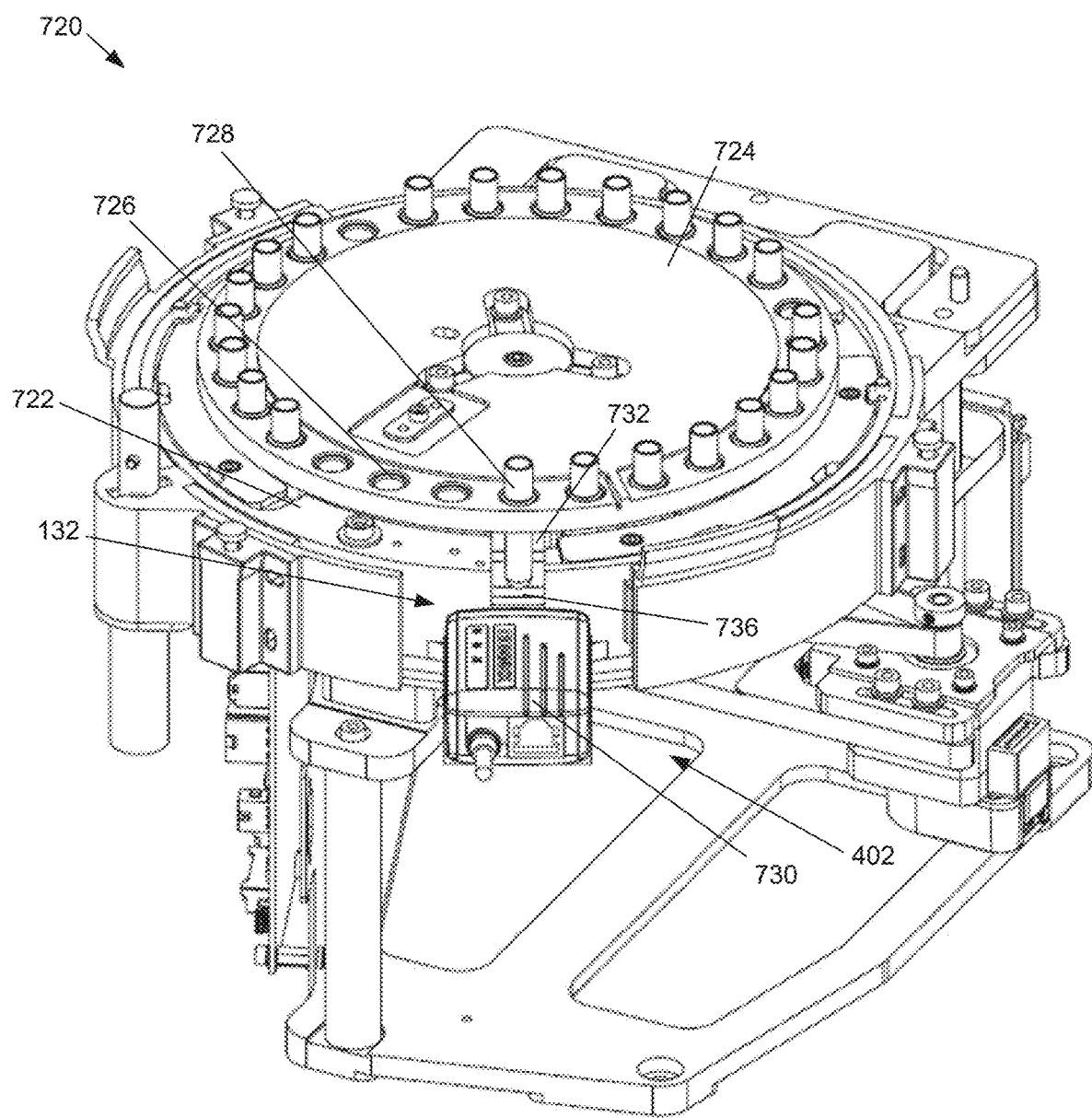
FIG. 24 is another perspective view of the container carriage device of FIG. 23, illustrating a vessel image capture unit of FIG. 23.
Figure 25:
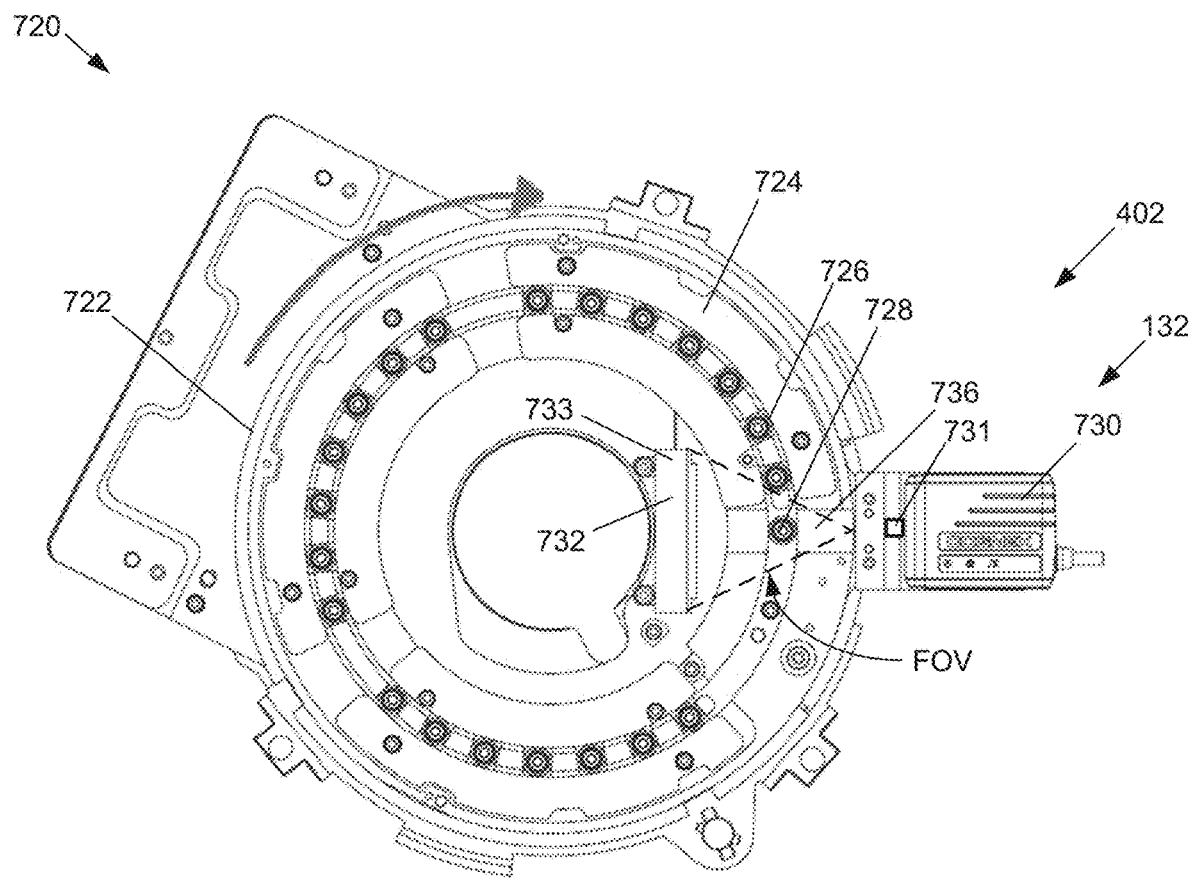
FIG. 25 is a top view of a wash wheel with the vessel volume detection device including the vessel image capture unit.

Referring to FIGS. 24 and 25, an example structure of the vessel volume detection device 402 is described including the vessel image capture unit 132. In particular, FIG. 24 is another perspective view of the container carriage device 720 of FIG. 23, illustrating the vessel image capture unit 132, and FIG. 25 is a top view of the wash wheel 720 with the vessel volume detection device 402 including the vessel image capture unit 132.

The vessel image capture unit 132 includes a camera unit 730 and a light source 732. In some embodiments, the camera unit 730 includes a complementary metal-oxide-semiconductor (CMOS) image sensor for obtaining a color digital image. In other embodiments, the camera unit 730 includes a charge-coupled device (CCD) image sensor for obtaining a color digital image. Other embodiments of the camera unit 730 are configured to obtain black-and-white or grayscale pictures. The light source 732 is used to illuminate a vessel 728, a slot 736, and/or the surroundings of the vessel 728 and/or the slot 736, which are to be photographed as desired. The light source 732 can be fixed in various locations. In the illustrated example, the light source 732 is positioned at the back of the vessel 728 facing the camera unit 730 and thus used as a backlight. Other locations of the light source 732 are also possible. One example of the light source 732 includes MDBL Series available from Moritex Corporation (Japan).

In other embodiments, the camera unit 730 includes a light source 731, such as a LED light, which is operable to emit light toward the vessel 728. In this configuration, the light source 732 can be replaced by a screen 733 which is arranged to be opposite to the camera unit 730 so that the vessel 728 is positioned between the camera unit 730 and the screen 733. The screen 733 is used to cast light back in the direction of the field of view (FOV) of the camera unit by reflecting light toward the camera's aperture. The screen 733 is made of one or more various materials which can provide different reflection intensities. For example, the screen 733 includes a retroreflective sheeting, one example of which includes 3M™ Scotchlite™ Sheeting 7610, available from 3M Company (Maplewood, MN). In other embodiment, the light source 732 can be used together with the light source 731 from the camera unit 730 and the screen 733. One example of the camera unit 730 includes a model named ADVANTAGE 102, which is available from Cognex Corporation (Natick, MA).

In some embodiments, the camera unit 730 and the light source 732 (or the screen 733) are attached to the housing unit 722 of the wash wheel 720. The camera unit 730 and the light source 732 (or the screen 733) are arranged such that the reaction vessels 728 supported by the rotatable plate 724 are positioned between the camera unit 730 and the light source 732 (or the screen 733) as the rotatable plate 724 rotates relative to the housing unit 722.

In some embodiments, the housing unit 722 defines a slot 736 that exposes one of the reaction vessels 728 between the camera unit 730 and the light source 732 (or the screen 733). When a reaction vessel 728 is aligned with the camera unit 730 and the light source 732 (or the screen 733) through the slot 736 of the housing unit 722, an image of the reaction vessel 728 can be captured by the camera unit 730. In other embodiments, where the housing unit 722 is made of an opaque material, the housing unit 722 includes a transparent or translucent region that replaces the slot 736. The transparent or translucent region allows the camera unit 730 to capture an image therethrough.

One example of the camera unit 730 is ADV102 Machine Vision Camera, such as part number ADV102-CQBCKFW1-B, available from Cognex Corporation (Natick, MA).

As described above, patient samples contained in reaction vessels are transported between various modules, units, or devices in the instrument 100. Various aspects of the diagnostic process in the instrument 100 are performed in the wash wheel 720. The wash wheel 720 transports multiple reaction vessels 728 therearound. The reaction vessels 728 on the wash wheel 720 can correspond to a plurality of test results. In this configuration, the camera unit 730 and the light source 732 (or the screen 733) are fixed to the wash wheel 720. The camera unit 730 faces into the wash wheel 720 where the light source 732 (or the screen 733) is located. The camera unit 730 captures an image of the reaction vessel 728 moving through the field of view (FOV) of the camera unit 730 between the camera unit 730 and the light source 732 (or the screen 733). In some embodiments, the reaction vessel 728 becomes stationary when the image of the reaction vessel 728 is captured by the camera unit 730. In other embodiments, the camera unit 730 captures the image of the reaction vessel 728 while the reaction vessel 728 moves. The image of the reaction vessel can be captured for each reaction vessel 728. The camera unit 730 takes images in multiple steps throughout diagnostic processes as the rotatable plate 724 rotates relative to the housing unit 722. In some embodiments, it is possible to bring a reaction vessel to a location between the camera unit 730 and the light source 732 (or the screen 733) (e.g., a container seat 726 located at the slot 736) when the diagnostic processes are not in progress.

The wash wheel 720 is operable in different operational modes. In some embodiments, the wash wheel 720 is operated in a test processing mode or in a diagnostic routine mode. In other embodiments, the wash wheel 720 is operable in a test preparation mode, such as priming. In the test processing mode, the wash wheel 720 holds one or more vessels on the rotatable plate 724 and rotates the vessels for predetermined analytic tests. In the diagnostic routine mode, which is also referred to herein as automated system diagnostics (ASD), the instrument 100 is in an idle state and does not run tests. In some embodiments, in the diagnostic routine mode, the wash wheel 720 is operated to perform at least one of the operations of the preparation evaluation system 104, such as vessels dispensing volume detection (e.g., by the reaction vessel dispensing volume detection device 700), vessel residual volume detection (e.g., by the reaction vessel residual volume detection device 702), dispensing adjustment (e.g., by the dispensing adjustment device 704), and vessel detection (e.g., by the reaction vessel detection device 706). In other embodiments, the operations of the preparation evaluation system 104 can be performed in the test processing mode.

In some embodiments, the wash wheel 720 is operated with a plurality of dispense tips that can have different profiles and accuracy based on hydraulic characteristics thereof. In the test processing mode, two or more of the plurality of dispense tips can dispense substances into vessels on the wash wheel 720. In the diagnostic routine mode, the dispense tips can be independently operated, and thus the operational condition of each dispense tip can be monitored and evaluated, such as in dispensing adjustment performed by, for example, the dispensing adjustment device 704.

Figure 26:
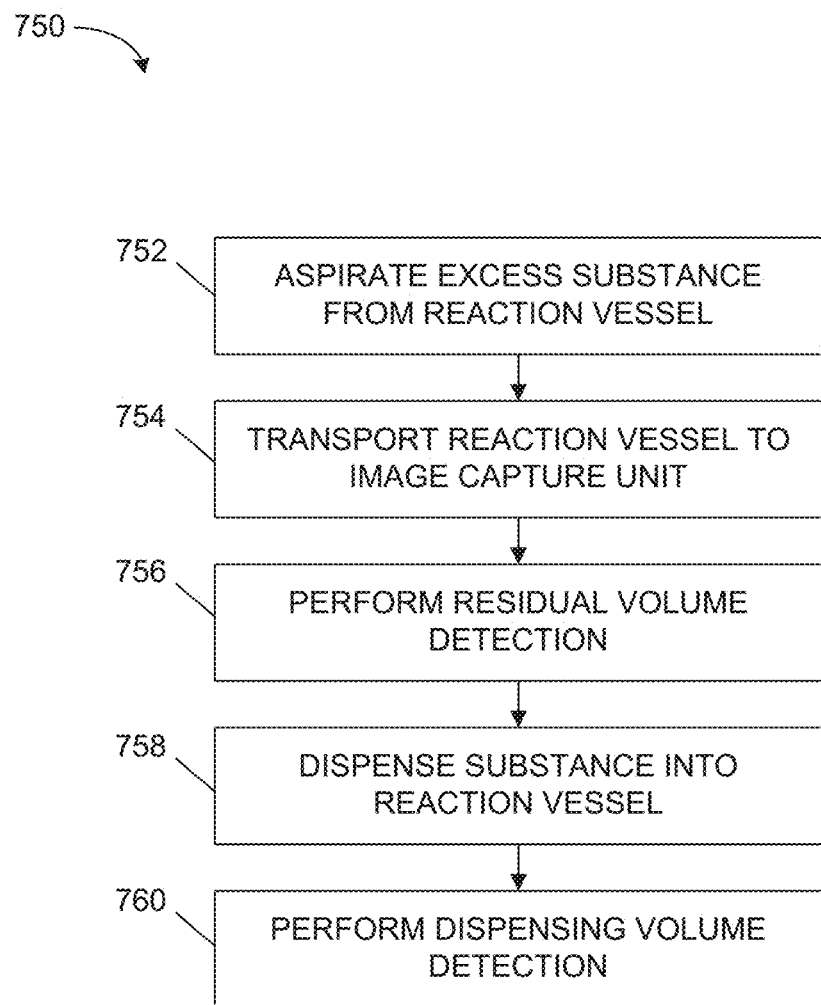
FIG. 26 is a flowchart illustrating an example method of operating the vessel volume detection device with the wash wheel.

FIG. 26 is a flowchart illustrating an example method 750 of operating the vessel volume detection device 402 with the wash wheel 720. In some embodiments, at least some of the operations in the method 750 are performed by the substance preparation system 102, the preparation evaluation system 104, and/or the substance evaluation system 106 of the instrument 100. In other embodiments, other components, units, and devices of the instrument 100 are used to perform at least one of the operations in the method 750. In some embodiments, the method 750 includes operations 752, 754, 756, 758, and 760.

At operation 752, the substance preparation system 102 operates to aspirate an excess volume of fluidic substance from a reaction vessel 738 on the wash wheel 720. In some embodiments, the excess volume of fluidic substance remains within the reaction vessel 738 after one or more predetermined analytic procedures on the wash wheel 720. Such an excess substance volume in a reaction vessel needs to be removed from the reaction vessel 738 for subsequent processes, such as before a substrate is dispensed into the reaction vessel as illustrated in FIG. 4.

At operation 754, the substance preparation system 102 transports the reaction vessel 738 to the vessel image capture unit 132 on the wash wheel 720.

At operation 746, the vessel volume detection device 402 performs residual volume detection in the reaction vessel 738. In some embodiments, the reaction vessel residual volume detection device 702 operates to execute the residual volume detection.

At operation 748, the substance preparation system 102 operates to dispense a fluidic substance (e.g., a substrate as illustrated in FIG. 4) into the reaction vessel 738.

At operation 760, the vessel volume detection device 402 performs dispensing volume detection in the reaction vessel 738. In some embodiments, the reaction vessel dispensing volume detection device 700 operates to execute the dispensing volume detection.

Figure 27:
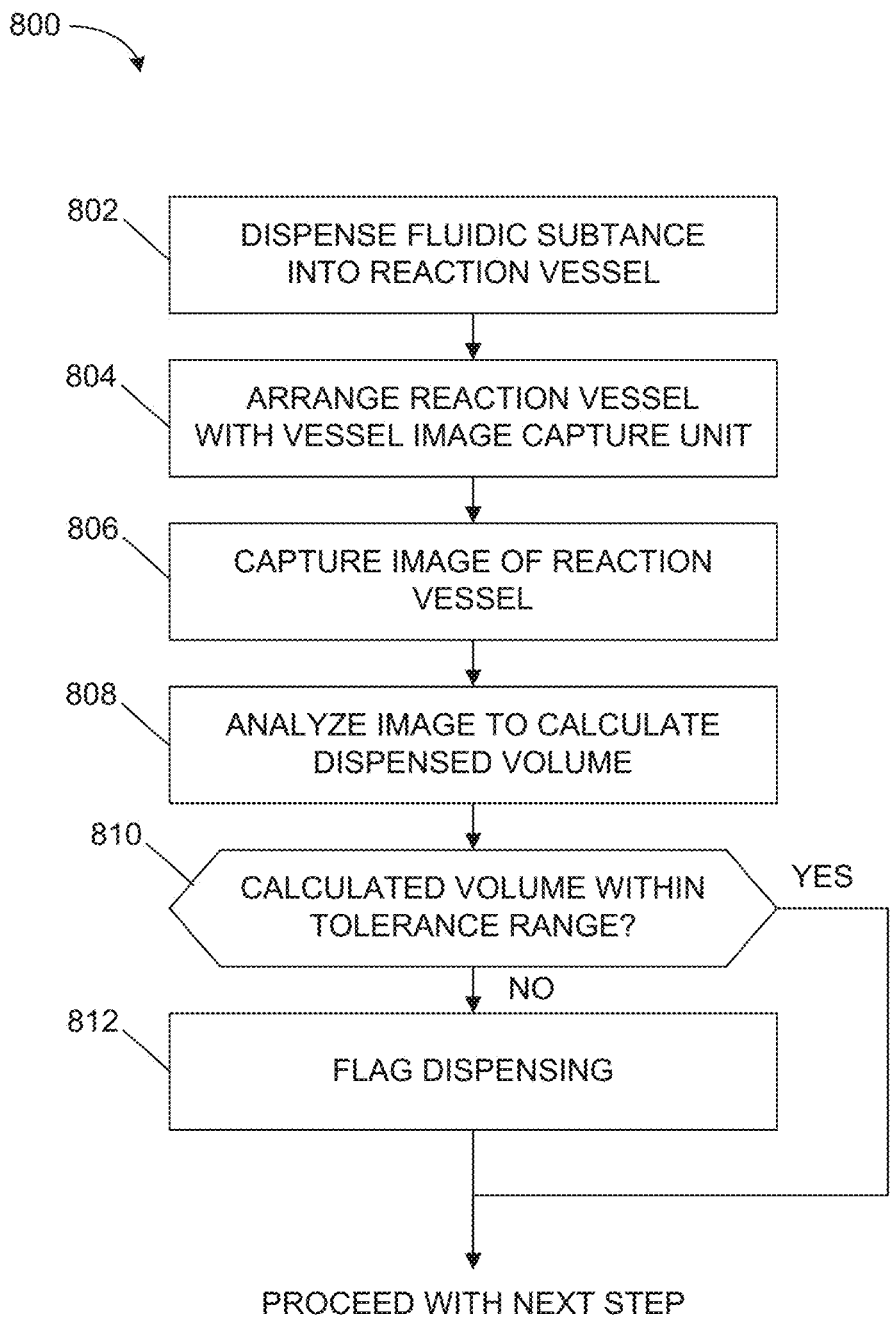
FIG. 27 is a flowchart illustrating an example method of operating a reaction vessel dispensing volume detection device of the vessel volume detection device.

FIG. 27 is a flowchart illustrating an example method 800 of operating the reaction vessel dispensing volume detection device 700. Although the method 800 is primarily described with respect to the reaction vessel dispensing volume detection device 700, the method 600 is also similarly applicable to other types of the vessel volume detection device 402. In some embodiments, the method 800 is performed by the container carriage device 720 (e.g., wash wheel) and the reaction vessel dispensing volume detection device 700.

In general, the method 800 performs analysis of a volume of fluidic substance dispenses or aspirated in a vessel and flags dispensing or aspiration results, or test results, if the calculated volume is outside a tolerance range.

At operation 802, a fluidic substance is dispensed to a reaction vessel 728 supported in, for example, the container carriage device 720, as programmed. Examples of the fluidic substance include a sample, diluent, reagent, substrate, or any combination thereof, as described herein. For example, diluents or reagents are used during a diagnostic mode for the wash wheel.

At operation 804, the container carriage device 720 transports the reaction vessel 738 containing the dispensed substance to the vessel image capture unit 132. In some embodiments, the vessel image capture unit 132 is arranged to capture an image of the reaction vessel 738 after dispensing without transportation. In other embodiments, the dispensing at the operation 802 occurs at a location where the vessel image capture unit 132 is arranged in place and captures an image of the reaction vessel 738 without moving the reaction vessel 738 after dispensing.

At operation 806, the vessel image capture unit 132 of the reaction vessel dispensing volume detection device 700 captures an image of the reaction vessel 738. In some embodiments, the image of the reaction vessel 738 is a digital image of a predetermined resolution.

At operation 808, the reaction vessel dispensing volume detection device 700 analyzes the image to determine a volume of the fluidic substance within the reaction vessel 738. An example of the operation 808 is described in more detail with respect to FIGS. 28 and 29.

At operation 810, the reaction vessel dispensing volume detection device 700 determines whether the determined volume falls within a tolerance range. When the determined volume is outside a tolerance range, the dispensing of the fluidic substance in the reaction vessel 738 is considered to be inappropriate. In some embodiments, such a tolerance range is determined based on an allowable deviation from a target dispensing volume of the fluidic substance that is intended to be dispensed into the reaction vessel 738. The tolerance range can vary depending on the target aspiration volume and other factors. By way of example, where the target dispensing volume (V) is 200 µL, it is considered to be acceptable if 194 µL≤V≤206 µL. In other examples, it is considered to be acceptable if the standard deviation (V(n)) is equal to or less than ±1 µL.

When the detected volume is determined to fall within the tolerance range ("YES" at the operation 810), the method 800 proceeds to perform a predetermined next step. Otherwise ("NO" at the operation 810), the method 800 moves on to operation 812.

At operation 812, the reaction vessel dispensing volume detection device 700 flags the dispensing to indicate that the dispensed volume in the reaction vessel 738 is not appropriate for subsequent processes. In other embodiments, the entire test result that has used the dispensed fluidic substance can be flagged to indicate or suggest that the test result can be improper. Alternatively, the reaction vessel dispensing volume detection device 700 operates to stop an associated test or analytic process in the instrument 100. In other embodiments, the evaluation result can be used to automatically adjust a test result that may be erroneous due to the inappropriate volume of the fluidic substance (by way of example, within certain volume range, RLUs are proportional to the substrate volume, and at certain point, it exceeds luminometer aperture range, then gets plateau and decreases because of dilution factor). In yet other embodiments, the evaluation result can be used to automatically adjust the volume of the fluidic substance in response to the volume determination.

Figure 28:
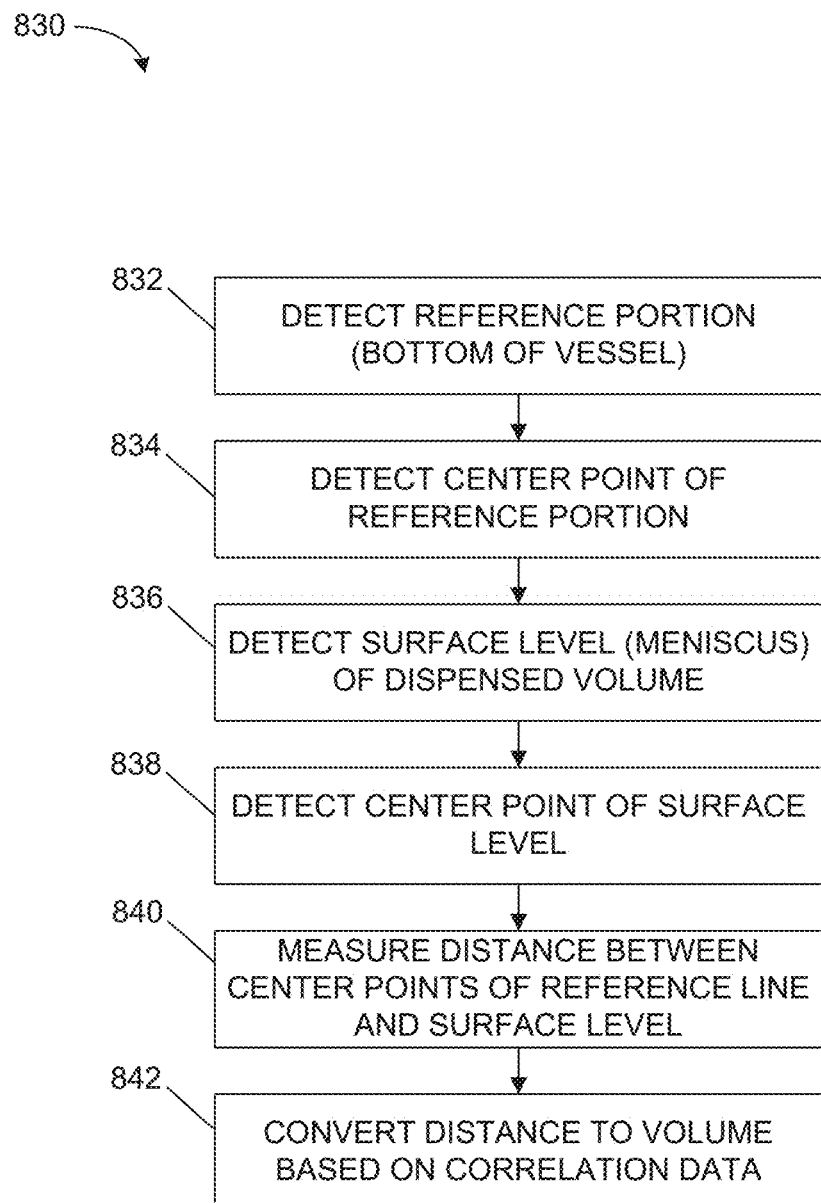
FIG. 28 is a flowchart illustrating an example method for performing an operation of the reaction vessel dispensing volume detection device of FIG. 27.
Figure 29:
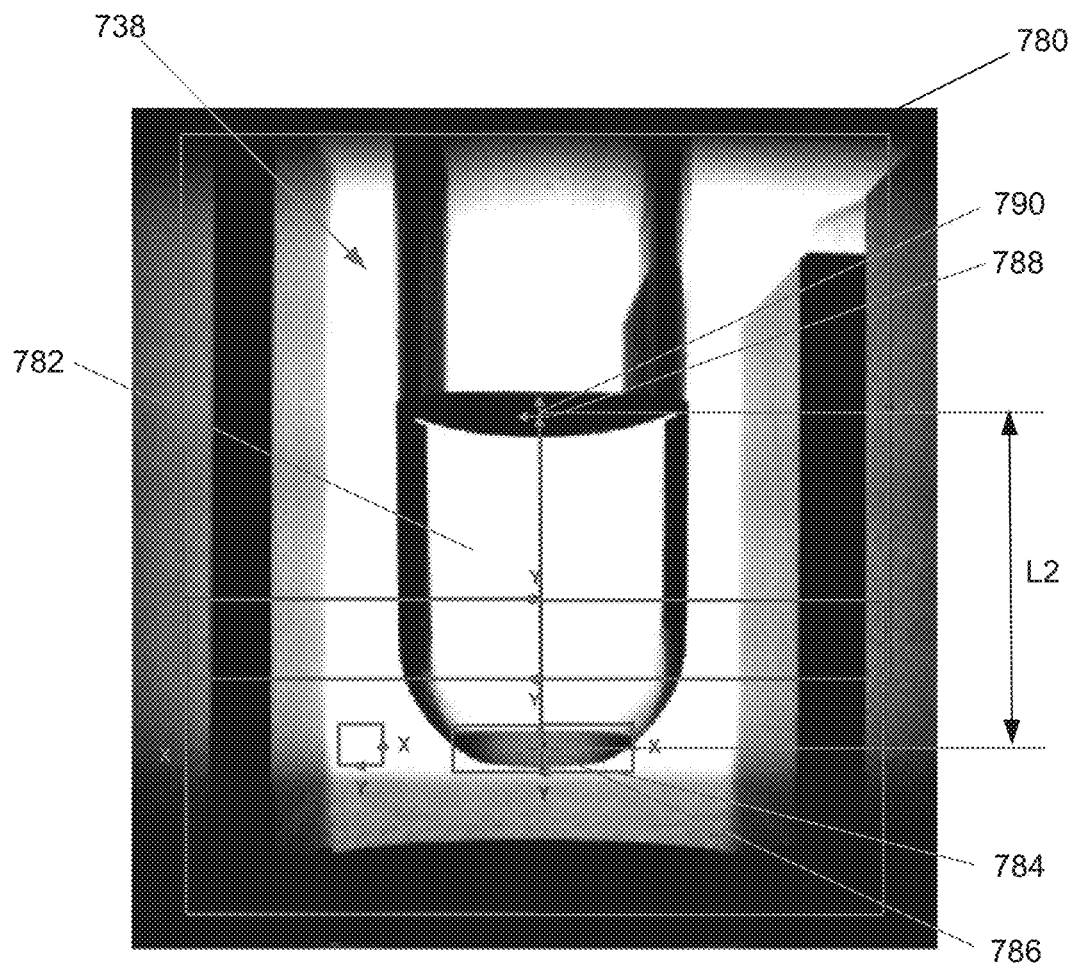
FIG. 29 illustrates an example analysis of a captured image of a reaction vessel.

Referring to FIGS. 28 and 29, an example of the operation 808 of FIG. 27, in which a captured image is analyzed to determine the volume dispensed in the reaction vessel, is described. In particular, FIG. 28 is a flowchart illustrating an example method 830 for performing the operation 608 of FIG. 27. The method 830 is described with also reference to FIG. 29, which illustrates an example analysis of a captured image 780 of the reaction vessel.

At operation 832, the reaction vessel dispensing volume detection device 700 detects a reference portion 784 of the reaction vessel 738 in the captured image 780. In some embodiments, the reference portion 784 includes a bottom portion of the reaction vessel 738. Other portions of the reaction vessel 738 can be used as a reference portion 784.

Various image processing methods can be used to detect the bottom portion 784 in the image 780. In some embodiments, the bottom portion 784 is detected by pattern matching function, which searches a pattern representative of the bottom portion based on a pre-trained reference image. For example, such pattern matching function executes a pattern search that scans the captured image for a pattern that has been stored in the system and recognized as the bottom portion. A correlation value, or matching rate (e.g., % matching), is adjustable. Other methods are also possible in other embodiments. One example of such image processing methods can be implemented by Cognex In-Sight Vision Software, available from Cognex Corporation (Natick, MA), which provides various tools, such as edge detection ("Edge"), pattern matching ("Pattern Match"), and histogram analysis ("Histogram").

At operation 834, the reaction vessel dispensing volume detection device 700 detects a center point 786 of the bottom portion 784. As illustrated in FIG. 29, once the bottom portion 784 is detected, the center point 786 can be calculated as the middle point of the bottom portion 784.

At operation 836, the reaction vessel dispensing volume detection device 700 detects a surface level 788 (FIG. 29) of the disposed volume in the reaction vessel 738. Various image processing methods can be used to detect the surface level 788 in the image 780. In some embodiments, similarly to the operation 832, the surface level 788 is detected by pattern matching function based on a pre-trained reference image. Other methods are also possible in other embodiments.

At operation 838, the reaction vessel dispensing volume detection device 700 detects a center point 790 of the surface level 788. As illustrated in FIG. 29, once the surface level 788 is detected, the center point 790 can be calculated as the middle point of the line of the surface level 788.

At operation 840, the reaction vessel dispensing volume detection device 700 measures a distance L2 (FIG. 29) between the center point 786 of the bottom portion 784 and the center point 790 of the surface level 788. In some embodiments, the distance L2 is measured by a pixel distance between the center points 786 and 790 in the image 780. In some embodiments, the pixel distance is calculated based on a Euclidean distance between two pixel points.

Figure 30:
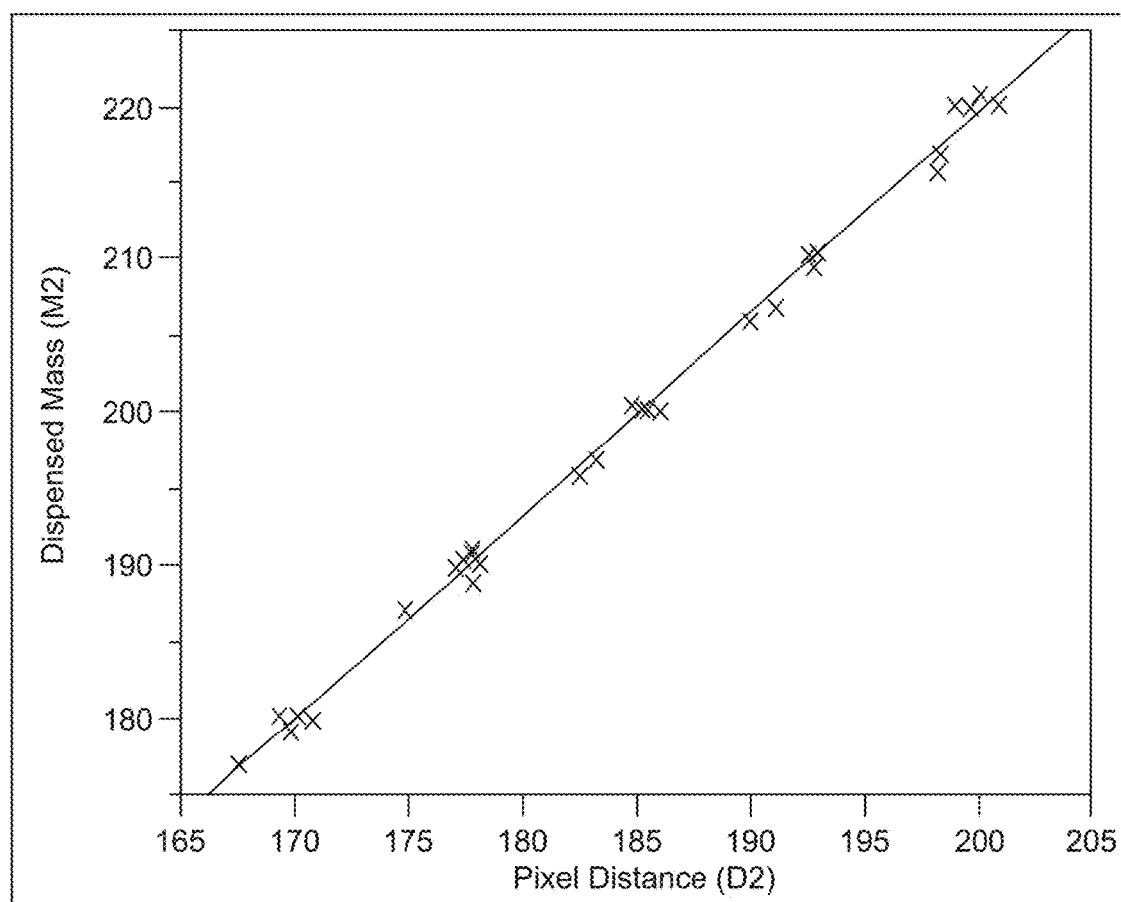
FIG. 30 is an example correlation curve corresponding to vessel volume correlation data.

At operation 842, the reaction vessel dispensing volume detection device 700 converts the distance L2 to a volume based on the vessel volume correlation data 712 (FIG. 22). The correlation data 712 include information about a correlation between volumes within the reaction vessel 738 and distances L2 between the center point 786 of the bottom portion 784 and the center points 790 of a plurality of different surface levels 788 in the reaction vessel 738. In some embodiments, the correlation data 712 can be plotted to a correlation curve 860 as illustrated in FIG. 30. An example method of generating the correlation data 712 is described with reference to FIG. 31.

FIG. 30 is an example correlation curve 860 corresponding to the correlation data 712. In some embodiments, the correlation curve 860 shows a relationship between the distance L2 (e.g., pixel distance) between the center points 786 and 790 and the volume V2 of dispensed fluidic substance 782 in the reaction vessel 738. In the illustrated example, the correlation curve 860 indicates a relationship between the mass of fluidic substance dispensed in the reaction vessel 738 and the pixel height of the fluidic substance in the reaction vessel 738. The mass can be converted to a volume based on a density of the fluidic substance. The pixel height of the fluidic substance in the reaction vessel corresponds to the distance D2.

The correlation curve 860 can be obtained by plotting a plurality of discrete data points include in the correlation data 712, which is described with reference to FIG. 31. As illustrated in FIG. 30, the correlation curve indicates that the dispense volume V2 (or the mass M2) generally increases as the distance L2 increases. Since the bottom portion 784 of the reaction vessel 738 is chosen as a reference point, the distance L2 is generally linearly correlated with the volume V2 (or the mass M2). For example, the distance L2 and the volume V2 are linearly correlated in general for volumes over 10 μL.

Figure 31:
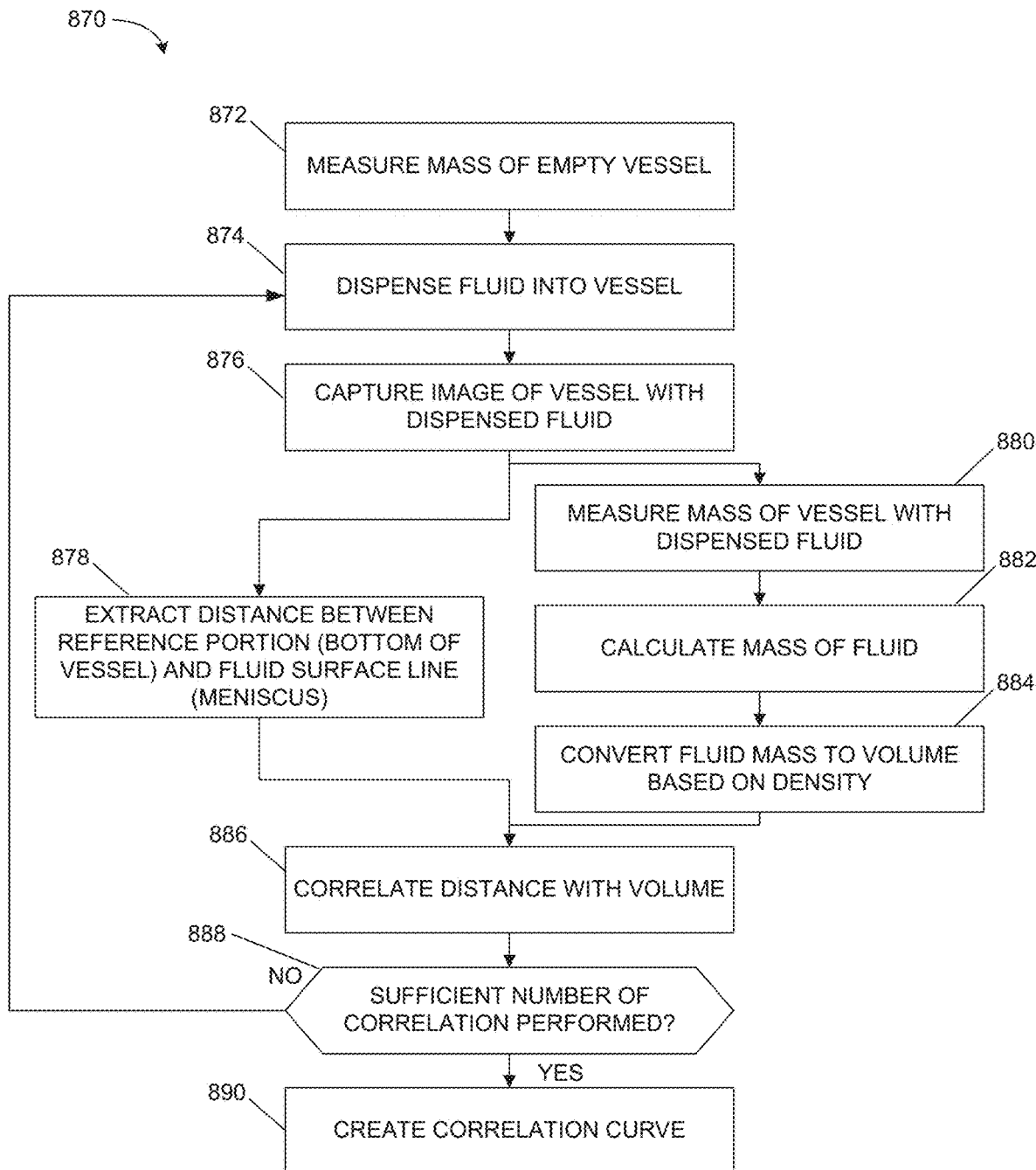
FIG. 31 is a flowchart illustrating an example method for operating a vessel volume correlation data generation system to generate the vessel volume correlation data.

FIG. 31 is a flowchart illustrating an example method 870 for operating the vessel volume correlation data generation system 710 to generate the vessel volume correlation data 712.

In some embodiments, the correlation data 712 is created using gravimetric analysis. For example, the vessel volume correlation data generation system 710 uses different volumes of fluid to show a correlation between extracted pixel distance information and fluidic volume information within a vessel. In some embodiments, the vessel volume correlation data generation system 710 selects a plurality of points within a target volume range (e.g., 190, 195, 200, 205, and 210 μL), dispense these volume settings into the vessel, and take images of the vessel for pixel distance calculation. Then, the vessel volume correlation data generation system 710 draws a calibration curve between pixel distances calculated from the images and masses measured by gravimetric analysis. The mass is then converted to a volume using the density of the fluid.

At operation 872, the vessel volume correlation data generation system 710 measures the mass of an empty vessel, such as a reaction vessel 738.

At operation 874, the vessel volume correlation data generation system 710 dispenses a fluid into the vessel.

At operation 876, the vessel volume correlation data generation system 710 captures an image of the vessel containing the fluid.

At operation 878, the vessel volume correlation data generation system 710 extracts a distance between the reference portion of the vessel, such as the bottom portion 784 of the reaction vessel 738, and a surface line of the fluid in the image captured in the operation 876. In some embodiments, the distance is measured by a pixel distance. In some embodiments, the distance is determined similarly to at least some of the operations of the method 830, such as the operations 832, 834, 836, 838, and 840. Other methods are also possible in other embodiments.

During operations 880, 882, and 884, the vessel volume correlation data generation system 710 measures a volume of the fluid dispensed in the vessel. Various methods can be used to determine the fluid volume. In the illustrated example, gravimetric approaches are used as described below.

At operation 880, the vessel volume correlation data generation system 710 measures the mass of the vessel containing the dispensed fluid.

At operation 882, the vessel volume correlation data generation system 710 calculates the mass of fluid contained in the vessel. In some embodiments, the mass of fluid in the vessel can be calculated by subtracting the mass of the empty vessel (which is obtained at the operation 872) from the total mass of the vessel containing the fluid (which is obtained at the operation 880).

At operation 884, the vessel volume correlation data generation system 710 converts the fluid mass to a volume based on the density of the fluid.

At operation 886, the vessel volume correlation data generation system 710 correlates the distance calculated at the operation 878 and the volume obtained at the operation 884.

At operation 888, the vessel volume correlation data generation system 710 determines whether a sufficient number of correlations have been performed to generate the vessel volume correlation data 712. If so ("YES" at the operation 888), the method 870 moves on to operation 890. Otherwise ("NO" at the operation 888), the method 870 returns to operation 874, in which another fluid is dispensed to the vessel, and the subsequent operations are performed to determine additional correlations between the distance and the volume of the fluid within the vessel. To obtain a sufficient range of correlation data, different quantities of fluid are dispensed to the vessel in different correlation cycles. In addition, the quantity of fluid dispensed to the vessel can remain generally the same for some of the correlation cycles so as to obtain reliable results of correlation.

At operation 890, the vessel volume correlation data generation system 710 creates the vessel volume correlation data 712 based on a plurality of correlations made at the operation 886. In some embodiments, the correlation data 712 is illustrated as a correlation curve (e.g., the correlation curve 860 in FIG. 30) by plotting each image's pixel distance with the corresponding dispensed volume. The correlation curve is used to estimate the relationship between the distance and the volume in the vessel.

Figure 32:
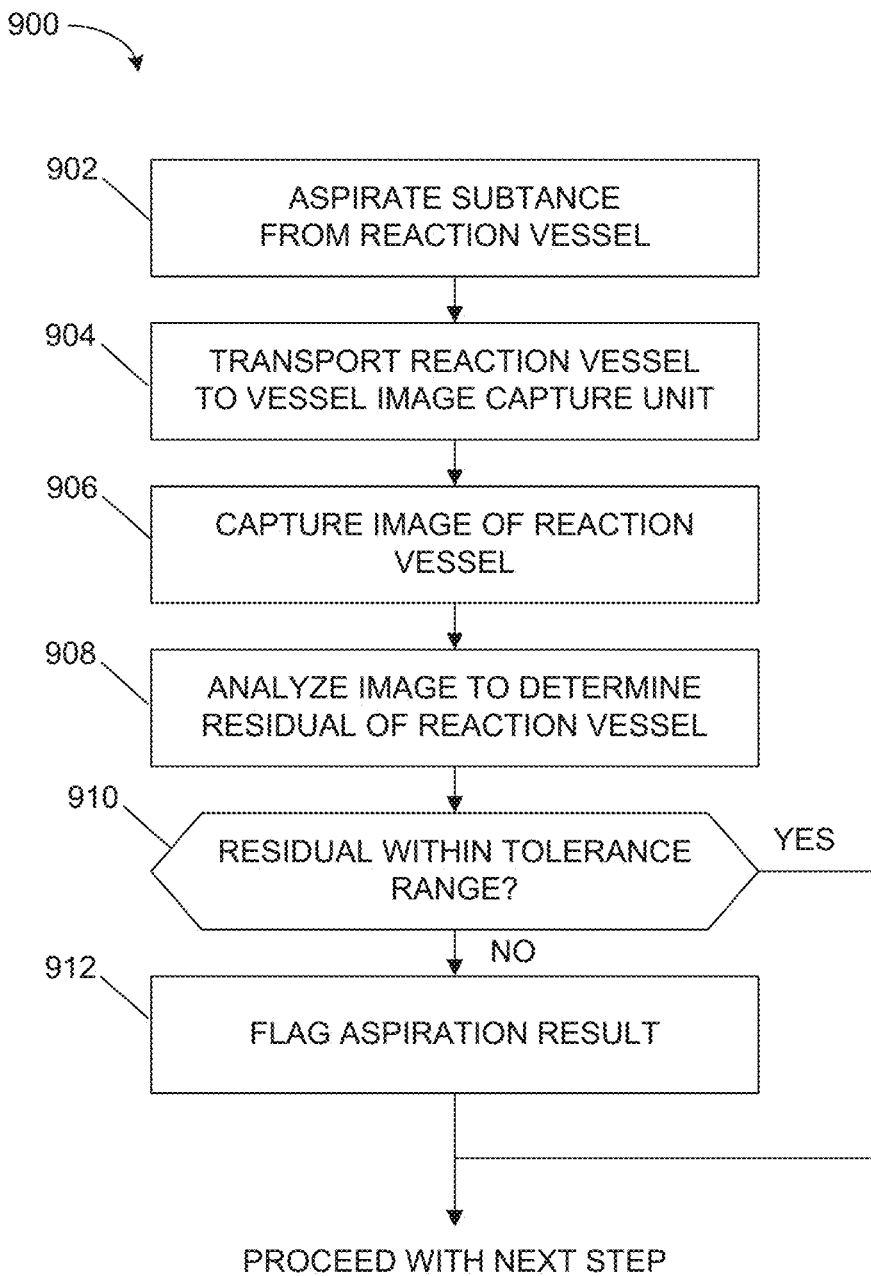
FIG. 32 is a flowchart illustrating an example method of operating a reaction vessel residual volume detection device of the vessel volume detection device.
Figure 33:
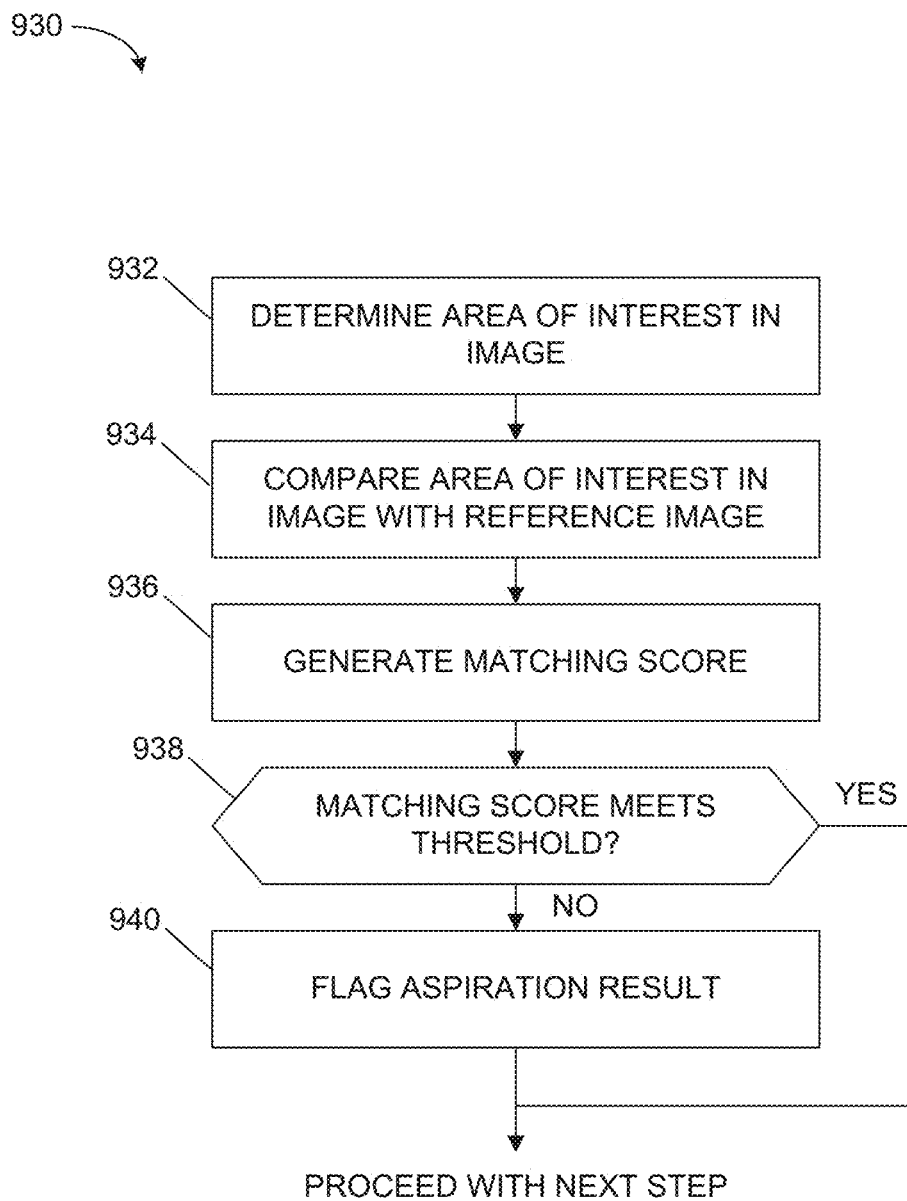
FIG. 33 is a flowchart illustrating an example method for performing an operation of the reaction vessel residual volume detection device of FIG. 32.
Figure 34:
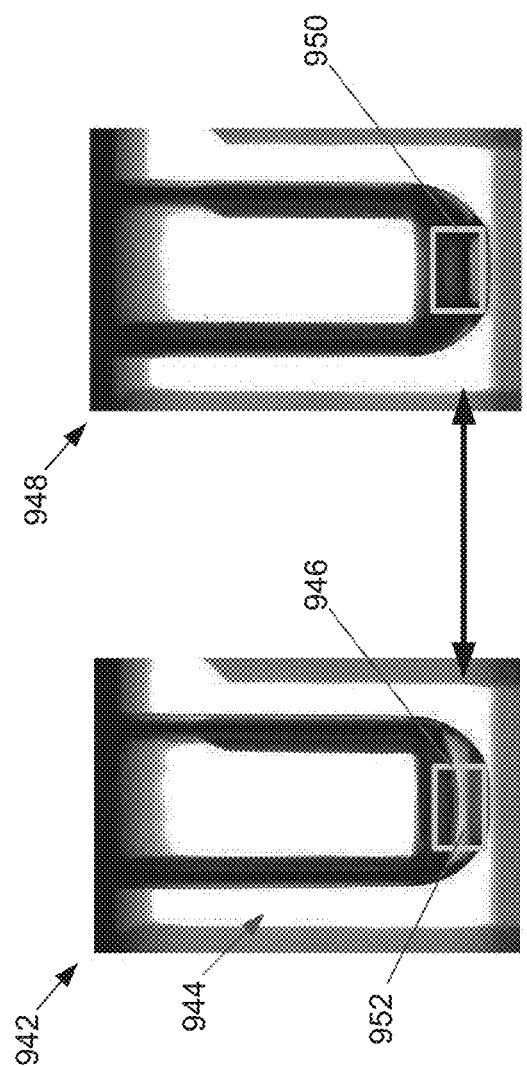
FIG. 34 illustrates an example analysis of a captured image of a vessel.

Referring to FIGS. 32-34, an example operation of the reaction vessel residual volume detection device 702 is described.

FIG. 32 is a flowchart illustrating an example method 900 of operating the reaction vessel residual volume detection device 702. In some embodiments, the method 900 includes operations 902, 904, 906, 908, 910, and 912.

In general, the method 900 performs analysis of a vessel to determine if the vessel contains a residual volume after the vessel is aspirated. If the vessel contains a volume that is outside a tolerance range, the aspiration result or the test result is flagged.

At operation 902, the reaction vessel residual volume detection device 702 aspirates the substance from a vessel, such as a reaction vessel 738.

At operation 904, the reaction vessel residual volume detection device 702 transports the vessel to the vessel image capture unit 132. In some embodiments, the vessel image capture unit 132 is arranged to capture an image of the vessel after aspiration without transportation. In other embodiments, the aspiration at the operation 902 occurs at a location where the vessel image capture unit 132 is arranged in place and captures an image of the vessel without moving the vessel after aspiration.

At operation 906, the vessel image capture unit 132 captures an image of the vessel. In some embodiments, the image of the vessel is a digital image of a predetermined resolution.

At operation 908, the reaction vessel residual volume detection device 702 analyzes the image to determine the presence of the substance within the vessel. An example of the operation 908 is described in more detail with respect to FIGS. 33 and 34.

At operation 910, the reaction vessel residual volume detection device 702 determines whether the presence of the residual volume falls within a tolerance range. When the presence of the residual volume is outside a tolerance range, the aspiration of the substance from the vessel is considered to be inappropriate. The tolerance range represents a range of residual volume in the reaction vessel that is tolerable for acceptable test outcome. For example, the reaction vessel does not have to be aspirated to become completely empty for acceptable test results. In some embodiments, such a tolerance range is determined in terms of a pattern matching score between the captured image and a pre-trained image, as further described in FIG. 33. By way of example, where a residual volume of 4 μL or less in a reaction vessel is considered to be acceptable, a pattern matching score that can be interpreted as resembling an image of a reaction vessel containing a volume of 4 μL will be used as a tolerance threshold.

When the presence of residual volume is determined to fall within the tolerance range ("YES" at the operation 910), the method 900 proceeds to perform a predetermined next step. Otherwise ("NO" at the operation 910), the method 900 moves on to operation 812.

At operation 912, the reaction vessel residual volume detection device 702 flags the aspiration result to indicate that the aspiration from the vessel is not appropriate for subsequent processes. In other embodiments, the entire test result that has used the aspirated vessel can be flagged to indicate or suggest that the test result can be improper. Alternatively, the reaction vessel residual volume detection device 702 operates to stop an associated test or analytic process in the instrument 100. In other embodiments, the evaluation result can be used to automatically adjust a test result that may be erroneous due to the inappropriate volume of the fluidic substance.

Referring to FIGS. 33 and 34, an example of the operation 908 of FIG. 32, in which a captured image is analyzed to determine the residual 952 within the vessel, is described. In particular, FIG. 33 is a flowchart illustrating an example method 930 for performing the operation 908 of FIG. 32. The method 930 is described with also reference to FIG. 34, which illustrates an example analysis of a captured image 942 of the vessel.

At operation 932, the reaction vessel residual volume detection device 702 detects an area of interest 946 in the captured image 942. In some embodiments, the area of interest 946 includes a bottom portion of a vessel 944. In some embodiments, the vessel 944 in the image represents the reaction vessel 738 discussed above. Other portions of the reaction vessel 738 can be used as a reference portion 784.

Various image processing methods can be used to detect the bottom portion 946 in the image 942. In some embodiments, the bottom portion 946 is detected by pattern matching function, which searches a pattern representative of the bottom portion based on a pre-trained reference image. For example, such pattern matching function executes a pattern search that scans the captured image for a pattern that has been stored in the system and recognized as the bottom portion. A correlation value, or matching rate (e.g., % matching), is adjustable. Other methods are also possible in other embodiments. One example of such image processing methods can be implemented by Cognex In-Sight Vision Software, available from Cognex Corporation (Natick, MA), which provides various tools, such as edge detection ("Edge"), pattern matching ("Pattern Match"), and histogram analysis ("Histogram").

At operation 934, the reaction vessel residual volume detection device 702 compares the area of interest 946 with a reference image 948. In some embodiments, the reference image 948 includes a portion 950 corresponding to the area of interest 946. In other embodiments, the reference image 948 is only the portion 950 corresponding to the area of interest 946 of the captured image 942.

In some embodiments, the reference image 948 represents an image of the same vessel 944 that is empty. Since an ideal aspiration leaves no residual fluid in the bottom portion of the vessel 944, a pre-trained image of the empty vessel 944 is used as the reference image 948. In other embodiments, other images can be used as the reference image 948.

At operation 936, the reaction vessel residual volume detection device 702 generates a matching score between the captured image 942 and the reference image 948. The matching score represents how closely the captured image 942 matches the reference image 948. The matching score is used as a metric to determine a cutoff for the presence of excess residual fluid in the vessel.

At operation 938, the reaction vessel residual volume detection device 702 determines whether the matching score meets a threshold. If the matching score meets the threshold ("YES" at the operation 938), it is considered that there is no or tolerable residual fluid in the vessel, and the method 930 moves on to a predetermined next step. Otherwise ("NO" at the operation 938), the method 930 continues on at operation 940. For example, if the matching score is below a predetermined threshold or cutoff value, it is considered that the excess residual fluid is present in the vessel, and the method 930 moves on to the operation 940.

At operation 940, the reaction vessel residual volume detection device 702 flags the aspiration result to indicate that the aspiration from the vessel is not appropriate for subsequent processes. In other embodiments, the entire test result that has used the aspirated vessel can be flagged to indicate or suggest that the test result can be improper. Alternatively, the reaction vessel residual volume detection device 702 operates to stop an associated test or analytic process in the instrument 100. In other embodiments, the evaluation result can be used to automatically adjust a test result that may be erroneous due to the inappropriate volume of the fluidic substance.

Alternatively, the method 930 uses other approaches to make image comparison and assign cutoff values. Examples of such approaches utilize common classification tools, such as logistic regression, support vector machines, neural networks, convolutional neural networks, and classification trees.

Figure 35:
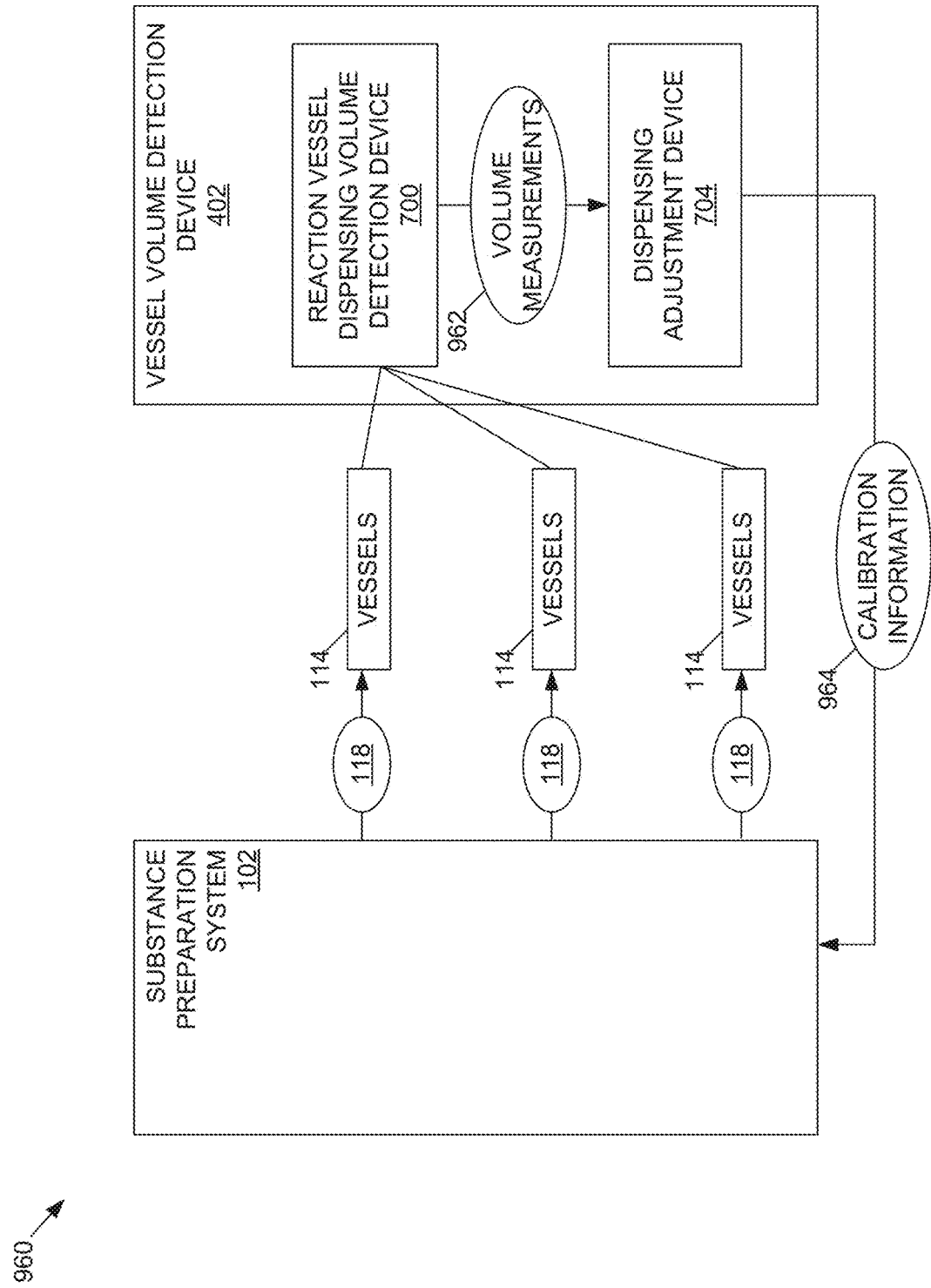
FIG. 35 is a block diagram of an example system in which a dispensing adjustment device of the vessel volume detection device is operated.
Figure 36:
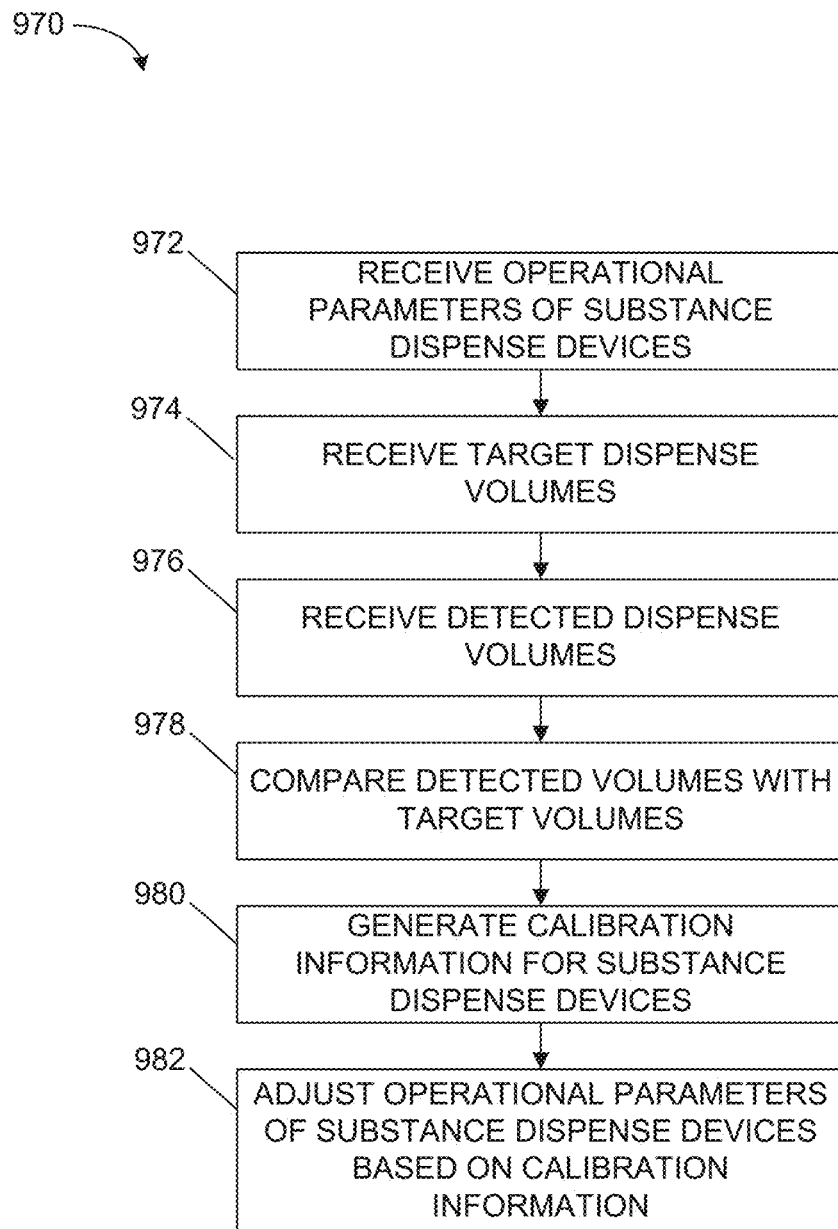
FIG. 36 is a flowchart illustrating an example method for operating the dispensing adjustment device of FIG. 35.

Referring to FIGS. 35 and 36, an example operation of the dispensing adjustment device 704 is described.

FIG. 35 is a block diagram of an example system 960 in which the dispensing adjustment device 704 is operated.

In general, the dispensing adjustment device 704 can use the volume-measurement capacities of the vessel image capture unit 132 to perform on-board adjustments of pipettors and pumps, thereby improving pipetting accuracy and overall system precision. In the illustrated example, single-volume or multiple-volume dispensings are made into a vessel, which is then transferred to the wash wheel for measurement. The results of the volume measurements, which can be performed by the reaction vessel dispensing volume detection device 700 as described above, are obtained, and the dispensing adjustment device 704 determines the accuracy for each combination of pumps and pipettors. In some embodiments, the measured volumes associated with pumps are used to adjust the operational parameters for the combinations of pumps and pipettors. By way of example, the step resolution for each pump can be adjusted, or offsets are added to the software instructions for each pump. After the adjustment, the dispensing adjustment device 704 can check the pumps again for accuracy, and readjust the pumps as needed. In some embodiments, the dispensing adjustment device 704 performs such adjustment operations while the instrument is idle for clinical testing. In other embodiments, the dispensing adjustment device 704 performs the adjustment operations during instrument initialization. In some embodiments, the dispensing adjustment device 704 performs the adjustment operations periodically to monitor the trend of pump performance so that a user or service department can monitor the status remotely and make a maintenance decision, such as when to send a service engineer for maintenance or part replacement.

As illustrated in FIG. 35, the substance preparation system 102 dispenses fluidic substances 118 to one or more vessels 114 (e.g., reaction vessels 728 on the wash wheel). The reaction vessel dispensing volume detection device 700 then performs volume measurements in the vessels 114, as described herein, and provides the result of volume measurements 962 to the dispensing adjustment device 704. In some embodiments, the dispensing adjustment device 704 analyzes the result of volume measurements 962 and generates calibration information 964, which can be then used to calibrate the substance preparation system 102 to improve dispensing accuracy.

FIG. 36 is a flowchart illustrating an example method 970 for operating the dispensing adjustment device 704. In some embodiments, the method 970 includes operations 972, 974, 976, 978, 980, and 982.

At operation 972, the dispensing adjustment device 704 receives one or more operational parameters of the substance preparation system 102. As described above, the substance preparation system 102 includes one or more substance dispense devices, such as the sample pipetting device 152, the reagent pipetting device, and the substrate pipetting device 178, which operate to dispense fluidic substances 118 to vessels 114. The operational parameters include various information about the configurations, settings, and operational status of the substance dispense devices. In some embodiments, such substance dispense devices include pump devices that operate dispense units (e.g., pipettors). Some examples of pump devices are operated by motors of various types, such as stepper motors. Where stepper motors are used, the operational parameters can include step resolutions, which are controlled to adjust an amount of dispensing via the pipettors.

At operation 974, the dispensing adjustment device 704 receives target dispense volumes of the fluidic substances 118. The target dispense volumes represent volumes of the fluidic substance 118 that are intended to be dispensed to the vessels 114 based on the operational parameters of the substance dispense devices.

At operation 976, the dispensing adjustment device 704 receives the detected volumes that have been dispensed to the vessels 114.

At operation 978, the dispensing adjustment device 704 compares the detected volumes with the target volumes. By way of example, a first substance dispense device, which includes a first pump device using a first pipettor, is configured to dispense a target volume of 100 μL to a vessel. After dispensing, the volume dispensed in the vessel is detected to be 99.9 μL. Then, the dispensing adjustment device 704 compares the target volume of 100 μL and the detected volume of 99.9 μL and determines there is 0.1 μL discrepancy between the target and detected volumes in the first substance dispense device.

In some embodiments, a plurality of dispensing instances from a single substance dispense device is considered as a group. By way of example, a particular substance dispense device performs a first dispensing, a second dispensing, and a third dispensing, using a pump device and a vessel (or three vessels), with a target volume of 100 μL. After three dispensing instances, the volumes dispensed to the vessel are detected to be 100.5 μL in the first dispensing instance, 99.5 μL in the second dispensing instance, and 100 μL in the third dispensing instance. In some embodiments, all of the detected volumes can be used together to calibrate the substance dispense device. For example, a standard deviation of the three detected volumes (e.g., 0.5 μL in this example) can be used to calibrate the substance dispense device by, for example, adjusting the step resolution of the stepper motor thereof. In this example, the calibration information 964 is generated and used to decrease the standard deviation. In other embodiments, as described above, each of the detected volumes can be used to calibrate the substance dispense device for each dispensing instance.

In other embodiments, a plurality of dispensing events from a plurality of substance dispense devices is considered as a group. By way of example, a first substance dispense device performs a first dispensing, a second substance dispense device performs a second dispensing, and a third substance dispense device performs a third dispensing, with a target volume of 100 μL. After dispensing, the volume dispensed by the first substance dispense device is detected to be 100.5 μL, the volume dispensed by the second substance dispense device is detected to be 99.5 μL, and the volume dispensed by the third substance dispense device is detected to be 100 μL. In some embodiments, all of the detected volumes can be used together to calibrate the substance dispense devices. For example, a standard deviation of the three detected volumes (e.g., 0.5 μL in this example) can be used to calibrate the substance dispense devices by, for example, adjusting the step resolutions of the stepper motors thereof. In this example, the calibration information 964 is generated and used to decrease the standard deviation. In other embodiments, as described above, the detected volumes can be used to calibrate the respective substance dispense devices.

At operation 980, the dispensing adjustment device 704 generates calibration information 964 for the substance dispense devices. The calibration information 964 includes information to control the substance dispense devices such that the volumes dispensed by the substance dispense devices are changed closer to the target volumes. Where the substance dispense devices include stepper motors, the calibration information 964 includes an adjustment to the step resolutions of the stepper motors to adjust the volumes dispensed by the stepper motors.

At operation 982, the dispensing adjustment device 704 adjusts the operational parameters of the substance dispense devices based on the calibration information 964. The substance dispense devices can operate to dispense the same or different volumes based on the modified operational parameters. In the example above where three dispensing instances are considered as a group, the volumes dispensed to the vessel after calibration are detected again.

Figure 37:
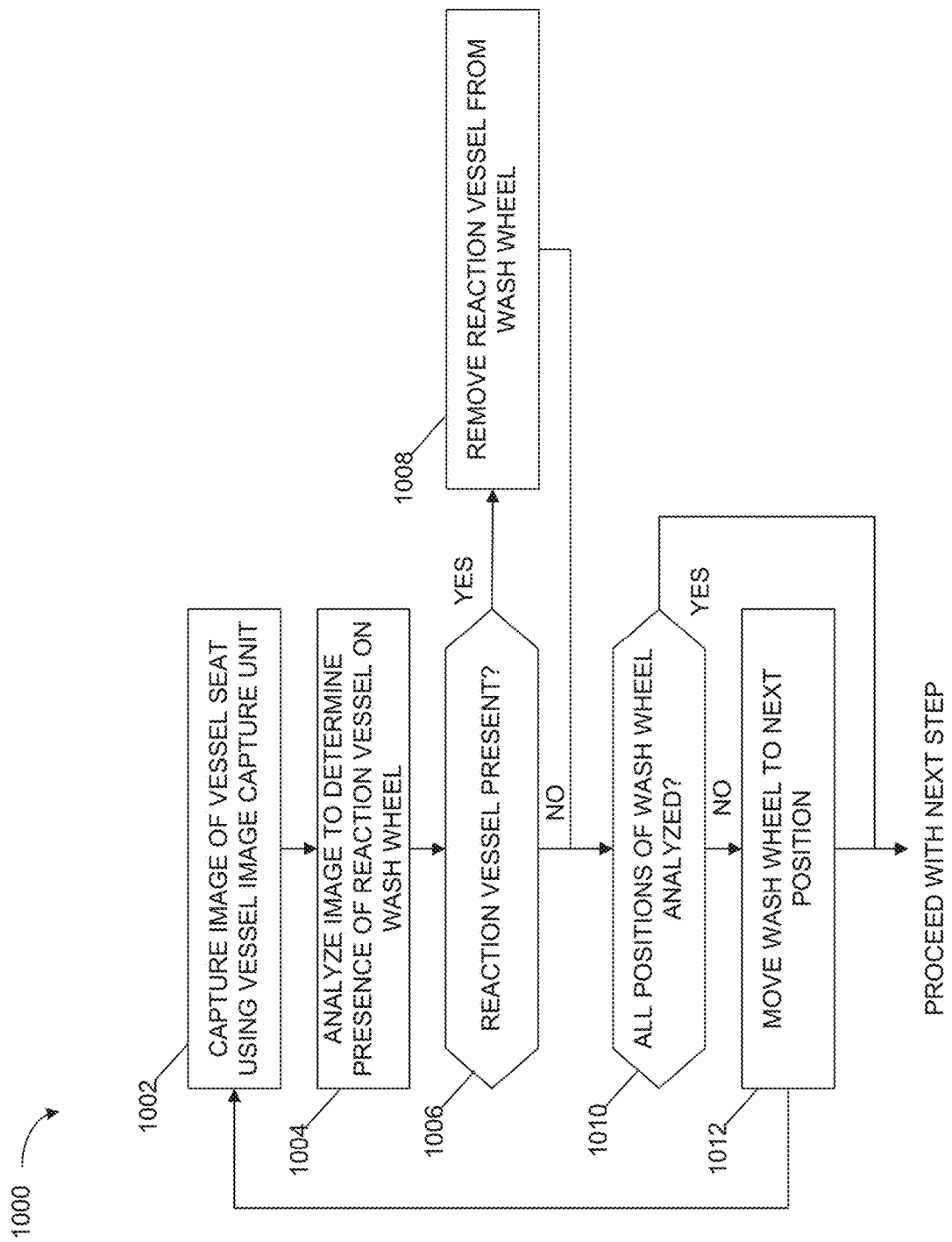
FIG. 37 is a flowchart illustrating an example method of operating a reaction vessel detection device of the vessel volume detection device.
Figure 38:
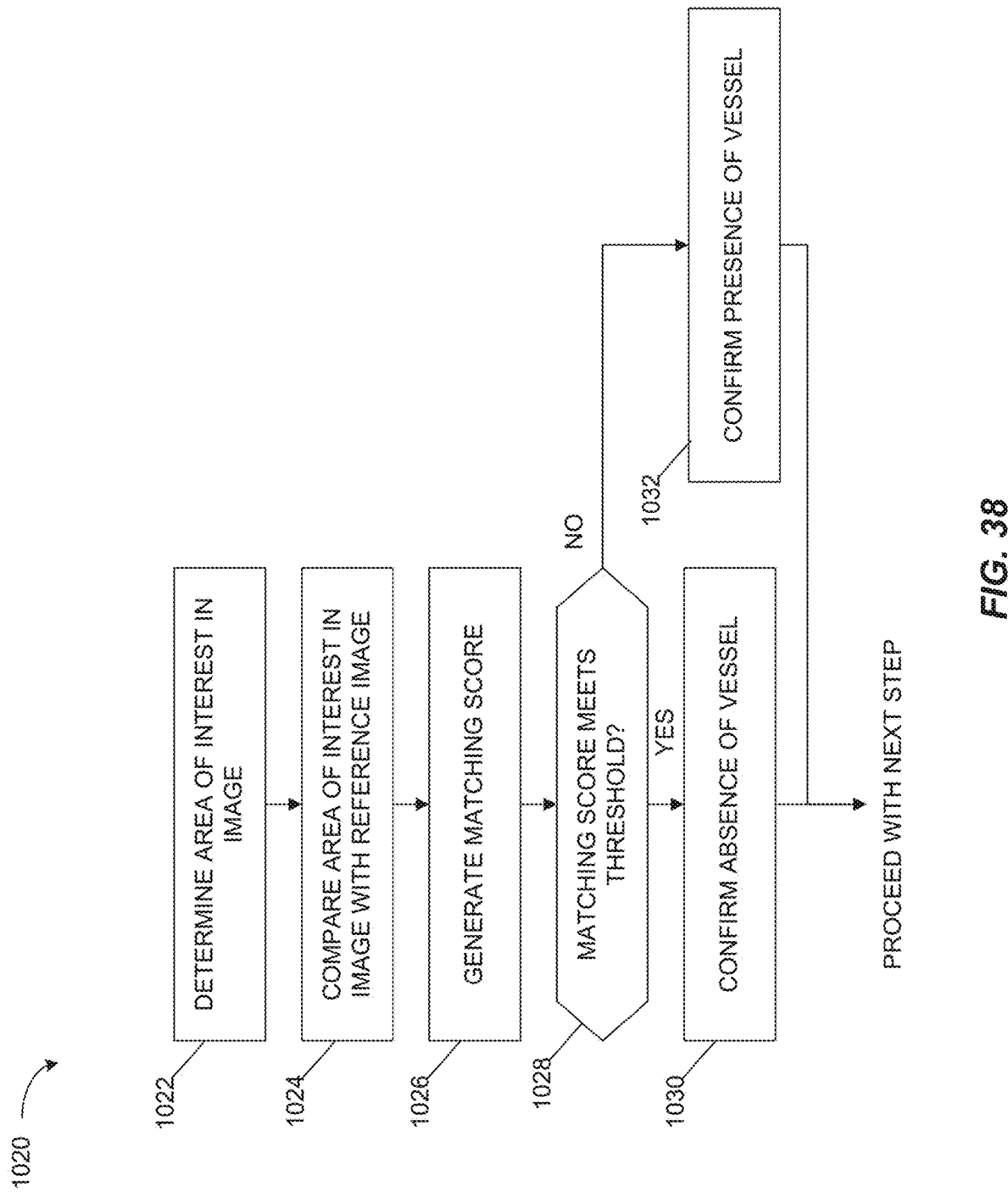
FIG. 38 is a flowchart illustrating an example method for performing an operation of the reaction vessel detection device of FIG. 37.
Figure 39:
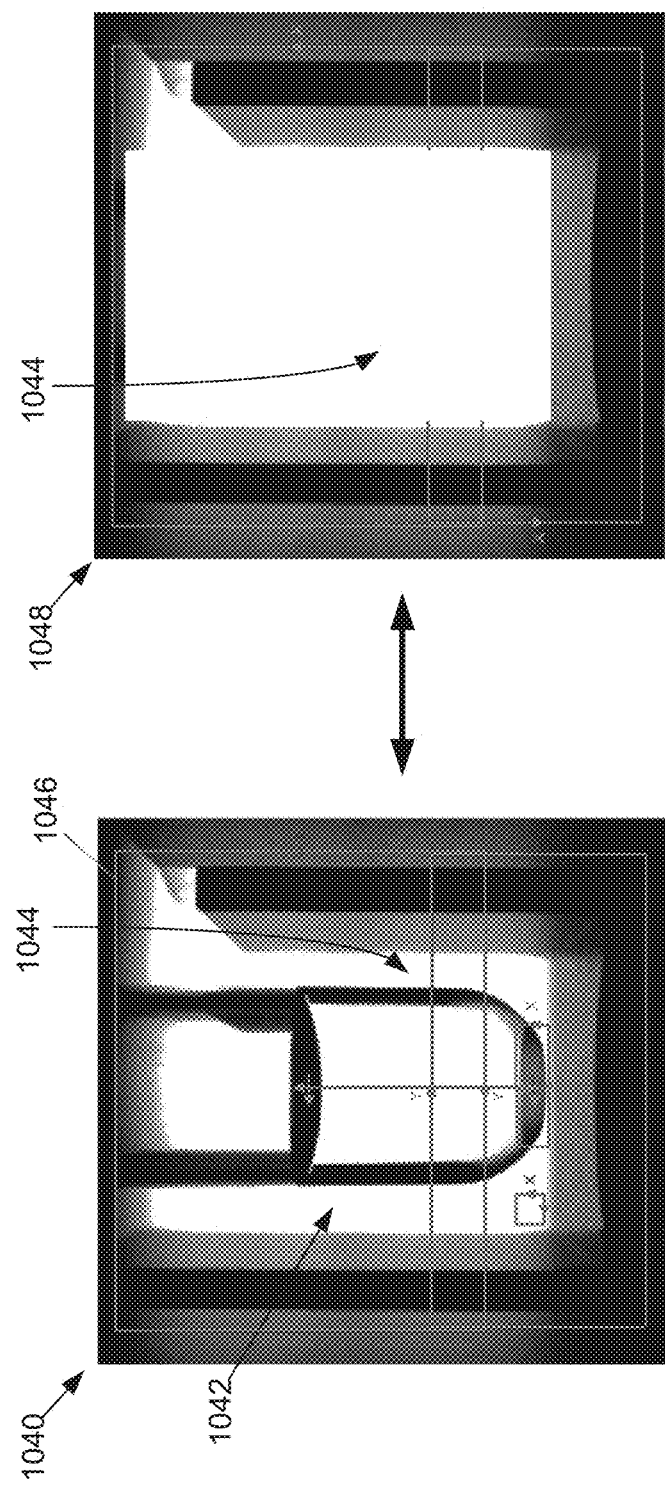
FIG. 39 illustrates an example analysis of a captured image of a vessel slot on a wash wheel.

Referring to FIGS. 37-39, an example operation of the reaction vessel detection device 706 is described.

FIG. 37 is a flowchart illustrating an example method 1000 of operating the reaction vessel detection device 706. In some embodiments, the method 1000 includes operations 1002, 1004, 1006, 1008, 1010, and 1012.

In general, during system initialization or reset, the vessels inside the wash wheel need to be removed. The reaction vessel detection device 706 can utilize the vessel image capture unit 132 to determine if all or some of the vessels have been removed during this initialization sequence. In some embodiments, the wash wheel operates to index every position so that each vessel location is checked by the image capture unit. At each wash wheel index position, the reaction vessel detection device 706 can perform image processing, such as a pattern-matching algorithm, to check for the presence of a vessel by comparing the captured image to a reference image (e.g., an image of the wash wheel without the vessel). The reaction vessel detection device 706 in accordance with an exemplary embodiment of the present disclosure provides reliable results, as opposed to other approaches that look at, or utilize, the volumes in vessels. As the reaction vessel detection device 706 looks for a close match to the geometry of the vessel, a large deviation from the reference image would indicate presence of the vessel, and a small deviation would indicate absence of the vessel. If the presence is determined, the system can remove the vessel and check again to confirm that the vessel has been removed successfully. Once it is determined that no vessels are present in the given wheel location, the wheel can index to the next position and repeat the process.

In the illustrate example, the reaction vessel detection device 706 is primarily described with respect to the wash wheel 720. In other embodiments, however, the reaction vessel detection device 706 is used with other types of container carriage device.

At operation 1002, the reaction vessel detection device 706 captures an image of a vessel slot 1044 (FIG. 39) (e.g., the slot 736) on the wash wheel 720, using the vessel image capture unit 132.

At operation 1004, the reaction vessel detection device 706 analyzes the image to determine presence or absence of a vessel 1042 (FIG. 39) (e.g., a reaction vessel 738) on the wash wheel 720. An example of the operation 1004 is described in more detail with reference to FIGS. 38 and 39.

At operation 1006, the reaction vessel detection device 706 determines whether the vessel is present at the vessel slot. If so ("YES" at the operation 1006), the method 1000 continues at operation 1008. Otherwise ("NO" at the operation 1006), the method 1000 moves on to operation 1010.

At operation 1008, the reaction vessel detection device 706 removes the vessel from the vessel slot of the wash wheel 720. In other embodiments, other devices (such as transfer or carriage devices as illustrated in FIG. 2) in the instrument 100 operate to remove the vessel from the wash wheel 720. In yet other embodiments, the vessel is manually removed from the wash wheel 720.

At operation 1010, the reaction vessel detection device 706 determines whether all of the positions of the wash wheel 720 have been analyzed through the precedent operations (e.g., the operations 1002, 1004, 1006, and 1008). If so ("YES" at the operation 1010), the method 1000 proceeds with a predetermined next step. Otherwise ("NO" at the operation 1010), the method 1000 moves on to operation 1012.

At operation 1012, the reaction vessel detection device 706 moves the wash wheel 720 to the next position and repeat the operation 1002 and the subsequent operations.

Referring to FIGS. 38 and 39, an example of the operation 1004 of FIG. 37, in which a captured image is analyzed to determine presence of a vessel on a wash wheel, is described. In particular, FIG. 38 is a flowchart illustrating an example method 1020 for performing the operation 1004 of FIG. 37. The method 1020 is described with also reference to FIG. 39, which illustrates an example analysis of a captured image 1040 of a vessel slot 1044 on the wash wheel.

At operation 1022, the reaction vessel detection device 706 detects an area of interest 1046 in the captured image 1040. In some embodiments, the area of interest 1046 includes at least a portion of the vessel slot 1044 (e.g., the slot 736) of the wash wheel 720. In some embodiments, the area of interest 1046 includes a bottom portion of the vessel, or a portion in the image that corresponds to a location of the bottom portion of the vessel. One example method for detecting the area of interest can be implemented by Cognex In-Sight Vision Software, available from Cognex Corporation (Natick, MA), which provides various tools, such as edge detection ("Edge"), pattern matching ("Pattern Match"), and histogram analysis ("Histogram").

At operation 1024, the reaction vessel detection device 706 compares the area of interest 1046 with a reference image 1048. In some embodiments, the reference image 1048 includes a portion corresponding to the area of interest 1046. In other embodiments, the reference image 1048 itself corresponds to the area of interest 1046 of the captured image 1040.

In some embodiments, the reference image 1048 represents an image of the vessel slot 1044 without a vessel 1042 therein (FIG. 39). In other embodiments, other images can be used as the reference image 948. For example, the reference image is an image of the vessel slot with a vessel therein.

At operation 1026, the reaction vessel detection device 706 generates a matching score between the captured image 1040 and the reference image 1048. The matching score represents how closely the captured image 1040 matches the reference image 1048. The matching score is used as a metric to determine a cutoff for presence of a vessel 1042 in the slot 1044 of the wash wheel 720.

At operation 1028, the reaction vessel detection device 706 determines whether the matching score meets a threshold. If the matching score meets the threshold ("YES" at the operation 1028), it is considered that a vessel is not present at the slot of the wash wheel, and the method 1020 moves on to operation 1030. Otherwise ("NO" at the operation 1028), it is considered that a vessel is present at the slot of the wash wheel, and the method 1020 continues on at operation 1032. For example, if the matching score is below a predetermined threshold or cutoff value, it is considered that a vessel is present at the slot of the wash wheel, and the method 1020 moves on to the operation 1032.

At operation 1030, the reaction vessel detection device 706 confirms absence of a vessel 1042 at the slot 1044 of the wash wheel 720.

At operation 1032, the reaction vessel detection device 706 confirms presence of a vessel 1042 at the slot 1044 of the wash wheel 720.

As described with reference to FIGS. 22-39, the vessel volume detection device 402 can be modified to be suitable for various applications. For example, the vessel volume detection device 402 can be applied for any analyzer that prepares and/or uses fluidic substances to detect an analyte of interest, such as in-vitro diagnostic (IVD) analyzers. In some embodiments, the vessel volume detection device 402 and the methods thereof can be applied for any devices or units other than the wash wheel. Some embodiments of the vessel volume detection device 402 can be applied for total reaction volume check. In some embodiments, the calibration curves used in the vessel volume detection device 402 are established between pixel distances and colorimetric volume results obtained using a spectrophotometer. In other embodiments, the calibration curves used in the vessel volume detection device 402 are established between pixel distances and alkaline phosphatase reaction results obtained using a photon counting module. In yet other embodiments, the calibration curves used in the vessel volume detection device 402 are established using JIG reaction vessel with lines at known volume height on the outside wall. For the residual volume detection (e.g., for a volume greater than 10 μL) in the vessel volume detection device 402, line-finding or gray scale matching can be applicable.

The vessel volume detection device 402 in accordance with an exemplary embodiment of the present disclosure can be used in other various applications. In some embodiments, the vessel volume detection device 402 is used to detect dispensing tip misalignment. For example, the vessel image capture unit 132 is used to determine whether a dispensing tip is off center when the dispensing tip enters the field of view. In other embodiments, the vessel volume detection device 402 is used to detect wheel positioning integrity. For example, the vessel image capture unit 132 is used to determine whether the wash wheel is tilted or mispositioned. In yet other embodiments, the vessel volume detection device 402 is used to detect any abnormal condition like splashes, foaming, or poor magnetization. In yet other embodiments, the vessel volume detection device 402 is used to detect RV integrity, such as scratches, discoloration, and translucency. In yet other embodiments, the vessel volume detection device 402 is used to detect tip alignment integrity.

The light source used in the vessel volume detection device 402 needs not to be located behind a reaction vessel. Other locations of the backlight device are also possible. Alternatively, the light source can be incorporated in the camera unit and configured to illuminate from the camera unit. Such a light source incorporated in the camera unit can be used with a screen which is located behind a reaction vessel, as illustrated herein. In some embodiments, the camera unit used in the vessel volume detection device 402 is configured to monitor a temperature of a vessel and/or a wash wheel using IR spectrum.

As described above, the reaction vessel detection device 706 of the vessel volume detection device 402 can be applied to any container carriage devices other than the wash wheel. As described above, the dispensing adjustment device 704 of the vessel volume detection device 402 can operate to measure levels of substrate volume and use the measured levels to adjust RLU's of test result, fine-tuning the calibration and improving accuracy.

The instrument 100 in accordance with an exemplary embodiment of the present disclosure employs various program solutions to implement the image evaluation operations as described herein, such as pattern matching. In some embodiments, such program solutions are developed using off-the-shelf software solutions. One example of program solutions is In-Sight Explorer Software (also referred to as In-Sight Vision Software), available from Cognex Corporation, Natick, MA.

Figure 40:
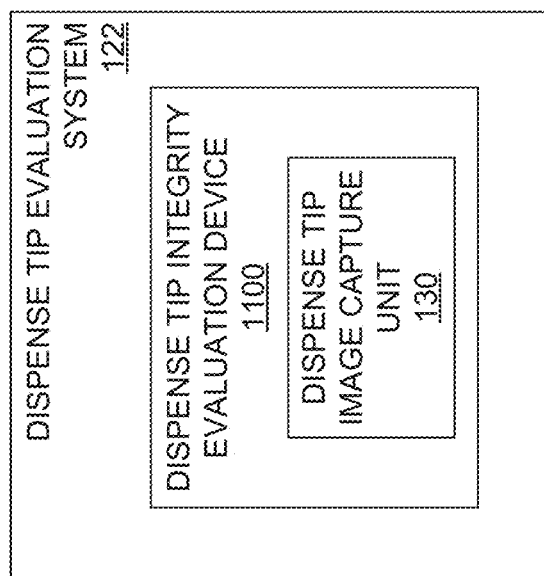
FIG. 40 is a block diagram of an example integrity evaluation system of FIG. 1.

Referring now to FIG. 40 and subsequent figures, an example of the dispense tip evaluation system 122 is described.

FIG. 40 is a block diagram of an example of the dispense tip evaluation system 122 of FIG. 1. In some embodiments, the dispense tip evaluation system 122 includes a dispense tip integrity evaluation device 1100.

The dispense tip integrity evaluation device 1100 operates to evaluate a quality of a fluidic substance 118 aspirated into a dispense tip 112 and an alignment of the dispense tip 112. As described herein, the dispense tip 112 can be of various types and used for different processes. One example of the dispense tip 112 is a pipetting tip that can be used with the sample pipetting device 152. The dispense tip integrity evaluation device 1100 can utilize the dispense tip image capture unit 130. An example of the dispense tip integrity evaluation device 1100 is illustrated and described in more detail with reference to FIG. 41.

Figure 41:
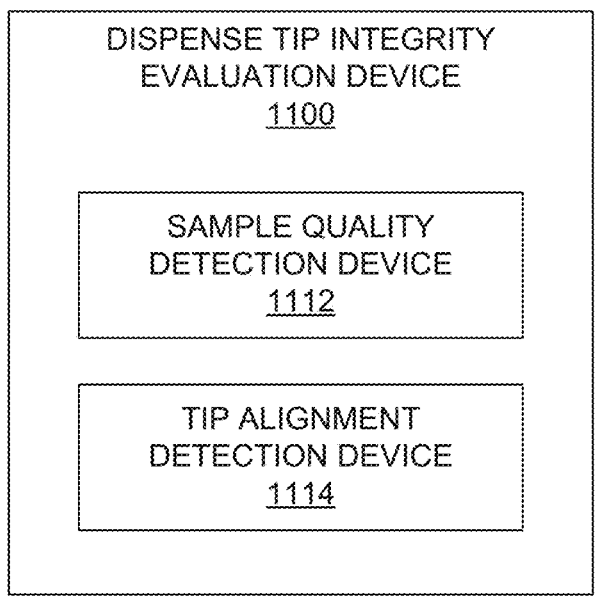
FIG. 41 is a block diagram of an example dispense tip integrity evaluation device of FIG. 40.

FIG. 41 is a block diagram of an example of the dispense tip integrity evaluation device 1100 of FIG. 40. In some embodiments, the dispense tip integrity evaluation device 1100 includes a sample quality detection device 1112 and a tip alignment detection device 1114.

In some embodiments, the dispense tip integrity evaluation device 1100 is implemented with the sample aspiration system 510 of FIG. 10. In other embodiments, the dispense tip integrity evaluation device 1100 can be used in other types of systems operable to aspirate or dispense a fluidic substance with a container.

The sample quality detection device 1112 operates to detect a quality of the sample aspirated into a sample pipetting tip of the sample pipetting device 152. An example of the structure and operation of the sample quality detection device 1112 is described with reference to FIGS. 42-55.

In addition to the detection of sample quality in the dispense tip, the sample quality detection device 1112 can also be used to detect a quality of a fluidic substance 118 contained within a vessel 114. As described herein, the vessel 114 can be of various types and used for different processes. Examples of the vessel 114 include a reaction vessel, a sample vessel, and a dilution vessel, which are used throughout the process in the instrument 100. In some embodiments, the sample quality detection device 1112 can utilize the vessel image capture unit 132.

The tip alignment detection device 1114 operates to detect a tolerance and misalignment of a dispense tip 112 with respect to the sample pipetting module 512 and/or the dispense tip image capture unit 130. An allowable tolerance of the dispense tip 112 and/or a misalignment of the dispense tip 112 can reduce accuracy in detecting aspirated sample volume in the dispense tip 112, as performed by the dispense tip volume detection device 400 herein, for example. The tip alignment detection device 1114 further operates to adjust or correct a detected volume of liquid aspirated in the dispense tip 112 based on the detection of tolerance and misalignment. An example of the structure and operation of the tip alignment detection device 1114 is described with reference to FIGS. 56-68.

With reference to FIGS. 42-55, an example of the sample quality detection device 1112 is described.

Figure 42:
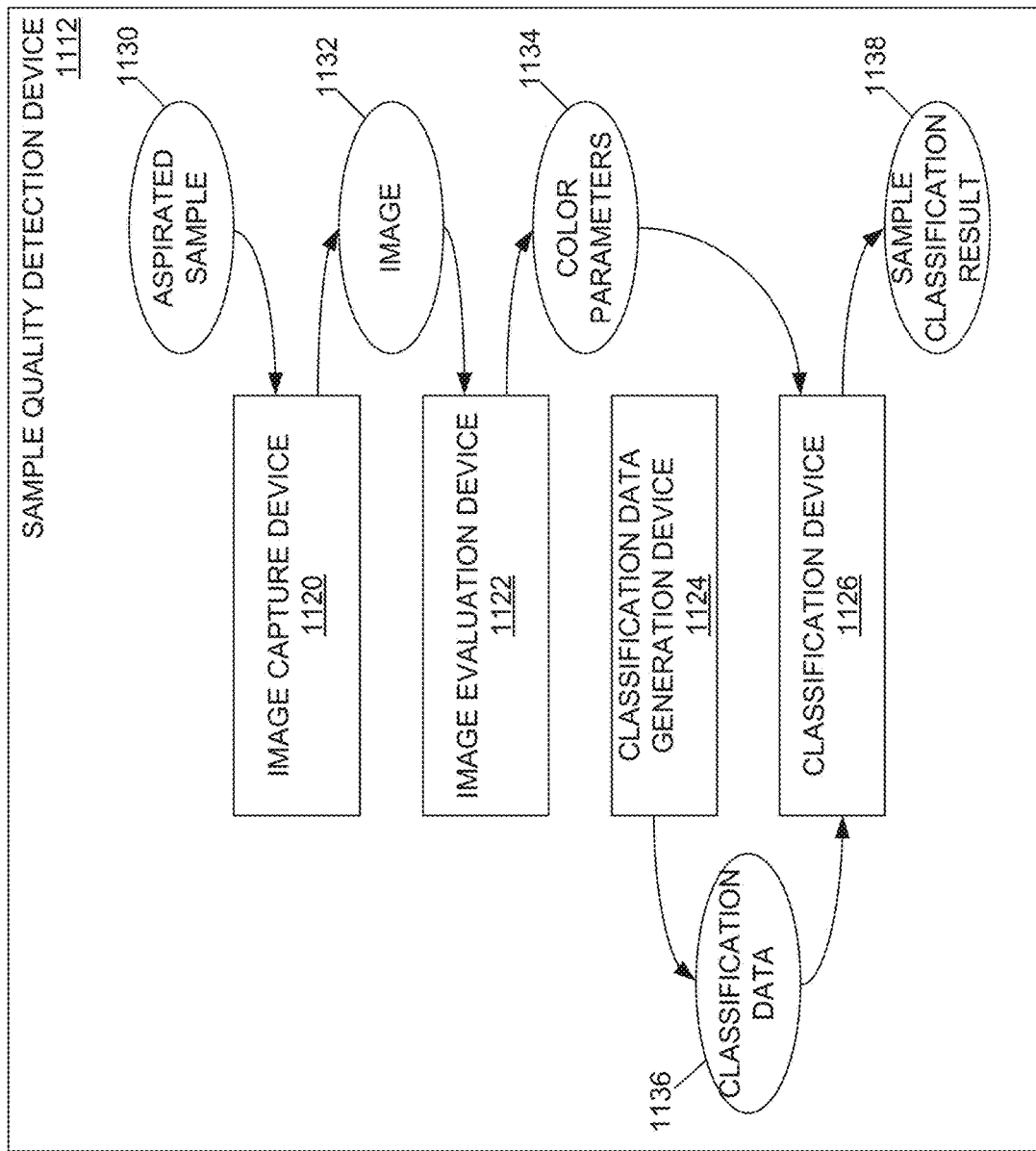
FIG. 42 illustrates an example sample quality detection device.

FIG. 42 illustrates an example of the sample quality detection device 1112. In some embodiments, the sample quality detection device 1112 includes an image capture device 1120, an image evaluation device 1122, a classification data generation device 1124, and a classification device 1126. Also shown are an aspirated sample 1130, an image 1132, one or more color parameters 1134, classification data 1136, and a sample classification result 1138.

The sample quality detection device 1112 operates to evaluate the quality of a sample aspirated with a dispense tip and determine whether the sample has a sufficient quality for subsequent analysis. If the sample quality is determined to be compromised, the instrument can inform a user of the sample quality and/or stop the test.

In some embodiments, a sample (e.g., the sample 324 in FIG. 4) provided in a sample tube contains various interference substances, or interferents, that can compromise the sample integrity and impact laboratory tests. Such a sample containing interferents greater than a tolerable level can cause erroneous, but believable, results, which cannot be easily detected. For chemistry and immunoassay systems, examples of the interferents include hemoglobin, bilirubin (also referred to herein as icterus, which is a medical condition caused by bilirubin), and lipid (also referred to herein as lipemia, which is a medical condition caused by lipid). Depending on the assay, the concentrations of hemoglobin, icterus, and lipemia should be limited to predetermined levels to ensure that no interference occurs causing a skewed result.

Various methods have been used to evaluate sample quality. Some examples of such methods include chemistry analyzers using spectrophotometers. Using such a spectrophotometer to determine sample quality is an independent event from a chemistry analysis of a sample, and thus may require an additional sample to determine the sample integrity, depending on the manufacturer. Since the spectrophotometer uses specific wavelengths for measurement, the system requires either LED or collimated light sources and uses complex mathematical processing due to spectral overlap of interferents with the end-products of some assays. Also, highly lipemic samples often exhibit volume displacement which can affect the sample volume in a test. As such, the methods for evaluating the sample quality have required a separate test for doing so and caused additional costs. As a result, a primary sample test is delayed because the primary sample test can be performed only after the quality check. Alternatively, where the primary sample test and the sample quality test are run simultaneously, the compromised sample can only be flagged during or after the primary sample test. In this case, a sample needs to be redrawn, which also causes a delay in test results.

In contrast, the sample integrity detection device 1112 is incorporated with the instrument 100 and uses various components of the instrument 100 that are configured for analysis of samples. Therefore, the single instrument can both evaluate the quality of a sample and perform analysis of the sample, without causing the delay and additional cost.

As described above, in some embodiments, the sample integrity detection device 1112 is used with the sample aspiration system 510 of FIG. 10. In other embodiments, the sample integrity detection device 1112 can be used in other types of systems operable to aspirate a fluidic substance with a container.

In the illustrated example, the sample integrity detection device 1112 is described primarily in the context of an immunoassay analyzer, as illustrated in FIGS. 2 and 4. For example, the sample integrity detection device 1112 operates to detect the concentration of interferents, such as hemoglobin, icterus, and lipemia, in a sample aspirated in a dispense tip. In other embodiments, however, the sample integrity detection device 1112 is used to evaluate the quality of a sample in other types of instruments.

In general, the sample integrity detection device 1112 acquires an image of a clear conical shaped container with a fluid inside. The sample integrity detection device 1112 then extracts information about respective pixels within a region of interest in the image. The information about the pixels is used to classify the fluid. The sample integrity detection device 1112 includes a classifier model that employs classifiers used to group fluids into categories. If the color of the fluid aspirated in the container is not within predetermined specifications, the aspiration, or the test, is flagged. In some embodiments, an operator of the instrument receives the information about the fluid aspiration when the fluid integrity is determined to be outside the specifications for the given fluid.

Figure 45:
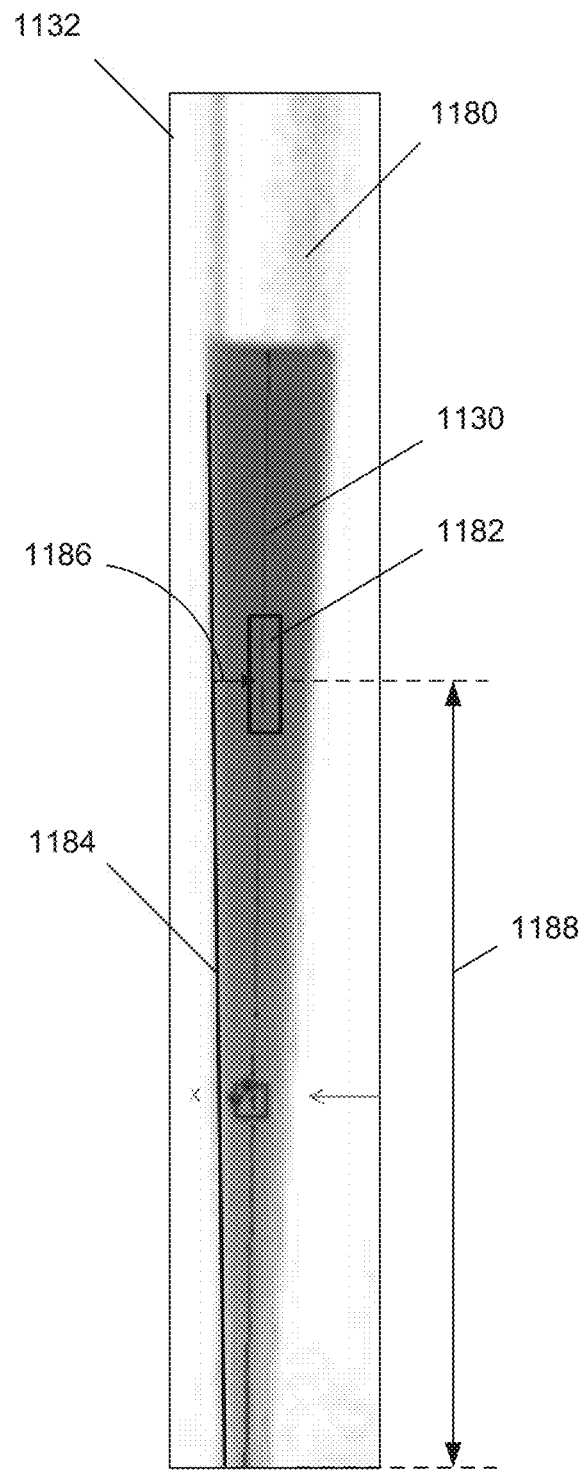
FIG. 45 illustrates an example analysis of a captured image.

Referring still to FIG. 42, the image capture device 1120 operates to capture an image 1132 of a sample 1130 aspirated with a dispense tip 1180 (FIG. 45). In some embodiments, the sample 1130 is an example of the sample 540, and the dispense tip 1180 is an example of the dispense tip 112, as shown in FIG. 10. In some embodiments, the image capture device 1120 operates to capture more than one image of a sample 1130 aspirated with a dispense tip 1180 at varying time intervals. For example, the image capture device 1120 operates to sequentially capture two images of the sample 1130 aspirated with a dispense tip 1180 at approximately thirty (30) milliseconds apart, or any other time interval. In some embodiments, the image capture device 1120 utilizes the dispense tip image capture unit 130, which includes the camera unit 550 and the light source 552. In some embodiments, the light source 552 of the image capture device 1120 generates a white back light. In other embodiments, the light source 552 provides one or more colored back lights, which can be either fixed or variable during image capturing. In some embodiments, the light source 552 can generate back light with different exposure times. For example, the light source 552 can generate back light with an exposure time of approximately six (6) milliseconds, and the image capture device 1120 operates to capture a first image immediately after the exposure time of approximately six (6) milliseconds, and a second image at approximately thirty (30) seconds. In one embodiment, the first image is obtained at approximately 0.2 second after the reagent is dispensed into the container. In an embodiment, the second image is obtained after approximately 6.5 seconds of mixing. In a further embodiment, the first image is obtained at approximately 0.2 second after the reagent is dispensed into the container, and wherein the second image is obtained after approximately 6.5 seconds of mixing. Varying exposure times may improve the evaluation of the captured image for color parameters. For example, if a sample has a high concentration, then a longer exposure time would likely result in a brighter image so that the image evaluation device 1122 can effectively evaluate for different color parameters.

The image evaluation device 1122 operates to process and evaluate the captured image 1132 and generate one or more color parameters 1134. The color parameters 1134 are used to determine the concentration levels of interferents contained in the sample 1130. An example of the image evaluation device 1122 is illustrated and described in more detail with reference to FIGS. 44-48.

The classification data generation device 1124 operates to generate classification data 1136. As described below, the classification data 1136 include a list of classification labels for different amounts of interferents, which are used by the classification device 1126 to generate a sample classification result 1138. An example of the classification data generation device 1124 is illustrated and described in more detail with reference to FIGS. 49-53.

The classification device 1126 operates to generate a sample classification result 1138 based on the color parameters 1134 and the classification data 1136. The sample classification result 1138 includes information indicative of the quality of the sample 1130. For example, the sample classification result 1138 includes information representative of the concentration levels of the interferents, such as hemoglobin, icterus, and lipemia, in the aspirated sample 1130, and indicates that the concentration levels of the interferents, either individually or in combination, are acceptable. Thus, the sample classification result 1138 is used to determine whether the sample 1130 has a sufficient quality for laboratory analysis in the instrument 100. An example of the classification device 1126 is illustrated and described in more detail with reference to FIGS. 54-55.

Figure 43:
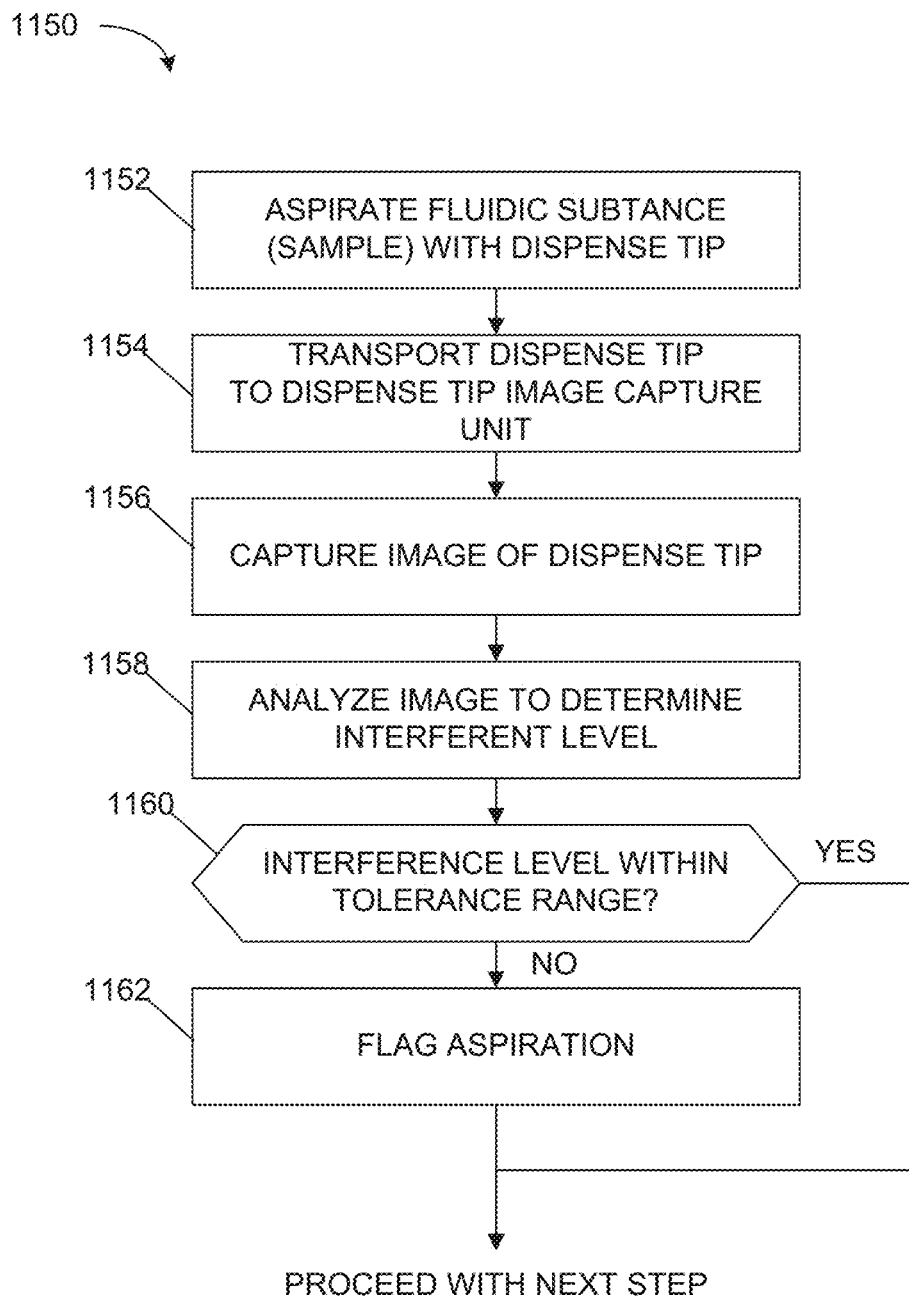
FIG. 43 is a flowchart illustrating an example method for operating the sample quality detection device of FIG. 42.

FIG. 43 is a flowchart illustrating an example method 1150 for operating the sample integrity detection device 1112. In some embodiments, the method 600 is performed by the sample aspiration system 510 (FIG. 10) and the sample integrity detection device 1112.

In general, the method 1150 performs analysis of a sample quality in a dispense tip in terms of the concentration of interferents, such as hemoglobin, icterus (bilirubin), and lipemia, and flags test results if the evaluated quality is classified outside of an acceptance range.

At operation 1152, the sample aspiration system 510 operates to aspirate a fluidic substance, such as a sample 1130, into a dispense tip 1180 (FIG. 45) (which is an example of the dispense tip 112 as shown in FIG. 10) as programmed.

At operation 1154, the sample aspiration system 510 transports the dispense tip 1180 containing the aspirated sample 1130 to the image capture device 1120 (which includes the dispense tip image capture unit 130). In some embodiments, the dispense tip image capture unit 130 of the image capture device 1120 is arranged to capture an image of the dispense tip 1180 after aspiration without transportation.

At operation 1156, the dispense tip image capture unit 130 captures an image 1132 of the dispense tip 1180. In some embodiments, the image 1132 of the dispense tip 1180 is a digital image of a predetermined resolution. In some embodiments, the dispense tip image capture unit 132 can capture more than one image of the dispense tip 1180 at varying time intervals. For example, the dispense tip image capture unit 132 can capture two images of the dispense tip 1180 at approximately thirty (30) milliseconds apart, or any other time interval. At operation 1158, the sample integrity detection device 1112 analyzes the image 1132 to determine the level of interferents in the sample 1130 within the dispense tip 1180. An example of the operation 1158 is described in more detail with respect to FIGS. 44-55.

At operation 1160, the sample integrity detection device 1112 determines whether the interferent level falls within a tolerance range. When the determined level is outside a tolerance range, the aspiration of the sample 1130 in the dispense tip 112 is considered to be inappropriate. The tolerance range can vary depending on the type of sample and/or the types of interferents therein. In some embodiments, whether the determined interferent level falls within the tolerance range can be evaluated using classification identifiers or classifiers, as described below.

When the detected interferent level is determined to fall within the tolerance range ("YES" at the operation 1160), the method 1150 proceeds to perform a predetermined next step. Otherwise ("NO" at the operation 1160), the method 1150 moves on to operation 1162.

At operation 1162, the sample integrity detection device 1112 flags the aspiration to indicate that the aspirated sample 1130 in the dispense tip 1180 is not appropriate for subsequent processes. In other embodiments, the entire test result that has used the aspirated sample can be flagged to indicate or suggest that the test result can be improper. Alternatively, the sample integrity detection device 1112 operates to stop an associated test or analytic process in the instrument 100. In other embodiments, the evaluation result can be used to automatically adjust a test result that may be erroneous due to the compromised sample quality.

With reference to FIGS. 44-55, an example of the operation 1158 of FIG. 43, in which a captured image 1132 is analyzed and the quality of the sample aspirated in the dispense tip is determined, is described. In some embodiments, the operation 1158 is performed by the image evaluation device 1122, the classification data generation device 1124, and the classification device 1126 of the sample integrity detection device 1112.

Figure 44:
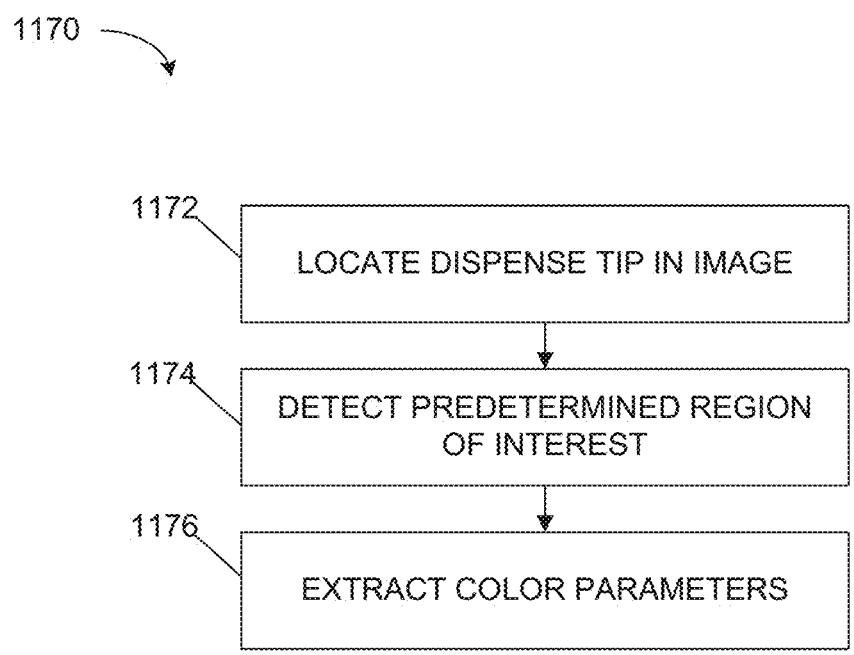
FIG. 44 is a flowchart illustrating an example method of operating an image evaluation device of FIG. 42.

FIG. 44 is a flowchart illustrating an example method 1170 of operating the image evaluation device 1122 of FIG. 42. In some embodiments, the method 1170 includes operations 1172, 1174, and 1176. The method 1170 is described with also reference to FIG. 45, which illustrates an example analysis of a captured image 1132.

At operation 1172, the image evaluation device 1122 locates a dispense tip 1180 in the image 1132. Various image processing methods can be used to detect the location of the dispense tip 1180 in the image 1132. In some embodiments, the dispense tip 1180 is located by pattern matching function, which searches a pattern representative of the dispense tip based on a pre-trained reference image. Such image processing methods can be implemented in various programming languages, such as Python (e.g., a contour finding function thereof). One example method for such image processing methods can be implemented by Cognex In-Sight Vision Software, available from Cognex Corporation (Natick, MA), which provides various tools, such as edge detection ("Edge"), pattern matching ("Pattern Match"), and histogram analysis ("Histogram").

At operation 1174, the image evaluation device 1122 detects a predetermined region of interest 1182. The region of interest 1182 is a region of the image 1132 that is evaluated to determine the quality of the sample 1130 in the dispense tip 1180. The region of interest 1182 is preset as a region that is repeatedly detectable as including samples 1130 in different images 1132. Various methods can be used to detect the region of interest 1182. One example of such methods is described with reference to FIG. 46. In some embodiments, there can be more than one predetermined region of interest and thus, the image evaluation device 1122 detects more than one predetermined region of interest. For example, there can be three predetermined regions of interest, a first region of interest above the region of interest 1182, a second region of interest such as the region of interest 1182, and a third region of interest below the region of interest 1182.

At operation 1176, the image evaluation device 1122 extracts color parameters 1134 (FIG. 42) for the captured image 1132. In some embodiments, the region of interest 1182 in the image 1132 is analyzed to generate the color parameters 1134. One example of extracting color parameters is described with reference to FIGS. 47 and 48.

Figure 46:
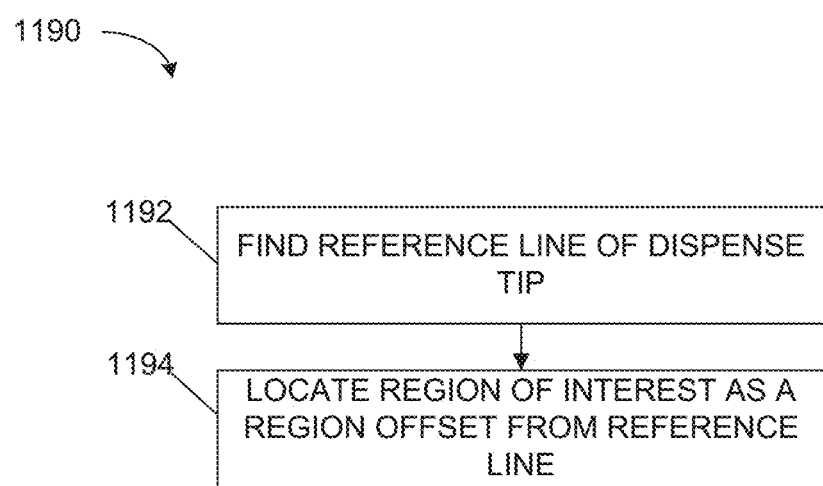
FIG. 46 is a flowchart illustrating an example method for finding a region of interest in the image.

FIG. 46 is a flowchart illustrating an example method 1190 for finding the region of interest 1182 in the image 1132. In some embodiments, the method 1190 includes operations 1192 and 1194. The method 1190 is described with also reference to FIG. 45.

In general, once the location of the dispense tip 1180 is determined, the image evaluation device 1122 uses a set of offset factors to determine the region of interest 1182. In some embodiments, the region of interest 1182 is optimized to include a subsection of the dispense tip image that is roughly central to the vertical and horizontal axes of the sample 1130 in the dispense tip 1180, so that the region of interest 1182 is generally at the center to the aspirated sample 1130. In other embodiments, other locations are possible for the region of interest 1182. In other embodiments, there can be more than one region of interest, as previously articulated.

At operation 1192, the image evaluation device 1122 finds a reference line associated with the dispense tip 1180. In some embodiments, the reference line is a longitudinal edge 1184 of the dispense tip 1180 in the image 1132. Other lines of the dispense tip 1180 can be used as the reference line.

At operation 1194, the image evaluation device 1122 locates a region that is located apart from the reference line 1184 by a predetermined offset 1186. In some embodiments, the predetermined offset 1186 determines a horizontal position of the region of interest 1182 while a vertical position of the region of interest 1182 is preset as a predetermined height 1188 from the bottom of the image 1132. In some embodiments, the vertical position of the region of interest remains generally identical among different images since the image capture unit is arranged repeatedly at a sample height relative to dispense tips.

One example of image processing methods used above can be implemented by Cognex In-Sight Vision Software, available from Cognex Corporation (Natick, MA), which provides various tools, such as edge detection ("Edge"), pattern matching ("Pattern Match"), and histogram analysis ("Histogram").

Figure 47:
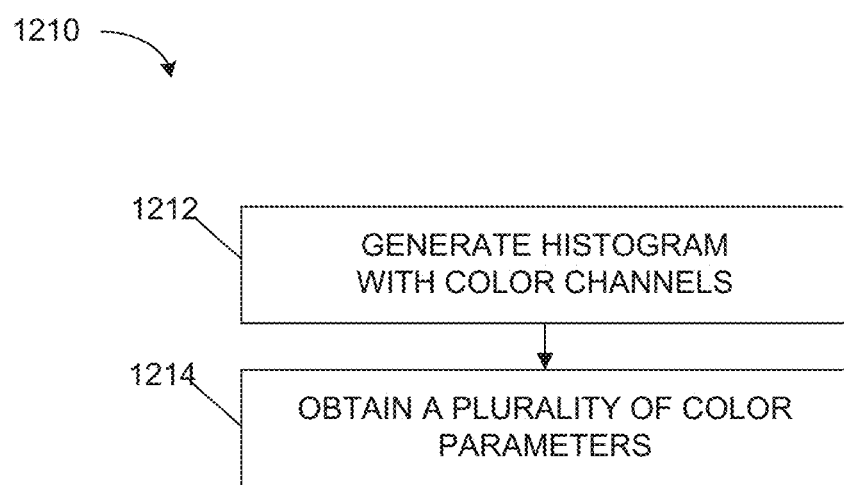
FIG. 47 is a flowchart of an example method for extracting color parameters for the image.

FIG. 47 is a flowchart of an example method 1210 for extracting color parameters for the image 1132. The method 1210 is described with also reference to FIG. 48, which illustrates an example histogram 1220 for the image 1132. In some embodiments, the method 1210 includes operations 1212 and 1214.

At operation 1212, the image evaluation device 1122 generates a histogram 1220 for the image 1132. In some embodiments, the histogram 1220 is generated from data for the region of interest 1182 in the image 1132. In some embodiments, there are more than one region of interest, and therefore, the image evaluation device 1122 generates a histogram 1120 for each region of interest in the image 1132. For example, if there are three regions of interest in the image 1132, then the image evaluation device 1122 generates three respective histograms.

Figure 48:
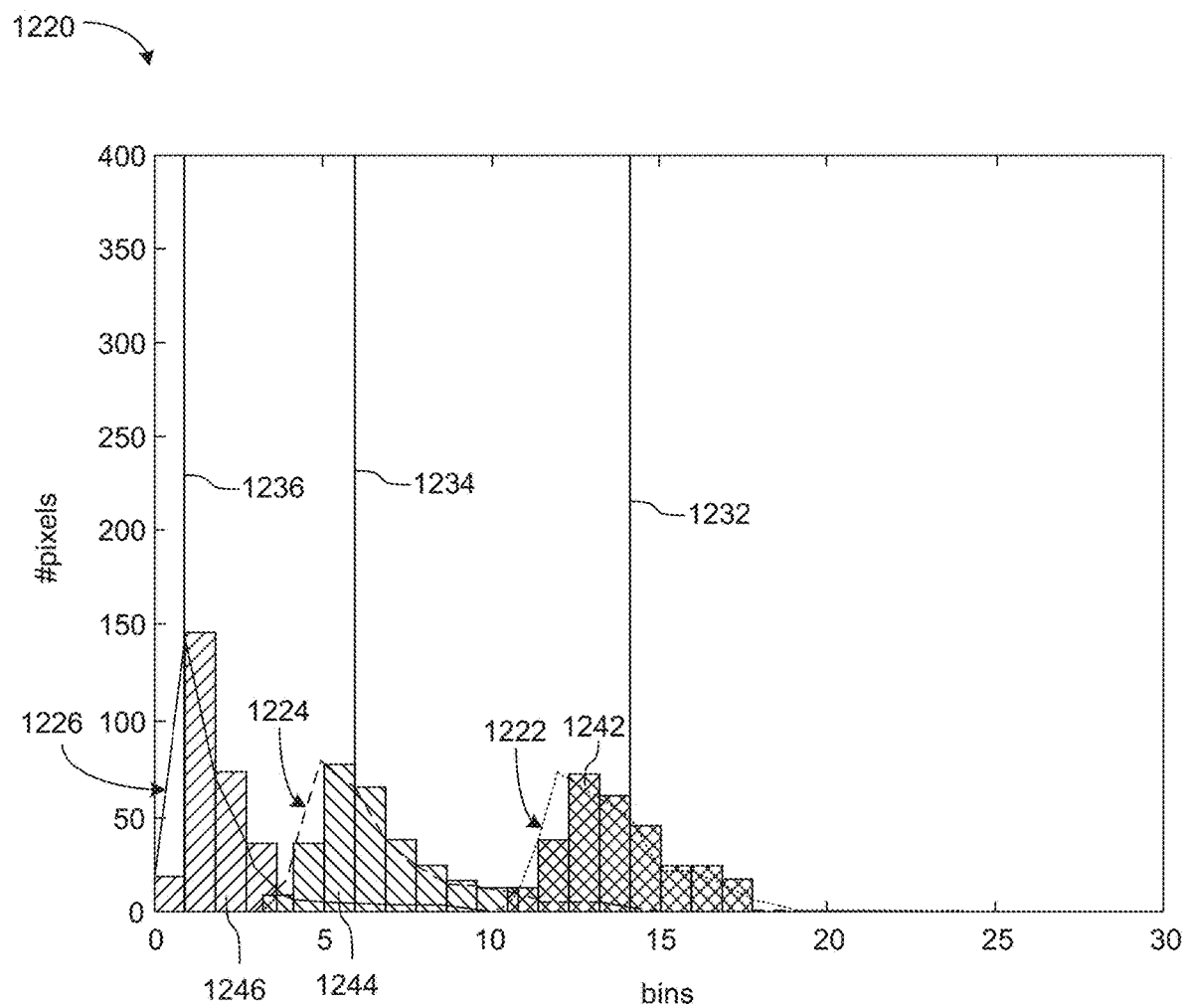
FIG. 48 illustrates an example histogram for the image.

As illustrated in FIG. 48, the histogram 1220 represents the distribution of different colors in the image 1132 (e.g., the region of interest 1182 thereof). In some embodiments, the histogram 1220 shows the number of pixels that have colors in each of a fixed list of color ranges (also referred to herein as bins). The histogram 1220 can be built for any type of color space. In the illustrated example, the RGB color model is used. In other embodiments, the CMYK color model and any other color models can be used.

The histogram 1220 can be produced first by discretizing the colors (i.e., red, green, and blue in the RGB model) in the image 1132 (e.g., the region of interest 1182 thereof) into a number of bins, and counting the number of pixels in each bin. For example, where the image 1132 is an 8-bit image, the values of zero to 255 for each color are grouped into a plurality of bins such that each bin includes a range of ten values. By way of example, a first bin includes values equal to and greater than zero and less than 10, a second bin includes values equal to and greater than 10 and less than 20, a third bin includes values equal to and greater than 20 and less than 30, etc. As illustrated in FIG. 48, a first color channel 1222, a second color channel 1224, and a third color channel 1226, which respectively represent the red, green, and blue components in the RGB model, are depicted in the histogram 1220. In other embodiments, different color components in the RGB model, CMYK color model, or any other color models can be used. In other embodiments, the image can be a different bit, such as 15-bit color, 16-bit color, 24-bit color, 30-bit color, 36-bit color, 48-bit color, or any other bit value.

At operation 1214, the image evaluation device 1122 obtains a plurality of color parameters 1134 from the histogram 1220. In some embodiments, the image evaluation device 1122 creates six color parameters. For example, a first color parameter 1232 is the mean of the first color channel 1222, a second color parameter 1234 is the mean of the second color channel 1224, and a third color parameter 1236 is the mean of the third color channel 1226. Further, a fourth color parameter 1242 is the Riemann sum of the first color channel 1222, a fifth color parameter 1244 is the Riemann sum of the second color channel 1224, and a sixth color parameter 1246 is the Riemann sum of the third color channel 1226. The Riemann sums of the first, second, and third color channels 1222, 1224, and 1226 represent the areas under the curves for the first, second, and third color channels 1222, 1224, and 1226, respectively.

In other embodiments, other color parameters are generated from the histogram 1220. For example, the color parameters can include a maximum of the first color channel 1222, a maximum of the second color channel 1224, a maximum of the third color channel 1226, a minimum of the first color channel 1222, a minimum of the second color channel 1224, a minimum of the third color channel 1226, a mode of the first color channel 1222, a mode of the second color channel 1224, a mode of the third color channel 1226, a histogram head of the first color channel 1222, a histogram head of the second color channel 1224, a histogram head of the third color channel 1226, a histogram tail of the first color channel 1222, a histogram tail of the second color channel 1224, a histogram tail of the third color channel 1226, a histogram head percentage of the first color channel 1222, a histogram head percentage of the second color channel 1224, a histogram head percentage of the third color channel 1226, a histogram tail percentage of the first color channel 1222, a histogram tail percentage of the second color channel 1224, and a histogram tail percentage of the third color channel 1226. A histogram head specifics the smallest grey scale value of the histogram. For example, a histogram head of the first color channel 1222 specifies the smallest grey scale value of the first color channel 1226 in the histogram. A histogram tail specifies the largest grey scale value of the histogram. For example, a histogram tail of the first color channel 1222 specifies the largest grey scale value of the first color channel 1226 in the histogram. A histogram head percentage specifies the percentage of the total pixels in the histogram that exist within a specified range of greyscale values that have the lowest grey scale values. For example, a histogram head percentage of the first color channel 1222 specifies the percentage of the total pixels of the first color channel 1222 in the histogram that exist within a range of the lowest grey scale values of the first color channel 1222. A histogram tail percentage specifies the percentage of the total pixels represented in the histogram that exist within a specified range of greyscale values that have the highest grey scale values. For example, a histogram tail percentage of the first color channel 1222 specifies the percentage of the total pixels of the first color channel 1222 in the histogram that exist within a range of the highest grey scale values of the first color channel 1222.

In other embodiments, the color parameters include the means of the color channels (e.g., the first, second, and third color channels), the peaks of the color channels (e.g., the first, second, and third color channels), and/or the standard deviations of the color channels (e.g., the first, second, and third color channels). In yet other embodiments, other types of color parameters are used.

Figure 49:
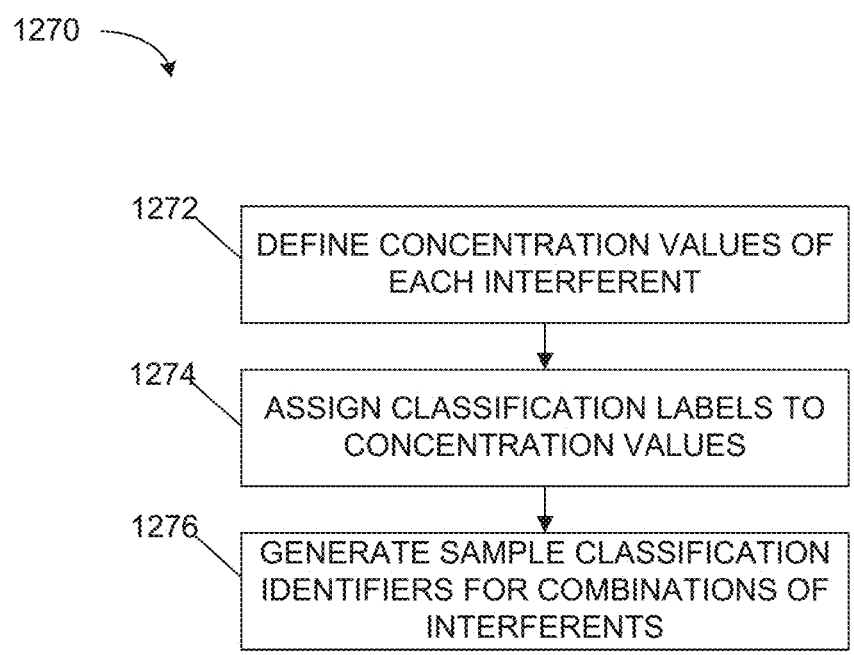
FIG. 49 is a flowchart of an example method for operating a classification data generation device of FIG. 42.
Figure 51:
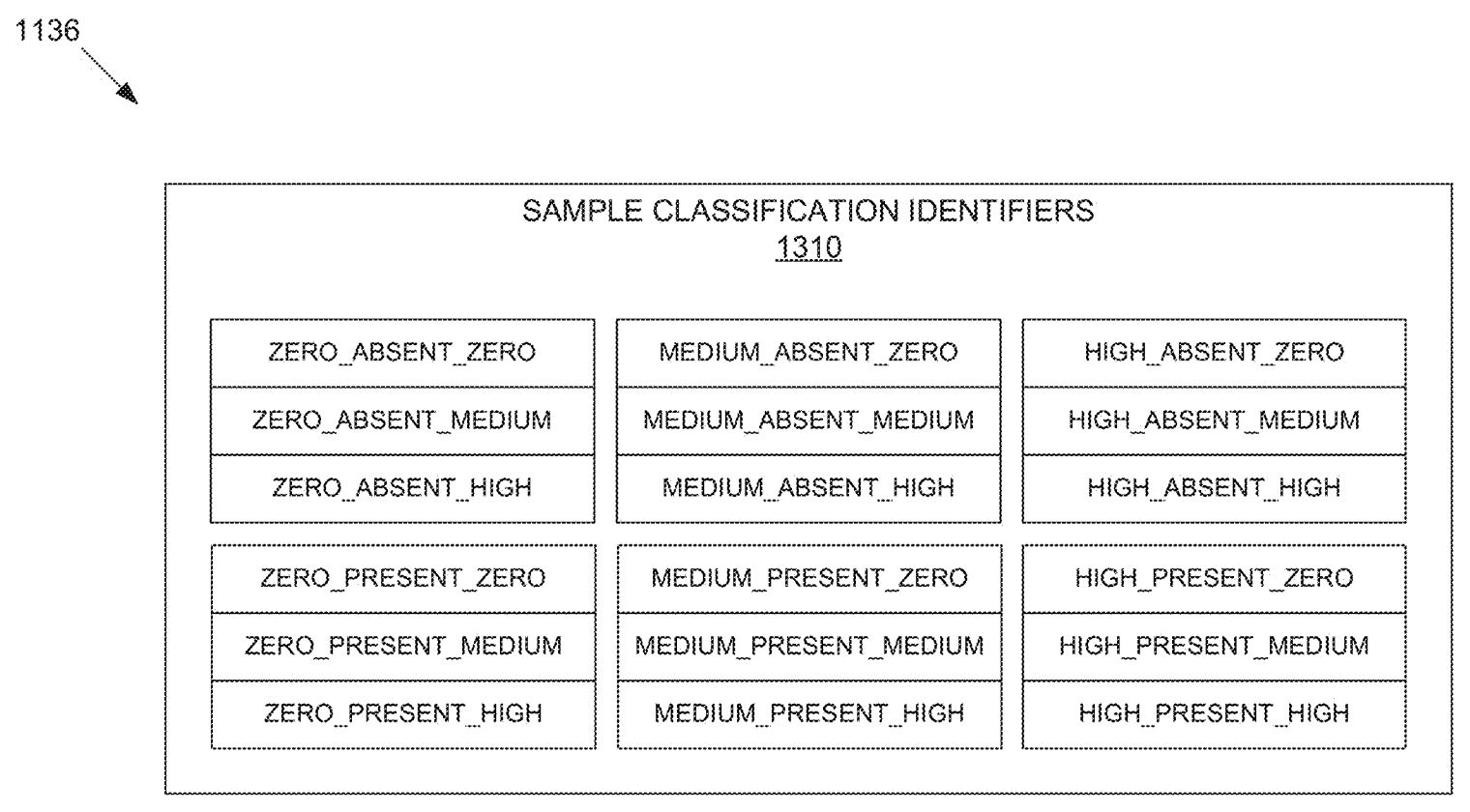

FIG. 49 is a flowchart of an example method 1270 for operating the classification data generation device 1124 of FIG. 42. The method 1270 is described with reference to FIGS. 50 and 51. FIG. 50 is an example table 1278 illustrating that interferent values are parsed into classification labels, and FIG. 51 is an example set of sample classification identifiers 1310 that can serve as outputs from the classification device 1126 of FIG. 42.

In some embodiments, as described below, the different levels of sample qualities are classified into a plurality of target variables, which are also referred to herein as sample classification identifiers. In particular, the classification device 1126 determines the quality of a sample as one of the sample classification identifiers. The classification data generation device 1124 operates to generate the sample classification identifiers for a particular interferent or a particular set of interferents. In some embodiments, the sample classification identifiers are constructed by first parsing interferent values for a particular sample into a set of labels based on the concentration values for individual interferents. The set of labels for the interferents are then combined into a single set of labels (i.e., sample classification identifiers) that classifies the ranges of all of the interferents in the sample.

Referring still to FIG. 49, at operation 1272, the classification data generation device 1124 defines concentration values of each interferent. By way of example, as illustrated in FIG. 50, three interferents, which are a first interferent 1280, a second interferent 1282, and a third interferent 1284, are evaluated for a sample 1130 aspirated in a dispense tip. Concentration values 1290, 1292, and 1294 are defined for the interferents 1280, 1282, and 1284, respectively. In some embodiments, the concentration values are defined as one or more discrete concentration values. In other embodiments, the concentration values are defined as a range of concentration value.

For example, three concentration values 1290 (e.g., Value(s) 1-1, Value(s) 1-2, and Value(s) 1-3) are defined for the first interferent 1280, three concentration values 1292 (e.g., Value(s) 2-1, Value(s) 2-2, and Value(s) 2-3) are defined for the second interferent 1282, and three concentration values 1294 (e.g., Value(s) 3-1, Value(s) 3-2, and Value(s) 3-3) are defined for the third interferent 1284. In other embodiments, other numbers of concentration values are defined for the same or different interferents.

At operation 1274, the classification data generation device 1124 assigns classification labels 1300, 1302, and 1304 to concentration values 1290, 1292, and 1294. In the same example, the concentration values 1290 for the first interferent 1280 are assigned three classification labels 1300, such as ZERO, MEDIUM, and HIGH. The concentration values 1292 for the second interferent 1282 are assigned two classification labels 1302, such as ABSENT and PRESENT. The concentration values 1294 for the third interferent 1284 are assigned three classification labels 1304, such as ZERO, MEDIUM, and HIGH. Other embodiments of classification labels are also possible. For example, in other embodiments, the concentration values 1292 for the second interferent 1282 can be assigned three classification labels such as ZERO, MEDIUM, and HIGH, similar to the three classification labels 1300 and 1304. In other embodiments, the concentration values 1290 and 1294 can be assigned classifications labels, such as ABSENT and PRESENT, similar to the two classification labels 1302.

At operation 1276, the classification data generation device 1124 generates a list of sample classification identifiers 1310 based on different combinations of interferent concentration values. The sample classification identifiers 1310 are used to generally represent the level, or concentration, of a combination of all interferents in question. As described below, the sample classification identifiers 1310 serve as target variables for the classification device 1126 or outputs from the classification device 1126.

As illustrated in FIG. 51, the list of sample classification identifiers 1310 includes all of the possible combinations of classification labels 1300, 1302, and 1304. An example notation of sample classification identifiers 1310 is a combination of a classification label 1300 for the first interferent 1280, a classification label 1302 for the second interferent 1282, and a classification label 1304 for the third interferent 1284 in order. In the illustrated example, since there are three classification labels (e.g., ZERO, MEDIUM, and HIGH) for the first interferent 1280, two classification labels (e.g., ABSENT and PRESENT) for the second interferent 1282, and three classification labels (e.g., ZERO, MEDIUM, and HIGH) for the third interferent 1284, there can be 18 (=3×2×3) sample classification identifiers 1310. The sample classification identifiers are also referred to herein as sample classifiers. Other sample classification identifiers are also possible. For example, the second interferent 1282 can have three classification labels (e.g., ZERO, MEDIUM, and HIGH) instead of two classification labels (e.g., ABSENT and PRESENT).

FIG. 50 illustrates an example of a color parameter data table 1320 for a mixture of three interferents, each interferent having five values. In the illustrated example, the first interferent 1280 is hemoglobin, the second interferent 1282 is icterus (bilirubin), and the third interferent 1284 is lipemia (lipid) where the instrument 100 is an immunoassay analyzer. By way of example, the first interferent 1280 is divided into three segments with five values, such as 0 mg/dL for Value(s) 1-1 with a classification label 1300 of ZERO, 250 and 500 mg/dL for Value(s) 1-2 with a classification label 1300 of MEDIUM, and 750 and 1000 mg/dL for Value(s) 1-3 with a classification label 1300 of HIGH. The second interferent 1282 is divided into three segments with five values, such as 0 mg/dL for Value(s) 2-1 with a classification label 1302 of ABSENT, 10 and 20 mg/dL for Value(s) 2-2 with a classification label 1302 of PRESENT, and 30 and 40 mg/dL for Values(s) 2-3 with a classification label 1302 of PRESENT. In other embodiments, the second interferent 1282 can be divided into three segments with five values, such as 0 mg/dL for Value(s) 2-1 with a classification label 1302 of ZERO, 10 and 20 mg/dL for Value(s) 2-2 with a classification label 1302 of MEDIUM, and 30 and 40 mg/dL for Values(s) 2-3 with a classification label 1302 of HIGH. The third interferent 1284 is divided into three segments with five values, such as 0 mg/dL for Value(s) 3-1 with a classification label 1304 of ZERO, 125 and 250 mg/dL for Value(s) 3-2 with a classification label 1304 of MEDIUM, and 375 and 500 mg/dL for Value(s) 3-3 with a classification label 1304 of HIGH.

Figure 52:
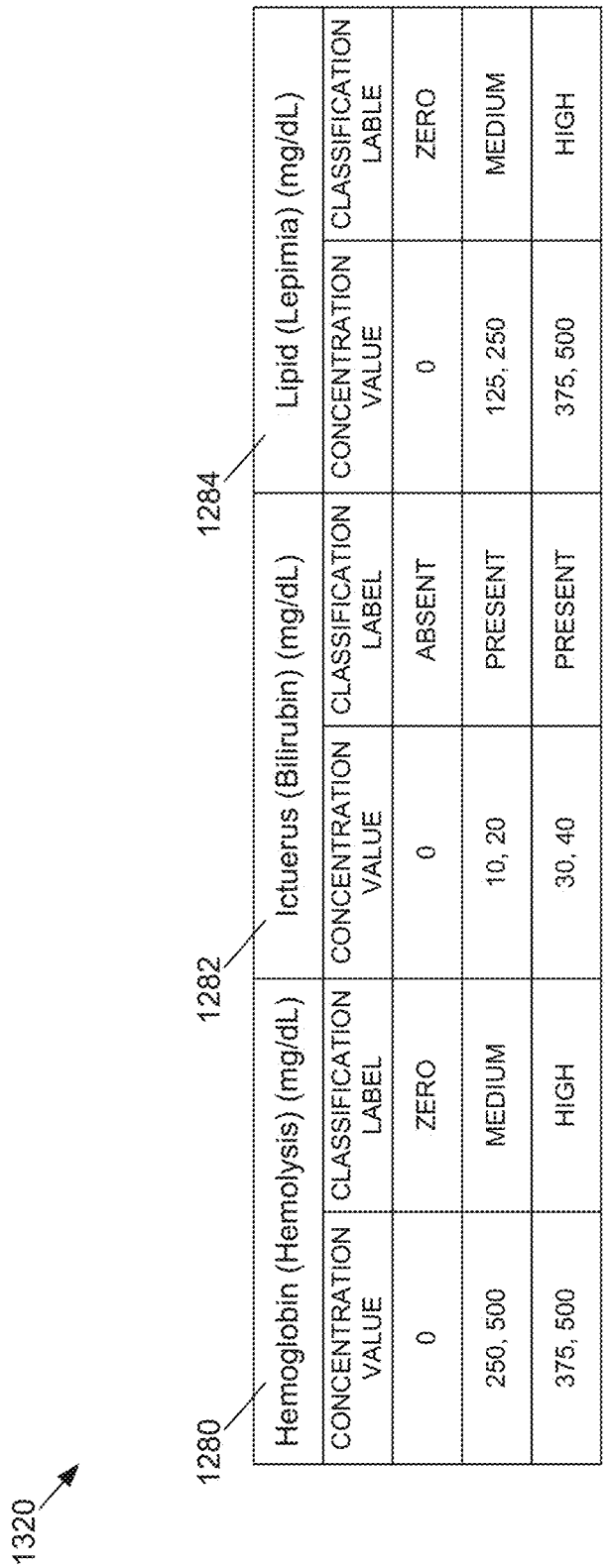
FIG. 52 illustrates an example color parameter data table for three interferents.
Figure 53:
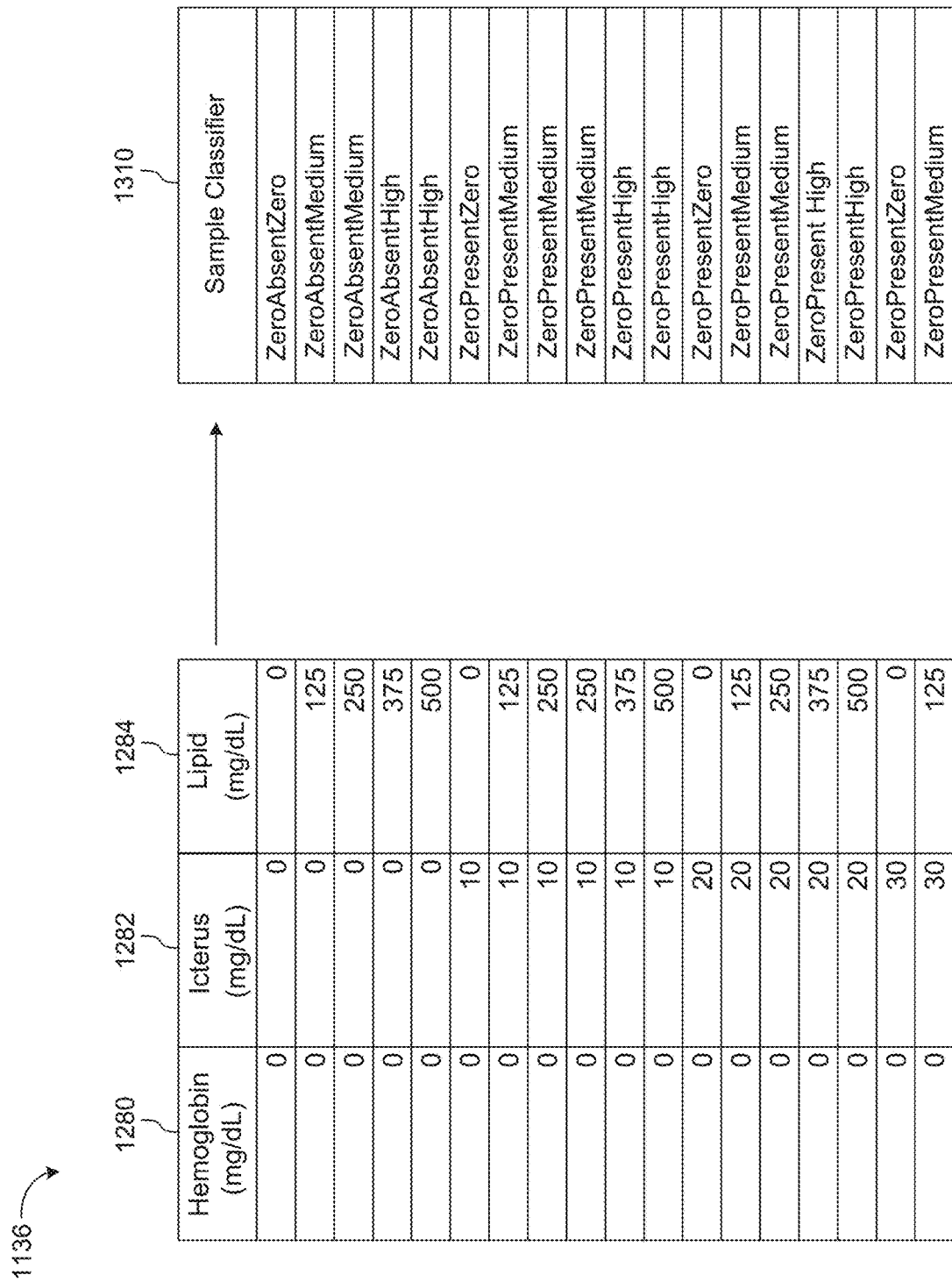
FIG. 53 shows an example set of sample classifiers from combinations of first, second, and third interferents as shown in FIG. 52.
Figure 54:
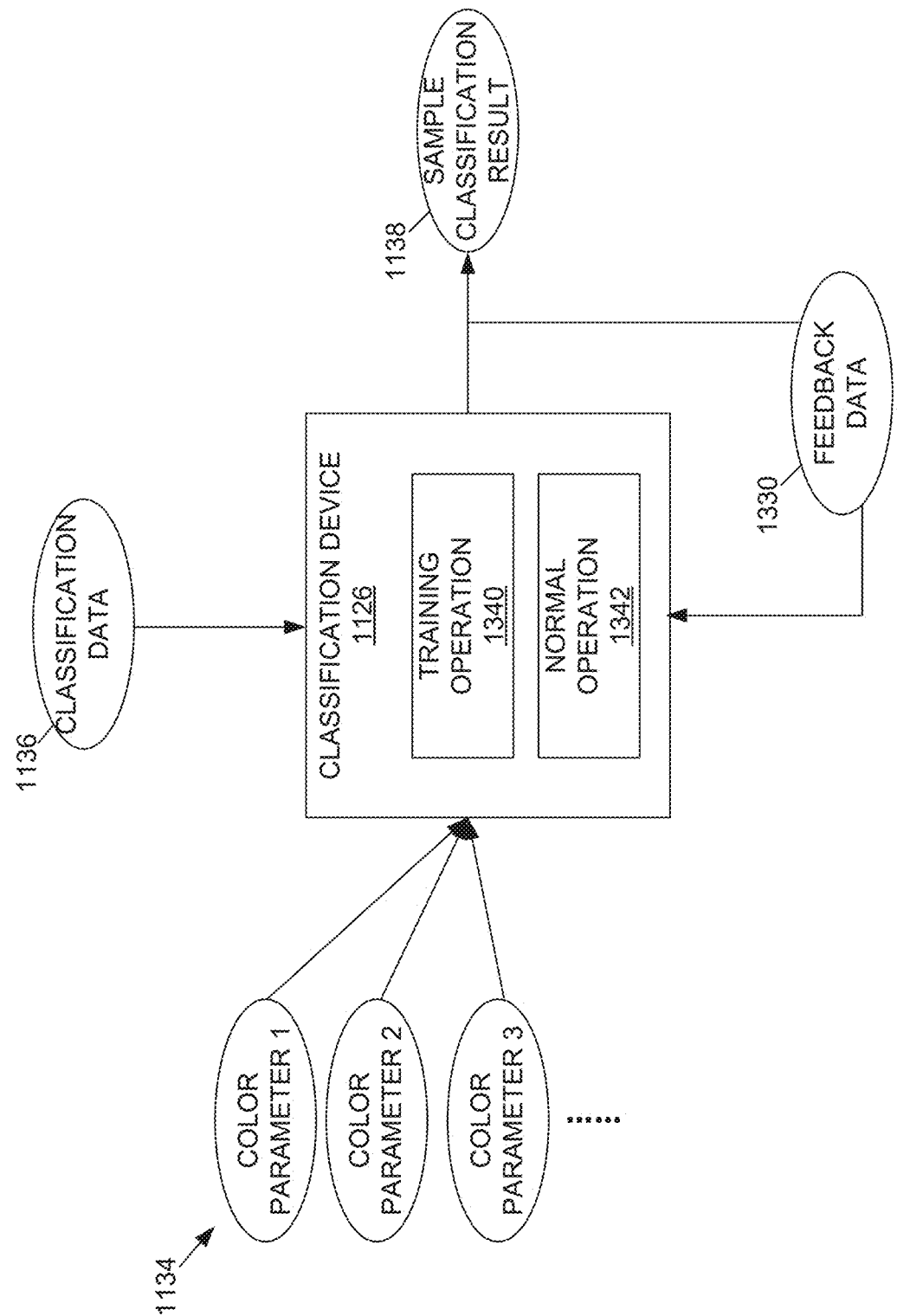
FIG. 54 is a block diagram that schematically illustrates an example classification device of FIG. 42.

FIG. 53 shows an example set of sample classifiers 1310 that are predicted to be outputted from combinations of the first, second, and third interferents as shown in FIG. 52. The classifiers 1310 in FIG. 53 illustrate only some of the possible outputs based on the first, second, and third interferents as shown in FIG. 52. The notation of sample classifiers 1310 are created as described with reference to FIG. 51. For example, where lipid exists 0 mg/dL in a sample ("ZERO" in the table 1320), 10 mg/dL of icterus is included in the sample ("PRESENT" in the table 1320), and 375 mg/dL of hemoglobin is included in the sample ("HIGH" in the table 1320), the sample classifier 1310 is designated as "ZeroPresentHigh." Other sample classifiers 1310 are also possible. For example, where lipid exists 0 mg/dL in a sample ("ZERO" as the classification label), where 10 mg/dL of icterus is included in the sample, it can have a classification label of "MEDIUM" instead of "PRESENT", and 375 mg/dL of hemoglobin is included in the sample ("HIGH" as the classification label), the sample classifier 1320 would be designated as "ZeroMediumHigh." By way of further example, where lipid exists 0 mg/dL in a sample ("ZERO" as the classification label), where 0 mg/dL of icterus is included in the sample, it can have a classification label of "ZERO" instead of "ABSENT", and 375 mg/dL of hemoglobin is included in the sample ("HIGH" as the classification label), the sample classifier 1320 would be designated as "ZeroZeroHigh." FIG. 54 is a block diagram that schematically illustrates an example of the classification device 1126 of FIG. 42. As described above, the classification device 1126 operates to receive one or more of the color parameters 1134 and generate a sample classification result 1138. The classification device 1126 further receives the classification data 1136 to generate the sample classification result 1138. In some embodiments, the classification device 1126 generates feedback data 1330. As described herein, the classification device 1126 is incorporated in the instrument 100 so that no separate device is needed to evaluate the sample quality.

In some embodiments, the color parameters 1134 includes at least one of the color parameters 1232, 1234, 1236, 1242, 1244, and 1246 as described above. In other embodiments, the classification device 1126 utilizes all of the color parameters 1232, 1234, 1236, 1242, 1244, and 1246. In yet other embodiments, the classification device 1126 uses other types of color parameters.

In some embodiments, the classification device 1126 operates to process the color parameters 1134 and select one from the list of sample classification identifiers 1310 as the sample classification result 1138. The sample classification result 1138 includes one of the sample classification identifiers 1310, which generally indicates the sample quality or integrity. As such, the output of the sample quality detection device 1112 is not a quantifiable number of the amount or concentration of interferents contained in a sample. Rather, the sample quality detection device 1112 outputs a classifier (i.e., a classification identifier), which is a simple indication of the sample quality.

Where a sample contains a plurality of interferents in question, such interferents can cause spectral overlap such that one interferent affects detection of the other interferents. For example, where hemoglobin (red or the like), bilirubin (yellow or the like), and lipid (white or the like) are interferents in a sample, the absorptions with respect to hemoglobin, bilirubin, and lipid at least partially overlap and thus make it difficult to distinguish between the interferents. Accordingly, it is desirable to simplify the sample quality result by using a sample classifier, as opposed to outputting specific amounts or concentrations of interferents.

In some embodiments, the classification device 1126 uses the feedback data 1330 adapted to improve the operation of the classification device 1126. The feedback data 1330 can include information about the correlation between the inputted color parameters 1134 and the outputted sample classification result 1138. The feedback data 1330 is fed back and used to improve future operations by further training the classification device 1126.

In some embodiments, the classification device 126 employs a machine learning model. For example, the classification device 126 uses a support vector machine (SVM) model, which is a supervised learning model with one or more associated learning algorithms that analyze data used for classification. Other models are also possibly used in other embodiments, such as logistic regression, neural networks, convolutional neural networks, and classification trees.

As illustrated in FIG. 54, some embodiments of the classification device 1126 perform a training operation 1340 and a normal operation 1342. In the training operation 1340, the classification device 1126 that employs a SVM training algorithm builds a model from a set of training example samples, each marked for belonging to one of sample classifications. The model assigns new examples into one classification or the other, making it a non-probabilistic binary linear classifier. An SVM model is a representation of examples as points in space, mapped so that the examples of the separate classifications are divided by a clear gap that is as wide as possible. New examples are then mapped into the same space and predicted to belong to a classification based on which side of the gap they fall in. Alternatively to a linear classification, the SVM model can perform a non-linear classification using kernel methods (e.g., radial basis function), mapping their inputs into high-dimensional feature spaces. For example, a SVM model constructs a hyper-plane or a set of hyper-planes in a high or infinite dimensional space, which can be used for classification. Good separation is achieved by the hyper-plane that has the largest distance to the nearest training data points of any class, since, in general, the larger the margin is, the lower the generalization error of the classifier is.

In the illustrated example herein, the dimensional space for the SVM is constructed from the RGB profile described above, resulting in a six-dimensional predictor space corresponding to the six color parameters. As described above, the target variable for the classification is constructed by parsing the measured interferent values (e.g., hemoglobin, icterus, and lipemia, which are collectively referred to herein as HIL) for each sample into a set of labels based on the concentration range for the individual HIL data. The sample labels for each interferent are combined into a single label that classifies the ranges of all three HIL components. It is this overall sample classification label that serves as the target variable for the SVM classifier.

In some embodiments, the SVM classifier is tuned with a hyper-parameter known as 'nu,' which regularizes the number of support vectors and training errors. The classifier is implemented in, for example, Python using the Sci-Kit Learn module, which has built-in support for Nu-regularized SVM classifiers (such as "sklearn.svm.NuSvc").

Once the SVM model is established in the training operation 1340, the classification device 1126 is ready for the normal operation 1342, in which the quality of a patient sample is evaluated for laboratory analysis in the instrument 100 at site. In some embodiments, the classification device 1126 is pretrained before the instrument 100 is installed at a customer's site. In other embodiments, the classification device 1126 continues to be updated with the feedback data 1330 in the normal operation 1342. In yet other embodiments, the classification device 1126 is configurable by a customer.

FIG. 55 is an example data set 1350 of sample classification results 1138 and associated flagging results 1352. As described with reference to FIG. 43, the sample integrity detection device 1112 generates a flagging result to indicate whether the aspirated sample 1130 has an appropriate quality for subsequent processes (the operation 1162 of FIG. 43). As illustrated in FIG. 55, one or more of the sample classification results 1138 are considered to indicate that the associated samples do not have sufficient quality for laboratory analysis in the instrument 100. The samples associated with such sample classification results 1138 can be flagged to indicate the compromised quality of the samples. By way of example, the data set 1350 illustrates which sample classification result represents a sample that needs to be flagged.

As described in FIGS. 42-55, the sample quality detection device 1112 operates to transform a complex variable space (associated with a plurality of color parameters) to a simple output (including a sample classifier) representative of the sample quality. The outputted sample classification result 1138 is used to inform a user whether the sample has been properly prepared so as to have an adequate quality or integrity for laboratory analysis.

The sample quality detection device 1112 can be modified to be suitable for various applications. For example, the sample quality detection device 1112 is applicable for any in-vitro diagnostic analyzer, for any sample tube or reaction vessel, and for any container shape. In some embodiments, the image evaluation device 1122 of the sample quality detection device 1112 need not use a predefined region of interest for image processing. The camera unit of the image capture device 1120 can be of any type or quality. The sample quality detection device 1112 in accordance with an exemplary embodiment can use a consumer-level camera unit, such as cameras accompanied with mobile devices. The light source used in the image capture device 1120 can be located in any position. In some embodiments, the classification device 1126 can be trained onsite at customer locations. In yet other embodiments, the classification device 1126 can be adapted by a learning algorithm to adjust the performance, based on the customer's unique population of patient samples and interferent (e.g., HIL) values.

Referring to FIGS. 56-68, an example of the tip alignment detection device 1114 is described.

Figure 56:
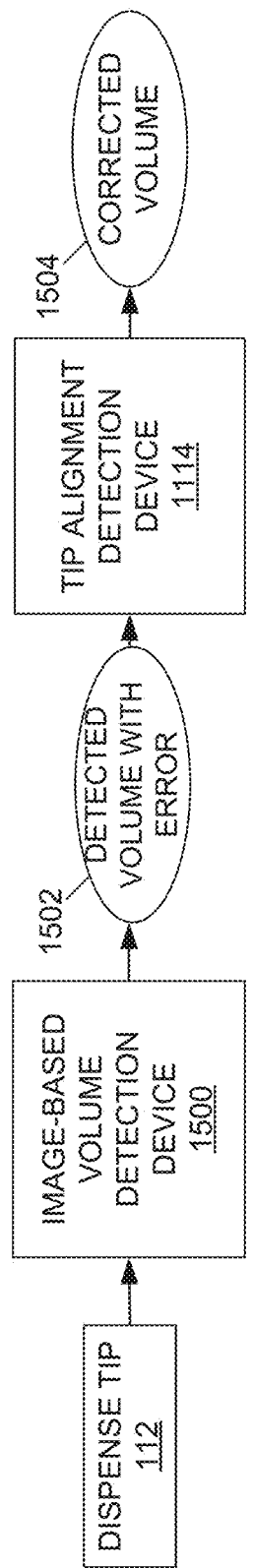
FIG. 56 is a block diagram of an example tip alignment detection device.

FIG. 56 is a block diagram of an example of the tip alignment detection device 1114. The tip alignment detection device 1114 operates to detect a misalignment of a dispense tip 112 and correct a detected volume of liquid substance contained in the dispense tip 112.

In some embodiments, an image-based volume detection device 1500 operates to capture an image of the dispense tip 112 that has aspirated a liquid substance, such as a sample, and calculate a volume of the liquid substance based on the image of the dispense tip 112. An example of the image-based volume detection device 1500 includes the dispense tip volume detection device 400 as described herein. For example, as described herein, the sample pipetting device 152 is used to aspirate a sample into the dispense tip 112, and the dispense tip volume detection device 400 captures an image of the dispense tip using the dispense tip image capture unit 130, and calculates the volume of aspirated sample by analyzing the captured image.

Figure 57:
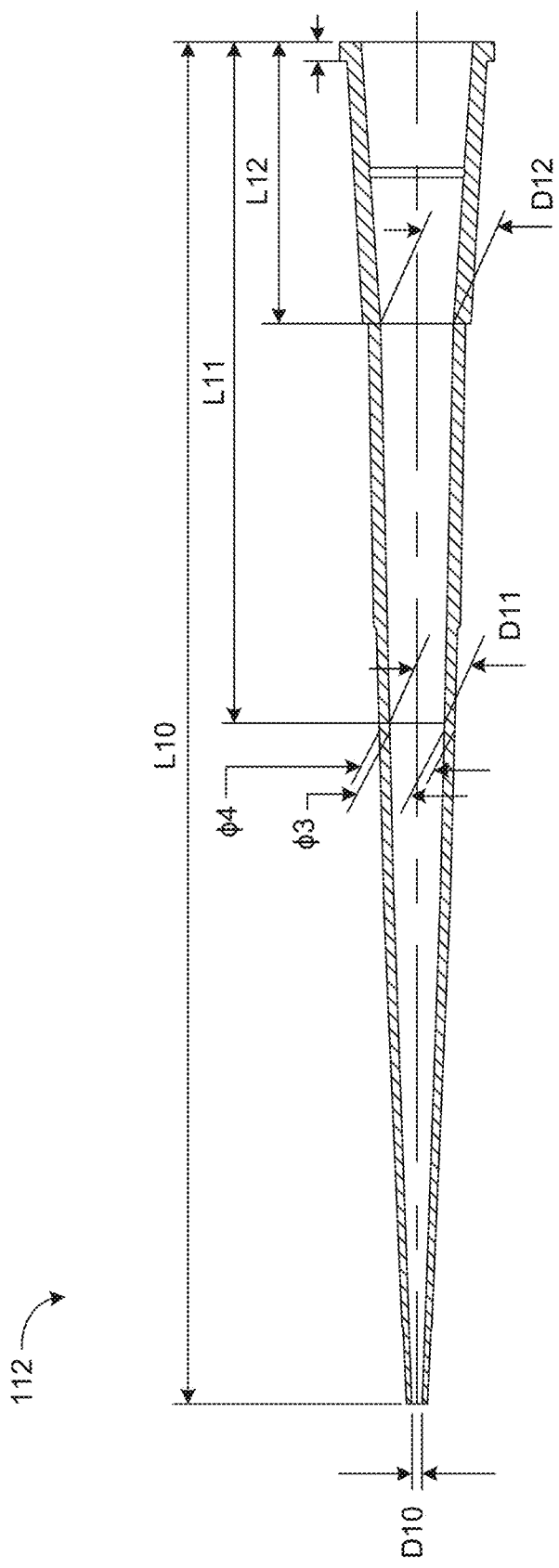
FIG. 57 is a cross sectional view of an example dispense tip, illustrating possible tolerances in the dispense tip.
Figure 58:
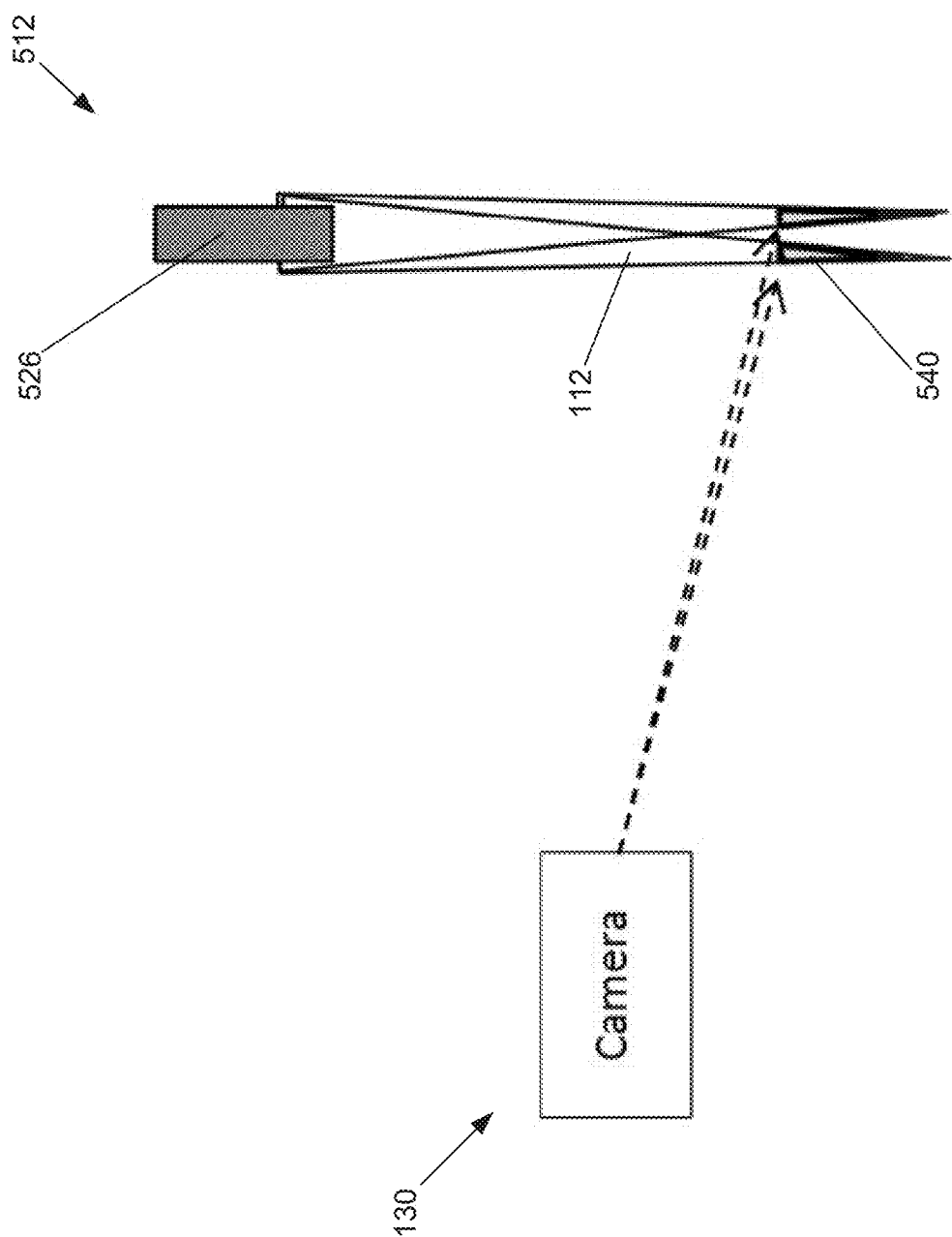
FIG. 58 schematically illustrates an example misalignment of a dispense tip.

In some embodiments, the detected volume of liquid substance (e.g., sample) in the dispense tip 112 is not always accurate due to various sources of tolerance and misalignment as described in FIGS. 57 and 58. Accordingly, the volume 1502 is detected with some errors.

The tip alignment detection device 1114 operates to at least detect a misalignment of the dispense tip 112 with respect to the sample pipetting module 512 and/or the dispense tip image capture unit 130. The misalignment of the dispense tip 112 causes errors in detecting aspirated sample volume in the dispense tip 112. The tip alignment detection device 1114 operates to correct the substance volume detected by the image-based volume detection device 1500 (e.g., the dispense tip volume detection device 400) and provide a corrected volume of aspirated substance 1504.

As described herein, the tip alignment detection device 1114 and the image-based volume detection device 1500 can be part of the instrument 100, and therefore are operated in connection with the systems, devices, components, engines, and other parts of the instrument 100 as described herein.

FIG. 57 is a cross sectional view of an example of the dispense tip 112, illustrating possible tolerances in the configuration of the dispense tip 112. The dispense tip 112 is designed with allowable tolerances in one or more dimensions. Some of such dimensions include lengths L10, L11, and L12, and widths or diameters D10, D11, and D12. The tolerances allowed for the dispense tip 112 can affect a volume of substance contained with the dispense tip 112.

FIG. 58 schematically illustrates an example misalignment of a dispense tip 112. As illustrated, when a dispense tip 112 (also referred to herein as 112) is engaged with the sample pipetting module 512, such as the mandrel 528 thereof, the dispense tip 112 is not always positioned as desired. In some embodiments, it can be desirable to position the dispense tip 112 vertically, or to be in line with the mandrel 526. However, the dispense tip 112 can be tilted relative to the mandrel 526, and the volume of substance 540 can be viewed differently from the perspective of the dispense tip image capture unit 130. Therefore, the misalignment of the dispense tip 112 may impact accuracy in detecting the volume of substance 540 aspirated in the dispense tip 112.

FIG. 59 illustrates possible types of misalignment of a dispense tip 112. Diagram 1 shows a position of the dispense tip 112 relative to a camera unit of the dispense tip image capture unit 130. While Z-axis is defined as an axis along which the dispense tip 112 generally extends, X-axis is defined as a direction along which the dispense tip 112 can be tilted left to right or right to left side with respect to the camera unit of the dispense tip image capture unit 130, as shown in Diagram 2. When the dispense tip 112 is tilted in the X-axis direction, the misalignment can be represented by a side-misalignment angle C, as shown in Diagram 2 ("side misalignment"). Y-axis is defined as a direction along which the dispense tip 112 can be tilted away from, or toward, the camera unit, as shown in Diagram 3. When the dispense tip 112 is tilted in the Y-axis direction, the misalignment can be represented by a depth-misalignment angle D, as in depicted in Diagram 3 ("depth misalignment"). Such a depth misalignment is not identified from a two-dimensional image captured by the tip image capture unit 130.

FIG. 60A is a cross sectional side view of an example dispense tip 1510 configured to be used with the tip alignment detection device 1114. The dispense tip 1510 in this example is configured similarly to the dispense tip 112 as described with reference to FIGS. 13 and 14. Therefore, the description for the dispense tip 1510 is limited primarily to the differences from the dispense tip 112, and the other descriptions are omitted for brevity.

In this example, the dispense tip 1510 includes a first reference line 1512 and a second reference line 1514, as illustrated better in FIGS. 60B and 60C (which are expanded views of portions of the dispense tip of FIG. 60A). In some embodiments, the first and second references lines 1512 and 1514 are used to detect the side-misalignment of the dispense tip, as described with reference to FIG. 62. In addition, at least one of the first and second reference lines 1512 and 1514 is used to detect the depth-misalignment of the dispense tip, as described in FIG. 62.

In some embodiments, the reference lines 1512 and 1514 are configured to be detectable by the dispense tip image capture unit 130. The reference lines 1512 and 1514 can be formed in various locations of the dispense tip 1510. In some embodiments, the first reference line 1512 is located such that a surface level or meniscus of an aspirated substance is arranged below the first reference line 1512 (i.e., between the first reference line 1512 and the distal end 562 of the dispense tip 1510). In other embodiments, the first reference line 1512 is located such that the meniscus of the aspirated substance is arranged above the first reference line 1512 relative to the distal end 562 (i.e., between the reference line 570 and the proximal end 560). In some embodiments, the first reference line 1512 corresponds to the reference line 570 as shown in FIG. 13.

The second reference line 1514 can be arranged close to the distal end 562 of the dispense tip 1510, relative to the first reference line 1512. By way of example, the first reference line 1512 is located such that a surface line of aspirated substance with 100 μL is arranged below the first reference line 1512 (i.e., between the first reference line 1512 and the distal end 562 of the dispense tip 1510), while the second reference line 1514 is located such that a surface line of aspirated substance with 2 μL is arranged above the second reference line 1512 (i.e., between the first reference line 1512 and the second reference line 1514).

The first and second reference line 1512 and 1514 are provided to the dispense tip 1510 in various manners. In some embodiments, the reference lines are detectable structures, such as projections, ridges, indentations, notches, or any other visible elements formed on the dispense tip. In other embodiments, the reference lines are markers or indicators that are painted or attached on the dispense tip. The reference lines can be integrally formed or molded to the dispense tip. Alternatively, the reference lines are separately made and attached to the dispense tip.

Figure 61:
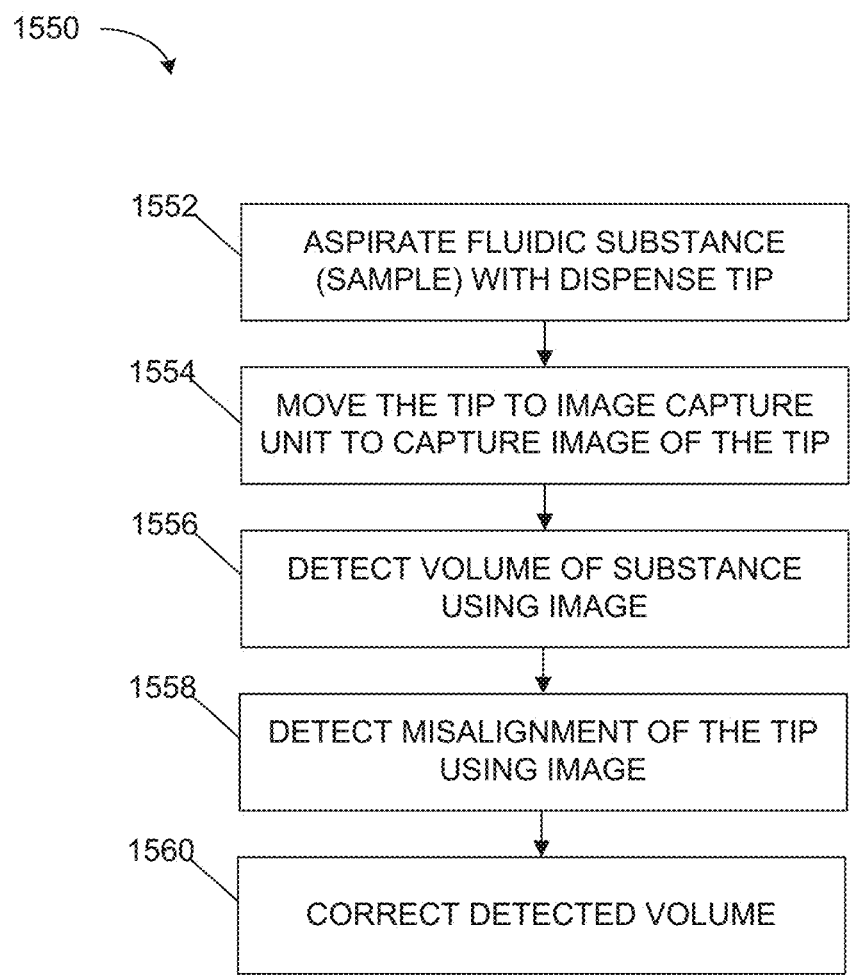
FIG. 61 is a flowchart illustrating an example method for evaluating a dispense tip alignment.

FIG. 61 is a flowchart illustrating an example method 1550 for evaluating a dispense tip alignment. In some embodiments, the method 1550 is performed by the tip alignment detection device 1114. In other embodiments, other part of the instrument 100 can execute the method 1550 together with, or in replacement of, the tip alignment detection device 1114.

At operation 1552, the instrument 100, such as the sample aspiration system 510, aspirates a fluidic substance, such as a sample, into a dispense tip 1510 as programmed.

At operation 1554, the instrument 100, such as the sample aspiration system 510, transports the dispense tip 1510 containing the aspirated sample to the dispense tip image capture unit 130. In some embodiments, the dispense tip image capture unit 130 is arranged to capture an image of the dispense tip after aspiration without transportation. Then, the dispense tip image capture unit 130 captures an image of the dispense tip 1510. In some embodiments, the image of the dispense tip 1510 is a digital image of a predetermined resolution.

At operation 1556, the instrument 100, such as the image-based volume detection device 1500 (e.g., the dispense tip volume detection device 400 or the sample aspiration volume detection device 500, as shown in FIG. 9), detects a volume of the substance in the dispense tip 1510, by analyzing the captured image. One example of the operation 1556 has been described with reference to, for example, FIGS. 16-19.

At operation 1558, the instrument 100, such as the tip alignment detection device 1114, detects a misalignment of the dispense tip 1510 using the captured image. An example of the operation 1558 is described with reference to FIGS. 62-68.

At operation 1560, the instrument 100, such as the tip alignment detection device 1114, operates to correct the detected volume (as detected in the operation 1556) based on the detection of misalignment (as detected in the operation 1558).

Figure 62:
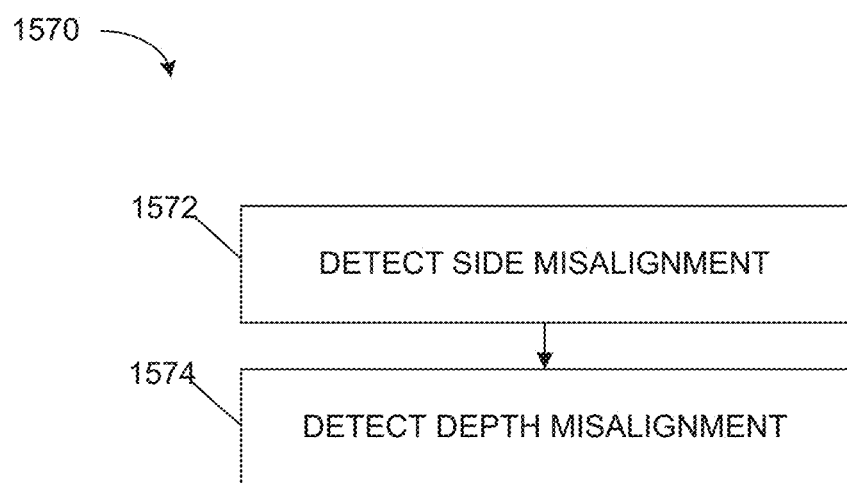
FIG. 62 is a flowchart illustrating an example method for detecting a dispense tip misalignment.

FIG. 62 is a flowchart illustrating an example method 1570 for detecting a dispense tip misalignment. In this method, the tip alignment detection device 1114 can detect a side misalignment as depicted in Diagram 2 of FIG. 59 (at operation 1572), and a depth misalignment as depicted in Diagram 3 of FIG. 59 (at operation 1574).

Figure 63:
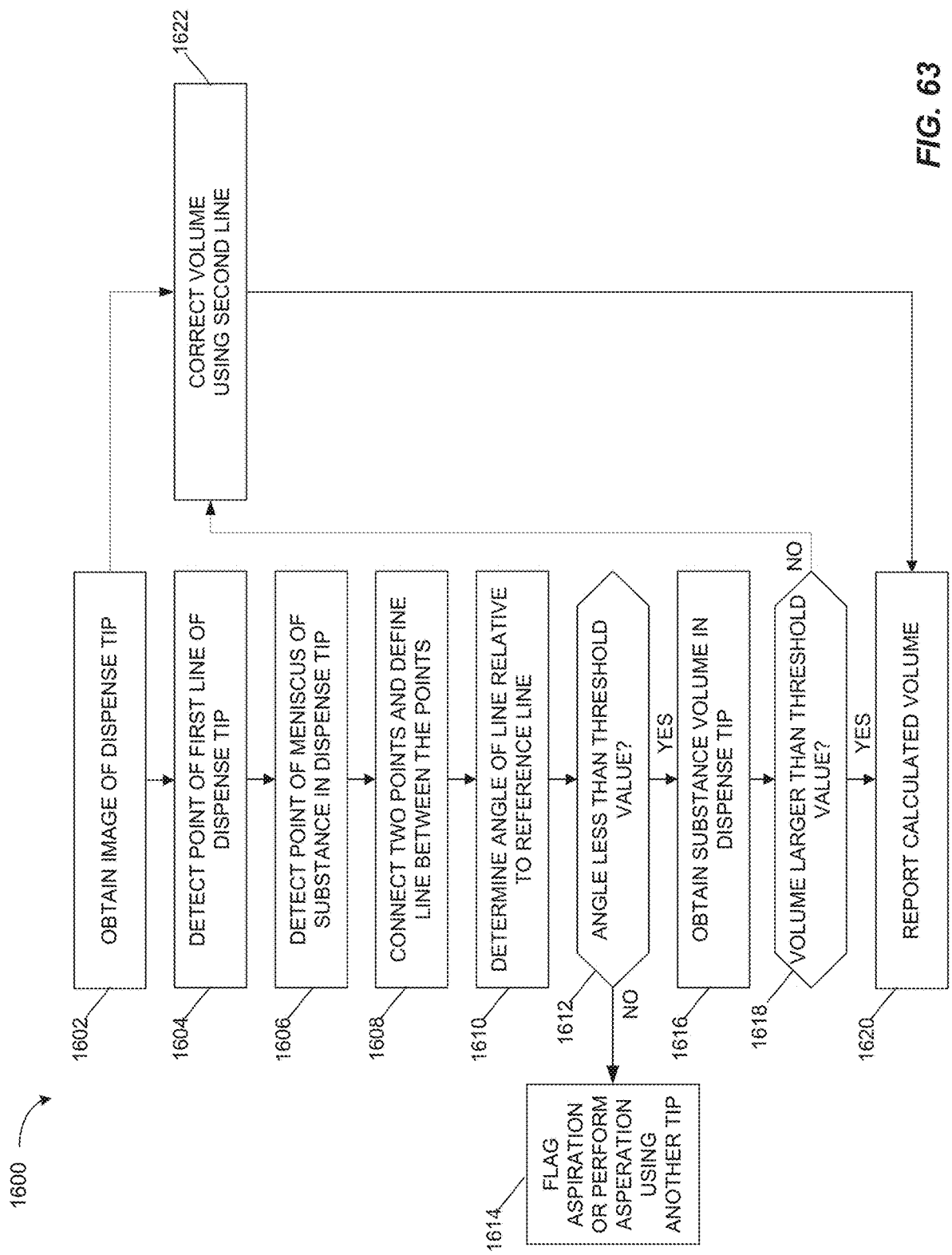
FIG. 63 is a flowchart illustrating another example method for detecting a dispense tip misalignment.
Figure 64:
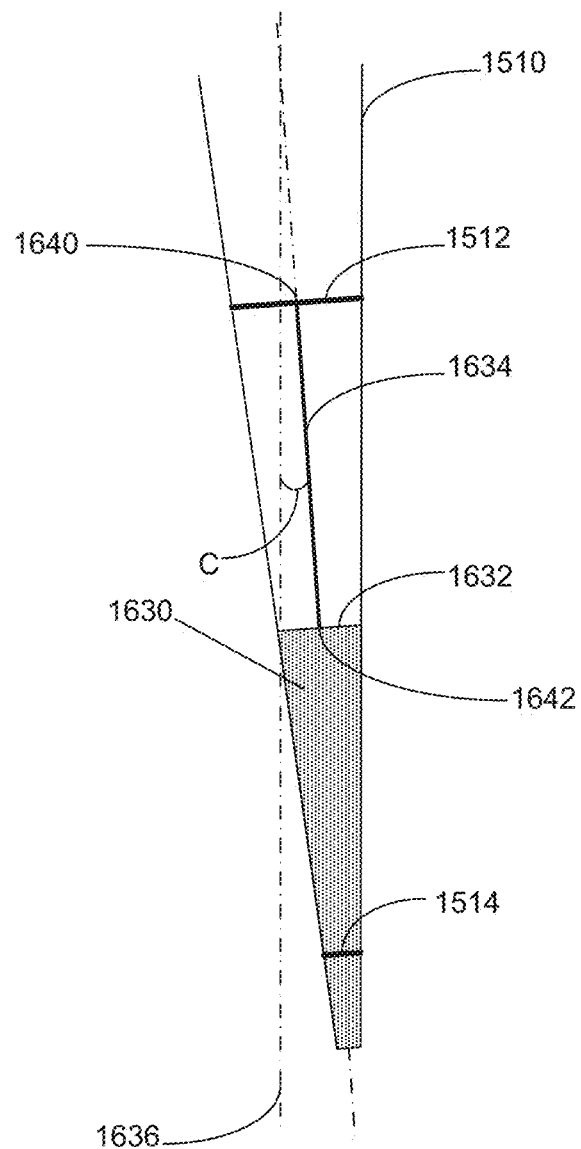
FIG. 64 schematically illustrates an example image showing a side misalignment of the dispense tip.

FIG. 63 is a flowchart illustrating another example method 1600 for detecting a dispense tip misalignment. The method 1600 is described with also reference to FIG. 64, which schematically illustrates an example image showing a side misalignment of the dispense tip.

In this method, the side misalignment can be detected with operations 1602, 1604, 1606, 1608, 1610, 1612, and 1614. The depth misalignment can be detected with operations 1602, 1622, 1624, and 1626. In some embodiments, the side misalignment can be detected as part of volume detection process which is for example performed by the dispense tip volume detection device 400 or the sample aspiration volume detection device 500 as described herein. For example, the operations 1602, 1604, 1606, 1608, and 1616 are identical or similar to some of the operations performed by the dispense tip volume detection device 400 or the sample aspiration volume detection device 500, and therefore can be replaced by such operations of the dispense tip volume detection device 400 or the sample aspiration volume detection device 500.

At operation 1602, the tip alignment detection device 1114 obtains an image of the dispense tip 1510. The image of the dispense tip 1510 can be captured by the dispense tip image capture unit 130.

At operation 1604, the tip alignment detection device 1114 detects a predetermined point 1640 of the first reference line 1512 of the dispense tip 1510. In some embodiments, the predetermined point 1640 is the center of the first reference line 1512. Other points of the first reference line 1512 can be used in other embodiments.

At operation 1606, the tip alignment detection device 1114 detects a predetermined point 1642 of the meniscus 1632 of the fluidic substance 1630 contained in the dispense tip 1510. In some embodiments, the predetermined point 1642 is the center of the meniscus of the substance in the dispense tip. Other points of the meniscus can be used in other embodiments.

In other embodiments, instead of the meniscus of the fluidic substance, the second reference line 1514 is used. In this application, the tip alignment detection device 1114 detects a predetermined point (e.g., the center) of the second reference line of the dispense tip.

At operation 1608, the tip alignment detection device 1114 connects the points 1640 and 1642 to define a line 1634 between the points 1640 and 1642.

At operation 1620, the tip alignment detection device 1114 determines an angle C of the line 1634 relative to a reference line 1636. In some embodiments, the reference line 1636 is in parallel with a vertical line in the image captured by the dispense tip image capture unit 130. Other lines can be used as the reference line 1636 in other embodiments.

Although the first reference line 1512 and the meniscus 1632 of the aspirated substance 1630 are used to determine the line 1634, other reference lines or points can be used to define the line 1634. For example, any combination of the first reference line 1512, the second reference line 1514, the meniscus 1632 of aspirated substance, other portions of the dispense tip 1510, and any portion of the sample pipetting module 512 engaging the dispense tip 1510.

At operation 1612, the tip alignment detection device 1114 determines whether the angle C is less than a threshold value. The threshold value represents a maximum acceptable angle at which the dispense tip can be tilted. When the dispense tip is tilted at an angle greater than the threshold angle value, the detected volume of substance is considered to be unacceptable for reliable result. In some embodiments, the threshold angle value ranges from about 0.5 to about 5 degrees. In other embodiments, the threshold angle value ranges from about 1 to about 3 degrees. In yet other embodiments, the threshold angle value is about 2 degrees.

If it is determined that the angle C of the line 1634 is less than the threshold angle value ("YES" at this operation), the method 1600 continues on at operation 1616. Otherwise ("NO" at this operation), the method 1600 moves on to operation 1614, at which the tip alignment detection device 1114 flags the aspiration to indicate that the aspirated volume in the dispense tip is not appropriate for subsequent processes. At operation 1614, another aspiration can be performed using another dispense tip for repeating the operation 1602 and the subsequent operations.

At operation 1616, a volume of the substance in the dispense tip is obtained using the captured image. In some embodiments, the dispense tip volume detection device 400 or the sample aspiration volume detection device 500 can perform this operation as described herein.

At operation 1618, the tip alignment detection device 1114 determines whether the detected volume is larger than a threshold volume value. The threshold volume value represents a maximum volume in the dispense tip which may be affected (or significantly affected) by the side misalignment and/or the depth misalignment. When the volume of substance contained in the dispense tip is larger than this threshold value, it is considered that the side and depth misalignments would not significantly affect the detection of volume in the dispense tip, and the calculation of such volume in the dispense tip is acceptable regardless of the side and depth misalignments. When the volume of substance contained in the dispense tip is equal to or smaller than this threshold value, it is considered that the side or depth misalignment can significantly impact the detection of volume based on the captured image, and the calculation of such volume would be unacceptable.

In some embodiments, the threshold volume value ranges from about 3 to about 30 μL. In other embodiments, the threshold volume value ranges from about 5 to about 20 μL. In yet other embodiments, the threshold angle value is about 10 μL.

If it is determined that the detected volume is larger than the threshold volume value ("YES" at this operation), the method 1600 continues on at operation 1620, in which the calculated volume is reported. Otherwise ("NO" at this operation), the method 1600 moves on to operation 1622 and subsequent operations.

At operation 1622, the tip alignment detection device 1114 operates to correct the detected volume using the second reference line 1514. An example method for correcting the volume using the second reference line is described with reference to FIGS. 65 and 66.

In the illustrated example, it is primarily described that, if the angle does not meets the threshold angle value, the aspiration that has been performed to the dispense tip is flagged. Alternatively, the method 1600 can be performed before aspirating a particular substance, such as a reagent, a sample, or a substrate, into a dispense tip. In this configuration, if the angle does not meets the threshold angle value, the tip alignment detection device 1114 can operate to prevent an intended substance from being aspirated into the dispense tip, or operate to generate a notification that the aspiration of such an intended substance should not be performed or should be performed with caution.

Figure 65:
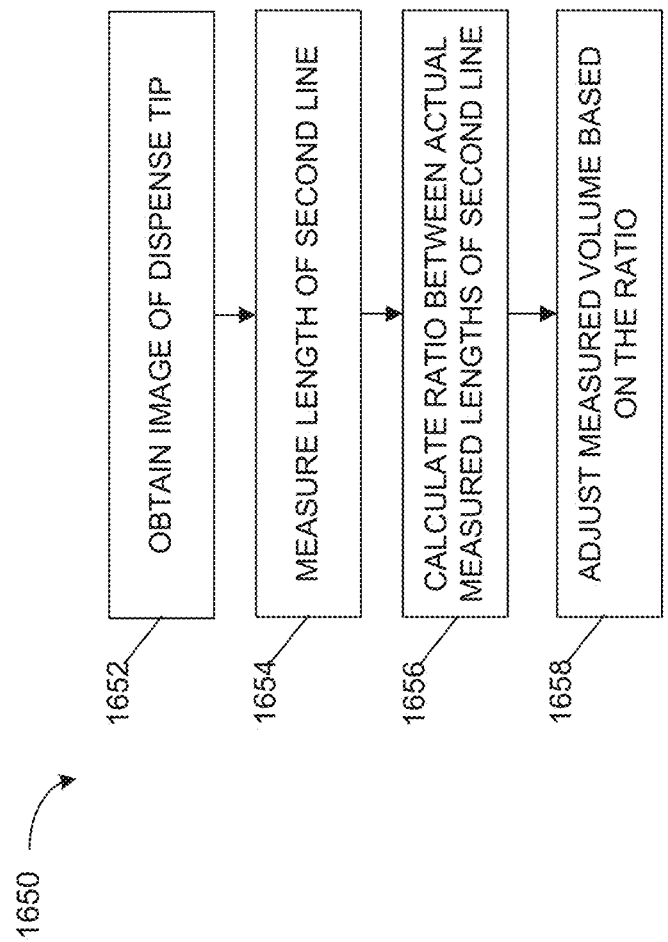
FIG. 65 is a flowchart illustrating an example method for correcting the volume using the second reference line.

FIG. 65 is a flowchart illustrating an example method 1650 for correcting the volume using the second reference line. The method 1650 can begin at operation 1652, in which the tip alignment detection device 1114 obtains an image of the dispense tip 1510, as in the operation 1602 in FIG. 63.

At operation 1654, the tip alignment detection device 1114 measures the length of the second reference line 1514 in the captured image.

At operation 1656, the tip alignment detection device 1114 calculates a ratio between the measured length of the second reference line 1514 and an actual length of the second reference line 1514. The actual length of the second reference line 1514 is known. For example, the actual length of the second reference line 1514 can be measured from an actual model or product of the dispense tip 1510, or from an image of the dispense tip 1510 that is not misaligned.

The length of the second reference line 1514 that is measured from the captured image will be different from the actual length of the second reference line 1514 where the dispense tip 1510 is tilted in the Y-direction as depicted in Diagram 3 of FIG. 59. Therefore, the ratio between the measured length and the actual length of the second reference line 1514 can indicate how much the depth misalignment occurs in the dispense tip (i.e., how much the dispense tip is tilted in the Y-direction as in Diagram 3 of FIG. 59).

At operation 1658, the tip alignment detection device 1114 operates to correct the detected volume of substance using the ratio. As the ratio between the measured length and the actual length of the second reference line 1514 is correlated with the degree of depth misalignment of the dispense tip, the ratio is also correlated with the volume of substance detected from the captured image. Therefore, the ratio can be used to adjust the volume of substance in the dispense tip that is estimated from the captured image.

Although it is primarily described that the second reference line 1514 is used in the operations 1652, 1654, 1656, and 1658, other reference lines or points can be used for the same operations. For example, the first reference line 1512 or other features in the dispense tip 1510 can be used instead of the second reference line 1514.

In the illustrated example, it is primarily described that, if the ratio between the measured length of the second reference line 1514 and an actual length of the second reference line 1514 is used to adjust the measured volume. However, in another embodiment, the method 1650 can be performed before aspirating a particular substance, such as a reagent, a sample, or a substrate, into a dispense tip. In this application, if the ratio does not meet a predetermined threshold, the tip alignment detection device 1114 can operate to prevent an intended substance from being aspirated into the dispense tip, or operate to generate a notification that the aspiration of such an intended substance should not be performed or should be performed with caution.

Figure 66:
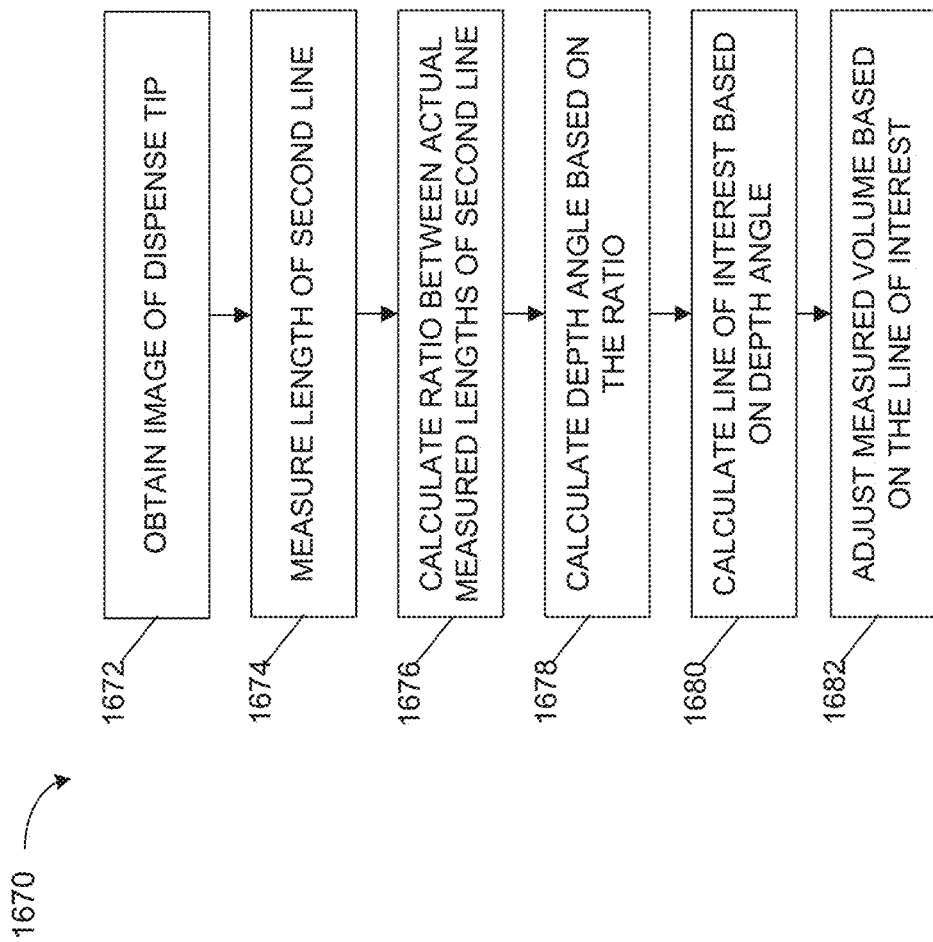
FIG. 66 is a flowchart illustrating another example method for correcting the volume using the second reference line.

FIG. 66 is a flowchart illustrating another example method 1670 for correcting the volume using the second reference line. The method 1650 is described with also reference to FIG. 67, which schematically illustrates a depth misalignment of the dispense tip with respect to the camera unit.

In this method 1670, operations 1672, 1674, and 1676 are identical or similar to the operations 1652, 1654, and 1656 in FIG. 65, and, therefore, the descriptions of these operations are omitted for brevity.

At operation 1678, the tip alignment detection device 1114 calculates a depth angle D (Diagram 3 of FIG. 59 and FIG. 67) based on the ratio calculated in the operation 1676. The depth angle D represents an angle at which the dispense tip is tilted in the Y-direction (i.e., the depth direction), and is correlated with the ratio.

At operation 1680, the tip alignment detection device 1114 calculates a line of interest E' based on the depth angle D. The line of interest E' represents a line that connects a proximate end 1684 of the dispense tip to a camera perspective line 1685 extending between the camera and a center 1686 of the second reference line 1514 of the properly aligned dispense tip (i.e., aligned with a vertical line 1687). The line of interest E' extends perpendicularly from the camera perspective line 1685 to the proximate end 1684 of the dispense tip.

In some embodiments, the line of interest E' can be calculated using a line E and an angle D' as depicted in FIG.

67. In some embodiments, the angle D' can be approximated to the depth angle D where the angles D' and D are relatively small. The line E is a line extending between the proximate end 1684 of the dispense tip and a camera perspective line 1688. The camera perspective line 1688 extends from the camera and a center 1689 of the second reference line 1514 of a misaligned dispense tip 1690 (i.e., misaligned at the depth angle D). As such, the line of interest E' corresponds to an adjustment or compensation to the line E that is obtained from the misaligned dispense tip.

In some embodiments, as illustrated in FIG. 67, the tip alignment detection device 1114 includes or utilizes the camera unit 2550, which is included in the dispense tip image capture unit 130 (FIG. 10). As illustrated in FIG. 2, the camera unit 2550 is mounted on the sample precise pipetting unit ("Sample Precision Gantry") 152B. As described above, the camera unit 2550 and its associated components are configured similar to the camera unit 550 and its associated components (e.g., the light source 551, the light source 552, and the screen 553). One example of the camera unit 2550 is AE3-IS Machine Vision Camera+IO board, such as part number AE3-IS-CQBCKFP2-B, available from Cognex Corporation (Natick, MA).

At operation 1682, the tip alignment detection device 1114 adjusts the detected volume based on the line of interest E'.

Figure 68:
FIG. 68 is an example data table of volume detection before and after correction performed by the tip alignment detection device.

FIG. 68 is an example table of data 1694 of volume detection before and after correction performed by the tip alignment detection device 1114. In the table 1994, the second column shows the detected volumes of substance aspirated into a dispense tip before correction, and the third column shows the volumes of substance after correction using the tip alignment detection device 1114.

Referring to FIGS. 69-79, an example of the particle concentration check system 124 is described.

Figure 69:
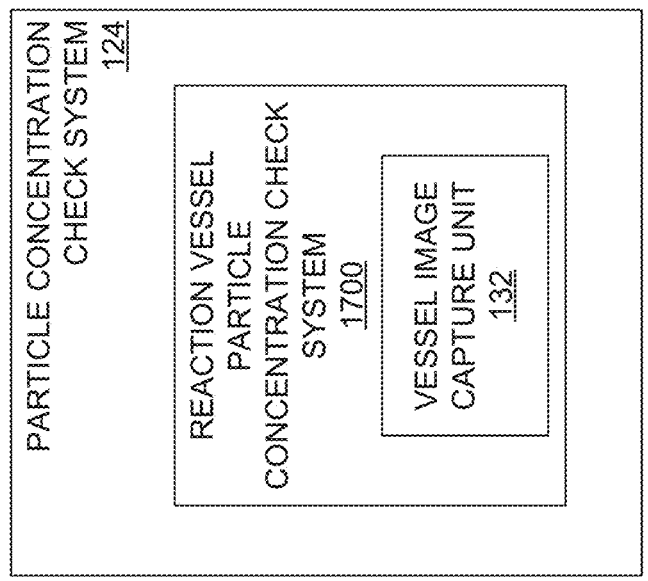
FIG. 69 is a block diagram of an example particle concentration check system of FIG. 1.

FIG. 69 is a block diagram of an example of the particle concentration check system 124 of FIG. 1. In some embodiments, the particle concentration check system 124 includes a reaction vessel particle concentration check system 1700.

The reaction vessel particle concentration check system 1700 operates to determine a particle concentration in a fluidic substance contained in a reaction vessel. In other embodiments, the reaction vessel particle concentration check system 1700 can also be used to detect a particle concentration in other types of vessels, such as a sample vessel, a dilution vessel, and a cuvette, which are used throughout the process in the instrument 100. In some embodiments, the reaction vessel particle concentration check system 1700 uses the vessel image capture unit 132 as described herein.

In clinical diagnostic applications, the bound-free separation using paramagnetic particles is typically used to generate a specific signal. However, due to certain tolerance, particles with different sizes can remain, which can make it difficult to have a consistent particle retention rate over one or more washing steps. There are several factors that impact particle loss through washing. Examples of the factors include dispensing tip alignment, reaction vessel positioning, and resuspension spin speed change. However, such factors cannot be precisely monitored.

As described in FIG. 4, one example method for measuring a particle concentration or particle retention rate is to use labeled paramagnetic particles (e.g., alkaline-phosphatase) as a tool to directly measure particles left after washing. Signal, such as light, that are generated by the labeled paramagnetic particles are measured to estimate the particle concentration, assuming that the signal is proportional to the particle amount. However, this method can require enzyme reaction with takes some time (e.g., at least about 5 minutes) to obtain results. The method also requires comparing a result after a single wash and a result after two washes to calculate the paramagnetic particle loss per wash. Additional cost is required to provide the diagnostic tool, such as the labeled particles. The Alkaline-phosphatase activity and binding capability do not last longer, and thus it needs to study and define a stability period.

The reaction vessel particle concentration check system 1700 operates to identify the particle retention rate by analyzing the image of a reaction vessel. The reaction vessel particle concentration check system 1700 can generate calibration data on site by creating different concentration particles in reaction vessels.

As described herein, the reaction vessel particle concentration check system 1700 is part of the instrument 100, and therefore is operated in connection with the systems, devices, components, engines, and other parts of the instrument 100 as described herein.

Figure 70:
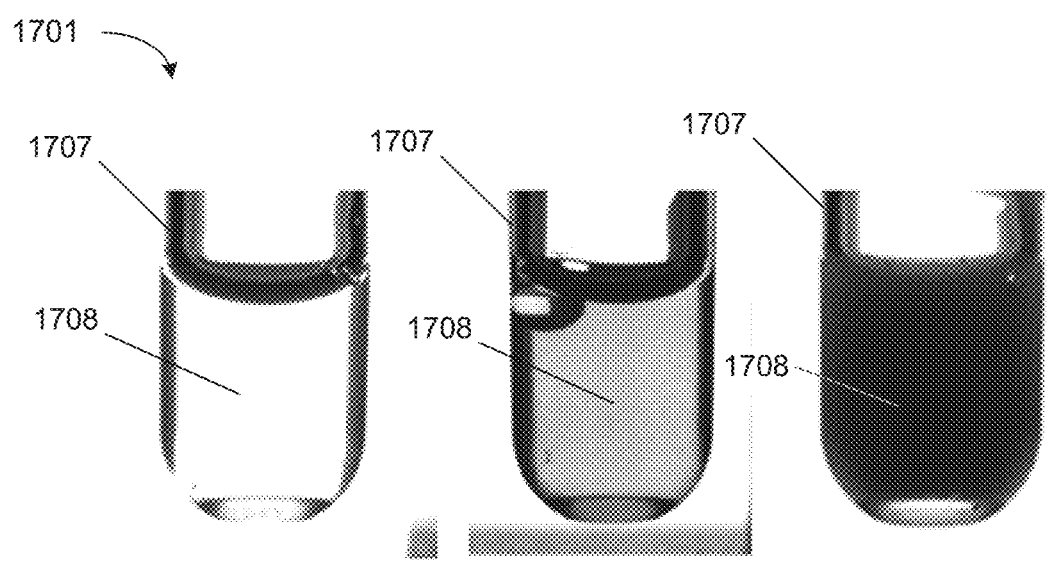
FIG. 70 shows example images of a reaction vessel with different particle concentrations.

FIG. 70 shows example images 1701 of a reaction vessel with different particle concentrations. The left image shows a fluidic substance 1708 in a reaction vessel 1707, such as the cuvette 320 (FIG. 4) and the reaction vessel 728 (FIG. 23), contains particles less than the other images. The center image shows a fluidic substance in the reaction vessel contains particles more than the left image and less than the right image. The right image shows that a fluidic substance in the reaction vessel contains particles more than the other images. As depicted, when a paramagnetic particle concentration becomes higher, the turbidity increases, and thus the brightness accordingly changes. As the number of particles increases in a reaction vessel, the number of photons that are generated from a backlight of the reaction vessel and transmitted through the reaction vessel becomes lower. Accordingly, the brightness changes on an image of the reaction vessel captured by a camera.

The brightness in the image of a reaction vessel can depend on not only a particle concentration in the reaction vessel but also a camera exposure time. An optimal camera exposure time can be determined depending on the type of assay and the amount of desired particle concentration. Further, the variability of particle concentration measurement varies as a function of particle concentration. Therefore, in some embodiments, a particular particle concentration range is to be used to obtain an accurate measurement.

Figure 71:
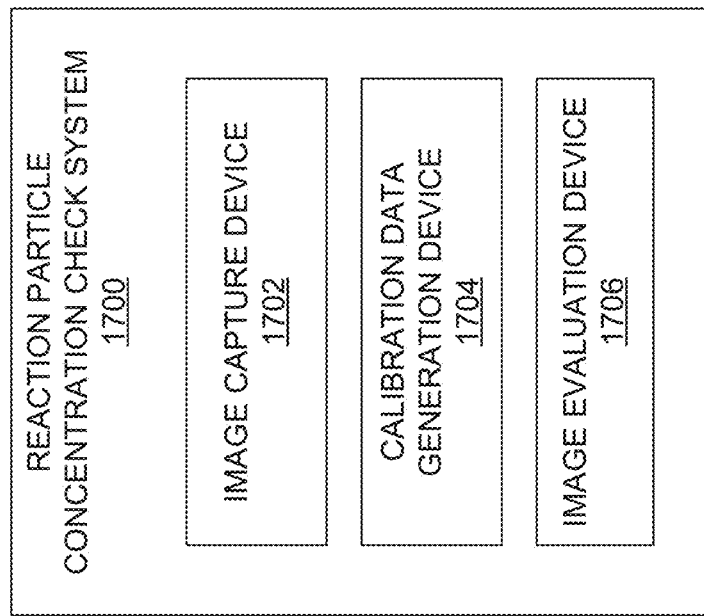
FIG. 71 is a block diagram of an example reaction vessel particle concentration check system.

FIG. 71 is a block diagram of an example of the reaction vessel particle concentration check system 1700. In some embodiments, the reaction vessel particle concentration check system 1700 includes an image capture device 1702, a calibration data generation device 1704, and an image evaluation device 1706.

The image capture device 1702 operates to capture an image 1701 of a fluidic substance 1708 contained in the reaction vessel 1707. In some embodiments, the image capture device 1702 utilizes the vessel image capture unit 132, which includes the camera unit 730 and the light source 732 (or the screen 733). In some embodiments, the light source 732 of the image capture device 1702 generates a white back light. In other embodiments, the light source 732 provides one or more colored back lights, which can be either fixed or variable during image capturing.

The fluidic substance 1708 in the reaction vessel 1707 contains particles of interest, and the concentration of the particles is to be measured by analyzing the image 1701. In some embodiments, the fluidic substance 1708 includes a mixture of sample, reagent, substrate, and/or other substances. One example of the fluidic substance 1708 is a mixture of the first reagent 322, the sample 324, the second reagent 332, and the substrate 340, as shown in FIG. 4. In the example of FIG. 4, the fluidic substance 1708 can be a substance after the operation 310, in which the substrate 340 is dispensed into the reaction vessel. The reaction vessel particle concentration check system 1700 can measure the concentration of labeled paramagnetic particles in the reaction vessel.

The calibration data generation device 1704 operates to generate calibration data usable to determine a particle concentration in a reaction vessel. An example of the calibration data generation device 1704 is described with reference to FIG. 73.

The image evaluation device 1706 operates to evaluate an image of a reaction vessel captured by the image capture device 1702. The captured image is evaluated to determine a concentration of particles contained in the reaction vessel 1707.

Figure 72:
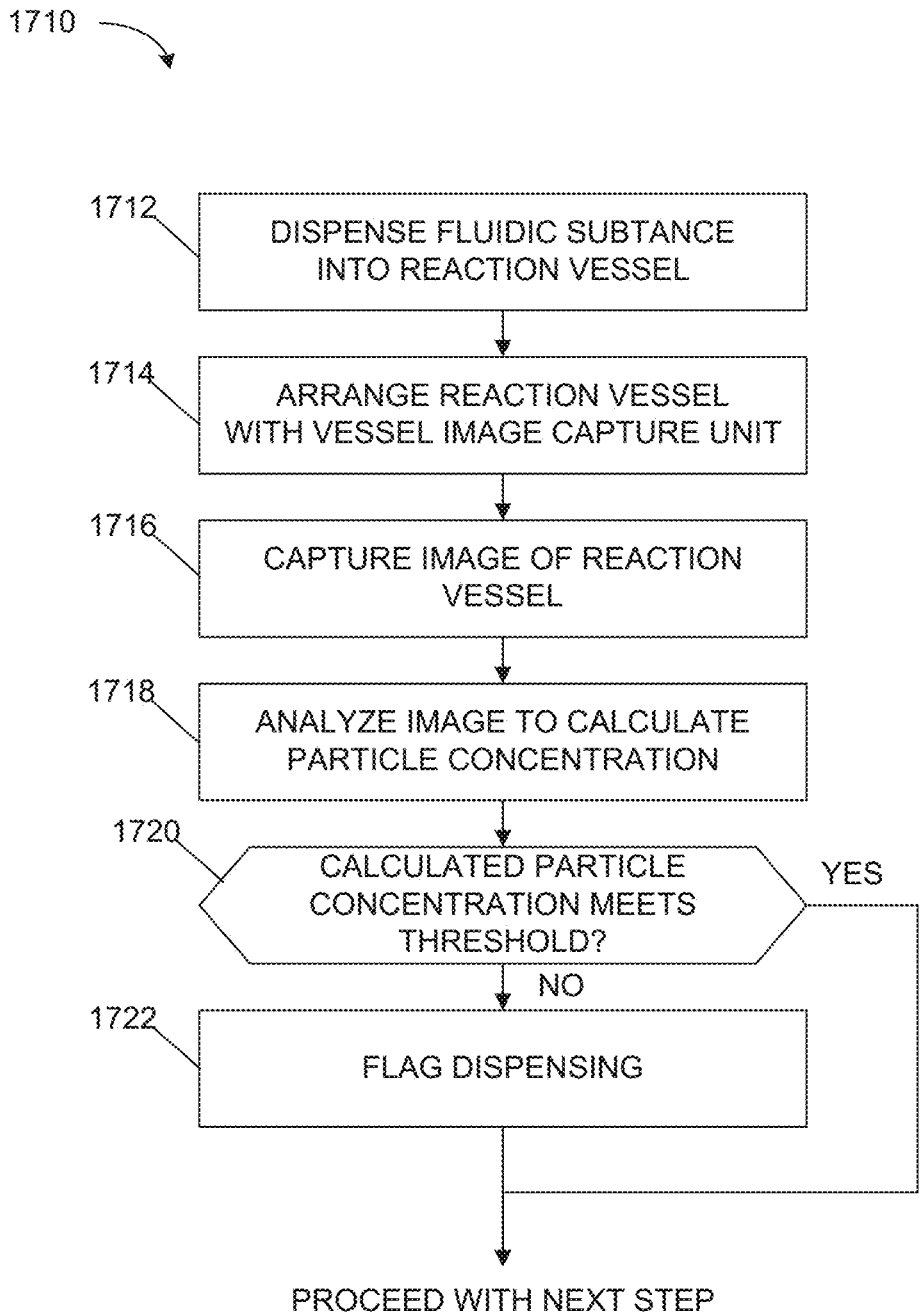
FIG. 72 is a flowchart illustrating an example method for measuring a particle concentration in a fluidic substance contained in a reaction vessel.

FIG. 72 is a flowchart illustrating an example method 1720 for measuring a particle concentration in a fluidic substance contained in a reaction vessel. In some embodiments, the method 1720 can be performed by the reaction vessel particle concentration check system 1700, and/or other parts of the instrument 100.

At operation 1712, a fluidic substance 1708 is dispensed to a reaction vessel 1707 as programmed. In some embodiments, the reaction vessel 1707 is supported in the container carriage device 720. Examples of the fluidic substance include a sample, diluent, reagent, substrate, or any combination thereof, as described herein. For example, diluents or reagents are used during a diagnostic mode for the wash wheel. In some embodiments, the reaction vessel 1707 already contains other fluidic substances, such as a sample, and after a fluidic substance 1708 is dispensed to a reaction vessel 1707, the fluidic substance 1708 is mixed with the other fluidic substances in the reaction vessel 1707. The mixing can be performed with a stirrer in direct contact with the fluidic substances, an ultrasonic probe in direct or indirect contact with the fluidic substances, or any other suitable mixing apparatus.

At operation 1714, the container carriage device 720 transports the reaction vessel 1707 containing the dispensed substance to the vessel image capture unit 132. In some embodiments, the vessel image capture unit 132 is arranged to capture an image of the reaction vessel 1707 after dispensing without transportation. In other embodiments, the dispensing at the operation 1712 occurs at a location where the vessel image capture unit 132 is arranged in place and captures an image of the reaction vessel 1707 without moving the reaction vessel 1707 after dispensing.

At operation 1716, the vessel image capture unit 132 captures an image 1701 of the reaction vessel 1707. In some embodiments, the image 1701 of the reaction vessel 1707 is a digital image of a predetermined resolution. In some embodiments, the vessel image capture unit 132 captures an image 1702 of the reaction vessel 1707 after mixing for a predetermined time period. For example, the vessel image capture unit 132 captures an image 1702 of the reaction vessel 1707 after approximately 6.5 seconds of mixing.

At operation 1718, the reaction vessel particle concentration check system 1700 analyzes the image to determine a retention rate of particles of interest within the reaction vessel 1707. An example of the operation 1718 is described in more detail with respect to FIG. 76.

At operation 1720, the reaction vessel particle concentration check system 1700 determines whether the measured particle concentration meets a concentration threshold. When the measured particle concentration is outside the threshold, the dispensing of the fluidic substance in the reaction vessel 1707 is considered to be inappropriate. In some embodiments, the concentration threshold varies depending on different types of test substances. Examples of the concentration threshold are described with reference to FIG. 77.

When the measured particle concentration is determined to meet the threshold ("YES" at the operation 1720), the method 1710 proceeds to perform a predetermined next step. Otherwise ("NO" at the operation 1720), the method 1710 moves on to operation 1722.

At operation 1722, the reaction vessel particle concentration check system 1700 flags the reaction vessel to indicate that the substance in the reaction vessel is not appropriate for subsequent processes. In other embodiments, the entire test result that has used the fluidic substance can be flagged to indicate or suggest that the test result can be improper. Alternatively, the reaction vessel particle concentration check system 1700 operates to stop an associated test or analytic process in the instrument 100. In other embodiments, the evaluation result can be used to automatically adjust a test result that may be erroneous due to the inappropriate volume of the fluidic substance.

Figure 73:
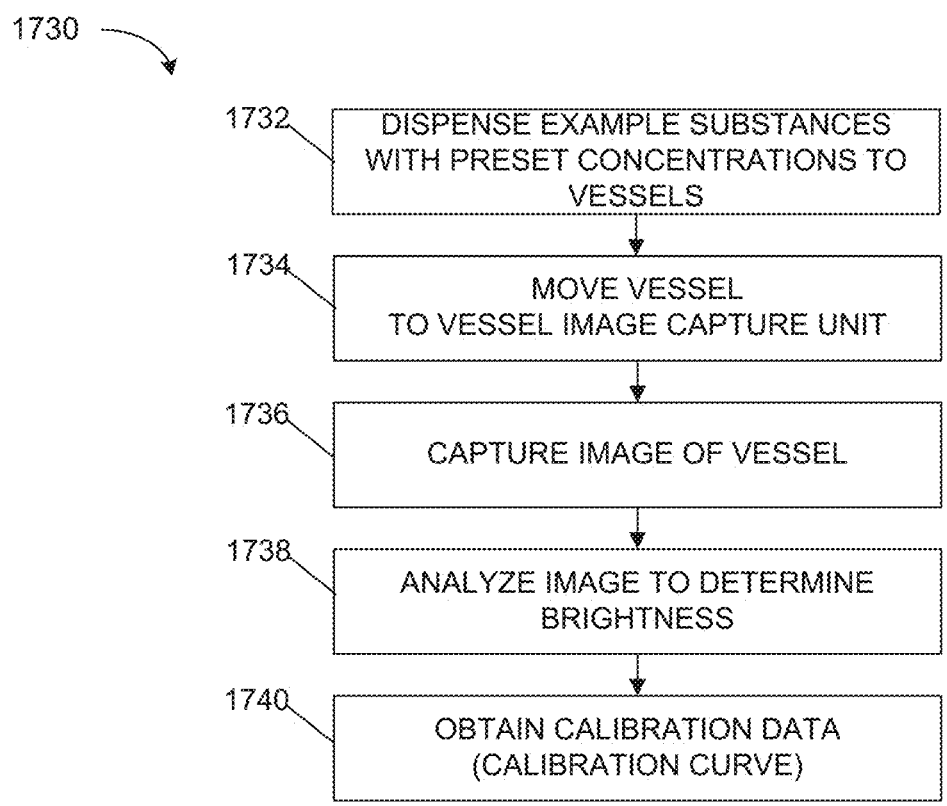
FIG. 73 is a flowchart illustrating an example method for generating calibration data.

FIG. 73 is a flowchart illustrating an example method 1730 for generating calibration data. The method 1730 is described with also reference to FIG. 74, which is a table 1750 of example substances used to generate the calibration data, and FIG. 75 which shows example calibration curves 1760 and 1762 plotted from the calibration data. In some embodiments, the method 1730 is performed by the calibration data generation device 1704.

At operation 1732, a plurality of substances with different particle concentrations are dispensed into respective reaction vessels. By way of example, as shown in FIG. 74, six substances with six known particle concentrations are dispensed into six reaction vessels. As the number of substances increases, the calibration data can be more accurate and reliable.

In some embodiments, a substance with a particular particle concentration can be prepared by first dispensing a predetermined amount of particles in a reaction vessel and dispensing a predetermined amount of substrate into the reaction vessel. In the example of FIG. 74, a first substance with 100% concentration rate is prepared by dispensing 200 μL of particles (e.g., paramagnetic particles) and 0 μL of substrate, a second substrate with 90% concentration rate is prepared by dispensing 180 μL of particles and 20 μL of substrate, a third substance with 80% concentration rate is prepared by dispensing 160 μL of particles and 40 μL of substrate, a fourth substance with 70% concentration rate is prepared by dispensing 140 μL of particles and 60 μL of substrate, a fifth substance with 60% concentration rate is prepared by dispensing 120 μL of particles and 80 μL of substrate, and a sixth substance with 50% concentration rate is prepared by dispensing 100 μL of particles and 100 μL of substrate.

In the illustrated embodiment, the operation 1732 is performed by simultaneously dispensing substances with different particle concentrations into multiple reaction vessels. In other embodiments, the substances with different concentrations are dispensed into reaction vessels one-by-one, and each reaction vessel is imaged and analyzed to determine brightness in the subsequent operations.

At operation 1734, the reaction vessels are moved to the vessel image capture unit 132. In other embodiments, the reaction vessels are arranged in place beforehand.

At operation 1736, the vessel image capture unit 132 captures an image of each of the reaction vessel 1707. In some embodiments, the captured image is a gray scale digital image. In other embodiments, the captured image is a color digital image.

At operation 1738, each of the captured images is analyzed to determine brightness of the substance contained in the reaction vessel. In some embodiments, the brightness is identified by a gray scale range, such as a range from 0 to 255. Other ranges are also possible in other embodiments.

At operation 1740, the calibration data is generated by correlating the brightness of the substance and the known particle concentration of the substance. When all the substances are evaluated, the calibration data can be plotted into a calibration curve, which can be used as the basis for evaluating a particle concentration in a test substance.

As described herein, each assay has a different particle type and particle concentration to optimize performance Therefore, the calibration data and the calibration curves need to be obtained for different assays to detect particle concentrations accurately.

As shown in FIG. 75, an example set of calibration data 1760 is presented regarding a substance type of troponin I (TnI) with exposure time of 2 ms. An example set of calibration data 1762 is presented for a substance type of total triiodothyronine (TT3) with exposure time of 1 ms. A calibration curve can be plotted using the data points as depicted in these examples.

Figure 76:
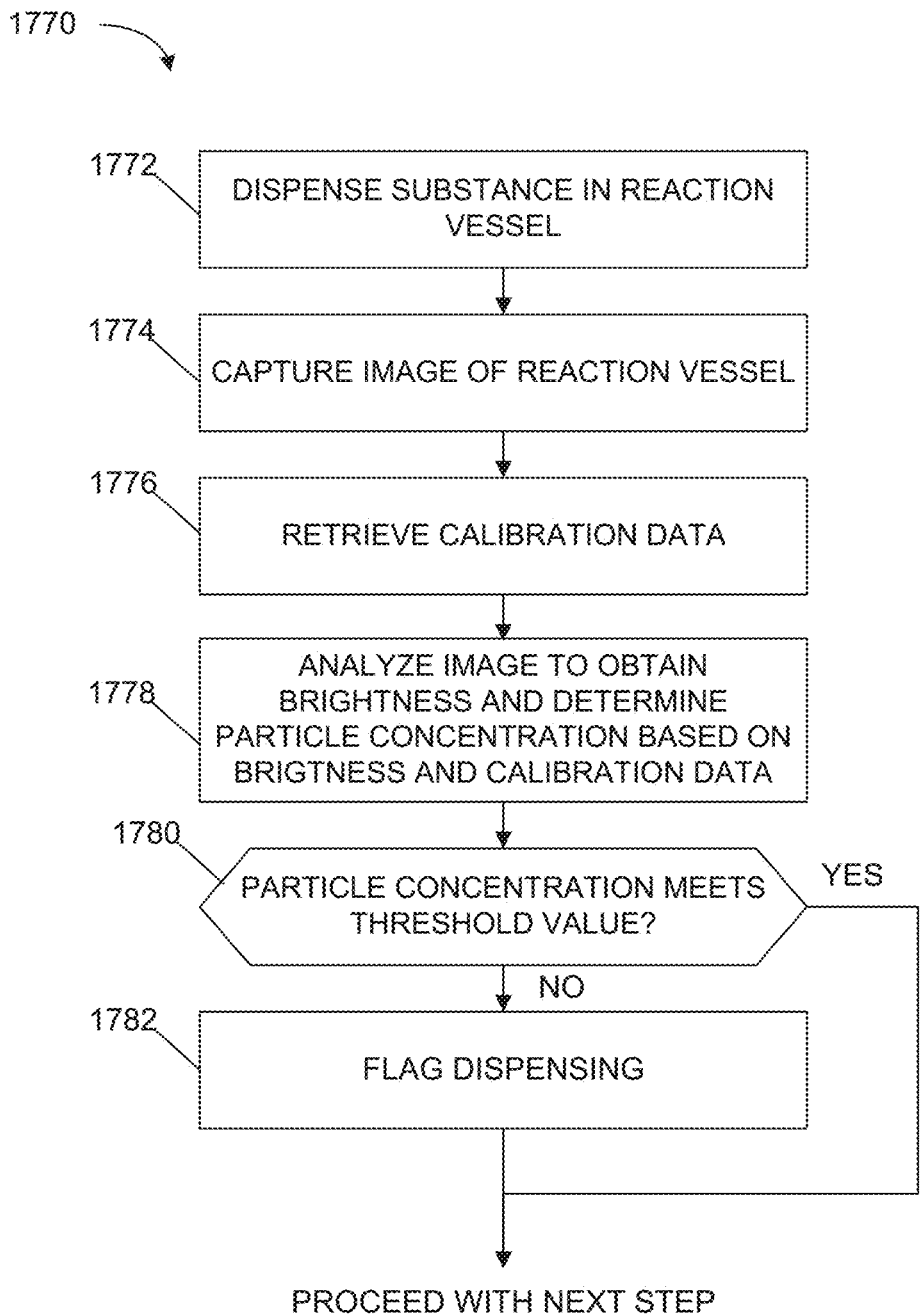
FIG. 76 is a flowchart illustrating an example method for measuring a particle concentration in a fluidic substance contained in a reaction vessel.

FIG. 76 is a flowchart illustrating an example method 1770 for measuring a particle concentration in a fluidic substance contained in a reaction vessel. In some embodiments, the method 1770 is performed by the reaction vessel particle concentration check system 1700 and/or other parts of the instrument 100.

In this method 1770, operations 1772 and 1774 are performed similarly to the operations 1712, 1714, and 1716 of FIG. 72. Therefore, the description of these operations is omitted for brevity.

At operation 1776, the reaction vessel particle concentration check system 1700 retrieves the calibration data as obtained in the method 1730.

At operation 1778, the reaction vessel particle concentration check system 1700 analyzes the captured image to determine the brightness of the substance in the reaction vessel. Then, the reaction vessel particle concentration check system 1700 determines a particle concentration in the reaction vessel based on the determined brightness and the calibration data.

In some embodiments, the brightness of substance in the captured image can be identified as a numerical value, such as a gray scale value of a predetermined range (e.g., gray scale from 0 to 255). In other embodiments, different identifications can be used to represent the brightness of substance in the captured image. Once the brightness of substance is determined in the captured image, the calibration data is looked up to find a particle concentration value corresponding to the determined brightness. Where the calibration data do not have an exact data point corresponding to the determined brightness, a concentration value can be extrapolated based on the known data points. Alternatively, the calibration curve obtained from the calibration data can be used to determine a particle concentration valued corresponding to the brightness of substance in the captured image.

At operation 1780, the reaction vessel particle concentration check system 1700 determines whether the measured particle concentration meets a concentration threshold. When the measured particle concentration is determined to meet the threshold ("YES" at the operation 1780), the method 1770 proceeds to perform a predetermined next step. Otherwise ("NO" at the operation 1780), the method 1770 moves on to operation 1782.

At operation 1782, the reaction vessel particle concentration check system 1700 flags the reaction vessel to indicate that the substance in the reaction vessel is not appropriate for subsequent processes. In other embodiments, the entire test result that has used the fluidic substance can be flagged to indicate or suggest that the test result can be improper. Alternatively, the reaction vessel particle concentration check system 1700 operates to stop an associated test or analytic process in the instrument 100. In other embodiments, the evaluation result can be used to automatically adjust a test result that may be erroneous due to the inappropriate volume of the fluidic substance.

FIG. 77 is an example table 1790 of example concentration thresholds for different assay substances. When a measured particle concentration is outside an associated threshold, the dispensing of fluidic substance in the reaction vessel is considered to be inappropriate and can be flagged. As shown, different assay substances 1792 have different concentration thresholds 1794. For example, for HBcAb, a desired particle concentration 1796 is 6.7 mg/mL, and the concentration threshold 1794 is equal to or greater than 85%. Therefore, if the particle concentration in HBcAb is equal to or greater than 85% of 6.7 mg/mL (approximately 5.695 mg/mL), the reaction vessel is considered to be acceptable for testing.

Figure 78:
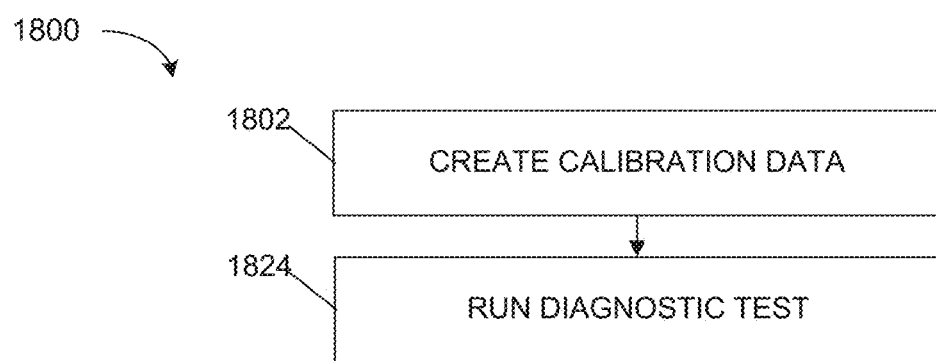
FIG. 78 is a flowchart of an example diagnostic function utilizing the functions of the reaction vessel particle concentration check system.
Figure 79:
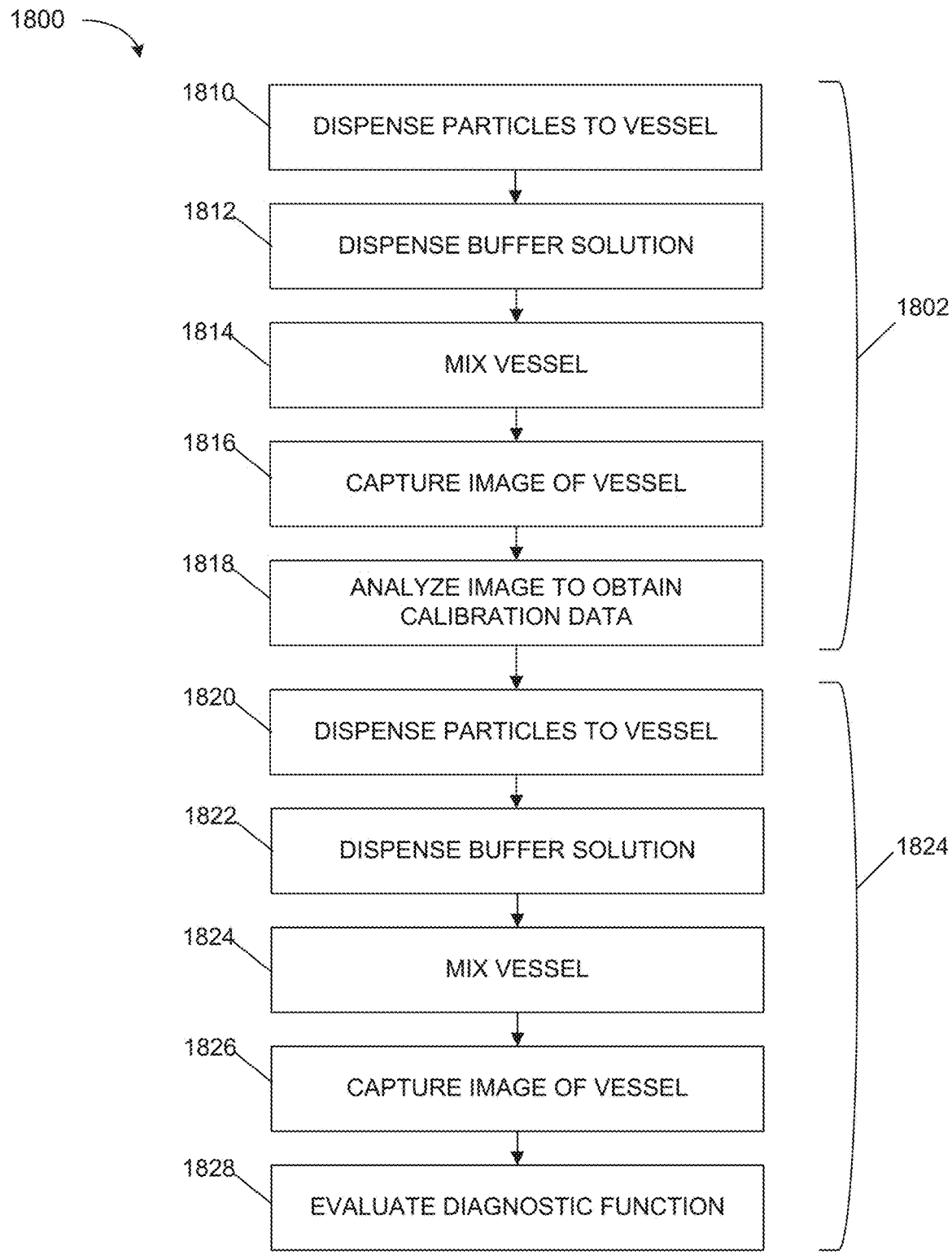
FIG. 79 is a flowchart of another example of the diagnostic function of FIG. 78.

Referring to FIGS. 78 and 79, the operations and functions of the reaction vessel particle concentration check system 1700 can also be used as part of diagnostic function where uncoated particles can be used to generalize the bound-free separation function and detect system failures. In particular, FIG. 78 is a flowchart of an example diagnostic method 1800. The method 1800 includes operation 1802 in which calibration data is created, and operation 1804 in which diagnostic test is performed. FIG. 79 further illustrates the method 1800. In some embodiments, the operation 1802 of the method 1800 includes operations 1810, 1812, 1814, 1816, and 1820, and the operation 1804 includes operations 1820, 1822, 1824, 1826, and 1830. These operations are performed identically or similarly to the operations performed by the reaction vessel particle concentration check system 1700 as described above. Therefore, the operations in the method 1800 are briefly described for brevity.

To perform the operation 1802, particles of interest are dispensed into a vessel (operation 1810). Then, a buffer solution is dispensed in the vessel (operation 1812), and the vessel is mixed (operation 1814). Then, an image of the vessel is captured after the vessel is moved to the image capture unit (operation 1816). The captured image is analyzed to obtain calibration data (operation 1818).

To perform the operation 1804, particles of interest are dispensed into a vessel (operation 1820). Then, a buffer solution is dispensed in the vessel (operation 1822), and the vessel is mixed (operation 1824). Then, an image of the vessel is captured after the vessel is moved to the image capture unit (operation 1826). The captured image is analyzed to measure a particle concentration based on the calibration data (operation 1828). The obtained particle concentration can be used to perform diagnostic function.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A system for evaluating a fluidic substance, the system comprising:
    a sample pipetting device configured to at least partly engage a dispense tip, the sample pipetting device configured to aspirate a fluidic substance into the dispense tip, the dispense tip having at least one reference line;
    an image capture unit configured to capture an image of at least a portion of the dispense tip;
    at least one computing device configured to:
        identify the at least one reference line of the dispense tip from the portion of the image of the dispense tip;
        determine at least one characteristic of the at least one reference line; and
        compare the at least one characteristic of the at least one reference line to a threshold value, which threshold value is representative of a misalignment of the dispense tip.

2. The system of claim 1, wherein the at least one reference line comprises a first reference line and a second reference line formed on the dispense tip;
    wherein the system is configured to, in response to determining the misalignment, prevent the sample pipetting device from aspirating the fluidic substance into the dispense tip;
    wherein the misalignment of the dispense tip includes a side misalignment and a depth misalignment;
    wherein the sample pipetting device is configured to aspirate a liquid into a further dispense tip;
    wherein the system is configured to determine a volume of the aspirated liquid;
    wherein the image capture unit is configured to capture a further image of the further dispense tip;
    wherein the computing device is configured to determine a pixel distance between a reference point in the image associated with the further dispense tip and is configured to correlate the determined volume with the determined pixel distance and to generate correlation data based on the determined volume and the determined pixel distance;
    wherein the correlation data are generated based on a plurality of correlations between a plurality of determined pixel distances and a plurality of determined volumes of liquid aspirated into the further dispense tip;
    wherein the aspirated liquid comprises a dye solution;
    wherein the system is configured to determine the volume of the aspirated liquid based on spectrophotometry; and/or
    wherein the system is configured to determine a mass of the aspirated liquid and to determine the volume of the aspirated liquid based on the determined mass of the aspirated liquid.

3. The system of claim 1, wherein the at least one reference line comprises a first reference line and a second reference line formed on the dispense tip; and
    wherein the at least one computing device is further configured to:
        obtain the at least one characteristic of the at least one reference line based on:
            determining a length of the first reference line;
            determining a length of the second reference line; and
            determining an angle of a line relative to at least one of the first reference line and the second reference line, the line connecting a predetermined point of the first reference line and a predetermined point of the second reference line; and
        determine the misalignment of the dispense tip based on at least one of the length of the first reference line, the length of the second reference line, and the angle of the line.

4. The system of claim 1, wherein the at least one computing device is further configured to:
    in response to determining the misalignment, flag and/or initiate aspiration of the fluidic substance into the dispense tip.

5. The system of claim 1, wherein the at least one computing device is further configured to:
    identify the at least one reference line of the dispense tip from the portion of the image of the dispense tip;
    identify a surface level of the fluidic substance within the dispense tip in the image;
    determine a distance between the at least one reference line and the surface level; and
    determine a volume of the fluidic substance by converting the distance to the volume of the fluidic substance based on correlation data, the correlation data including information about a correlation between volumes within the dispense tip and distances from the at least one reference line to a plurality of surface levels within the dispense tip.

6. The system according to claim 5,
    wherein the computing device is configured to search a pattern representative of the reference line in the captured image.

7. The system according to claim 5,
    wherein the computing device is configured to compare at least a part of the captured image with a reference image and the computing device is configured to determine a matching rate and/or a correlation value of the part of the captured image and the reference image.

8. The system of claim 1, wherein the at least one reference line comprises a first reference line and a second reference line formed on the dispense tip;
    wherein the at least one computing device is further configured to:
    determine a length of the first reference line in the image;
    determine a length of the second reference line in the image;
    determine an angle of a line relative to at least one of the first reference line and the second reference line; the line connecting a predetermined point of the first reference line and a predetermined point of the second reference line;
    determine the misalignment of the dispense tip based on at least one of the length of the first reference line, the length of the second reference line, and the angle of the line; and
    adjust a volume of the fluidic substance based on the determination of the misalignment.

9. The system of claim 1, wherein the at least one reference line comprises a first reference line and a second reference line formed on the dispense tip; and wherein the at least one computing device is further configured to:
identify a predetermined point of the first reference line in the image;
identify a predetermined point of the second reference line in the image;
define an alignment line that connects the predetermined point of the first reference line and the predetermined point of the second reference line;
determine an angle of the alignment line relative to at least one of the first reference line and the second reference line; and
compare the angle to a threshold angle value, which threshold angle value is representative of a side misalignment of the dispense tip.

10. The system of claim 3, wherein the predetermined point of the first reference line is a center point of the first reference line in in the image, and the predetermined point of the second reference line is a center point of the second reference line in the image.

11. The system of claim 9, wherein the at least one computing device is further configured to:
in response to determining that the angle of the alignment line relative to at least one of the first reference line and the second reference line meets and/or exceeds the threshold angle value, flag aspiration of the fluidic substance into the dispense tip and/or initiate aspiration of the fluidic substance into the dispense tip.

12. The system of claim 1, wherein the at least one computing device is further configured to:
determine a length of the at least one reference line based on the captured image of the tip;
obtain an actual length of the at least one reference line;
calculate a ratio between the length of the at least one reference line and the actual length of the at least one reference line;
determine a depth misalignment of the dispense tip based on the ratio; and adjust a determined volume of the fluidic substance based on the ratio.

13. The system of claim 1, further comprising:
a light source and a sample pipetting module,
wherein the light source and the image capture unit are attached to the sample pipetting module, and/or
wherein the light source and the image capture unit are configured to move together with the sample pipetting module so that an image of the dispense tip can be captured in any position of the sample pipetting module.

14. A method of evaluating a fluidic substance in a container, the method comprising:
capturing, using an image capture unit, an image of at least a portion of the container;
determining, using at least one computing device, a first reference line and a second reference line of the container from the image of the container;
determining at least one characteristic of at least one of the first reference line and the second reference line,
wherein the at least one characteristic comprises at least one of a length of the first reference line; a length of the second reference line; and an angle of a line relative to at least one of the first reference line and the second reference line;
wherein the line connects a predetermined point of the first reference line and a predetermined point of the second reference line; and
comparing the at least one characteristic of at least one of the first reference line and the second reference line to a threshold value representative of a misalignment of the dispense tip.

15. The method according to claim 14, wherein the container contains a fluidic substance, the method further comprising:
identifying a surface level of the fluidic substance within the container in the captured image;
determining a distance between at least one of the first reference line and the second reference line and the surface level;
wherein the first reference line and the second reference line are determined based on pattern matching and/or based on segmentation of the captured image;
determining a volume of the fluidic substance by converting the distance to the volume of the fluidic substance based on correlation data, the correlation data including information about a correlation between volumes within the container and distances from at least one of the first reference line and the second reference line to a plurality of surface levels within the container; and
wherein the misalignment of the container includes a side misalignment and a depth misalignment.

16. The method according to claim 14,
wherein determining the first reference line and the second reference line comprises searching a pattern representative of the first reference line and/or the second reference line in the captured image.

17. The method according to claim 14,
wherein determining the first reference line and the second reference line comprises comparing at least a part of the captured image with a reference image, and the method further comprises determining a matching rate and/or a correlation value of the part of the captured image and the reference image.

18. The method of claim 14, the method further comprising:
determining a length of the first reference line in the image;
determining a length of the second reference line in the image;
determining an angle of a line relative to at least one of the first reference line and the second reference line; the line connecting a predetermined point of the first reference line and a predetermined point of the second reference line;
determining the misalignment of the container based on at least one of the length of the first reference line, the length of the second reference line, and the angle of the line; and
adjusting a volume of the fluidic substance based on the determination of the misalignment.

19. The method of claim 14, further comprising:
identifying a predetermined point of the first reference line in the image;
identifying a predetermined point of the second reference line in the image;
defining an alignment line that connects the predetermined point of the first reference line and the predetermined point of the second reference line;
determining an angle of the alignment line relative to at least one of the first reference line and the second reference line; and
comparing the angle to a threshold angle value, which threshold angle value is representative of a side misalignment of the container.

20. The method of claim 19, wherein the predetermined point of the first reference line is a center point of the first reference line in in the image, and the predetermined point of the second reference line is a center point of the second reference line in the image.

21. The method of claim 19, further comprising:
in response to determining that the angle of the alignment line relative to at least one of the first reference line and the second reference line meets and/or exceeds the threshold angle value, flagging aspiration of the fluidic substance into the container and/or initiating aspiration of the fluidic substance into the container.

22. The method of claim 14, further comprising:
determining a length of at least one of the first reference line and the second reference line based on the captured image of the container;
obtaining an actual length of at least one of the first reference line and the second reference line;
calculating a ratio between the length of at least one of the first reference line and the second reference line and the actual length of the at least one of the first reference line and the second reference line;
determining a depth misalignment of the container based on the ratio; and
adjusting a determined volume of the fluidic substance based on the ratio.

23. A non-transitory computer-readable medium on which a computer program element is stored,
which when executed on a computing device of a system for evaluating a fluidic substance, instructs the computing device to carry out the steps of the method according to claim 14.

* * * * *